(12) United States Patent
Stewart et al.

(10) Patent No.: US 6,232,320 B1
(45) Date of Patent: May 15, 2001

(54) CELL ADHESION-INHIBITING ANTIINFLAMMATORY COMPOUNDS

(75) Inventors: Andrew O. Stewart, Libertyville; Steven A. Boyd, Mundelein; David L. Arendsen; Pramila Bhatia, both of Libertyville; Kevin R. Condroski, Evanston; Jennifer C. Freeman, Grayslake; Indrani W. Gunawardana, Libertyville; Gui-Dong Zhu, Gurnee; Kraig Lartey, Waukegan, all of IL (US); Catherine M. McCarty, Brookline, MA (US); Nicholas A. Mort, Highland Park; Meena V. Patel, Chicago, both of IL (US); Michael A. Staeger, Greenfield, WI (US); David M. Stout, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/325,336

(22) Filed: Jun. 3, 1999

Related U.S. Application Data
(60) Provisional application No. 60/087,907, filed on Jun. 4, 1998.

(51) Int. Cl.⁷ .................. A61K 31/4365; C07D 513/02; C07D 495/02
(52) U.S. Cl. .................. 514/301; 564/114; 544/127; 514/233.8
(58) Field of Search ................ 514/301, 233.8; 546/114; 544/127

(56) References Cited

U.S. PATENT DOCUMENTS

| | | | |
|---|---|---|---|
| 3,903,095 | 9/1975 | Shen et al. | 260/294.8 |
| 4,988,707 | 1/1991 | Stealey et al. | 514/303 |
| 5,006,532 | 4/1991 | Baker et al. | 514/301 |
| 5,227,384 | 7/1993 | Khanna et al. | 514/303 |
| 5,597,823 | 1/1997 | Meyer et al. | 514/250 |

FOREIGN PATENT DOCUMENTS

| | | |
|---|---|---|
| 0257830 | 6/1988 | (DD) . |
| 2330109 | 1/1974 | (DE) . |
| 3533331 | 3/1987 | (DE) . |
| 0310386 | 5/1987 | (EP) . |
| 0260613 | 3/1988 | (EP) . |
| 0294074 | 7/1988 | (EP) . |
| 0388909 | 9/1990 | (EP) . |
| 2336132 | 7/1977 | (FR) . |
| 2334356 | 8/1977 | (FR) . |
| 2452490 | 10/1980 | (FR) . |
| 2010249 | 6/1979 | (GB) . |
| 8908653 | 9/1989 | (WO) . |
| 9611192 | 4/1996 | (WO) . |
| 9820007 | 5/1998 | (WO) . |
| 9962908 | 12/1999 | (WO) . |
| 962934 | 4/1996 | (ZA) . |

OTHER PUBLICATIONS

Journal of Medicinal Chemistry, vol. 38 (1995), pp. 4597–4614, D.H. Boschelle et al., "Inhibition of E–Selectin–, ICAM–1–, and VCAM–1–Mediated Cell Adhesion by Benzo[b]thiophene–, Benzofuran–, Indole–, and Naphthalene–2–carboxamides: Identification of Pd 144795 as an Inflammatory Agent".
A. D. Dunn et al., *J. Prakt. Chem./Chem.–ZTG*, 334 (6), 483–6 (1992).
J. M. Barker et al., *J. Chem. Res.* (S), 4, 122–3 (1986).
M. A. Khan et al., *J. Heterocyclic Chem.*, 14 (5), 807–12, (1977).
L. H. Klemm et al., *J. Heterocyclic Chem.*, 16 (6) 1289–91 (1979).
L. H. Klemm et al., *J. Heterocyclic Chem.*, 13 (6), 1197–1200, (1976).

*Primary Examiner*—C. S. Aulakh
(74) *Attorney, Agent, or Firm*—B. Gregory Donner

(57) ABSTRACT

Compounds having Formula I

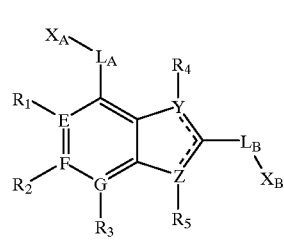

are useful for treating inflammation. Also disclosed are pharmaceutical compositions comprising compounds of Formula I, and methods of inhibiting/treating inflammatory diseases in a mammal.

25 Claims, No Drawings

CELL ADHESION-INHIBITING ANTIINFLAMMATORY COMPOUNDS

This application is a continuation-in-part of U.S. provisional application serial No. 60/087,907, filed Jun. 4, 1998, incorporated herein by reference.

TECHNICAL FIELD

The present invention relates to compounds that are useful for treating inflammatory diseases, to pharmaceutical compositions comprising these compounds, and to methods of inhibiting inflammation in a mammal.

BACKGROUND OF THE INVENTION

Inflammation results from a cascade of events that includes vasodilation accompanied by increased vascular permeability and exudation of fluid and plasma proteins. This disruption of vascular integrity precedes or coincides with an infiltration of inflammatory cells. Inflammatory mediators generated at the site of the initial lesion serve to recruit inflammatory cells to the site of injury. These mediators (chemokines such as IL-8, MCP-1, MIP-1, and RANTES, complement fragments and lipid mediators) have chemotactic activity for leukocytes and attract the inflammatory cells to the inflamed lesion. These chemotactic mediators which cause circulating leukocytes to localize at the site of inflammation require the cells to cross the vascular endothelium at a precise location. This leukocyte recruitment is accomplished by a process called cell adhesion.

Cell adhesion occurs through a coordinately regulated series of steps that allow the leukocytes to first adhere to a specific region of the vascular endothelium and then cross the endothelial barrier to migrate to the inflamed tissue (Springer, T. A., 1994, Traffic Signals for Lymphocyte Recirculation and Leukocyte Emigration: The Multistep Paradigm, Cell 76: 301–314; Lawrence, M. B., and Springer, T. A., 1991, Leukocytes' Roll on a Selectin at Physiologic Flow Rates: Distinction from and Prerequisite for Adhesion Through Integrins, Cell.65: 859–873; von Adrian, U., Chambers, J. D., McEnvoy, L. M., Bargatze, R. F., Arfos, K. E, and Butcher, E. C., 1991, Two-Step Model of Leukocyte-Endothelial Cell Interactions in Inflammation, Proc. Natl. Acad. Sci. USA 88: 7538–7542; and Ley, K., Gaehtgens, P., Fennie, C., Singer, M. S., Lasky, L. H. and Rosen, S. D., 1991, Lectin-Like Cell Adhesion Molecule 1 Mediates Rolling in Mesenteric Venules in vivo, Blood 77: 2553–2555). These steps are mediated by families of adhesion molecules such as integrin, Ig supergene family members, and selectins which are expressed on the surface of the circulating leukocytes and on the vascular endothelial cells. The first step consists of leukocyte rolling along the vascular endothelial cell lining in the region of inflammation. The rolling step is mediated by an interaction between leukocyte surface oligosacchamides (such as Sialylated Lewis-X antigen (Slex)) and a selectin molecule expressed on the surface of the endothelial cell in the region of inflammation. The selectin molecule is not normally expressed on the surface of endothelial cells but rather is induced by the action of inflammatory mediators such as TNF-α and interleukin-1. Rolling decreases the velocity of the circulating leukocyte in the region of inflammation and allows the cells to more firmly adhere to the endothelial cell. The firm adhesion is accomplished by the interaction of integrin molecules that are present on the surface of the rolling leukocytes and their counter-receptors-the Ig superfamily molecule-on the surface of the endothelial cell. The Ig superfamily molecules or CAMs (Cell Adhesion Molecules) are either not expressed or are expressed at low levels on normal vascular endothelial cells. The CAM's, like the selectins, are induced by the action of inflammatory mediators like TNF-alpha and IL-1. The final event in the adhesion process is the extravasation of the leukocyte through the endothelial cell barrier and the migration of the leukocyte along the chemotactic gradient to the site of inflammation. This transmigration is mediated by the conversion of the leukocyte integrin from a low avidity state to a high avidity state. The adhesion process relies on the induced expression of selectins and CAM's on the surface of vascular endothelial cells to mediate the rolling and firm adhesion of leukocytes to the vascular endothelium.

The induced expression of e-selectin and CAM's is mediated by the transcription factor NFkB. NFkB is a family of dimeric transcription factors made from monomers containing the 300 amino acid Rel domain. These factors can bind to DNA, interact with each other and bind to an inhibitor molecule termed IkB (Vermaa, I. M., Stevenson, J. K., Schwarz, E. M., Antwerp, D. V., and Miyamoto, S, 1995, Rel/NFlB/IkB Family: Intimate Tales of Association and Dissociation, Genes Dev. 9: 2723–2735; and Baldwin, A. S. 1996, The NFkB and IkB proteins: New Discoveries and Insights, Annu. Rev. Immunol. 14: 649–681). NFkB is found in the cytoplasm complexed with IkB. Activation of NFkB occurs in response to inflammatory mediators such as TNF-α, IL-1, and lipopolysacchamide. Activation of NFkB requires phosphorylation of IkB followed by ubiquitinylation of the IkB molecule and subsequent degradation by proteosomes. Release of NFkB from association with IkB results in translocation of the dimer to the nucleus where it can associate with specific DNA sequences. The e-selectin gene and CAM's contain NFkB-recognition sequences upstream from their coding regions. The DNA-bound NFkB acting with other proteins in the transcription complex directs the expression of the e-selectin and CAM genes among others controlled by this transcription factor.

The present invention discloses compounds that inhibit the expression of e-selectin and ICAM-1 relative to VCAM-1. These compounds are useful for the treatment or prophylaxis of diseases caused by expression of adhesion molecules. These diseases include those in which leukocyte trafficking plays a role, notably acute and chronic inflammatory diseases, autoimmune diseases, tumor metastasis, allograft rejection, and reperfusion injury.

SUMMARY OF THE INVENTION

In one embodiment of the present invention are disclosed compounds represented by structural Formula I:

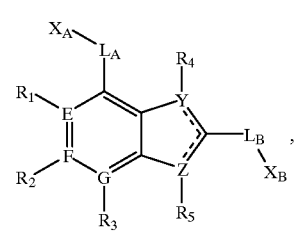

or a pharmaceutically acceptable salt or prodrug thereof, where the symbol—represents a single bond or a double bond, provided that when one bond is a double bond, the adjacent bond is a single bond;

E, F, and G are independently selected from
- (1) carbon,
- (2) nitrogen, and
- (3) $N^+$—$O^-$, provided that at least one of E, F or G is nitrogen or $N^+$—$O^-$, and further provided that at least one of E, F or G is carbon;

Y and Z are independently selected from
- (1) carbon,
- (2) nitrogen,
- (3) oxygen, and
- (4) $S(O)_t$ where t is an integer 0–2, provided that at least one of Y or Z is other than carbon;

$L_A$ is selected from
- (1) a covalent bond,
- (2) —O—,
- (3) —$S(O)_t$—,
- (4) —$NR_6$— where $R_6$ is selected from
  - (a) hydrogen,
  - (b) alkyl of one to ten carbons optionally substituted with 1 or 2 substituents independently selected from,
    - (i) aryl and
    - (ii) cycloalkyl of three to ten carbons,
  - (c) alkanoyl where the alkyl part is of one to ten carbons, and
  - (d) cycloalkyl of three to ten carbons,
- (5) —C(W)— where W is selected from
  - (a) O and
  - (b) S, and
- (6) alkenylene;

$X_A$ is selected from
- (1) halo,
- (2) alkyl of one to ten carbons optionally substituted with 1, 2, or 3 substituents independently selected from
  - (a) oxo,
  - (b) cycloalkyl of three to ten carbons,
  - (c) —$CO_2R_7$ where $R_7$ is selected from
    - (i) hydrogen and
    - (ii) alkyl of one to ten carbons optionally substituted with 1, or 2 substituents independently selected from
      - aryl and
      - cycloalkyl of three to ten carbons,
  - (d) —$NR_8R_9$ where $R_8$ and $R_9$ are independently selected from
    - (i) hydrogen,
    - (ii) alkyl of one to six carbons optionally substituted with 1 or 2 substituents independently selected from
      - —OH,
      - aryl,
      - heterocycle,
      - cycloalkyl of three to ten carbons, and
      - —$NR_AR_B$ where $R_A$ and $R_B$ are independently selected from
        - hydrogen and
        - alkyl of one to six carbons optionally substituted with
          - 1 or 2 substituents selected from —OH,
    - (iii) alkanoyl where the alkyl part is of one to to ten carbons,
    - (iv) cycloalkyl of three to ten carbons,
    - (v) alkoxy,
    - (vi) heterocycle, and
    - (vii) aryl,
      - where (vi) and (vii) are substituted with 1 or 2 substituents independently selected from
        - alkyl of one to six carbons and
        - halo,
  - (e) —$C(W)R_{10}$ where W is previously defined and $R_{10}$ is selected from
    - (i) hydrogen,
    - (ii) alkyl of one to ten carbons optionally substituted with 1, or 2 substituents independently selected from
      - aryl and
      - cycloalkyl of three to ten carbons,
    - (iii) —$NR_8R_9$, and
    - (iv) —$OR_7$,
  - (f) —OH,
  - (g) aryl, and
  - (h) heterocycle,
    where (g) and (h) can be optionally substituted with 1, 2, 3, 4, or 5 substituents independently selected from
    - (i) alkyl of one to twenty carbons,
    - (ii) —$NR_8R_9$,
    - (iii) alkoxy of one to ten carbons,
    - (iv) thioalkoxy of one to ten carbons,
    - (v) halo,
    - (vi) perfluoroalkyl of one to three carbons,
    - (vii) alkenyl of two to ten carbons,
    - (viii) alkyl of one to ten carbons optionally substituted with 1 or 2 substituents independently selected from
      - alkoxy of one to ten carbons and
      - —OH,
    - (ix) —$CO_2R_7$,
    - (x) aryl, and
    - (xi) —CHO,
- (3) cycloalkyl of three to ten carbons,
- (4) aryl,
- (5) heterocycle
  where (4) and (5) can be optionally substituted with 1, 2, 3, 4, or 5 substituents independently selected from
  - (a) alkyl of one to twenty carbons,
  - (b) alkyl of one to ten carbons substituted with 1, 2, or 3 substituents independently selected from
    - (i) —$OR_{11}$ where $R_{11}$ is selected from
      - hydrogen,
      - —$C(W)R_{12}$ where $R_{12}$ is selected from
        - alkyl of one to ten carbons,
        - cycloalkyl of three to ten carbons,
        - aryl, and
        - heterocycle, and
        - heterocycle optionally substituted with 1, 2, 3, or 4 substituents independently selected from
          - —OH and
          - alkyl of one to six carbons optionally substituted with 1 or 2 substituents selected from
            - —OH,
    - (ii) alkoxy of one to ten carbons optionally substituted with 1 or 2 substituents independently selected from
      - alkoxy and
      - alkoxyalkoxy,
    - (iii) spiroalkyl of three to ten carbons, and
    - (iv) halo,
  - (c) alkoxy of one to ten carbons optionally substituted with 1 or 2 substituents independently selected from
    - (i) alkoxy, and
    - (ii) alkoxyalkoxy, (d) thioalkoxy of one to ten carbons,
(e) halo,
(f) perfluoroalkyl of one to three carbons,
(g) alkenyl of two to ten carbons optionally substituted with 1 or 2 substituents independently selected from
  (i) —C(W)R$_{10}$ and
  (ii) —C(W)R$_{12}$,
(h) —CO$_2$R$_7$,
(i) —NR$_8$R$_9$,
(j) aryl,
(k) —C(W)R$_{12}$,
(l) —CHO,
(m) —C(O)NR$_8$R$_9$,
(n) —CN,
(o) heterocycle optionally substituted with 1 or 2 substituents independently selected from
  (i) alkyl of one to ten carbons and
  (ii) perfluoroalkyl of one to three carbons,
(p) —C(W)R$_{10}$,
(q) ethylenedioxy, and
(r) —OCF$_3$,
(6) —OR$_7$,
(7) hydrogen, and
(8) —NR$_8$R$_9$;

L$_B$ is selected from
(1) a covalent bond,
(2) —O—,
(3) —S(O)$_t$—,
(4) —NR$_6$—,
(5) —C(W)—, and
(6) —C(=NR$_{13}$)— where R$_{13}$ is selected from
  (a) hydrogen,
  (b) —NO$_2$,
  (c) —CN, and
  (d) —OR$_{14}$ where R$_{14}$ is selected from
    (i) hydrogen,
    (ii) aryl, and
    (iii) alkyl of one to ten carbons optionally substituted with 1 or 2 substituents independently selected from
      aryl and
      —C(O)R$_{15}$ where R$_{15}$ is selected from
        hydrogen,
        —OH,
        alkoxy, and
        NR$_A$R$_B$;

X$_B$ is selected from
(1) hydrogen,
(2) alkyl of one to ten carbons optionally substituted with 1, 2, or 3 substituents independently selected from
  (a) —CO$_2$R$_7$,
  (b) —NR$_8$R$_9$,
  (c) —C(W)NR$_8$R$_9$,
  (d) heterocycle,
  (e) aryl optionally substituted with 1 or 2 substituents independently selected from
    (i) alkyl of one to ten carbons,
    (ii) —NO$_2$, and
    (iii) —NR$_A$R$_B$,
  (f) —OR$_{16}$ where R$_{16}$ is selected from
    (i) hydrogen and
    (ii) —C(W)NR$_A$R$_B$, and
  (g) —NR$_A$C(W)NR$_8$R$_9$,
(3) alkenyl of two to six carbons optionally substituted with 1 or 2 substituents independently selected from
  (a) —C(W)NR$_A$R$_B$,
  (b) —CO$_2$R$_7$, and
  (c) heterocycle,
(4) —NR$_{17}$R$_{18}$ where R$_{17}$ and R$_{18}$ are independently selected from
  (a) hydrogen,
  (b) alkyl of one to ten carbons optionally substituted with 1, 2, or 3 substituents independently selected from
    (i) —OH,
    (ii) —C(W)R$_{10}$,
    (iii) —NR$_A$C(=NR$_{13}$)NR$_B$R$_{19}$ where R$_A$, R$_B$, and R$_{13}$ are previously defined and R$_{19}$ is selected from
      hydrogen,
      alkyl of one to ten carbons, and
      —NO$_2$,
    (iv) heterocycle,
    (v) aryl,
    (vi) halo, and
    (vii) —NR$_A$R$_B$,
  (c) alkoxy,
  (d) aryl optionally substituted with 1, 2, or 3 substituents independently selected from
    (i) halo,
    (ii) alkyl of one to ten carbons,
    (iii) alkoxy of one to ten carbons, and
    (iv) perfluoroalkyl of one to three carbons,
  (e) heterocycle,
  (f) —NR$_A$R$_B$,
  (g) —C(O)R$_{20}$ where R$_{20}$ is selected from
    (i) hydrogen,
    (ii) alkyl of one to ten carbons,
    (iii) —OR$_{12}$, and
    (iv) —NR$_A$R$_B$,
  (h) cycloalkyl of three to ten carbons, and
  (i) —OH,
(5) alkoxy,
(6) —OH,
(7) —NR$_A$C(=NR$_{13}$)NR$_B$R$_{19}$,
(8) —C(W)NR$_8$R$_9$,
(9) aryl,
(10) heterocycle,
  where (9) and (10) can be optionally substituted with 1, 2, 3, 4, or 5 substituents independently selected from
  (a) halo,
  (b) alkyl of one to ten carbons optionally substituted with 1, 2, or 3 substituents independently selected from
    (i) halo,
    (ii) alkoxy of one to ten carbons,
    (iii) —NR$_A$R$_B$,
    (iv) —OH,
    (v) —CO$_2$R$_7$,
    (vi) —C(W)NR$_A$R$_B$, and
    (vii) aryl,
  (c) —NR$_A$R$_B$,
  (d) alkoxy of one to ten carbons,
  (e) thioalkoxy of one to ten carbons,
  (f) perfluoroalkyl of one to three carbons,
  (g) —OH,
  (h) —C(W)NR$_8$R$_9$,
  (i) —CO$_2$R$_7$,
  (j) —NR$_A$C(W)OR$_{21}$ where R$_A$ is previously defined and R$_{21}$ is selected from
    (i) alkyl of one to ten carbons optionally substituted with 1 or 2 substituents selected from aryl and
cycloalkyl of three to ten carbons,
(ii) aryl, and
(iii) cycloalkyl of three to ten carbons,
(k) alkenyl of two to ten carbons,
(l) heterocycle,
(m) aryl, and
(n) —$NO_2$,
(11) —CN,
(12) —CHO,
(13) halo, and
(14) —$B(OR_A)(OR_B)$;
provided that when $R_1$, $R_2$, $R_3$, $R_4$, and $R_5$ are hydrogen or absent, —$L_A$— is a covalent bond, and —$L_B$— is a covalent bond, then one of $X_A$ or $X_B$ is other than hydrogen; and $R_1$, $R_2$, $R_3$, $R_4$, and $R_5$ are absent or independently selected from
(1) hydrogen,
(2) alkyl of one to six carbons optionally substituted with 1 or 2 substituents independently selected from
  (a) —$OC(O)R_{22}$, where $R_{22}$ is selected from
    (i) alkyl,
    (ii) alkoxy, and
    (iii) $NR_AR_B$,
  (b) alkoxy,
  (c) —OH,
  (d) —$NR_AR_B$,
  (e) heterocycle, and
  (f) aryl,
(3) —$CO_2R_7$,
(4) —$C(O)NR_AR_B$,
(5) —$SR_{23}$ where $R_{23}$ is selected from
  (a) hydrogen,
  (b) alkyl of one to six carbons,
  (c) aryl optionally substituted with 1 or 2 substituents selected from
    (i) alkyl of one to six carbons and
    (ii) halo,
(6) —$NR_AR_B$,
(7) halo,
(8) alkoxy,
(9) perfluoroalkyl of one to three carbons,
(10) —OH, and
(11) heterocycle,
provided that when E, F, and Y are carbon, G is nitrogen, Z is sulfur, —$L_A$— is a covalent bond, and $X_A$ is halo, $R_1$ is other than —$CO_2R_7$.

In another embodiment of the invention are disclosed methods of treating diseases comprising administering an effective amount of a compound having Formula I.

In yet another embodiment of the invention are disclosed pharmaceutical compositions containing compounds of Formula I.

DETAILED DESCRIPTION OF THE INVENTION

Definition of Terms

The term "alkanoyl" as used herein refers to an alkyl group attached to the parent molecular group through a carbonyl group.

The term "alkenyl" as used herein refers to a monovalent straight or branched chain group of 2–12 carbon atoms containing at least one carbon-carbon double bond derived from an alkene by the removal of one hydrogen atom.

The term "alkenylene" as used herein refers to a divalent straight or branched chain group of 2–10 carbon atoms containing a carbon-carbon double bond derived from an alkene by the removal of two hydrogen atoms.

The term "alkoxy" as used herein refers to an alkyl group attached to the parent molecular group through an oxygen atom.

The term "alkoxyalkoxy" as used herein refers to an alkoxy group attached to the parent molecular group through another alkoxy group.

The term "alkoxycarbonyloxy," as used herein, refers to an alkoxy group, as defined herein, appended to the parent molecular moiety through a carbonyloxy group, as defined herein.

The term "alkoxycarbonyloxymethylene," as used herein, refers to an alkoxycarbonyloxy group, as defined herein, appended to the parent molecular moiety through a methylene group, as defined herein.

The term "alkyl" as used herein refers to a saturated straight or branched chain group of 1–20 carbon atoms derived from an alkane by the removal of one hydrogen atom.

The term "alkylcarbonyl," as used herein, refers to an alkyl group, as defined herein, appended to the parent molecular moiety through a carbonyl group.

The term "alkylcarbonyloxy," as used herein, refers to an alkyl group, as defined herein, appended to the parent molecular moiety through a carbonyloxy group, as defined herein.

The term "alkylcarbonyloxymethylene," as used herein, refers to an alkylcarbonyloxy group, as defined herein, appended to the parent molecular moiety through a methylene group, as defined herein.

The term "alkylene," denotes a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, —$CH_2CH(CH_3)CH_2$—, and the like.

The term "amino," as used herein, refers to a —$NR_{80}R_{81}$ group, where $R_{80}$ and $R_{81}$ are independently selected from hydrogen and alkyl.

The term "aminocarbonyl," as used herein, refers to an amino group, as defined herein, appended to the parent molecular moiety through a carbonyl group, as defined herein.

The term "aminocarbonyloxy," as used herein, refers to an aminocarbonyl group, as defined herein, appended to the parent molecular moiety through an oxy group, as defined herein.

The term "aminocarbonyloxymethylene," as used herein, refers to an aminocarbonyloxy group, as defined herein, appended to the parent molecular moiety through a methylene group, as defined herein.

The term "aryl" refers to a mono- or bicyclic carbocyclic ring system having one or two aromatic rings. The aryl group can also be fused to a cyclohexane, cyclohexene, cyclopentane or cyclopentene ring. The aryl groups of this invention can be optionally substituted.

The term "carbonyl," as used herein, refers to a —C(O)— group.

The term "carbonyloxy," as used herein, refers to a carbonyl group as defined herein, appended to the parent molecular moiety through an oxy group, as defined herein.

The term "cycloalkyl" as used herein refers to a monovalent saturated cyclic hydrocarbon group of 3–12 carbons derived from a cycloalkane by the removal of a single hydrogen atom.

The term "ethylenedioxy," as used herein, refers to a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The terms "halo" or "halogen" as used herein refers to F, Cl, Br, or I.

The term "heterocycle" represents a represents a 4-, 5-, 6- or 7-membered ring containing one, two or three heteroatoms independently selected from the group consisting of nitrogen, oxygen and sulfur. The 4- and 5-membered rings have zero to two double bonds and the 6- and 7-membered rings have zero to three double bonds. The term "heterocycle" also includes bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring. Heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, oxadiazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, and the like.

Heterocyclics also include bridged bicyclic groups where a monocyclic heterocyclic group is bridged by an alkylene group such as

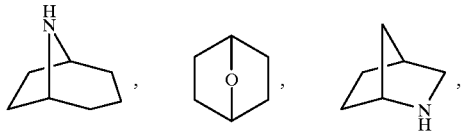

and the like.

Heterocyclics also include compounds of the formula

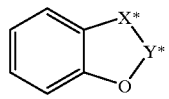

where X* is selected from —CH$_2$—, —CH$_2$O— and —O—, and Y* is selected from —C(O)— and —(C(R")$_2$)$_v$—, where R" is hydrogen or alkyl of one to four carbons, and v is 1–3. These heterocycles include 1,3-benzodioxolyl, 1,4-benzodioxanyl, and the like. The heterocycle groups of this invention can be optionally substituted.

The term "oxo," as used herein, refers to =O.

The term "oxy," as used herein, refers to —O—.

The term "methylene," as used herein, refers to a —CH$_2$— group.

The term "perfluoroalkyl" as used herein refers to an alkyl group in which all of the hydrogen atoms have been replaced by fluoride atoms.

The term "phenyl" as used herein refers to a monocyclic carbocyclic ring system having one aromatic ring. The aryl group can also be fused to a cyclohexane or cyclopentane ring. The phenyl groups of this invention can be optionally substituted.

The term "pharmaceutically acceptable prodrugs" as used herein represents those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to the parent compound of the above formula, for example, by hydrolysis in blood. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "spiroalkyl" as used herein refers to an alkylene group wherein two carbon atoms of the alkylene group are attached to one carbon atom of the parent molecular group thereby forming a carbocyclic ring of three to eleven carbon atoms.

The term "tautomer" as used herein refers to a proton shift from one atom of a molecule to another atom of the same molecule wherein two or more structurally distinct compounds are in equilibrium with each other.

The term "thioalkoxy" as used herein refers to an alkyl group attached to the parent molecular group through a sulfur atom.

Compounds of the present invention can exist as stereoisomers wherein asymmetric or chiral centers are present. These compounds are designated by the symbols "R" or "S," depending on the configuration of substituents around the chiral carbon atom. The present invention contemplates various stereoisomers and mixtures thereof. Stereoisomers include enantiomers and diastereomers, and mixtures of enantiomers or diastereomers are designated (±) Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can exist in the compounds of the present invention. The present invention contemplates the various geometric isomers and mixtures thereof resulting from the arrangement of substituents around a carbon-carbon double bond or arrangement of substituents around a carbocyclic ring. Substituents around a carbon-carbon double bond are designated as being in the Z or E configuration wherein the term "Z" represents substituents on the same side of the carbon-carbon double bond and the term "E" represents substituents on opposite sides of the carbon-carbon double bond. The arrangement of substituents around a carbocyclic ring are designated as cis or trans wherein the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated cis/trans.

Tautomers can also exist in the compounds of the present invention. The present invention contemplates tautomers due to proton shifts from one atom to another atom of the same molecule generating two distinct compounds that are in equilibrium with each other.

Compounds of the present invention include, but are not limited to methyl 2-[(6-ethylthieno[2,3-d]pyrimidin-4-yl)thio]acetate,
6-ethyl-4-[(4-methylphenyl)thio]thieno[2,3-d]pyrimidine,
6-ethyl-4-(2-pyridinylthio)thieno[2,3-d]pyrimidine,
6-ethyl-4-[(2-methylethyl)thio]thieno[2,3-d]pyrimidine,
6-ethyl-4-[(phenylmethyl)thio]thieno[2,3-d]pyrimidine,
6-ethyl-4-[(5-methyl-1,3,4-thiadiazol-2-yl)thio]thieno[2,3-d]pyrimidine,
ethyl 6-ethyl-4-[(4-methylphenyl)thio]thieno[2,3-d]pyrimidine-6-carboxylate,
6-ethyl-N-(phenylmethyl)thieno[2,3-d]pyrimidin-4-amine,
6-ethyl-N-(5-methyl-1,3,4-thiadiazol-2-yl)thieno[2,3-d]pyrimidin-4-amine,
4-[(5-amino-1,3,4-thiadiazol-2-yl)thio]-6-ethyl-2-(phenylmethyl)thieno[2,3-d]pyrimidine,
4-chloro-6-ethyl-2-(phenylmethyl)thieno[2,3-d]pyrimidine,
4-[(5-amino-1,3,4-thiadiazol-2-yl)thio]-6-ethyl-2-(phenylmethyl)thieno[2,3-d]pyrimidine,
7-methyl-4-[(4-methylphenyl)thio]thieno[3,2-d]pyrimidine,
7-methyl-4-[(5-methyl-1,3,4-thiadiazol-2-yl)thio]thieno[3,2-d]pyrimidine,
7-methyl-4-[[5-(methylthio)-1,3,4-thiadiazol-2-yl]thio]thieno[3,2-d]pyrimidine,
4-[(5-amino-1,3,4-thiadiazol-2-yl)thio]-7-methylthieno[3,2-d]pyrimidine,
7-methyl-N-[(4-(methylthio)phenyl]thieno[3,2-d]pyrimidin-7-amine,
7-methyl-4-[(4-methylphenyl)thio]thieno[3,2-d]pyrimidine-6-carboxamide,
methyl 4-[(4-methylphenyl)thio]thieno[2,3-c]pyridine-2-carboxylate,
4-[(4-methylphenyl)thio]thieno[2,3-c]pyridine-2-carboxylic acid,
4-[(4-methylphenyl)thio]thieno[2,3-c]pyridine-2-carboxamide,
4-(2-pyridinylthio)thieno[2,3-c]pyridine-2-carboxamide,
4-[(4-chlorophenyl)thio]thieno[2,3-c]pyridine-2-carboxamide,
N-methoxy-N-methyl-4-[(4-methylphenyl)thio]thieno[2,3-c]pyridine-2-carboxamide,
N-methoxy-4-[(4-methylphenyl)thio]thieno[2,3-c]pyridine-2-carboxamide,
N-(4-chlorophenyl)-4-[(4-methylphenyl)thio]thieno[2,3-c]pyridine-2-carboxamide,
4-[(4-methylphenyl)thio]thieno[2,3-c]pyridine-2-carboxaldehyde,
4-[(4-methylphenyl)thio]thieno[2,3-c]pyridine-2-carboxaldehyde, O-methyloxime,
4-[(4-methylphenyl)thio]thieno[2,3-c]pyridine-2-carboxaldehyde, O-(phenylmethyl)oxime,
2-[[[4-[(4-methylphenyl)thio]thieno[2,3-c]pyridin-2-ylmethylene]amino]oxy]acetic acid,
4-[(4-methylphenyl)thio]thieno[2,3-c]pyridine-2-carboxaldehyde, O-phenyloxime,
4-[(4-methylphenyl)thio]thieno[2,3-c]pyridine-2-carboxaldehyde, oxime,
2-[[[4-[(4-methylphenyl)thio]thieno[2,3-c]pyridine-2-ylmethylene]amino]oxy]acetamide,
(E)-3-[(4-methylphenyl)thio]thieno[2,3-c]pyridin-2-yl]-2-propenamide,
1-[4-[(4-methylphenyl)thio]thieno[2,3-c]pyridin-2-yl]ethanone,
2-benzoyl-4-[(4-methylphenyl)thio]thieno[2,3-c]pyridine,
2-ethyl-4-[(4-methylphenyl)thio]thieno[2,3-c]pyridine,
1-[4-[(4-methylphenyl)thio]thieno[2,3-c]pyridin-2-yl]ethanone, oxime,
N-(2,3-dihydroxypropyl)-4-[(4-methylphenyl)thio]thieno[2,3-c]pyridine-2-carboxamide,
4-[(4-methylphenyl)thio]thieno[2,3-c]pyridine-2-carboxylic acid, hydrazide,
$N^2$-4-[(4-methylphenyl)thio]thieno[2,3-c]pyridin-2-yl]carbonyl]-$N^6$-[(nitroamino)iminomethyl]-L-lysine, methyl ester,
N-(aminoiminomethyl)-4-[(4-methylphenyl)thio]thieno[2,3-c]pyridine-2-carboxamide,
4-[(4-methylphenyl)thio]thieno[2,3-c]pyridine-2-carbothioamide,
4-[(4-methylphenyl)thio]thieno[2,3-c]pyridine,
methyl 4-[(2-methoxy-2-oxoethyl)thio]thieno[2,3-c]pyridine-2-carboxylate,
4-[(2-amino-2-oxoethyl)thio]thieno[2,3-c]pyridine-2-carboxamide,
4-[(4-bromophenyl)thio]thieno[2,3-c]pyridine-2-carboxamide,
4-(phenylthio)thieno[2,3-c]pyridine-2-carboxamide,
4-[[4-(trifluoromethyl)phenyl]thio]thieno[2,3-c]pyridine-2-carboxamide,
4-[(2-methylphenyl)thio]thieno[2,3-c]pyridine-2-carboxamide,
4-[(3-methylphenyl)thio]thieno[2,3-c]pyridine-2-carboxamide,
4-[(3,4-dimethylphenyl)thio]thieno[2,3-c]pyridine-2-carboxamide,
4-[(3,5-dimethylphenyl)thio]thieno[2,3-c]pyridine-2-carboxamide,
4-[(2,4-dimethylphenyl)thio]thieno[2,3-c]pyridine-2-carboxamide,
4-[(2-methyl-3-furanyl)thio]thieno[2,3-c]pyridine-2-carboxamide,
4-[[(4-chlorophenyl)methyl]thio]thieno[2,3-c]pyridine-2-carboxamide,
4-[(3,4-dichlorophenyl)thio]thieno[2,3-c]pyridine-2-carboxamide,
4-[(4-methoxyphenyl)thio]thieno[2,3-c]pyridine-2-carboxamide,
4-(cyclohexylthio)thieno[2,3-c]pyridine-2-carboxamide,
4-[(4-methylphenyl)thio]-N-[3-(4-morpholinyl)propyl]thieno[2,3-c]pyridine-2-carboxamide, trifluoromethylacetate salt, 4-[(4-methylphenyl)sulfinyl]thieno[2,3-c]pyridine-2-carboxamide,
methyl 4-[(4-methylphenyl)sulfinyl]thieno[2,3-c]pyridine-2-carboxylate,
4-(4-methylphenoxy)thieno[2,3-c]pyridine-2-carboxamide,
methyl 4-(4-methylphenoxy)thieno[2,3-c]pyridine-2-carboxylate,
4-(4-chlorophenoxy)thieno[2,3-c]pyridine-2-carboxamide,
methyl 4-(4-chlorophenoxy)thieno[2,3-c]pyridine-2-carboxylate,
4-[4-(trifluoromethyl)phenoxy]thieno[2,3-c]pyridine-2-carboxamide,
4-(4-octylphenoxy)thieno[2,3-c]pyridine-2-carboxainide,
4-[4-(1-methylethyl)phenoxy]thieno[2,3-c]pyridine-2-carboxamide,
4-(2-bromo-4-chlorophenoxy)thieno[2,3-c]pyridine-2-carboxamide,
4-(4-ethylphenoxy)thieno[2,3-c]pyridine-2-carboxamide,
4-(4-ethenylphenoxy)thieno[2,3-c]pyridine-2-carboxamide,
4-[4-(1,2-dihydroxyethyl)phenoxy]thieno[2,3-c]pyridine-2-carboxamide,
4-[2-(2-propenyl)phenoxy]thieno[2,3-c]pyridine-2-carboxamide,
4-[2-(2,3-dihydroxypropyl)phenoxy]thieno[2,3-c]pyridine-2-carboxamide,
4-[4-(trifluoromethyl)phenoxy]thieno[2,3-c]pyridine-2-carboxamide, 1-oxide,
4-[3-(pentadecyl)phenoxy]thieno[2,3-c]pyridine-2-carboxamide,
4-(4-bromophenoxy)thieno[2,3-c]pyridine-2-carboxanlide,
4-(3-chlorophenoxy)thieno[2,3-c]pyridine-2-carboxamide,
4-(4-t-butylphenoxy)thieno[2,3-c]pyridine-2-carboxamide,
4-(4-chloro-3-methylphenoxy)thieno[2,3-c]pyridine-2-carboxamide,
4-(4-chloro-2-methylphenoxy)thieno[2,3-c]pyridine-2-carboxamide,
4-(4-methoxyphenoxy)thieno[2,3-c]pyridine-2-carboxamide,
ethyl 3-[[2-(aminocarbonyl)thieno[2,3-c]pyridin-4-yl]oxy]benzoate,
4-phenoxythieno[2,3-c]pyridine-2-carboxamide,
4-(3-bromophenoxy)thieno[2,3-c]pyridine-2-carboxamide,
4-(4-fluorophenoxy)thieno[2,3-c]pyridine-2-carboxamide,
4-(3,5-dimethylphenoxy)thieno[2,3-c]pyridine-2-carboxamide,
4-(3-choro-4-methylphenoxy)thieno[2,3-c]pyridine-2-carboxamide,
4-(4-iodophenoxy)thieno[2,3-c]pyridine-2-carboxamide,
4-(4-(methoxymethyl)phenoxy]thieno[2,3-c]pyridine-2-carboxamide,
2-(aminocarbonyl)-4-(4-chlorophenoxy)thieno[2,3-c]pyridinium, iodide,
4-(4-chlorophenoxy)thieno[2,3-c]pyridine-2-carboxylic acid,
N-(4-(4-chlorophenoxy)thieno[2,3-c]pyridin-2-yl)-O-(3-tetrahydrofuranyl)carbamate,
4-(4-chlorophenoxy)thieno[2,3-c]pyridine-2-methanol,
(E)-3-[4-(4-chlorophenoxy)thieno[2,3-c]pyridin-2-yl]-2-propenoic acid,
4-(4-chlorophenoxy)thieno[2,3-c]pyridine-2-carboxaldehyde,
(E)-3-[4-(4-chlorophenoxy)thieno[2,3-c]pyridin-2-yl]-2-propenamide,
4-bromothieno[2,3-c]pyridine-2-carboxamide,
methyl 4-bromothieno[2,3-c]pyridine-2-carboxylate,
4-chlorothieno[2,3-c]pyridine-2-carboxamide,
4-[4-(trifluoromethyl)phenyl]thieno[2,3-c]pyridine-2-carboxamide,
methyl 4-[4-(trifluoromethyl)phenyl]thieno[2,3-c]pyridine-2-carboxylate,
N-methyl4-[4-(trifluoromethyl)phenyl]thieno[2,3-c]pyridine-2-carboxamide,
4-phenylthieno[2,3-c]pyridine-2-carboxamide,
methyl 4-phenylthieno[2,3-c]pyridine-2-carboxylate,
4-([1,1'-biphenyl]-4-ylthio)thieno[2,3-c]pyridine-2-carboxamide,
4-(5-formyl-2-furanyl)thieno[2,3-c]pyridine-2-carboxamide,
ethyl 4-[[2-(aminocarbonyl)thieno[2,3-c]pyridin-4-yl]oxylbenzoate,
4-[[2-(aminocarbonyl)thieno[2,3-c]pyridin-4-yl]oxy]benzoic acid,
4-(1-phenylethenyl)thieno[2,3-c]pyridine-2-carboxamide,
methyl 4-(1-phenylethenyl)thieno[2,3-c]pyridine-2-carboxalate,
4-[(4-methylphenyl)thio]thieno[2,3-c]pyridine-2-methanol,
4-(4-Chlorophenoxy)-N-methylthieno[2,3-c]pyridine-2-carboxamide,
4-(4-chlorophenoxy)-N,N-dimethylthieno[2,3-c]pyridine-2-carboxamide,
4-(4-chlorophenoxy)-N,N-diethylthieno[2,3-c]pyridine-2-carboxamide,
4-(4-chlorophenoxy)-N-cyclopropylthieno[2,3-c]pyridine-2-carboxamide,
1-[[4-(4-chlorophenoxy)thieno[2,3-c]pyridin-2-yl]carbonyl]pyrrolidine,
1-[[4-(4-chlorophenoxy)thieno[2,3-c]pyridin-2-yl]carbonyl]piperidine,
4-[[4-(4-chlorophenoxy)thieno[2,3-c]pyridin-2-yl]carbonyl]morpholine,
1-[[4-(4-chlorophenoxy)thieno[2,3-c]pyridin-2-yl]carbonyl]-4-methylpiperazine,
1-[[4-(4-chlorophenoxy)thieno[2,3-c]pyridin-2-yl]carbonyl]-4-phenyl]piperazine,
1-[[4-(4-chlorophenoxy)thieno[2,3-c]pyridin-2-ylcarbonyl]-4-(phenylmethyl)piperazine,
1-[[4-(4-chlorophenoxy)thieno[2,3-c]pyridin-2-ylcarbonyl]-4-(2-pyridinyl)piperazine,
4-(4-chlorophenoxy)-N-(2-hydroxyethyl)lthieno[2,3-c]pyridine-2-carboxamide,
4-[[4-(4-chlorophenoxy)thieno[2,3-c]pyridin-2-yl]carbonyl]-N-(1-methylethyl)-1-piperazineacetamide, trifluoroacetate salt, 4-(4-chlorophenoxy)-N-[1-(hydroxymethyl)ethyl]thieno[2,3-c]pyridine-2-carboxamide,
4-(4-chlorophenoxy)-N-[1,1-bis(hydroxymethyl)ethyl]thieno[2,3-c]pyridine-2-carboxamide,
(D,L)-4-(4-chlorophenoxy)-N-(2-hydroxypropyl)thieno[2,3-c]pyridine-2-carboxamide,
4-(4-chlorophenoxy)-N-[2-(4-morpholinyl)ethyl]thieno[2,3-c]pyridine-2-carboxamide,
4-(4-chlorophenoxy)thieno[2,3-c]pyridine-2-sulfonamide,
4-[(4-methylphenyl)methyl]thieno[2,3-cpyridine-2-carboxamide,
methyl 4-[(4-methylphenyl)methyl]thieno[2,3-c]pyridine-2-carboxylate,
4-(4-morpholinyl)thieno[2,3-c]pyridine-2-carboxamide,
4-(4-chlorophenoxy)thieno[2,3-c]pyridine-2-carboxamide, N-oxide,
methyl (4-chlorophenoxy)thieno[2,3-c]pyridine-2-carboxylic acid, N-oxide,
4-(4-chlorophenoxy)-2-(2-methoxyphenyl)thieno[2,3-c]pyridine,
4-(4-Chlorophenoxy)thieno[2,3-c]pyridine,
4-(4-Chlorophenoxy)-3-methylthieno[2,3-c]pyridine-2-carboxamide,
Methyl 4-(4-chlorophenoxy)-3-methylthieno[2,3]-c]pyridine-2-carboxylate,
4-(4-Chorophenoxy)-3-hydroxythieno[2,3-c]pyridine-2-carboxamide,
methyl 4-(4-chlorophenoxy)-3-hydroxythieno[2,3-c]pyridine-2-carboxylate,
4-(4-Chlorophenoxy)-3-(1-methylethoxy)thieno[2,3-c]pyridine-2-carboxamide,
3-bromo-4-(4-chlorophenoxy)thieno[2,3-c]pyridine,
4-(4-Chlorophenoxy)thieno[2,3-c]pyridine-3-carboxylic acid,
4-(4-Chlorophenoxy)thieno[2,3-c]pyridine-3-carboxamide,
3-amino-4-(4-chlorophenoxy)thieno[2,3-c]pyridine-2-carboxamide,
methyl 3-amino-4-(4-chlorophenoxy)thieno[2,3-c]pyridine-2-carboxylate,
3-amino-4-(4-chlorophenoxy)thieno[2,3-c]pyridine-2-carboxylc acid,
4-[(4-methylphenyl)thio]thieno[2,3-b]pyridine,
4-[(4-methylphenyl)thio]thieno[2,3-b]pyridine-2-carboxamide,
4-chloro-N-(4-chlorophenyl)thieno[2,3-b]pyridine-5-carboxamide,
ethyl 4-[(5-methyl-1,3,4-thiadiazol-2-yl)thio]thieno[2,3-b]pyridine-5-carboxylate,
7-[(4-methylphenyl)thio]thieno[3,2-b]pyridine-2-carboxamide,
methyl 6-[(4-methylphenyl)thio]thieno[2,3-b]pyridine-2-carboxylate,
methyl 3-amino-6-chlorothieno[2,3-b]pyridine-2-carboxylate,
6-[(4-methylphenyl)thio]thieno[2,3-b]pyridine-2-carboxamide,
2-bromo-4-[(4-methylphenyl)thio]thieno[3,2-c]pyridine,
4-[(4-methylphenyl)thio]thieno[3,2-c]pyridine-2-carboxamide,
4-[(4-methylphenyl)thio]thieno[3,2-c]pyridine-2-carbonitrile,
4-(4-Methylphenoxy)thieno[3,2-c]pyridine-2-carboxamide,
4-(4-Methylphenoxy)thieno[3,2-c]pyridine-2-carbonitrile,
7-(4-methylphenoxy)oxazolo[5,4-c]pyridine-2-carboxamide,
methyl 7-(4-methylphenoxy)oxazolo[5,4-c]pyridine-2-carboxylate,
7-(4-methylphenoxy) [1,3]thiazolo[5,4-c]pyridine-2-carboxamide,
methyl 7-(4-methylphenoxy)[1,3]thiazolo[5,4-c]pyridine-2-carboxylate,
7-(4-methylphenoxy)-3H-imidazo[4,5-c]pyridine-2-carboxamide,
methyl 7-(4-methylphenoxy)-3H-imidazo[4,5-c]pyridine-2-carboxylate,
4-(4-chlorophenoxy)thieno[2,3-d]pyridazine-2-carboxamide,
4-(4-chlorophenoxy)thieno[2,3-d]pyridazine-2-carboxylic acid,
7-(4-chlorophenoxy)thieno[3,2-c]pyridine-2-carbamide,
7-(4-chlorophenoxy)thieno[3,2-c]pyridine-2-carboxylic acid,
4-(4-chlorophenoxy)thieno[2,3-c]pyridine-2-carbothioamide,
4-(4-chlorophenoxy)-N-ethylthieno[2,3-c]pyridine-2-carboxamide,
4-(4-chlorophenoxy)-N-(2,3-dihydroxypropyl)thieno[2,3-c]pyridine-2-carboxamide,
4-(4-bromophenoxy)-N-(2,3-dihydroxypropyl)thieno[2,3-c]pyridine-2-carboxamide,
N-(2-chloroethyl)-4-(4-chlorophenoxy)thieno[2,3-c]pyridine-2-carboxamide,
4-(4-bromophenoxy)-N-(2-hydroxyethyl)thieno[2,3-c]pyridine-2-carboxamide,
4-(2-bromo-4-chlorophenoxy)-N-(2-hydroxyethyl)thieno[2,3-c]pyridine-2-carboxamide,
N-(2-hydroxyethyl)-4-[4-trifluoromethyl)phenoxy]thieno[2,3-c]pyridine-2-carboxamide,
N-(2-aminoethyl)-4-(4-chlorophenoxy)thieno[2,3-c]pyridine-2-carboxamide,
4-(4-chlorophenoxy)-N-hydroxythieno[2,3-c]pyridine-2-carboxamide,
4-(4-chlorophenoxy)thieno[2,3-c]pyridine-2-carbohydrazide,
4-(4-bromophenoxy)thieno[2,3-c]pyridine-2-carbohydrazide,
4-[4-(trifluoromethyl)phenoxy]thieno[2,3-c]pyridine-2-carbohydrazide,
4-(4-chlorophenoxy)-N-hydroxythieno[2,3-c]pyridine-2-carboxamide,
2-({[4-(4-chlorophenoxy)thieno[2,3-c]pyridin-2-yl]carbonyl}amino)acetic acid,
N-(2-amino-2-oxoethyl)-4-(4-chlorophenoxy)thieno[2,3-c]pyridine-2-carboxamide,
N-(2-aamino-2-oxoethyl)-4-(4-bromophenoxy)thieno[2,3-c]pyridine-2-carboxamide,
(2S)-2-({[4-(4-chlorophenoxy)thieno[2,3-c]pyridin-2-yl]carbonyl}amino)-3-hydroxypropanoic acid, N-[(1S)-2-amino-1-(hydroxymethyl)-2-oxoethyl]-4-(4-chlorophenoxy)thieno[2,3-c]pyridine-2-carboxamide,
(2R)-2-({[4-(4-chlorophenoxy)thieno[2,3-c]pyridin-2-yl]carbonyl}amino)-3-hydroxypropanoic acid,
(2R)-2-({[4-(4-chlorophenoxy)thieno[2,3-c]pyridin-2-yl]carbonyl}amino)propanoic acid,
4-(4-chlorophenoxy)-N-[(1R)-1-methyl-2-(methylamino)-2-oxoethyl]thieno[2,3-c]pyridine-2-carboxamide,
(2S)-2-({[4-(4-chlorophenoxy)thieno[2,3-c]pyridin-2-yl]carbonyl}amino)propanoic acid,
4-(4-chlorophenoxy)-N-[(1S)-1-methyl-2-(methylamino)-2-oxoethyl]thieno[2,3-c]pyridine-2-carboxamide,
4-(4-chlorophenoxy)-N-[(1R)-1-(hydroxymethyl)-2-(methylamino)-2-oxoethyl]thieno[2,3-c]pyridine-2-carboxamide,
4-(4-chlorophenoxy)-N-[(1S)-1-(hydroxymethyl)-2-(methylamino)-2-oxoethyl]thieno[2,3-c]pyridine-2-carboxamide,
4-(3-pyridinyloxy)thieno[2,3-c]pyridine-2-carboxamide,
4-(4-bromophenoxy)-N-methylthieno[2,3-c]pyridine-2-carboxamide,
4-(4-bromophenoxy)-N,N-dimethylthieno[2,3-c]pyridine-2-carboxamide,
N,N-dimethyl-4-[4-(trifluoromethyl)phenoxy]thieno[2,3-c]pyridine-2-carboxamide,
4-(4-chloro-3-fluorophenoxy)-N-methylthieno[2,3-c]pyridine-2-carboxamide,
4-(4-chloro-3-fluorophenoxy)thieno[2,3-c]pyridine-2-carboxamide,
4-(4-chloro-3-ethylphenoxy)thieno[2,3-c]pyridine-2-carboxamide,
4-(3-fluorophenoxy)thieno[2,3-c]pyridine-2-carboxamide,
4-(2,3-difluorophenoxy)thieno[2,3-c]pyridine-2-carboxamide,
4-(2,3-difluorophenoxy)-N-methylthieno[2,3-c]pyridine-2-carboxamide,
4-(3-fluorophenoxy)-N-methylthieno[2,3-c]pyridine-2-carboxamide,
N-methyl-4-(2,3,4-trifluorophenoxy)thieno[2,3-c]pyridine-2-carboxamide,
4-(2,3,4-trifluorophenoxy)thieno[2,3-c]pyridine-2-carboxamide,
N-methyl-4-[4-(trifluoromethyl)phenoxy]thieno[2,3-c]pyridine-2-carboxamide,
4-[3-(trifluoromethyl)phenoxy]thieno[2,3-c]pyridine-2-carboxamide,
N,N-dimethyl-4-(4-vinylphenoxy)thieno[2,3-c]pyridine-2-carboxamide,
4-(4-cyanophenoxy)-N-methylthieno[2,3-c]pyridine-2-carboxamide,
4-(4-cyanophenoxy)thieno[2,3-c]pyridine-2-carboxamide,
4-(4-aminophenoxy)thieno[2,3-c]pyridine-2-carboxamide,
4-[4-(acetylamino)phenoxy]thieno[2,3-c]pyridine-2-carboxamide,
N-methyl-4-[4-(4-morpholinyl)phenoxy]thieno[2,3-c]pyridine-2-carboxamide,
4-[4-(hydroxymethyl)phenoxy]thieno[2,3-c]pyridine-2-carboxamide,
4-[4-(hydroxymethyl)phenoxyl-N-methylthieno[2,3-c]pyridine-2-carboxamide,
4-[4-(methoxymethyl)phenoxy]-N-methylthieno[2,3-c]pyridine-2-carboxamide,
4-{4-[(2-methoxyethoxy)methyl]phenoxy}thieno[2,3-c]pyridine-2-carboxamide,
4-{4-[(2-methoxyethoxy)methyl]phenoxy}-N-methylthieno[2,3-c]pyridine-2-carboxamide,
4-(4-{[2-(2-methoxyethoxy)ethoxy]methyl}phenoxy)thieno[2,3-c]pyridine-2-carboxamide,
4-(4-{[2-(2-methoxyethoxy)ethoxy]methyl}phenoxy)-N-methylthieno[2,3-c]pyridine-2-carboxamide,
4-{4-[(tetrahydro-2H-pyran-2-yloxy)methyl]phenoxy}thieno[2,3-c]pyridine-2-carboxamide,
N-methyl-4-{4-[(tetrahydro-2H-pyran-2-yloxy)methyl]phenoxy}thieno[2,3-c]pyridine-2-carboxamide,
4-{[2-(aminocarbonyl)thieno[2,3-c]pyridin-4-yl]oxy}benzyl 2-furoate,
4-[4-({[(2R,4R,5S,6R)-4,5-dihydroxy-6-(hydroxymethyl)tetrahydro-2H-pyran-2yl]oxy}methyl)phenoxy]-N-methylthieno[2,3-c]pyridine-2-carboxamide,
4-(4-acetylphenoxy)-N-methylthieno[2,3-c]pyridine-2-carboxamide,
4-[4-(4-morpholinylcarbonyl)phenoxy]thieno[2,3-c]pyridine-2-carboxamide,
N-methyl-4-[4-(4-morpholinylcarbonyl)phenoxy]thieno[2,3-c]pyridine-2-carboxamide,
4-[4-({[2-(4-morpholinyl)ethyl]amino}carbonyl)phenoxy]thieno[2,3-c]pyridine-2-carboxamide,
N-methyl-4-[4-({[2-(4-morpholinyl)ethyl]amino}carbonyl)phenoxy]thieno[2,3-c]pyridine-2-carboxamide,
4-{4-[(E)-3-(4-morpholinyl)-3-oxo-1-propenyl]phenoxy}thieno[2,3-c]pyridine-2-carboxamide,
4-[4-((E)-3-{[2-(4-morpholinyl)ethyl]amino}-3-oxo-1-propenyl)phenoxy]thieno[2,3-c]pyridine-2-carboxamide,
N-methyl-4-[4-((E)-3-{[2-(4-morpholinyl)ethyl]amino}-3-oxo-1-propenyl)phenoxy]thieno[2,3-c]pyridine-2-carboxamide,
4-(4-{(E)-3-[(2,3-dihydroxypropyl)amino]-3-oxo-1-propenyl}phenoxy)thieno[2,3-c]pyridine-2-carboxamide,
4-(4-{(E)-3-[(2,3-dihydroxypropyl)amino]-3-oxo-1-propenyl}phenoxy)-N-methylthieno[2,3-c]pyridine-2-carboxamide,
4-[4-((E)-3-{[2-(1H-imidazol-4-yl)ethyl]amino}-3-oxo-1-propenyl)phenoxy]-N-methylthieno[2,3-c]pyridine-2-carboxamide,
4-{4-[(E)-3-({2-[bis(2-hydroxyethyl)amino]ethyl}amino)-3-oxo-1-propenyl]phenoxy}-N-methylthieno[2,3-c]pyridine-2-carboxamide,
4-{4-[(E)-3-({2-[bis(2-hydroxyethyl)amino]ethyl}amino)-3-oxo-1-propenyl]phenoxy}thieno[2,3-c]pyridine-2-carboxamide, 4-[4-(,H-imidazol-1-yl)phenoxy]thieno[2,3-c]pyridine-2-carboxamide,
N-methyl-4-[4-(1H-pyrazol-1-yl)phenoxy]thieno[2,3-c]pyridine-2-carboxamide,
N-methyl-4-[4-(1H-1,2,4-triazol-1-yl)phenoxy]thieno[2,3-c]pyridine-2-carboxamide,
N-methyl-4-{4-[5-(trifluoromethyl)-1,2,4-oxadiazol-3-yl]phenoxy}thieno[2,3-c]pyridine-2-carboxamide, 4-[4-(4,5-dihydro-1H-imidazol-2-yl)phenoxy]-N-methylthieno[2,3-c]pyridine-2-carboxamide,
N-methyl-4-[4-(2-thienyl)phenoxy]thieno[2,3-c]pyridine-2-carboxamide,
4-([1,1'-biphenyl]-4-yloxy)-N-methylthieno[2,3-c]pyridine-2-carboxamide,
N-methyl-4-[4-(1-methyl-1H-imidazol-5-yl)phenoxy]thieno[2,3-c]pyridine-2-carboxamide,
4-{4-[1-(hydroxymethyl)cyclopropyl]phenoxy}-N-methylthieno[2,3-c]pyridine-2-carboxamide,
4-[4-(1-{[2-(2-ethoxyethoxy)ethoxy]methyl}cyclopropyl)phenoxy]-N-methylthieno[2,3-c]pyridine-2-carboxamide,
N-methyl-4-[4-(trifluoromethoxy)phenoxy]thieno[2,3-c]pyridine-2-carboxamide,
5-{4-[4-(1-{[2-(2-ethoxyethoxy)ethoxy]methyl}cyclopropyl)phenoxy]thieno[2,3-c]pyridin-2-yl}-1,3,4-oxadiazol-2-amine,
4-[4-(1,1-difluoro-2-hydroxyethyl)phenoxy]-N-methylthieno[2,3-c]pyridine-2-carboxamide,
4-(4-{2-[2-(2-ethoxyethoxy)ethoxy]-1,1-difluoroethyl}phenoxy)-N-methylthieno[2,3-c]pyridine-2-carboxamide,
4-(4-chlorophenoxy)-6-{[(2,2-dimethylpropanoyl)oxy]methyl}-2-[(methylamino)carbonyl]thieno[2,3-c]pyridin-6-ium,
4-(4-bromophenoxy)-6-{[(2,2-dimethylpropanoyl)oxy]methyl}-2-[(methylamino)carbonyl]thieno[2,3-c]pyridin-6-ium,
2-(aminocarbonyl)-4-(4-chlorophenoxy)-6-{[(isopropoxycarbonyl)oxy]methyl}thieno[2,3-c]pyridin-6-ium,
4-(benzyloxy)thieno[2,3-c]pyridine-2-carboxamide,
4-[(4-chlorophenyl)(hydroxy)methyl]thieno[2,3-c]pyridine-2-carboxamide,
4-(4-chlorobenzoyl)-N-methylthieno[2,3-c]pyridine-2-carboxamide,
$N^4$-(4-chlorophenyl)thieno[2,3-c]pyridine-2,4-dicarboxamide,
[4-(4-bromophenoxy)thieno[2,3-c]pyridin-2-yl]methanol,
4-(4-bromophenoxy)thieno[2,3-c]pyridine-2-carbaldehyde,
4-(4-chlorophenoxy)thieno[2,3-c]pyridine-2-carbaldehyde oxime,
4-(4-chlorophenoxy)thieno[2,3-c]pyridine-2-carbaldehyde O-methyloxime,
1-[4-(4-chlorophenoxy)thieno[2,3-c]pyridin-2-yl]-1-ethanone O-methyloxime,
1-[4-(4-chlorophenoxy)thieno[2,3-c]pyridin-2-yl]-1-ethanone O-methyloxime,
1-[4-(4-chlorophenoxy)thieno[2,3-c]pyridin-2-yl]-1-ethanone oxime,
1-[4-(4-chlorophenoxy)thieno[2,3-c]pyridin-2-yl]-1-ethanone oxime,
1-[4-(4-chlorophenoxy)thieno[2,3-c]pyridin-2-yl]-1-propanone,
1-[4-(4-chlorophenoxy)thieno[2,3-c]pyridin-2-yl]-1-propanone oxime,
2-[4-(4-chlorophenoxy)thieno[2,3-c]pyridin-2-yl]-N-methoxy-N-methyl-2-oxoacetamide,
4-(4-chlorophenoxy)thieno[2,3-c]pyridine-2-carbonitrile,
4-(4-chlorophenoxy)-N'-hydroxythieno[2,3-c]pyridine-2-carboximidamide,
4-(4-chlorophenoxy)-N'-cyanothieno[2,3-c]pyridine-2-carboximidamide,
[4-(4-chlorophenoxy)thieno[2,3-c]pyridin-2-yl](2-nitrophenyl)methanol,
[4-(4-chlorophenoxy)thieno[2,3-c]pyridin-2-yl](2-nitrophenyl)methanone,
(2-aminophenyl)[4-(4-chlorophenoxy)thieno[2,3-c]pyridin-2-yl]methanone,
(2-aminophenyl)[4-(4-chlorophenoxy)thieno[2,3-c]pyridin-2-yl]methanol,
[4-(4-chlorophenoxy)thieno[2,3-c]pyridin-2-yl](3-nitrophenyl)methanol,
(3-aminophenyl)[4-(4-chlorophenoxy)thieno[2,3-c]pyridin-2-yl]methanone,
(3-aminophenyl)[4-(4-chlorophenoxy)thieno[2,3-c]pyridin-2-yl]methanol,
4-(4-bromophenoxy)-2-vinylthieno[2,3-c]pyridine,
1-[4-(4-chlorophenoxy)thieno[2,3-c]pyridin-2-yl]-1,2-ethanediol,
1-[4-(4-bromophenoxy)thieno[2,3-c]pyridin-2-yl]-1,2-ethanediol,
[4-(4-chlorophenoxy)thieno[2,3-c]pyridin-2-yl]methanamine,
[4-(4-chlorophenoxy)thieno[2,3-c]pyridin-2-yl]methyl carbamate,
N-{[4-(4-chlorophenoxy)thieno[2,3-c]pyridin-2-yl]methyl}urea,
(E)-3-[4-(4-bromophenoxy)thieno[2,3-c]pyridin-2-yl]-2-propenamide,
(E)-3-[4-(4-bromophenoxy)thieno[2,3-c]pyridin-2-yl]-N-methyl-2-propenamide,
3-[4-(4-bromophenoxy)thieno[2,3-c]pyridin-2-yl]-2,3-dihydroxy-N-methylpropanamide,
3-[4-(4-bromophenoxy)thieno[2,3-c]pyridin-2-yl]-2,3-dihydroxypropanamide,
4-(4-chlorophenoxy)thieno[2,3-c]pyridin-2-ylamine,
4-(4-chlorophenoxy)thieno[2,3-c]pyridin-2-ylformamide,
N-[4-(4-chlorophenoxy)thieno[2,3-c]pyridin-2-yl]urea,
N-[4-(4-chlorophenoxy)thieno[2,3-c]pyridin-2-yl]-N'-methylthiourea,
4-(4-chlorophenoxy)-N-methylthieno[2,3-c]pyridine-2-sulfonamide,
4-(4-chlorophenoxy)-N-(2,3-dihydroxypropyl)thieno[2,3-c]pyridine-2-sulfonamide,
4-(4-chlorophenoxy)-N-(2-hydroxyethyl)thieno[2,3-c]pyridine-2-sulfonamide,
4-[4-(4-chlorophenoxy)thieno[2,3-c]pyridin-2-yl]phenol,
3-[4-(4-chlorophenoxy)thieno[2,3-c]pyridin-2-yl]aniline,
4-[4-(4-chlorophenoxy)thieno[2,3-c]pyridin-2-yl]aniline,
4-(4-chlorophenoxy)-2-(5-nitro-2-pyridinyl)thieno[2,3-c]pyridine,
6-[4-(4-chlorophenoxy)thieno[2,3-c]pyridin-2-yl]-3-pyridinamine,
5-[4-(4-chlorophenoxy)thieno[2,3-c]pyridin-2-yl]-2-pyridinamine,
5-[4-(4-chlorophenoxy)thieno[2,3-c]pyridin-2-yl]-1,3,4-oxadiazol-2-amine,
5-[4-(4-bromophenoxy)thieno[2,3-c]pyridin-2-yl]-1,3,4-oxadiazol-2-ylamine, 5-[4-(4-chlorophenoxy)thieno[2,3-c]pyridin-2-yl]-4H-1, 2,4-triazol-3-amine,
5-[4-(4-chlorophenoxy)thieno[2,3-c]pyridin-2-yl]-1,3,4-thiadiazol-2-amine,
4-(4-chlorophenoxy)-2-(5-methyl-1,2,4-oxadiazol-3-yl)thieno[2,3-c]pyridine,
5-{4-[4-(trifluoromethyl)phenoxy]thieno[2,3-c]pyridin-2-yl}-1,3,4-oxadiazol-2-amine,
4-(4-chlorophenoxy)-2-[5-(methylsulfanyl)-1,3,4-oxadiazol-2-yl]thieno[2,3-c]pyridine,
4-(4-chlorophenoxy)-2-(2-methyl-2H-1,2,3,4-tetraazol-5-yl)thieno[2,3-c]pyridine,
5-[4-(4-chlorophenoxy)thieno[2,3-c]pyridin-2-yl]-4-methyl-4H-1,2,4-triazol- 3-amine,
4-(4-chlorophenoxy)-2-[5-(trifluoromethyl)-1,2,4-oxadiazol-3-yl]thieno[2,3-c]pyridine,
5-[4-(4-chlorophenoxy)thieno[2,3-c]pyridin-2-yl]-1,2,4-oxadiazol-3-amine,
5-[4-(4-chlorophenoxy)thieno[2,3-c]pyridin-2-yl]-N-methyl-1,3,4-thiadiazol-2-amine,
4-(4-chlorophenoxy)-2-(1,2,4-oxadiazol-3-yl)thieno[2,3-c]pyridine,
2-(1,3,4-oxadiazol-2-yl)-4-[4-(trifluoromethyl)phenoxy]thieno[2,3-c]pyridine,
3-[4-(4-chlorophenoxy)thieno[2,3-c]pyridin-2-yl]-1,2,4-oxadiazol-5-amine,
2-(5-methyl-1,3,4-oxadiazol-2-yl)-4-[4-(trifluoromethyl)phenoxy]thieno[2,3-c]pyridine,
methyl 2-[4-(4-chlorophenoxy)thieno[2,3-c]pyridin-2-yl]-1,3-thiazole-4-carboxylate,
2-[4-(4-chlorophenoxy)thieno[2,3-c]pyridin-2-yl]-1,3-thiazole-4-carboxamide,
tert-butyl 2-[4-(4-chlorophenoxy)thieno[2,3-c]pyridin-2-yl]-1,3-thiazol-4-ylcarbamate,
2-[4-(4-chlorophenoxy)thieno[2,3-c]pyridin-2-yl]-1,3-thiazol-4-amine,
4-(4-chlorophenoxy)-2-(1,3-oxazol-2-yl)thieno[2,3-c]pyridine,
4-(4-chlorophenoxy)-2-(1H-imidazol-2-yl)thieno[2,3-c]pyridine,
4-chloro-3-methylthieno[2,3-c]pyridine-2-carboxamide,
3-amino-4-chlorothieno[2,3-c]pyridine-2-carboxamide,
4-(4-chlorophenoxy)-N,3-dimethylthieno[2,3-c]pyridine-2-carboxamide,
4-(4-bromophenoxy)-3-methylthieno[2,3-c]pyridine-2-carboxamide,
7-choro-4-(4-chlorophenoxy)-3-methylthieno[2,3-c7pyridine-2-carboxamide,
tert-butyl 2-(aminocarbonyl)-4-(4-chlorophenoxy)thieno[2,3-c]pyridine-3-carboxylate,
N-methyl-4-(4-toluidino)thieno[2,3-c]pyridine-2-carboxamide,
4-(4-chloroanilino)-N-methylthieno[2,3-c]pyridine-2-carboxamide,
N-methyl-4-(4-morpholinyl)thieno[2,3-c]pyridine-2-carboxamide,
7-chloro-4-(4-chlorophenoxy)thieno[2,3-c]pyridine-2-carboxamide,
7-chloro-4-(4-chlorophenoxy)-N-methylthieno[2,3-c]pyridine-2-carboxamide,
7-chloro-4-(4-chlorophenoxy)-N-(2-hydroxyethyl)thieno[2,3-c]pyridine-2-carboxamide,
7-bromo-4-(4-chlorophenoxy)thieno[2,3-c]pyridine-2-carboxamide,
7-bromo-4-(4-chlorophenoxy)-N-methylthieno[2,3-c]pyridine-2-carboxamide,
4-(4-bromophenoxy)-7-chlorothieno[2,3-c]pyridine-2-carboxamide,
4-(4-bromophenoxy)-7-chloro-N-methylthieno[2,3-c]pyridine-2-carboxamide,
7-chloro-4-[4-(trifluoromethyl)phenoxy]thieno[2,3-c]pyridine-2-carboxamide,
7-chloro-N-methyl-4-[4-(trifluoromethyl)phenoxy]thieno[2,3-c]pyridine-2-carboxamide,
7-chloro-N-(2-hydroxyethyl)-4-[4-(trifluoromethyl)phenoxy]thieno[2,3-c]pyridine-2-carboxamide,
4-(4-chlorophenoxy)-N,7-dimethylthieno[2,3-c]pyridine-2-carboxamide,
4-(4-chlorophenoxy)-7-methoxythieno[2,3-c]pyridine-2-carboxamide,
4-(4-chlorophenoxy)-7-oxo-6,7-dihydrothieno[2,3-c]pyridine-2-carboxamide,
4-(4-chlorophenoxy)-N-methyl-7-(methylamino)thieno[2,3-c]pyridine-2-carboxamide,
7-(4-methylphenoxy)[1,3]thiazolo[5,4-c]pyridine-2-carboxamide,
N-methyl-7-(4-methylphenoxy)[1,3]thiazolo[5,4-c]pyridine-2-carboxamide,
4-(4-chlorophenoxy)furo[2,3-c]pyridine-2-carboxamide,
4-(4-chlorophenoxy)furo[2,3-c]pyridine-2-carbothioamide,
4-[(E)-2-phenylethenyl]thieno[2,3-c]pyridine-2-carboxamide,
4-(4-chlorophenyl)thieno[2,3-c]pyridine-2-carboxamide,
4-[3-(trifluoromethyl)phenyl]thieno[2,3-c]pyridine-2-carboxamide,
4-(3-chlorophenyl)thieno[2,3-c]pyridine-2-carboxamide,
4-(4-bromophenyl)thieno[2,3-c]pyridine-2-carboxamide,
4-(3-aminophenyl)thieno[2,3-c]pyridine-2-carboxamide,
4-(3,5-dichlorophenyl)thieno[2,3-c]pyridine-2-carboxamide,
4-(2,4-dichlorophenyl)thieno[2,3-c]pyridine-2-carboxamide,
4-(3,4-dichlorophenyl)thieno[2,3-c]pyridine-2-carboxamide,
4-(2,4-difluorophenyl)thieno[2,3-c]pyridine-2-carboxamide,
4-(4-fluorophenyl)thieno[2,3-c]pyridine-2-carboxamide, and
4-(4-bromophenyl)-5-chlorothieno[2,3-c]pyridine-2-carboxamide.

Determination of Biological Activity

Pooled primary human umbilical vein endothelial cells (HUVEC's) (Clonetics) between passages 3 and 7 were plated in 96-well plates (Costar), 100 μL/well, 5×10$^4$ cells/mL in Clonetics EBM/2% FBS/EGF/Bovine brain extract/gentamicin in the absence of hydrocortisone. The following day, compounds of the invention were added in 10 μL/well medium, and the plates were incubated at 37° C. 24 hours after compound addition, TNF (Gibco/BRL) in 10 μL/well medium was added to a final concentration of 5 ng/mL, and the cells were incubated an additional 6 hours at 37° C. Then media was removed, and the plates were washed once with D-PBS (Gibco/BRL) and treated with primary antibodies (Becton Dickinson, City), 100 μL/well in D-PBS/2% BSA (Sigma)/0.01% azide. Primary antibodies at an initial concentration of 1 mg/mL were used at the following dilutions: anti-ELAM-1, 1:2000, anti-ICAM-1, 1:2000 and anti-VCAM-1, 1:3000. Plates were stored overnight at 4° C., washed 3 times with D-PBS, and treated with secondary antibody (Jackson Labs), 100 μL/well 1:8000 dilution HRP-conjugated donkey anti-mouse IgG(H+L) in D-PBS/2%BSA. Plates were incubated a minimum of 1 hour at room temperature, washed 3 times with D-PBS and treated with 100 μL of ortho-phnylene diamine 2 HCl reagent per well. Plates were developed approximately 15 minutes and neutralized with 100 μL/well 1N sulfuric acid. Absorbance was read at 490 nm. Inhibitory potencies for representative compounds of the invention are shown in Table 1.

TABLE 1

| | CAM ELISA % Inhibition at 1 μM | | |
|---|---|---|---|
| Example | E-Selectin | ICAM-1 | VCAM-1 |
| 2 | 28 | 35 | 4 |
| 3 | 37 | 32 | 19 |
| 16 | 35 | 32 | 19 |
| 17 | 29 | 30 | 14 |
| 19 | 79 | 67 | 41 |
| 20 | 55 | 46 | 26 |
| 21 | 63 | 55 | 23 |
| 22 | 64 | 64 | 33 |
| 32 | 75 | 63 | 41 |
| 33 | 69 | 60 | 28 |
| 53 | 70 | 67 | 48 |
| 54 | 74 | 59 | 33 |
| 60 | 74 | 71 | 42 |
| 61 | 82 | 74 | 50 |
| 79 | 66 | 63 | 38 |
| 89 | 62 | 64 | 50 |
| 90 | 47 | 51 | 27 |
| 95 | 85 | 71 | 61 |
| 102 | 78 | 68 | 53 |
| 104 | 78 | 72 | 53 |
| 110 | 44 | 48 | 39 |
| 119 | 59 | 61 | 36 |
| 120 | 72 | 72 | 49 |
| 135 | 29 | 22 | 34 |
| 123 | 39 | 31 | 12 |
| 124 | 18 | 29 | 26 |
| 125 | 72 | 69 | 44 |
| 142 | | | |
| 151 | 69 | 73 | 44 |
| 158 | 61 | 65 | 26 |
| 159 | 30 | 45 | 13 |
| 161 | 51 | 58 | 51 |
| 170 | 66 | 67 | 53 |
| 171 | 67 | 72 | 50 |
| 183 | 63 | 69 | 48 |
| 184 | 52 | 56 | 30 |
| 187 | 78 | 72 | 54 |
| 190C | 70 | 65 | 37 |
| 202 | 80 | 68 | 49 |
| 210 | 64 | 58 | 42 |
| 217 | 64 | 63 | 42 |
| 218 | 66 | 64 | 51 |
| 219 | 62 | 68 | 50 |
| 220 | 60 | 51 | 32 |
| 222 | 40 | 42 | 44 |
| 223 | 34 | 36 | 36 |
| 224 | 61 | 55 | 41 |
| 225 | 75 | 78 | 60 |
| 226 | 77 | 74 | 56 |
| 227 | 61 | 62 | 44 |
| 228 | 70 | 68 | 54 |
| 228 | 67 | 64 | 52 |
| 229 | 54 | 55 | 46 |
| 230 | 56 | 53 | 45 |
| 233 | 74 | 79 | 62 |

TABLE 1-continued

| | CAM ELISA % Inhibition at 1 μM | | |
|---|---|---|---|
| Example | E-Selectin | ICAM-1 | VCAM-1 |
| 236 | 59 | 59 | 33 |
| 237I | 71 | 77 | 54 |
| 238 | 46 | 47 | 17 |
| 249 | 75 | 69 | 61 |
| 254 | 24 | 28 | 24 |
| 255 | 67 | 65 | 19 |
| 259 | 63 | 59 | 57 |
| 261 | 20 | 16 | 0 |
| 274 | 65 | 71 | 44 |
| 275 | 73 | 72 | 64 |
| 276 | 66 | 61 | 52 |
| 279 | 30 | 40 | 24 |
| 280 | 73 | 77 | 69 |
| 281 | 18 | 25 | 20 |
| 282A | 8 | 15 | 5 |
| 283 | 39 | 57 | 52 |
| 284 | 56 | 68 | 45 |
| 285 | 56 | 65 | 50 |
| 286 | 54 | 64 | 46 |
| 287 | 49 | 49 | 27 |
| 289 | 64 | 62 | 52 |
| 290 | 42 | 53 | 48 |
| 294 | 46 | 45 | 24 |
| 295 | 59 | 56 | 44 |
| 301 | 44 | 48 | 34 |
| 303 | 65 | 66 | 33 |
| 311 | 72 | 77 | 36 |
| 312 | 64 | 76 | 42 |
| 313 | 57 | 68 | 39 |
| 316 | 76 | 68 | 42 |
| 320 | 64 | 67 | 55 |
| 325 | 76 | 68 | 42 |
| 329 | 72 | 62 | 64 |
| 340 | 18 | 33 | 20 |

Thus the compounds of the present invention act as antiinflammatory agents with potencies below 1 μM and are therefore useful for treating inflammatory diseases.

Pharmaceutical Compositions and Methods of Treatment

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et The compounds of the present invention may be used in the form of pharmaceutically acceptable salts derived from inorganic or organic acids. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in J. Pharmaceutical Sciences, 1977, 66: 1 et seq. The salts may be prepared in situ during the final isolation and purification of the compounds of the invention or separately by reacting a free base function with a suitable acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the invention include phosphate, tris and acetate.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention
Abbreviations

Abbreviations which have been used in the descriptions of the schemes and the examples that follow are: $BH_3$ for borane, $BH_3.DMS$ for borane dimethylsulfide complex, BINAP for 2,2'-bis(diphenylphosphino)-1,1'-binaphthyl, $BF_3OEt_2$ for boron trifluoride diethyl ether complex, n-BuLi for n-butyllithium, $CCl_4$ for carbon tetrachloride, $Cs_2CO_3$ for cesium carbonate, DBU for 1,8-diazabicyclo[5.4.0]undec-7-ene, DMA for N,N-dimethylacetamide, DIBAL for diisobutylaluminum hydride, DME for dimethoxyethane, DMF for N,N-dimethylformamide, DMSO for dimethylsulfoxide, DIPEA for diisopropylethylamine, DPPA for diphenylphosphoryl azide, EDCI or EDC for 1-ethyl-3-[3-(dimethylamino)propyl]-carbodiimide hydrochloride, $Et_3N$ for triethylamine, $Et_2O$ for diethyl ether, EtOAc for ethyl acetate, EtOH for ethanol, $K_2CO_3$ for potassium carbonate, $LiAlH_4$ for lithium aluminum hydride, LDA for lithium diisopropylamide, MeOH for methanol, NaOMe for sodium methoxide, NaOH for sodium hydroxide, HCl for hydrochloric acid, NMP for 1-methyl-2-pyffolidinone, $H_2/Pd$ for hydrogen and a palladium catalyst, iPrOH for isopropyl alcohol, $PPh_3$ for triphenylphosphine, THF for tetrahydrofuran, THP for tetrahydropyran, TFA for trifluoroacetic acid, and pyBOP for benzotriazol-1-yloxytripyffolidinophosphonium hexafluorophosphate.

Synthetic Methods

The compounds and processes of the present invention will be better understood in connection with the following synthetic schemes which illustrate the methods by which the compounds of the invention can be prepared. Further, all citations herein are incorporated by reference.

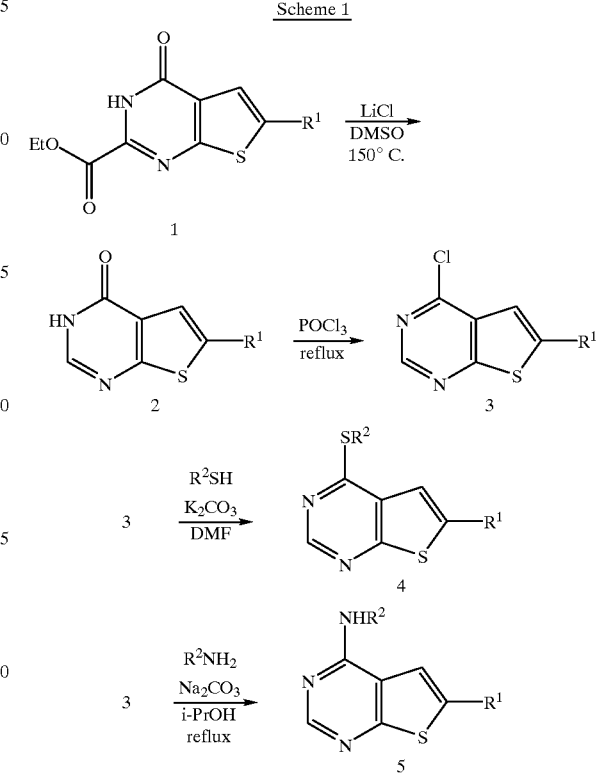

Scheme 1 shows the preparation of thieno[2,3-d] pyrimidines from esters of general formula 1 by published procedures. 4-Chlorothieno[2,3-d]pyrimidines of general formula 3 were substituted with thiols to provide 4-thioethers of general formula 4 or substituted with amines to provide 4-aminothieno[2,3-d]pyrimidines of general formula 5.

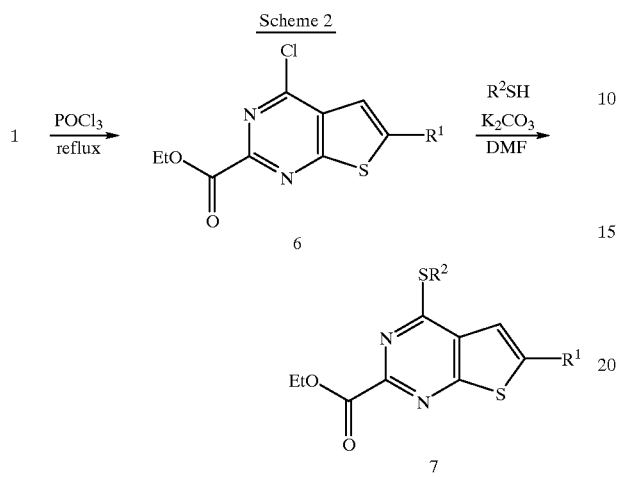

Scheme 2 shows the preparation of 2-carboxy-substituted thieno[2,3-d]pyrimidines. Pyrimidinones of general formula 1 weres reacted with phosphoryl chloride to produce 4-chloro pyrimidines of general formula 6, which were then ttuted with thiols to provide thioethers of general formula 7.

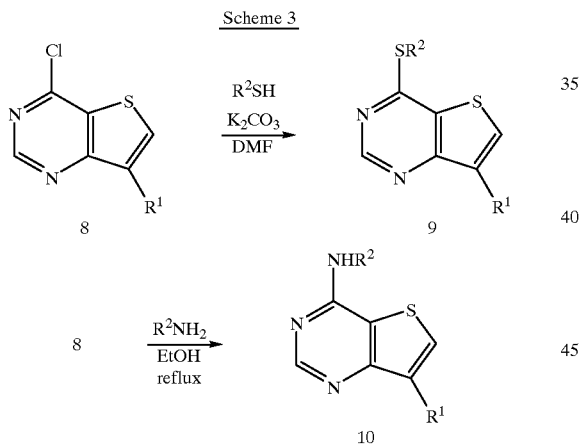

Scheme 3 shows the preparation of thieno[3,2-d]pyrimidines derived from chloropyrimidines of general formula 8. Substitution of the chlorides with thiols provided thioethers of general formula 9, and substitution of the chlorides with amines provided aminopyrimidines of general formula 10.

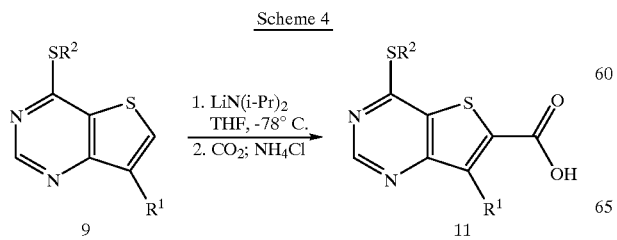

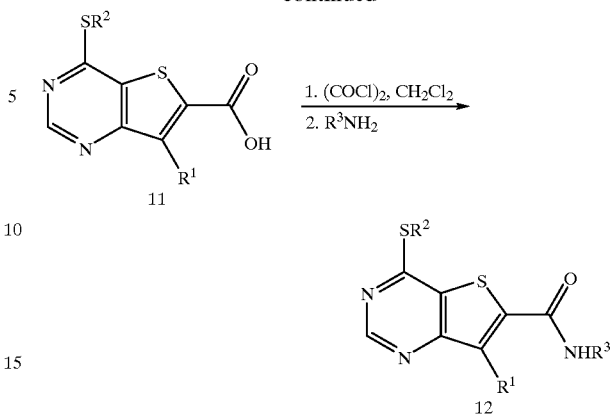

Analogs having 2-carboxamide groups on the thieno[3,2-d]pyrimidine were prepared as shown in Scheme 4. The thiophene-2-position was deprotonated with a strong base such as lithium diisopropylamide, and the corresponding carbanion was treated with carbon dioxide to provide acids of general formula 11. The acids were converted to the corresponding amides of general formula 12 through the intermediate acid chlorides.

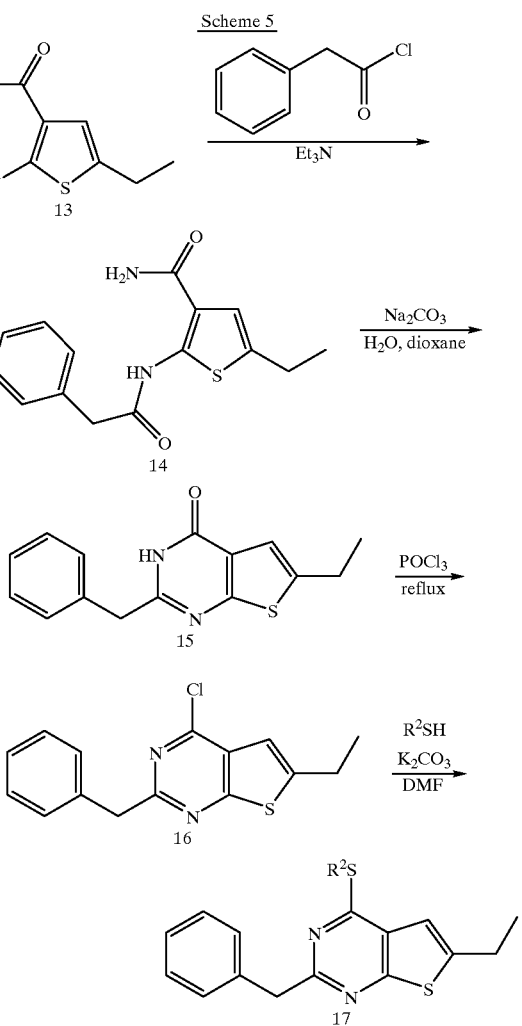

Scheme 5 shows the preparation of 6-alkyl substituted thieno[2,3-d]pyrimidines with alkylthio groups at the 4-position. Using known procedures, 2-aminothiophene 13 was acylated to provide amide 14 which was cyclized to provide thienopyrimidinone 15. The pyrimidinone was converted to chloride 16 and further to thioether 17 by standard procedures.

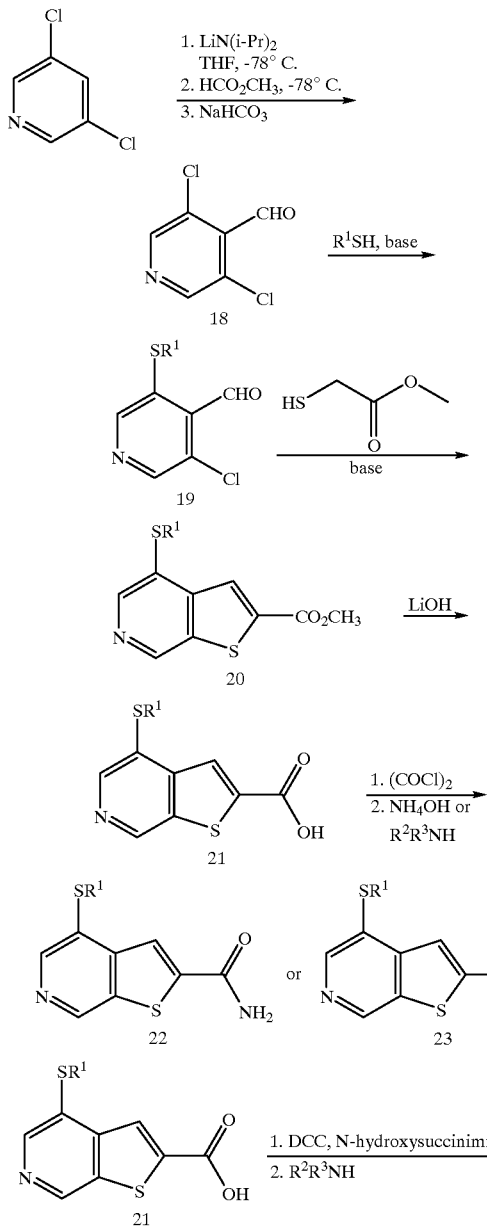

Scheme 6

The general process for preparing 2,4-disubstituted thieno[2,3-c]pyridines is shown in Scheme 6. Commercially available 3,5-dichlorpyridine was treated with strong base such as lithium diisopropylamide in an anhydrous solvent at low temperature followed by reaction with methyl formate (or alternatively, dimethylformamide) to provide the known pyridine-4-carboxaldehyde 18. Aldehyde 18 was then substituted with one equivalent of thiol ($R^1$=substituted or unsubstituted aryl, alkyl, or heterocyclic) to produce chloroaldehyde of general formula 19. Treatment of 19 with methyl thioglycolate and a base such as cesium carbonate or potassium carbonate provided the 4-thioether[2,3-c]-thienopyridine esters of general formula 20. The esters were converted to the corresponding acids of general formula 21 by basic hydrolysis, for example using lithium, sodium, or potassium hydroxide in a mixture of water and alcohol or tetrahydrofuran. Acids of general formula 21 may also be converted to amides of general formula 22 or 23 through the intermediate acid chlorides by treatment first with oxalyl chloride or thionyl chloride, then with the amine of choice ($R^2$, $R_3$ can be substituted or unsubstituted alkyl, aryl, heterocyclic). Alternatively, aicds 21 may be converted to amides 22 or 23 by other coupling methods, such as carbodiimide (for example, N-ethyl-N'-(3-dimethylamino)propyl carbodiimide hydrochloride (EDC)), mixed anhydrides (derived from pivaloyl chloride or isobutyl chloroformate treatment), and active esters (for example, derived from N-hydroxysuccinimide, p-nitrophenol).

Scheme 7

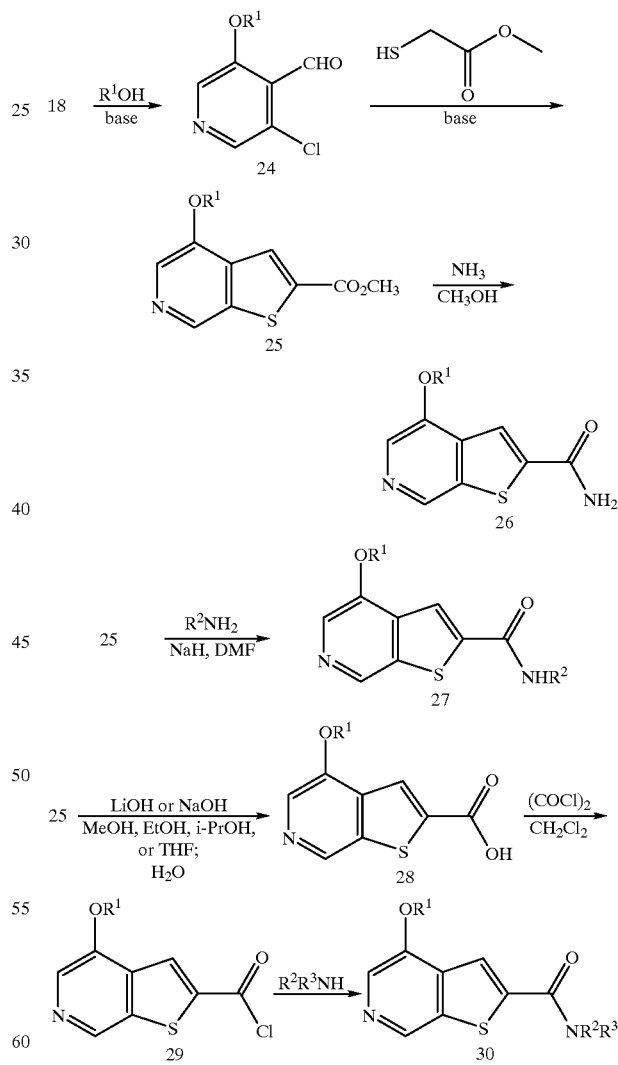

Scheme 7 illustrates the analogous preparation of 4-ether-substituted thienopyridines of general formula 30. Aldehyde 18 was substituted with alcohols ($R^1$=substituted or unsubstituted aryl, heterocyclic) under basic conditions (for example, potassium tert-butoxide or cesium carbonate in anhydrous tetrahydrofuran or dimethylformamide) to give pyridine-ethers of general formula 24, and then further reacted with methyl thioglycolate to provide the thieno[2,3-c]pyridine esters of general formula 25. These esters may be converted to the corresponding primary amides of general formula 26 by heating in methanolic ammonia solution. Alternatively, esters of general formula 25 may be reacted with mono or disubstituted amines in polar solvents such as dimethylformamide or methanol. Esters of general formula 25 were hydrolyzed to carboxylic acids of general formula 28 by basic hydrolysis with sodium or lithium hydroxide in aqueous methanol or tetrahydrofuran. The acids were then converted to amides of general formula 30 by reaction of the corresponding acid chlorides of general formula 29 with amines. Alternatively, the acids 30 were coupled to amines by standard peptide-coupling conditions as described in Scheme 6 for amides 22 or 23.

Tetrahedron Lett. 1975, 4467–70). Esters of general formula 33 were converted to amides of general formula 34 by the procedures described for 26, 27 or 30 in Scheme 7.

Scheme 8

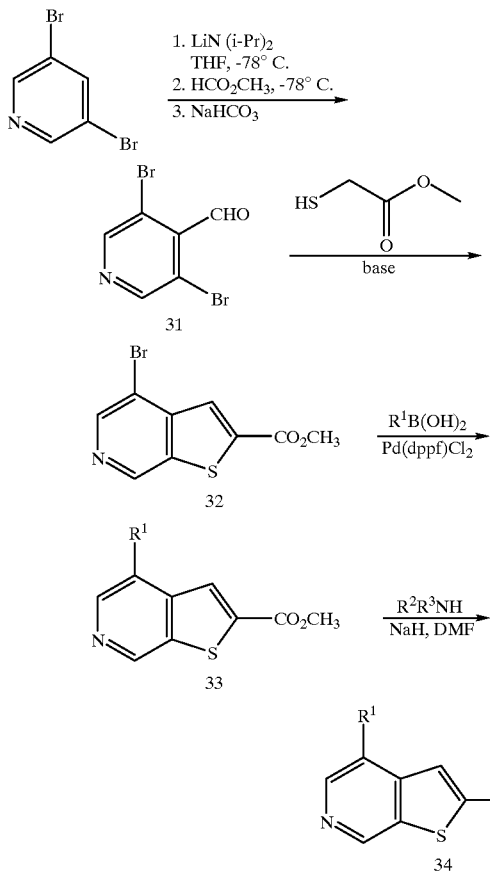

Similar methods may be utilized for the preparation of 4-bromothieno[2,3-c]pyridine 32, as shown in Scheme 8. 3,5-Dibromopyridine was converted to aldehyde 31 by the procedure described for preparation of compound 18 in Scheme 6. Reaction of 31 with methyl thioglycolate, for example in the presence of cesium carbonate in DMF, produced 4-bromothieno[2,3-c]pyridine ester 32. Bromide 32 served as starting material for the preparation of 4-aryl, heterocyclic, alkyl, or alkenyl derivatives of general formula 33, using Suzuki coupling methodology as shown. Bromide 32 may also be coupled with terminal alkynes to provide alkynyl derivatives ($R^1$=alkynyl) following Sonogashira methodology (Sonogashira, K.; Tohda, Y.; Hagihara, N.

Scheme 9

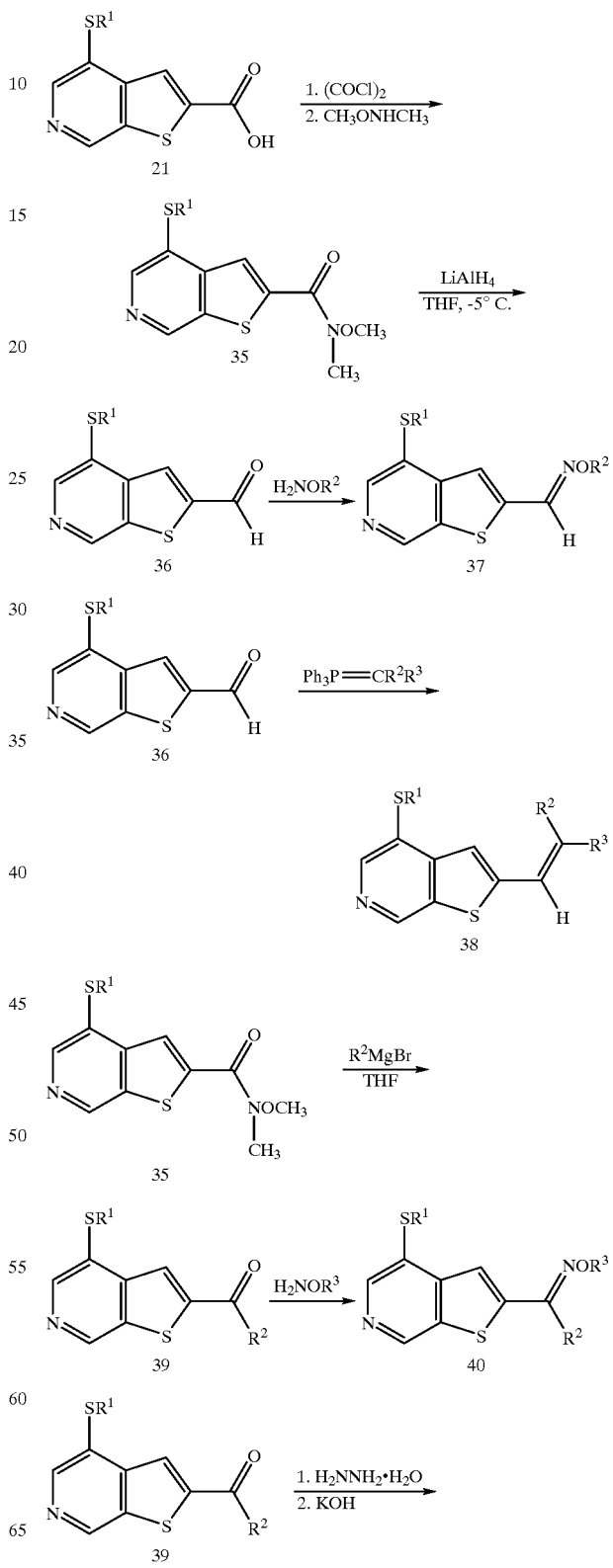

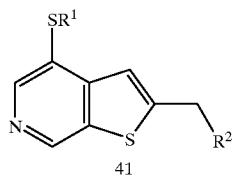

Scheme 9 shows the conversion of acids of general formula 21 to aldehyde or ketone-derived compounds. For example, aldehydes of general formula 36 were produced by reduction of the N-methyl-N-methoxylamides of general formula 35. The amides of general formula 35 were also reacted with Grignard reagents to produce unsymmetrical ketones of general formula 39. Aldehydes of general formula 36 and Ketones of general formula 39 were utilized for the production of oximes of general formula 37 or 40 by reaction with hydroxylamine derivatives. Aldehyde of general formula 36 were reacted with phosphoranes (or phosphonoacetate salts) to produce 2-alkenyl substituted derivatives of general formula 38. Ketones of general formula 39 were reduced to the corresponding alkanes of general formula 41 by treatment with hydrazine and strong base, such as potassium hydroxide. Analogous 2-position derivatives of thienopyridine ethers of general formula 28 in Scheme 7 would follow similar synthetic routes as described in Scheme 9. Thus, acids 28 may be converted to aldehydes, ketones, oximes, alkenes, or alkanes substitutions at the 2-position.

formula 20 with an oxidant such as m-chloroperoxybenzoic acid under controlled conditions.

Scheme 12

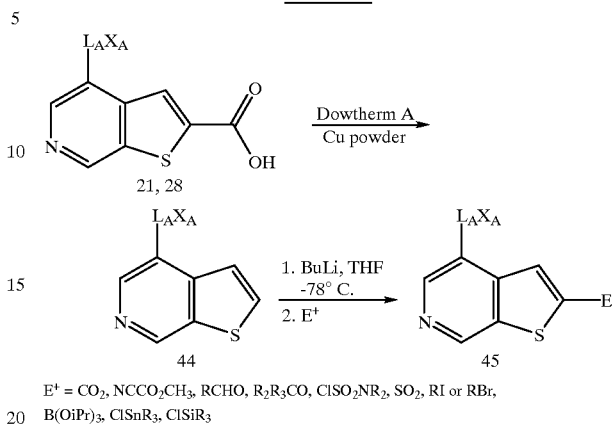

$E^+ = CO_2, NCCO_2CH_3, RCHO, R_2R_3CO, ClSO_2NR_2, SO_2, RI$ or $RBr$, $B(OiPr)_3, ClSnR_3, ClSiR_3$

Alternative functionality was introduced at the 2-position of thienopyridines of general formula 44 by metallation of the 2-position, followed by reaction with appropriate electrophiles, as shown in Scheme 12. Acids of general formula 21 ($L_AX_A$=thioalkoxy, alkoxy, alkyl, alkenyl, aryl, heterocyclic) were decarboxylated at elevated temperatures (optionally in the presence of copper powder) to afford 2-unsubstituted derivatives of general formula 44. Compounds of general formula 44 were deprotonated with strong Scheme 10

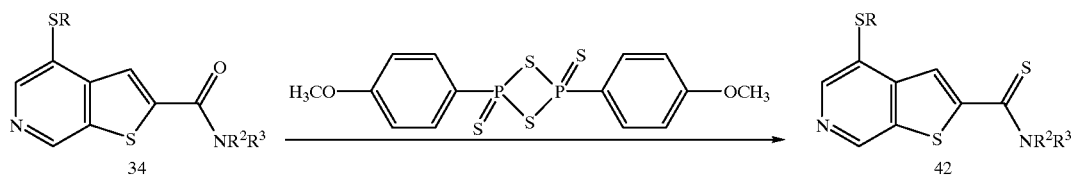

Amides of general formula 34 (or 26, 27 or 30), may be converted to the corresponding thionoamides of general formula 42 by treatment with Lawesson's reagent as shown in Scheme 10.

organic bases such as n-butyllithium, and then reacted with electrophiles such as borates, cyanoformates, aldehydes, or trialkyltin chlorides according to standard procedures (Masakatsu, N.; Kazuhiro, N.; Ichiro, M.; Iwao; W. Chem. Lett. 1983, 6, 905–908).

Scheme 11

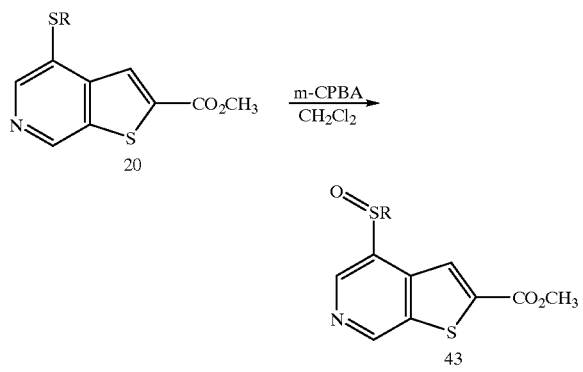

As shown in Scheme 11, 4-sulfoxides of general formula 43 were produced by reaction of thioethers of general Scheme 13

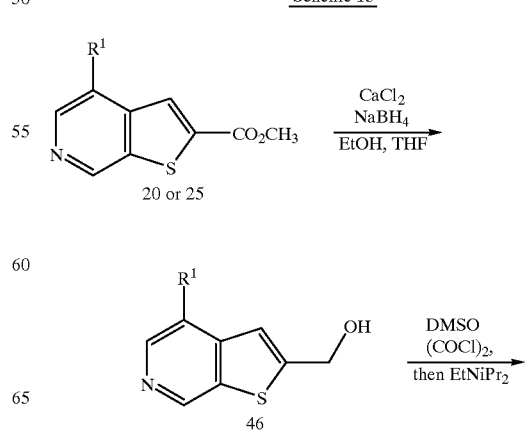

produce the acrylate derivatives of general formula 48 (Jung, M. E. and Kiankarami, M. J. Org. Chem. 1998, 63, 2968–2974).

Scheme 14

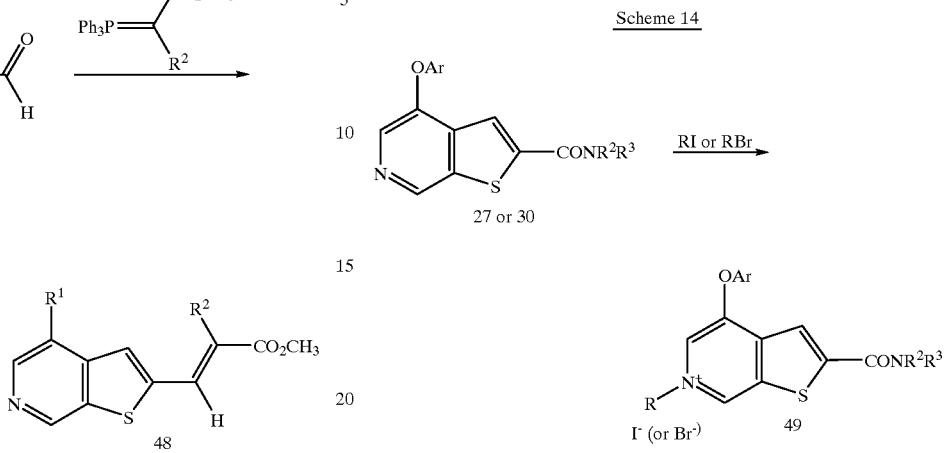

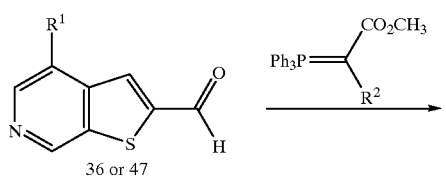

Scheme 13 illustrates an alternative method for the preparation of 2-carboxaldehydes of general formula 36 or 47. Esters of general formula 20 or 25 ($R^1$=thioalkoxy, alkoxy, alkyl, alkenyl, aryl, heterocyclic) were reduced to the corresponding alcohols of general formula 46 using calcium borohydride. The alcohols were then oxidized to the aldehydes using Swern conditions. The aldehydes were then reacted with Wittig reagents (for example phosphoranes to As shown in Scheme 14, thienopyridines of general formula 27 or 30 were alkylated on the pyridine nitrogen using alkyl iodides (or alkyl bromides or triflates) to produce the pyridinium salts of general formula 49. For example, R may be alkylcarbonyloxymethylene, aminocarbonyloxymethylene, alkoxycarbonyloxymethylene, or alkyl. Such derivatives may serve as prodrug forms of the thienopyridine amides 27 or 30.

Scheme 15

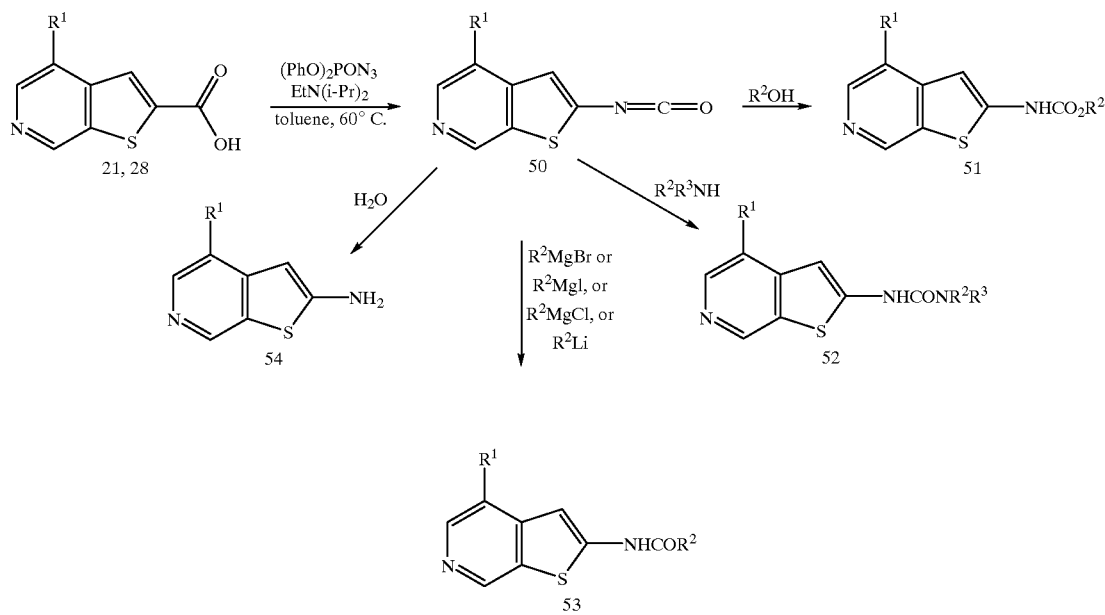

A variety of 2-aminothieno[2,3-c]pyridine derivatives were available starting from the 2-carboxylic acids of general formula 21 or 28, as shown in Scheme 15, wherein $R^1$ may be thioalkoxy, alkoxy, alkyl, alkenyl, aryl, heterocyclic. Curtius rearrangement led to isocyanates of general formula 50, which were reacted with alcohols (alkyl, aryl, heterocyclic, or dialkylaminoalkyl) to provide carbamates of general formula 51. Isocyanates 50 may be reacted with amines (ammonia, primary alkyl or secondary alkyl) to provide ureas of general formula 52. Also, 50 may be reacted with alkyl or arylmagnesium halides, or alkyl lithium salts, to provide amides of general formula 53. Isocyanate 50 was hydrolyzed under aqueous conditions to produce 2-amino derivatives of general formula 54.

Scheme 16

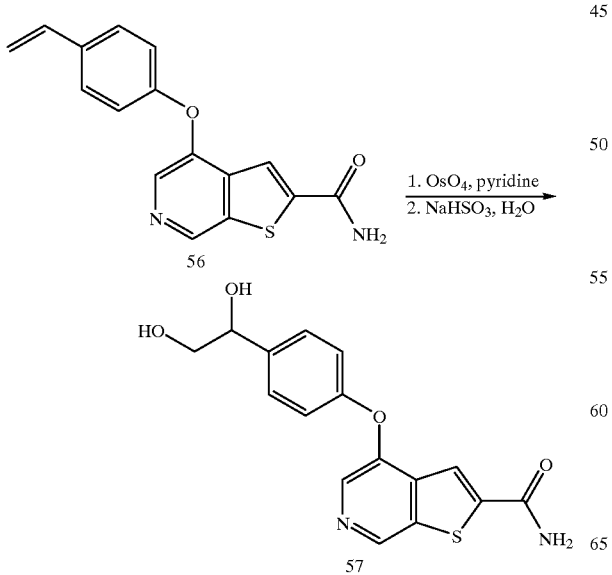

Amines of general formula 54 were reacted with appropriate electrophiles to further derivatize this position. Thus reaction of 54 with aryl or alkylsulfonyl chlorides ($R^2$=alkyl, aryl, heterocyclic) or sulfamoyl chlorides, ($R^2$=$NH_2$, mono- or di-alkylamino) to give sulfonamides of general formula 55. Amino derivative 54 was also reacted with acyl chlorides ($R^2$=alkyl, heterocyclic, or aryl) to produce amides of general formula 53 as shown in Scheme 16.

Scheme 17

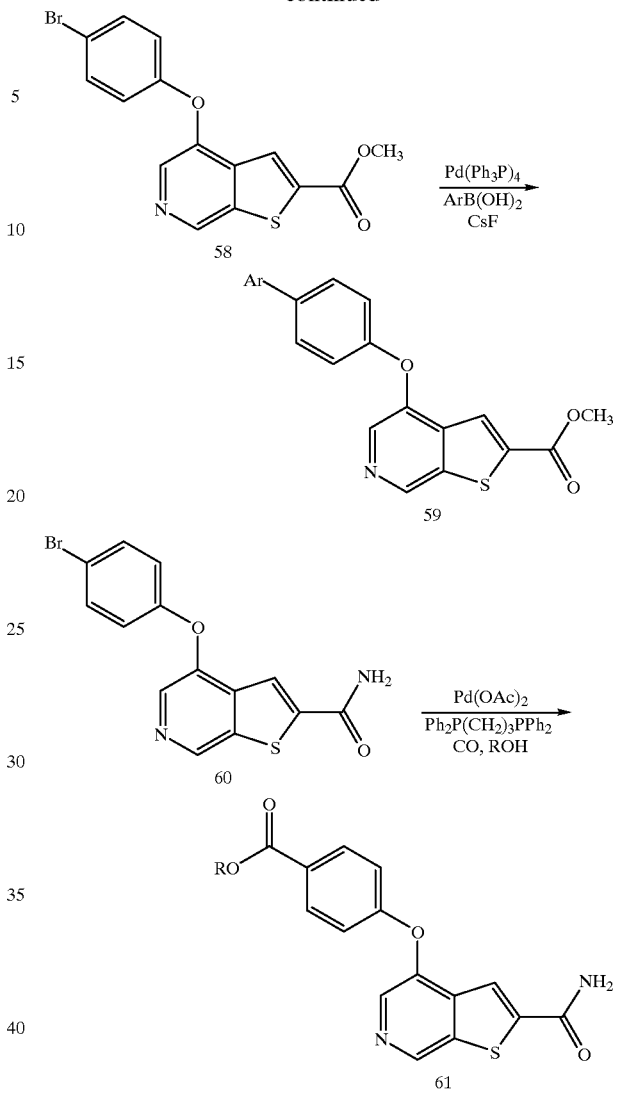

Functionality present on the aryl rings attached at the 4-position of the thieno[2,3-c]pyridines may be further reacted to advantage, as illustrated in Scheme 17. For example, styryl derivative 56 was converted to the 1,2-diol 57 by treatment with osmium tetroxide under standard conditions. The 4-(4-bromophenoxy) derivative 58 underwent fascile substitution with aryl boronic acids under palladium catalysis under Suzuki conditions to provide biaryl derivatives of general formula 59. Alternatively, alkoxycarbonylation under palladium catalysis efficiently provides esters of general formula 61.

Scheme 19

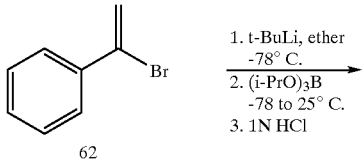

1. t-BuLi, ether
   -78° C.
2. (i-PrO)$_3$B
   -78 to 25° C.
3. 1N HCl

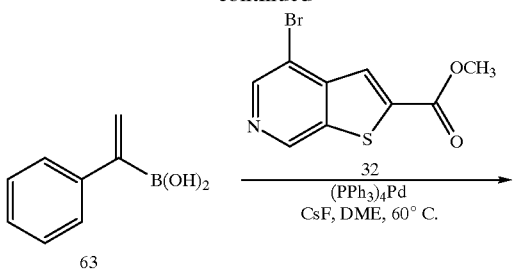

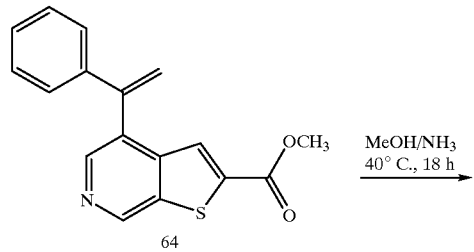

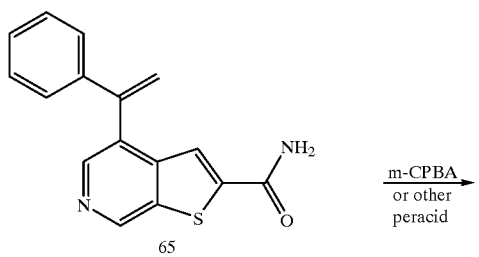

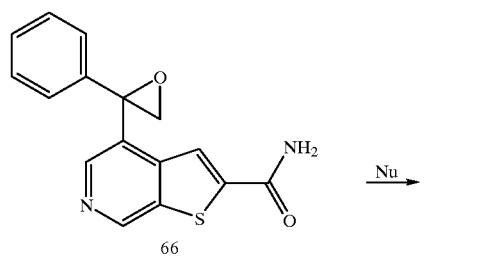

Nu = RS——, RNH$_2$, R$_2$CuCNLi, etc.

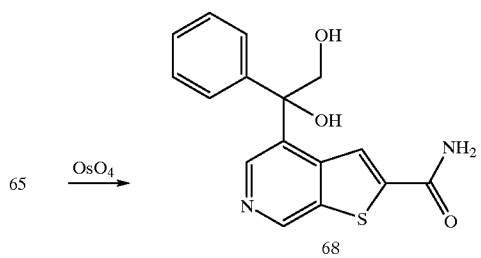

Scheme 19 shows the use of boronic acid derivatives to functionalize the 4-position of the thieno[2,3-c]pyridines. The chemistry depicted may be applied to a broad range of aryl olefins analogous to bromostyrene 62. In the case shown, bromostyrene 62 was converted to the boronic acid 63 under standard conditions, and the boronic acid was coupled to 4-bromothienopyridine 32 under Suzuki conditions, affording the styryl analog 64. The ester 64 was converted to the amide 65 by the previously described method (Miyara, N and Suzuki, A. Chem. Rev. 1995, 95, 2457–2463). The olefinic group may then be converted to the epoxide 66, which can undergo reactions with nucleophilic reagents at the less-hindered position of the epoxide to producing analogs of general formula 67. Alternatively, styryl derivative 65 may be converted to the diol 68 by standard methods.

Scheme 20

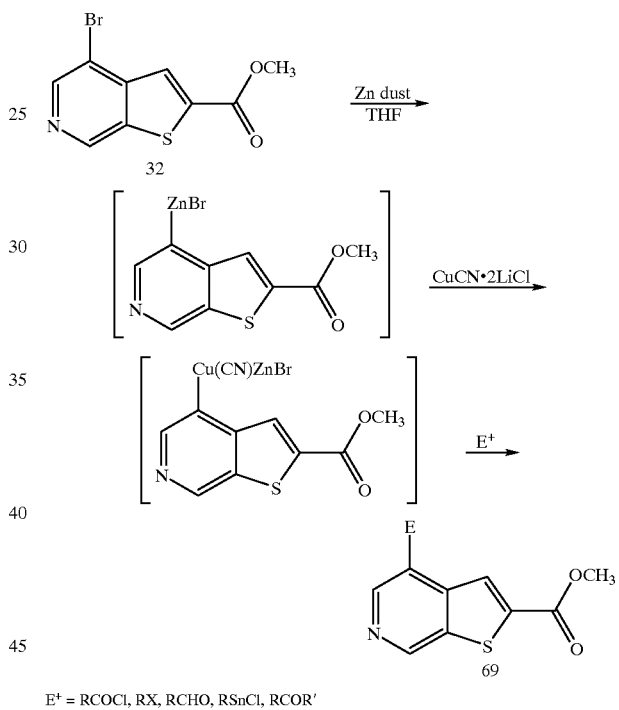

E$^+$ = RCOCl, RX, RCHO, RSnCl, RCOR'

Another method for introduction of substituents at the 4-position of the thieno[2,3-c]pyridines is shown in Scheme 20. Bromide 32 may be converted to the corresponding cuprate through the intermediate zinc bromide reagent, which then may be reacted with appropriate electrophiles (acid chlorides, alkyl halides, aldehydes, ketones) to afford the substituted compounds of general formula 69 (Zhu, L.; Wehmeyer, R. M.; Rieke, R. D. J. Org. Chem. 1991, 56, 1445–1453).

Scheme 21

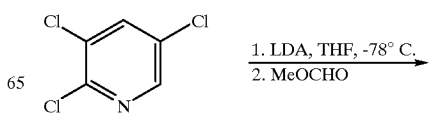

1. LDA, THF, -78° C.
2. MeOCHO

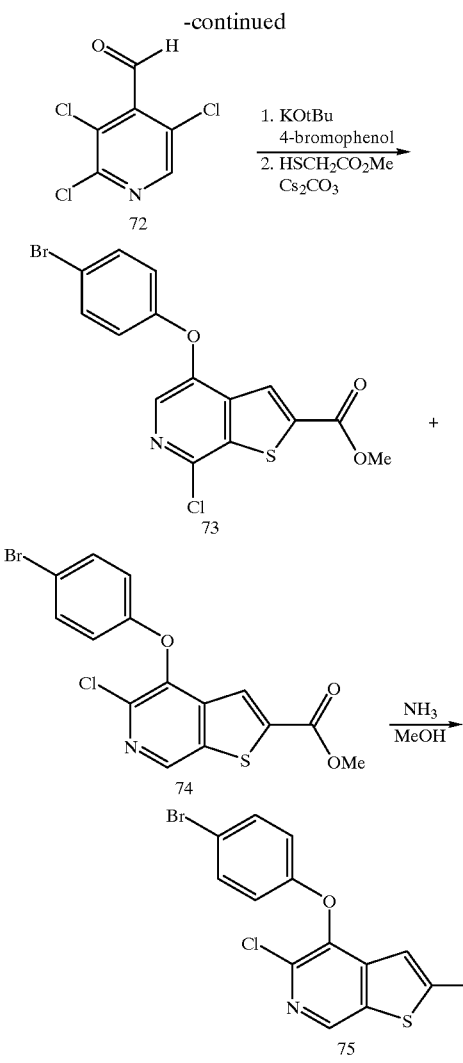

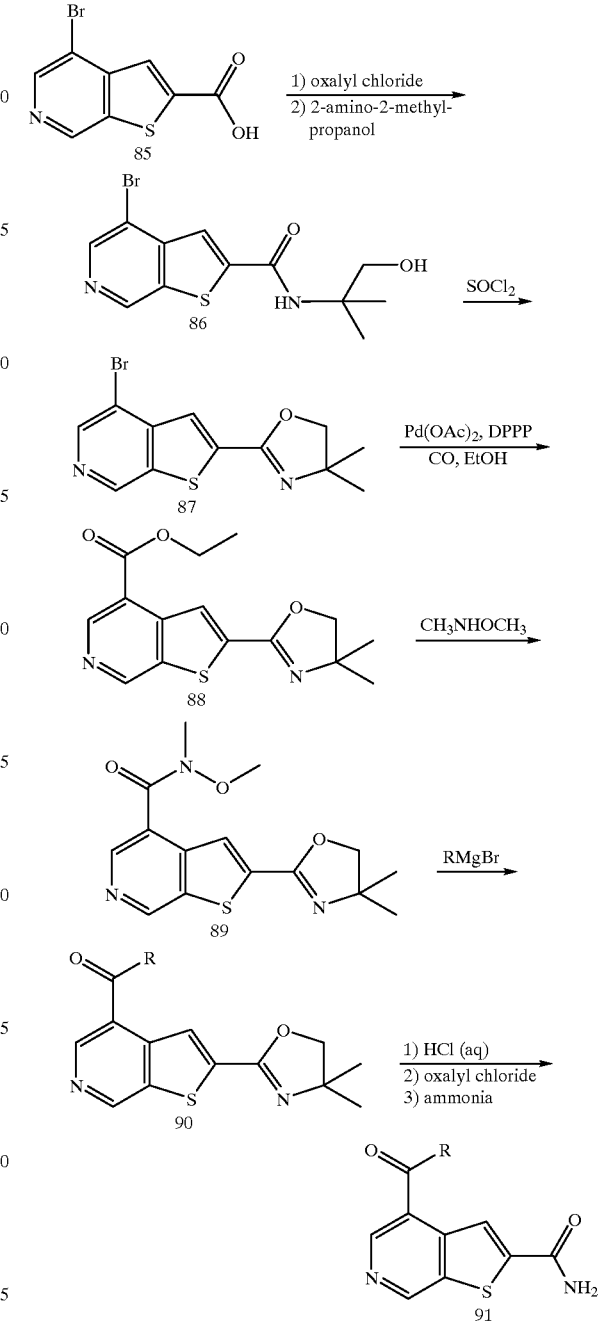

prepared according to Scheme 12, was coupled to aryl halides under palladium catalysis to produce 2-aryl derivatives of general formula 80.

Scheme 21 depicts the preparation of 5-halo thienopyridine derivatives, as exemplified by the preparation of the 5-chloro analog 75. Formylation of lithiated 2,3,5-trichloropyridine with methyl formate gave aldehyde 72. Displacement of the 3 and 5 chlorines with excess 4-bromophenol and reaction with methylthioglycolate gave the 5-chlorothienopyridine 74 in low yield, together with the major product 73. The 5-chloro isomer was treated with ammonia in methanol in a pressure tube to generate the amide 75. It should be noted that this chemistry may be applied using a range of phenols or hydroxy heterocyclic compounds in place of 4-bromophenol.

Scheme 22

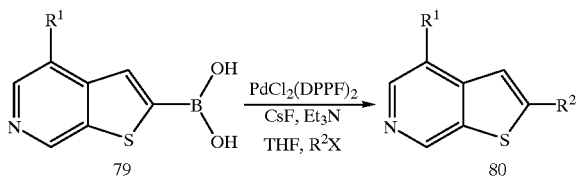

The 2-position of thienopyridines was substituted with aryl, vinyl, acetylenic or alkyl groups using the procedure shown in Scheme 22. Boronic acids of general formula 79

Scheme 23 illustrates the preparation of 4-acyl derivatives of thieno[2,3-c]pyridines. Carboxylic acid 85 was converted to amide 86 via the acid chloride, then the hydroxymide 86 underwent thionyl chloride-mediated cyclization to the oxazoline 87 (Meyers, A. I.; Stoianova, D. J. Org. Chem. 1997, 62, 5219–5221). Palladium mediated alkoxycarbonylation of 87 yielded ester 88 (Heck, R. F.; et al. J. Org. Chem. 1974, 39, 3318). Ester 88 may be converted to the Weinreb amide 89 by standard methods. Amide 89 was reacted with the appropriate Grignard reagents to provide the desired 4-acyl products of general formula 90. Hydrolysis of the oxazoline and conversion of the resultant carboxylic acid to the amide yields the desired products of general formula 91.

Scheme 24

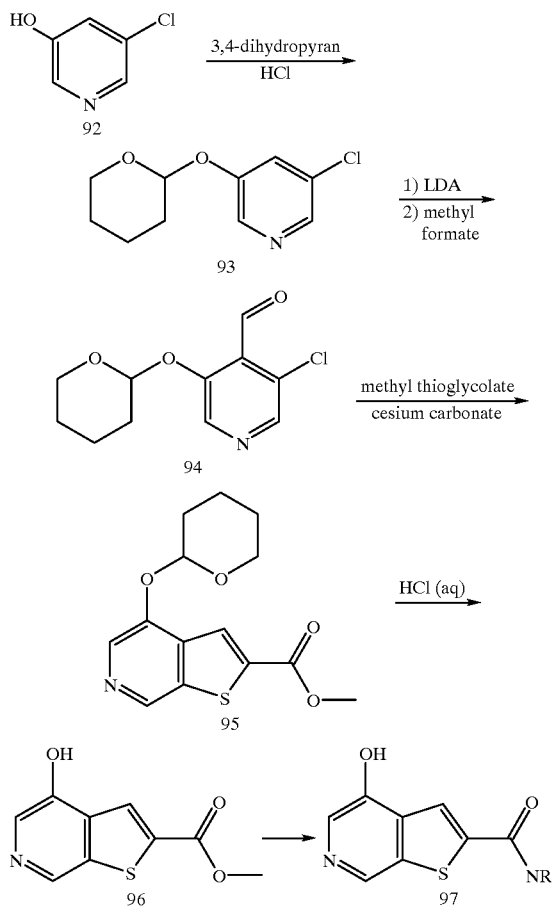

Scheme 24 depicts a proposed method for the formation of 4-hydroxy substituted thieno[2,3-c]pyridine. Reaction of phenol 92 with dihydropyran under acidic conditions yields tetrahydropyranyl ether 93 (Grant, H. N., et al. Helv. Chim. Acta. 1963, 46, 41). Lithiation of 93 and subsequent quench with methyl formate gives aldehyde 94. Displacement of the halide with methyl thioglycolate and subsequent cyclization with cesium carbonate yields the ester 95. Removal of the tetrahydropyranyl ether with aqueous HCl gives hydroxypyridine 96, which may be converted to the amide as described previously.

Scheme 25

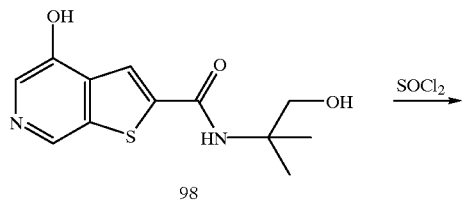

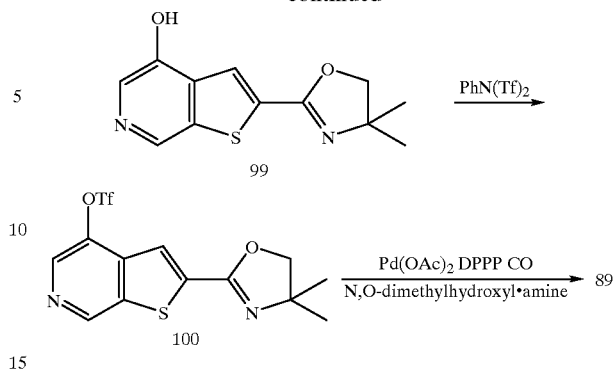

Scheme 25 proposes the use of the 4-hydroxy group for introduction of functionality to the 4-position of the thieno[2,3-c]pyridines. The 2-carboxylic acid group is first protected as the oxazoline 99 (through the intermediate amide 98), then the hydroxy group is converted to the aryl triflate 100 by standard conditions. Triflate 100 may then be converted to the N-methyl-N-methoxy amide 89 under conditions similar to that for bromide 87. It should be noted that 4-triflate 100 may serve as a coupling partner in a variety of transition-metal mediated couplings with appropriate nucleophilic partners (for example, boronic acids, boranes, alkyl or aryl-zinc reagents).

Scheme 26

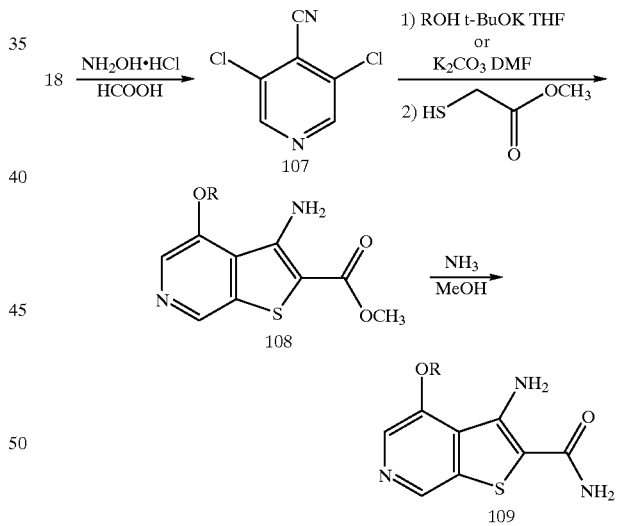

Compounds with amino substitutions at the 3-position of the thieno[2,3-c]pyridines were prepared according to the procedures outlined in Scheme 26. Aldehyde 18 was converted to the cyanopyridine 107 by treatment with hydroxylamine under dehydrating conditions. In a manner similar to the reactions involving aldehyde 18, cyanopyridine 107 was sequentially substituted with phenols and methyl thioglycolate to provide the 3-amino thieno[2,3-c]pyridines of general formula 108. Esters of general formula 108 were then converted to amides of general formula 109 by standard procedures.

Scheme 27

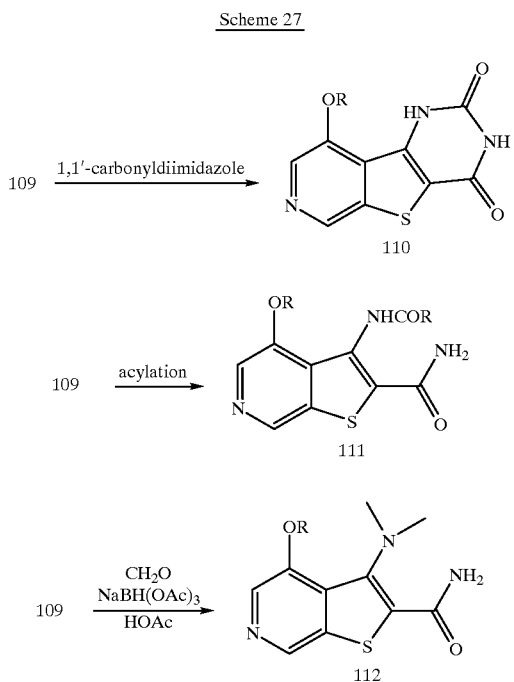

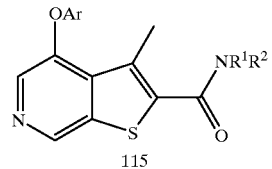

Scheme 27 illustrates additional derivatives which can be derived from amino esters of general formula 108 or amino amides of general formula 109. For example, amino amides of general formula 109 may be treated with 1,1'-carbonyldiimidazole to produce cyclic imides of general formula 110. The 3-amino group was acylated (for example, with acid chlorides and weak base, or by coupling with acids using carbodiimides) to give the diamides of general formula 111. The 3-amino group may be alkylated under reductive conditions using aldehydes and a reducing agent (such as triacetoxyborohydride), to provide alkylated amines of general formula 112.

Scheme 28

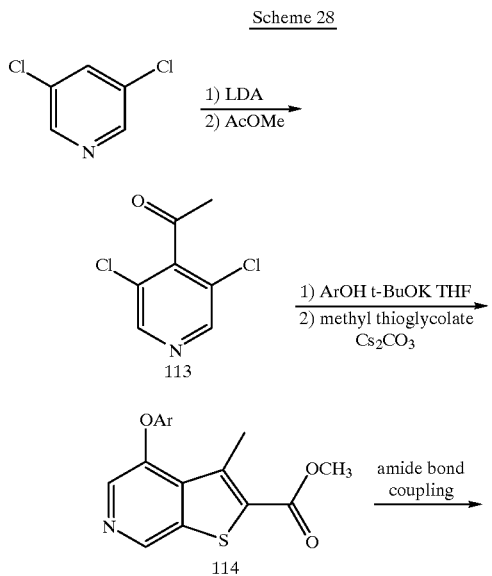

Scheme 28 shows the preparation of compounds bearing alkyl substituents at the 3-position of the thieno[2,3-c] pyridines. Using similar chemistry to that described for compound 30, 3,5-dichloropyridine was deprotonated with strong base (for example, lithium diisopropylamide), and then reacted with an acylating reagent (ester, N-methyl-N-methoxyamide, acyl pyrazole, or others) to provide ketone 113. Alternatively, the anion can be reacted with an aldehyde (for example, acetaldehyde) and then subsequently the product may be oxidized (for example, with tetrapropylammonium perruthenate) to provide ketone 113. Following the protocol outlined for example 30, the dichloroketone was reacted sequentially with phenols and then with methyl thioglycolate to provide cyclic products of general formula 114. The esters of general formula 114 may be converted to various derivatives as outlined previously.

Scheme 29

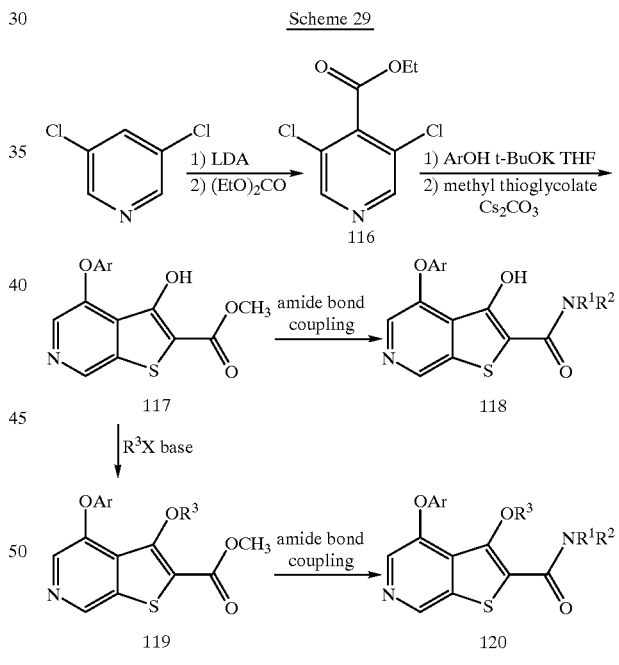

Scheme 29 describes a similar strategy used to obtain derivatives with alkoxy groups at the 3-position of thieno[2,3-c]pyridines. Ester 116 was substituted and cyclized to provide 3-hydroxy analogs of general formula 117. The hydroxy group may be left unsubstituted, leading to amides of general formula 118 (or other derivatives). Alternatively, hydroxy esters of general formula 117 may be alkylated by standard procedures to produce 3-alkoxy derivates of general formula 119, followed by amide formation to provide compounds of general formula 120.

Scheme 30

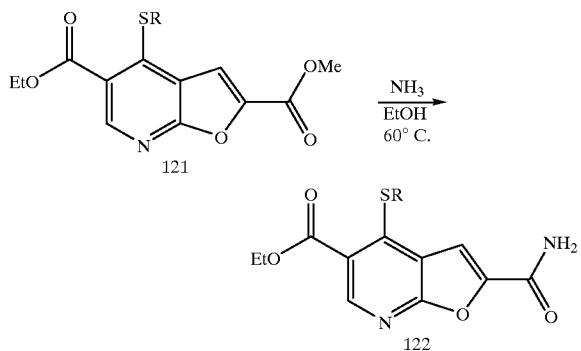

Scheme 30 shows the procedure used for the transformation of a commercially available furo[2,3-b]pyridine 121 into an amide 122.

Scheme 31

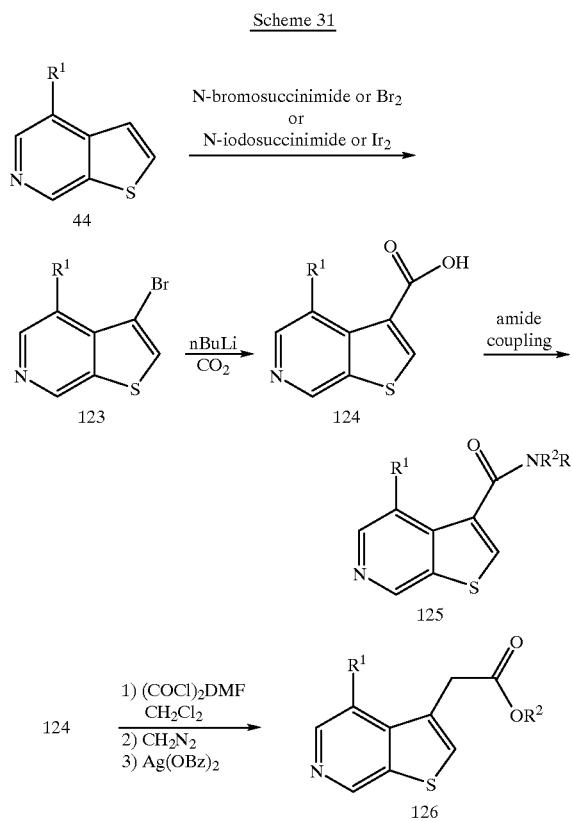

Scheme 31 proposes the preparation of thienopyridine derivatives containing an amide group at the 3-position. Thienopyridines of general formula 44 are halogenated using electophilic halide sources (for example, N-bromosuccinimide, $I_2$), to produce 3-halothienopyridines of general formula 123. Metal-halogen exchange, followed by trapping with carbon dioxide, provides acids of general formula 124. The acids are converted into amides of general formula 125 by standard procedures, or may be homologated to esters of general formula 126 (for example, by the Arndt-Eisert procedure). Esters of general formula 126 may then be converted to amides or other functionality by the methods described above.

Scheme 32

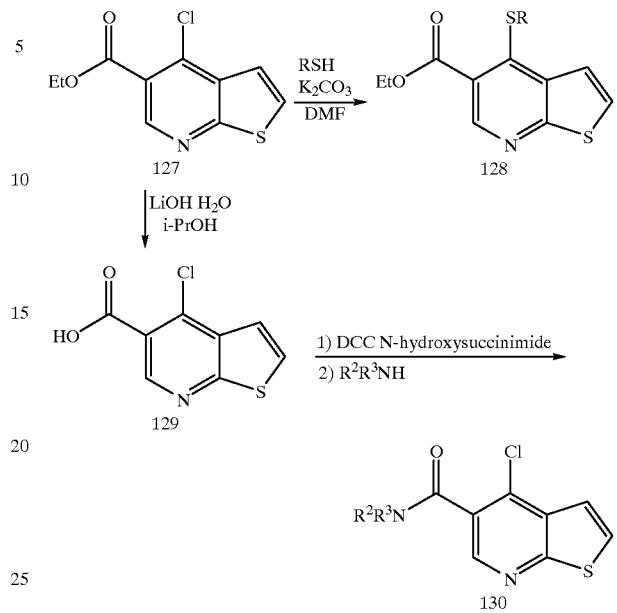

Scheme 32 describes the methods used for the preparation of a variety of thieno[2,3-b]pyridines starting from the known 4-chloro-5-ester 127. Displacement of the chlorine of 127 proceeded with thiols in the presence of potassium carbonate to provide 4-thioethers of general formula 128. Ester 127 was also hydrolyzed to the acid 129, which was converted to amides of general formula 130 by standard coupling conditions.

Scheme 33

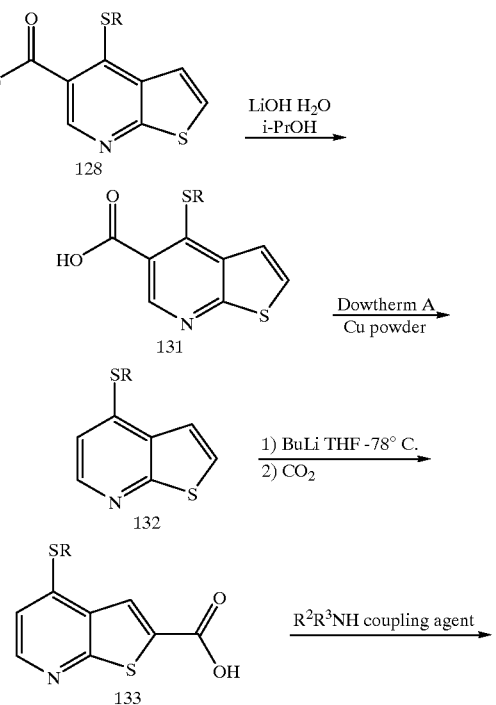

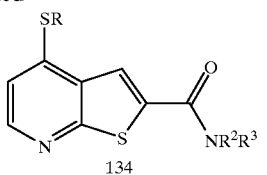

Scheme 33 shows the conversion of thioethers of general formula 128 to 2,4-disubstituted analogs. The corresponding acids of general formula 131 may be thermally decarboxylated to provide the 5-unsubstituted analogs of general formula 132. Compounds of general formula 132 were treated with strong base (for example, n-butyllithium), and reacted with carbon dioxide to provide the 2-carboxylic acids of general formula 133. The acids were then transformed into amides of general formula 134 by previously described procedures.

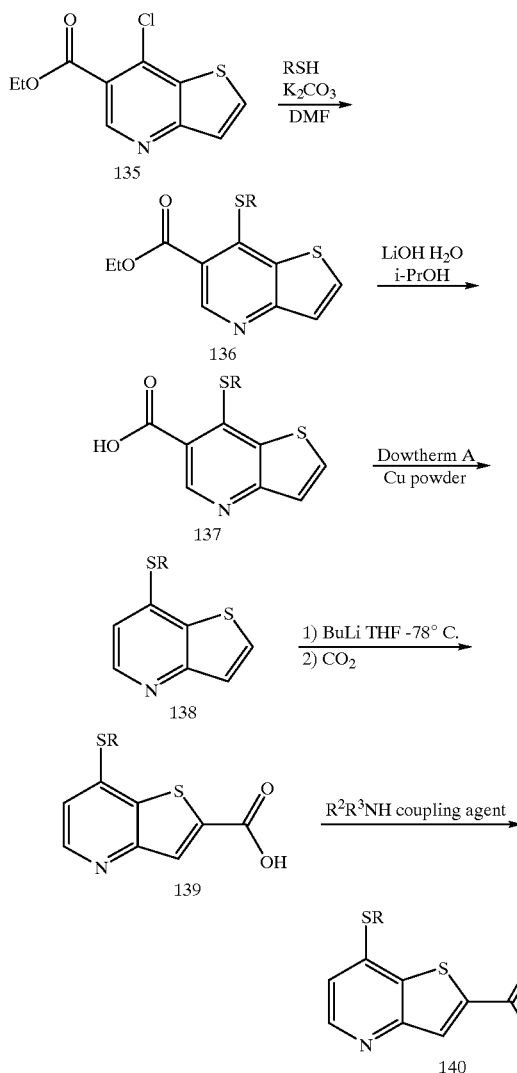

Scheme 34 illustrates the preparation of thieno[3,2-b] pyridines. Chloride 135 was transformed by a similar set of conditions to that described in Scheme 33 to produce acids of general formula 139 and amides of general formula 140.

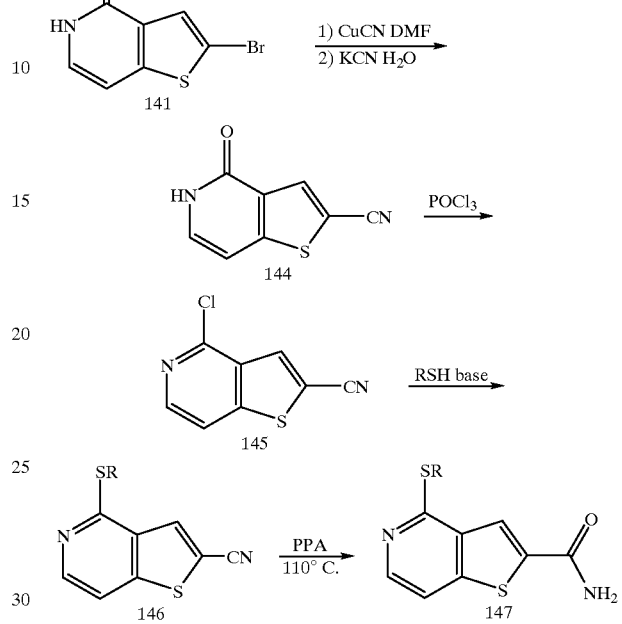

Scheme 35 depicts the preparation of thieno[3,2-c] pyridines. Starting with thienopyridone 141, 4-oxo-4,5-dihydrothieno[3,2-c]pyridine-2-nitrile 144 was prepared according to literature methods (Eloy, F.; Deryckere, A. Bul. Soc. Chim. Belg. 1970, 79, 301; Troxler, F.; Wiskott. E. U.S. Pat. No. 3,998,835). Treatment of thienopyridone 144 with phosphoryl chloride at 130° C. provided chloride 145, which upon exposure to thiols under basic conditions afforded thioethers of general formula 146. Hydrolysis of the nitrile group with polyphosphoric acid gave the corresponding amides of general formula 147.

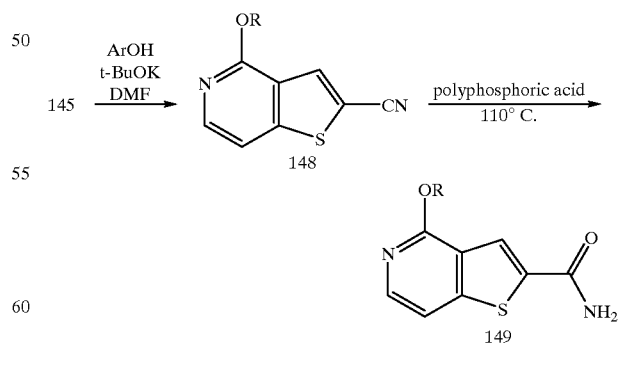

Scheme 36 show that ethers of general formula 149 were prepared in an analogous fashion as previously described in Scheme 35.

Scheme 37

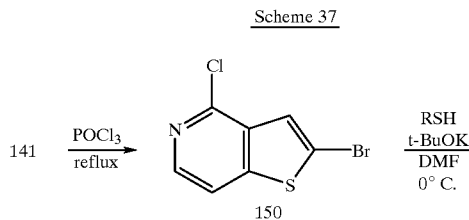

Scheme 37 shows the preparation of intermediates of general formula 151 useful for the preparation of alternative 2-derivatives. Treatment of the known 2-bromo-4-chlorothieno[3,2-c]pyridine 150 with 1 equivalent of a thiol afforded 2-bromothieno[3,2-c]pyridines of general formula 151.

Scheme 38

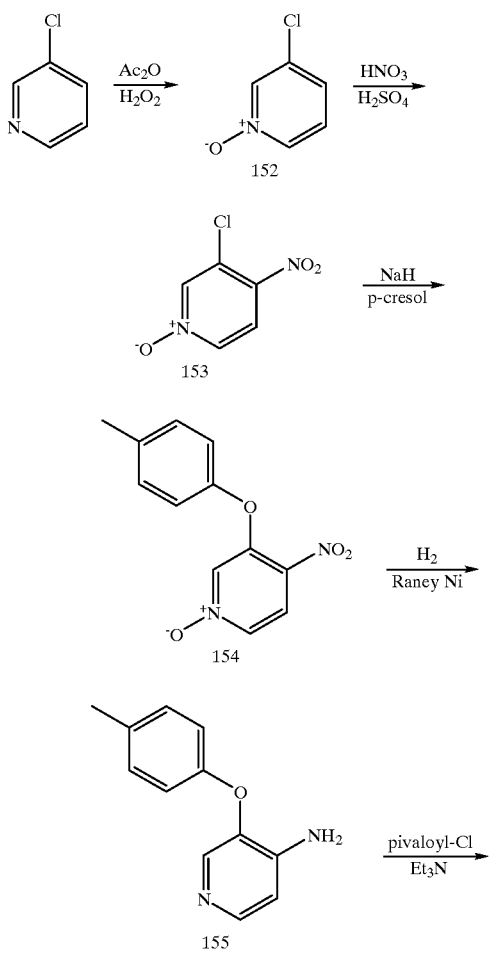

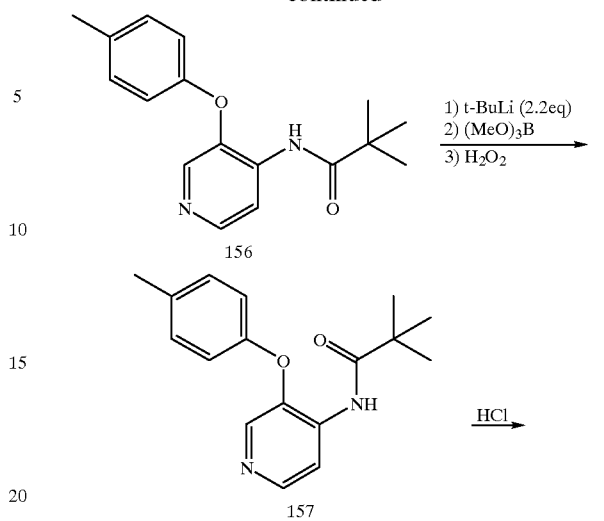

Scheme 38 depicts an example of the preparation of a related class of inhibitors based on an oxazolopyridine structure. Commercially available 3-chloropyridine is oxidized to the N-oxide 152 with peracetic acid, which is then nitrated in a mixture of concentrated nitric, concentrated sulfuric, and fuming sulfuric acids to give the 4-nitro derivative 153. The chlorine in 153 is then displaced with the sodium salt of p-cresol, and the resulting biaryl ether 154 is hydrogenated (Raney nickel catalysis) to reduce both the nitro functional group and the N-oxide to give 155. The amino group of 155 is protected with an N-trimethylacetyl group, and the 5-hydroxyl group is introduced according the procedure of Chu-Moyer and Berger (J. Org. Chem. 1995, 60, 5721) by formation of the dianion of 156, quenching with trimethyl borate, and oxidation of the intermediate boronate ester followed by hydrolysis with basic hydrogen peroxide to give hydroxypyridine 157. The amide is hydrolyzed with hydrochloric acid to give 158, which is condensed with methyl oxalyl chloride to give the oxazolopyridine 158. The methyl ester in 159 was then converted to the primary amide by treatment with ammonia in methanol to give the target compound 160.

other aryl, heterocyclic, or alkyl ethers. The dianion of 4-(N-trimethylacetyl)-amino-3-(4-methylphenoxy)-pyridine is quenched with tetramethylthiuram disulfide to introduce the 5-mercapto group into the substituted pyridine ring as dithiocarbamate 161. Subsequent deprotection of the amine under acidic conditions is followed by acylation of the free aniline 162 with methyl oxalyl chloride to afford the oxalamide 163. The thiazolopyridine bicyclic core 164 is then

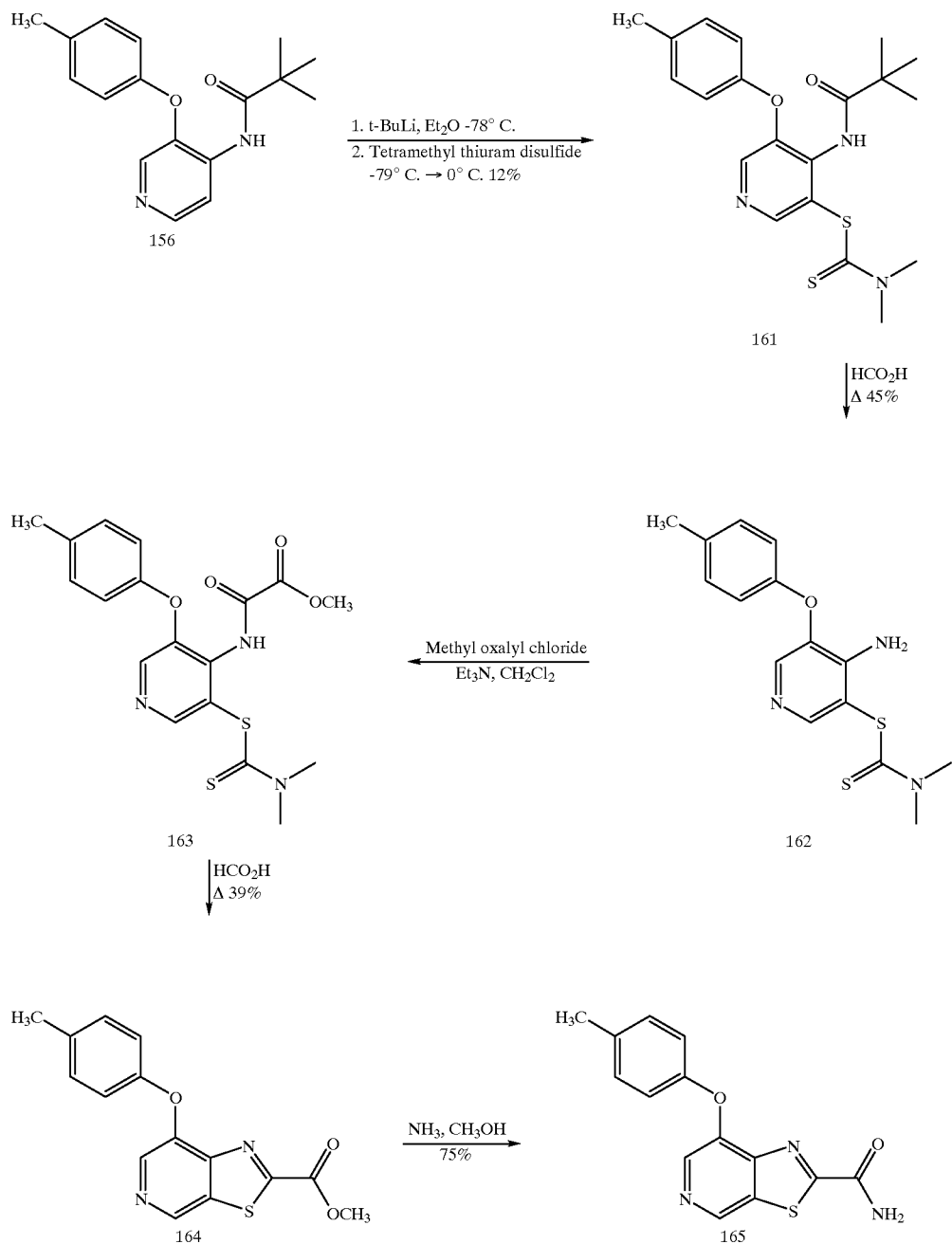

Scheme 39

Scheme 39 illustrates an example of the preparation of an analogous thiazolopyridine-based inhibitor. The scheme illustrates the use of para-cresol substituted pyridine as starting material, but the synthesis may be generalized to prepared by treatment with mild acid (for example formic acid at reflux). The ester functionality was converted to the corresponding amide 165 with a solution of an amine in methanol with warming.

Scheme 40

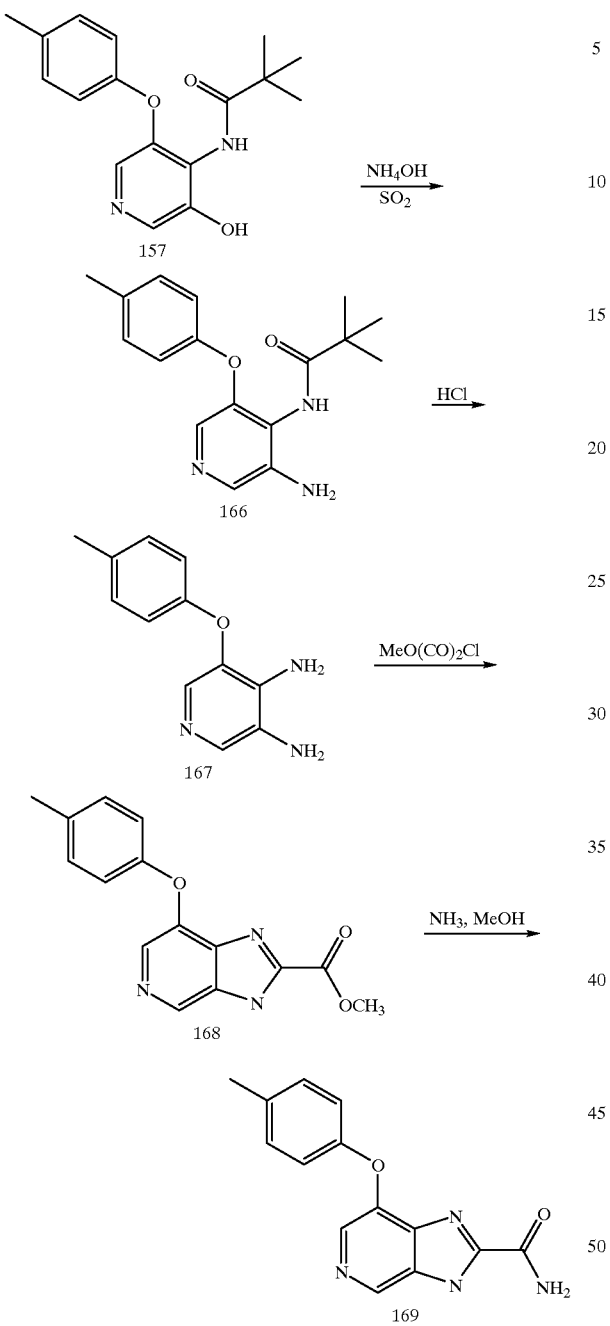

Scheme 41

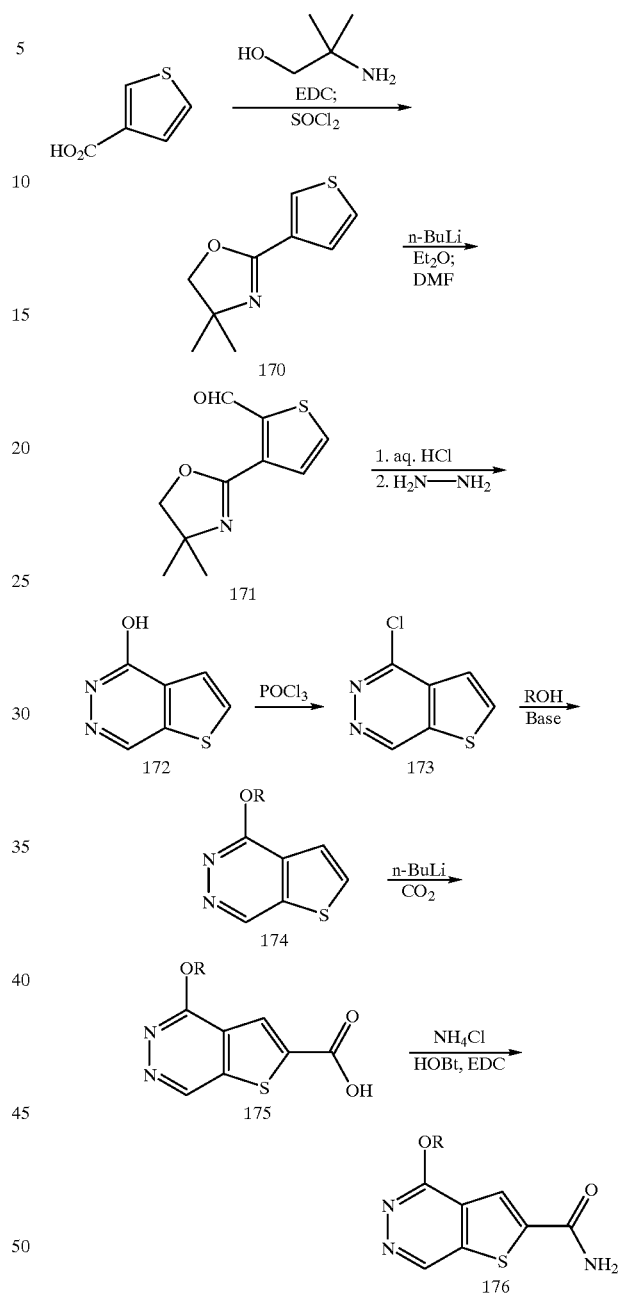

A related imidazopyridine class of compounds may be prepared from intermediates shown in Scheme 40. 5-Hydroxypyridine 157 may be converted to the corresponding aniline 166 by heating in ammonium hydroxide saturated with sulfur dioxide in a pressure vessel (Newman and Galt, J. Org. Chem. 1960, 25, 214). After removal of the pivaloyl group of 166 with hydrochloric acid, the resulting diaminopyridine 167 may be condensed with methyl oxalyl chloride to give the imidazopyridine 168. The ester functionality may then be converted to amide 169 by treatment with ammonia in methanol, as described previously.

Scheme 41 is an illustration of the preparation of thienopyridazine-containing inhibitors. The protected thiophene acid 170 was deprotonated with strong base (e.g. n-butyllithium), and reacted with a formylating reagent. The resultant oxazoline aldehyde 171 was hydrolyzed and cyclized with hydrazine to provide the hydroxy thienopyridazine 172. The hydroxy group was converted to the chloride 173 by the action of phosphorous oxychloride and subsequent substitution by alkoxides produced the ethers 174. The amide group is introduced in a manner analogous to that described above for the thienopyridines, providing amide 176.

Scheme 42

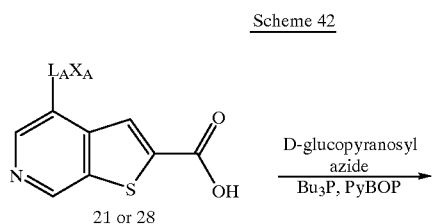

The syntheses of water-soluble glycosyl amide derivatives of general formula 178 are shown in Scheme 42. Tributylphosphine-mediated coupling of thienopyridine carboxylic acids of general formula 21 or 28 with 2,3,4,6-tetra-O-acetyl-D-glucopyranosyl aziide with assistance of PyBOP smoothly furnished the protected β-glycosyl amides of general formula 177. No other isomers were detected in the reaction. Cleavage of the acetyl groups with methyl amine provided compounds of general formula 178.

Scheme 43

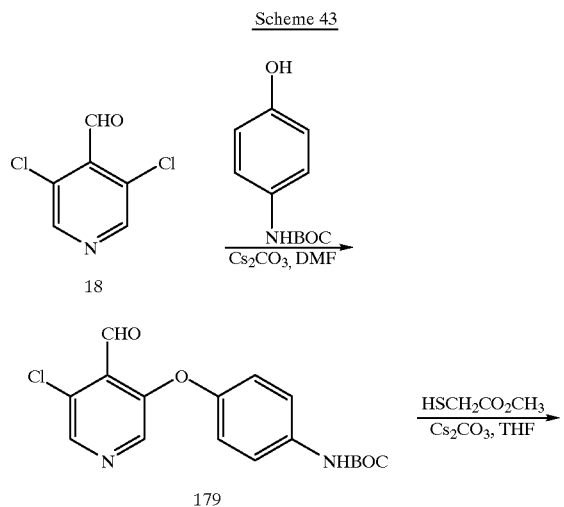

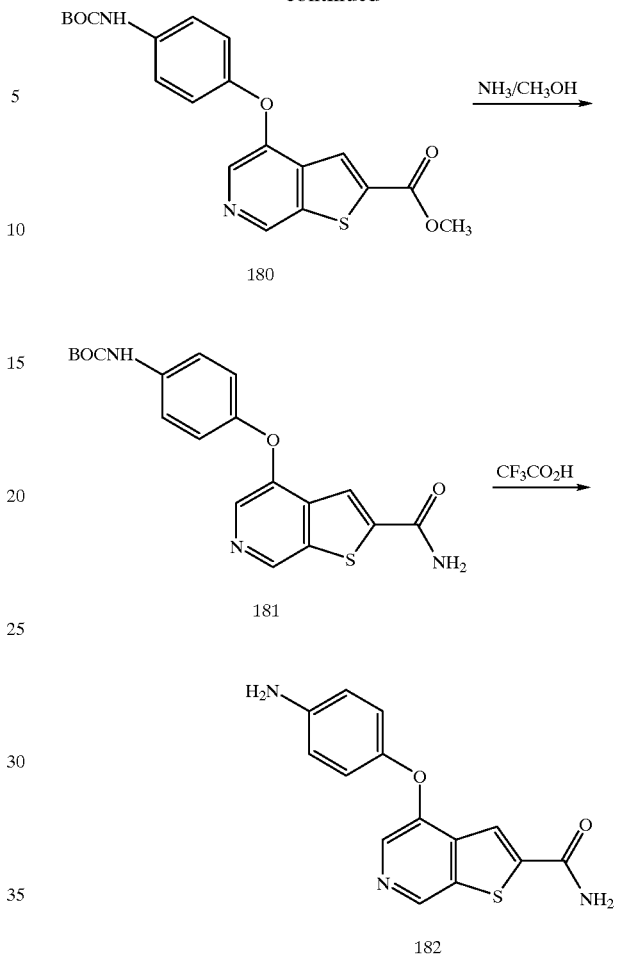

Scheme 43 outlines the preparation of 4-(4-aminophenoxy)thieno[2,3-c]pyridine-2-carboxamide using a modification of the route described in Scheme 7. A two step sequence was adopted for assembling the thienopyridine core in the synthesis of 182. Treatment of the dichloropyridine aldehyde with one equivalent of N-BOC-protected 4-hydroxyaniline afforded compound 179, which was cyclized to give ester 180. Transformation to the amide 181 followed the previously described procedure, and the Boc-group was removed by treatment with trifluoroacetic acid. It should be noted that aniline 182 also serves as starting material for Sandmeyer reactions via the diazonium salt, in which the amino group may be converted to a variety of functional groups, including halo, hydroxy, cyano, among other standard Sandmeyer products.

Scheme 44

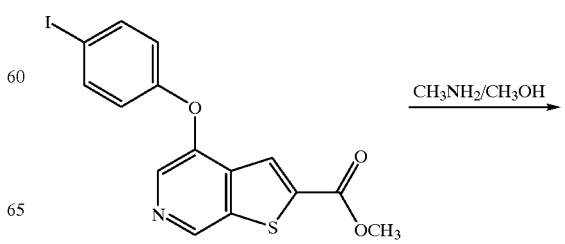

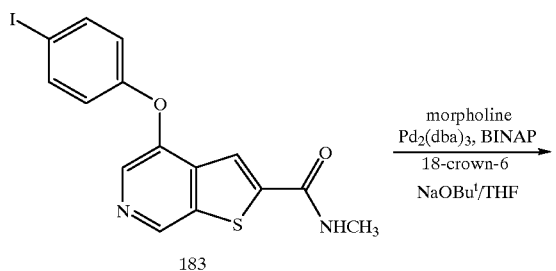

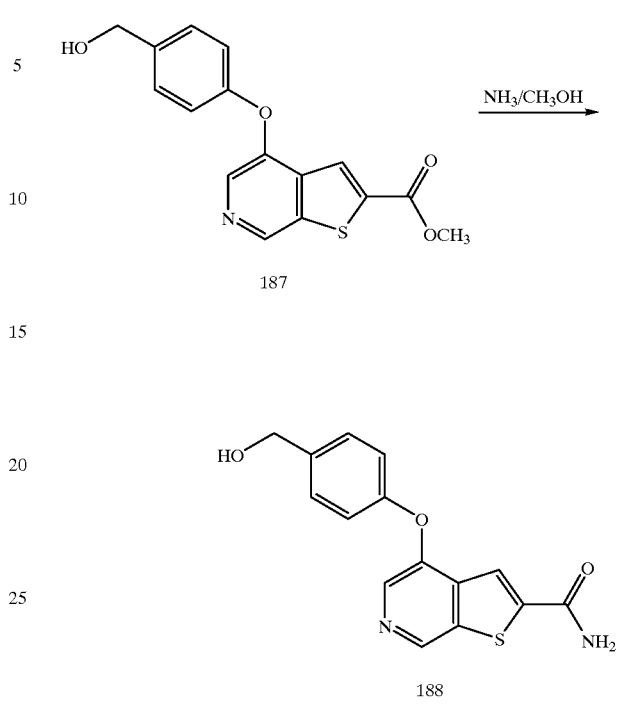

Scheme 44 exemplifies a general method for the preparation of 4-substituted aminophenoxythieno[2,3-c]pyridines using methodology described by Buchwald, et al. (Wolfe, John; Buchwald, Stephen L. J. Org. Chem. 1997, 62, 6066). Iodide 183, prepared by the previously described methods, was coupled with disubstituted amines (such as morpholine in the above example) in the presence of bis(dibenzylideneacetone)dipalladium and BINAP to provide the substituted aniline 184.

Scheme 45 describes the preparation of 4-(4-hydroxymethylphenyl)thieno[2,3-c]pyridine 188, utilizing a modification of the route shown in Scheme 7. Starting with mono-tritylated 4-hydroxybenzyl alcohol, condensation with dichloroaldehyde 18, followed by cyclization with methyl thioglycolate, provided protected benzyl alcohol 188. Standard transformations provided alcohol 188.

Scheme 45

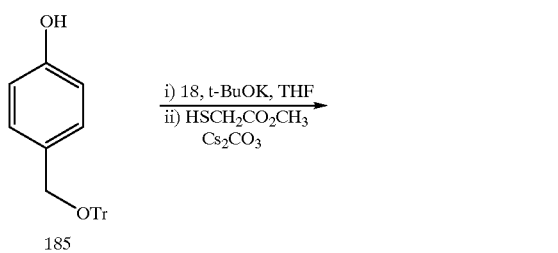

Scheme 46

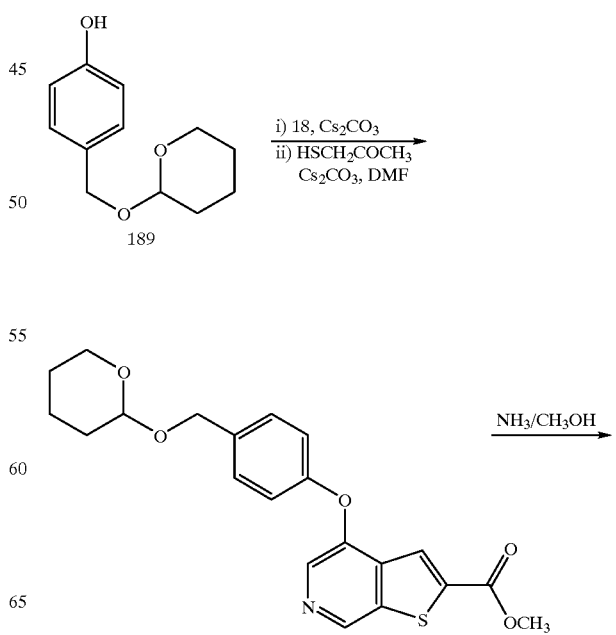

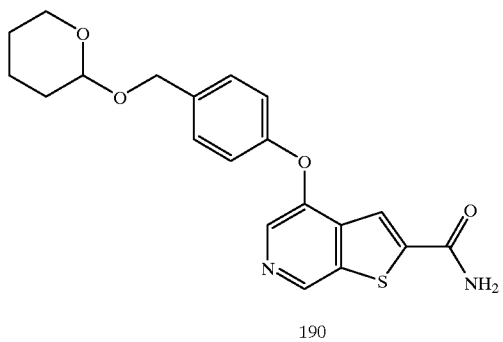

190

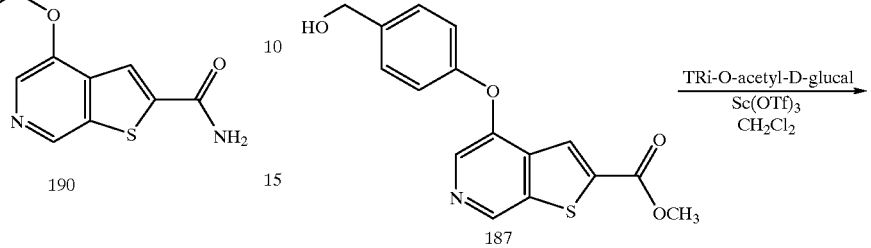

Scheme 46 describes the preparation of a protected benzyl alcohol 190, starting from mono-tetrahydropyran-protected hydroxybenzyl alcohol 189. Standard acid-catalyzed hydrolysis of the THP group can also yield the benzyl alcohol analog 188.

Scheme 47

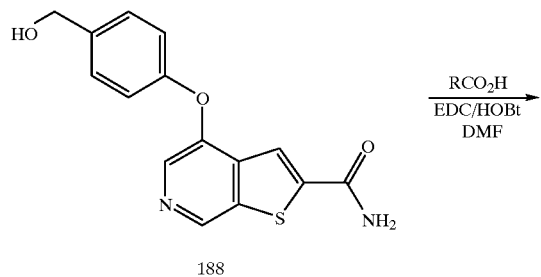

188

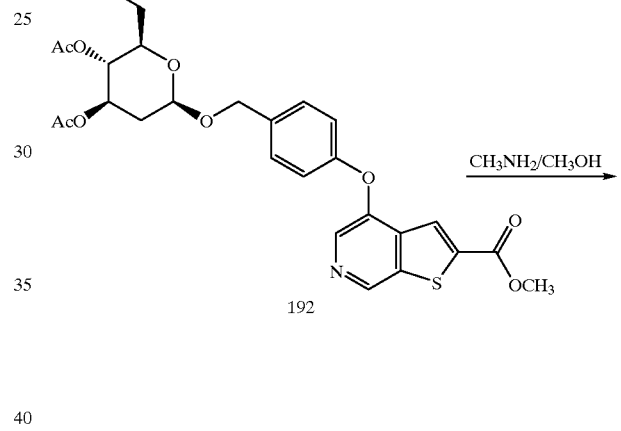

191

R = alkyl, heterocyclic, aryl

As shown in Scheme 47, benzyl alcohol 188 may be further derivatized to esters, using standard coupling procedures, for example by carbodiimide conditions shown above, or by use of acid chloride. In addition, the alcohol may be converted to carbamates (R=NH$_2$, mono or disubstituted amino) by treatment with isocyanates or carbamoyl chlorides.

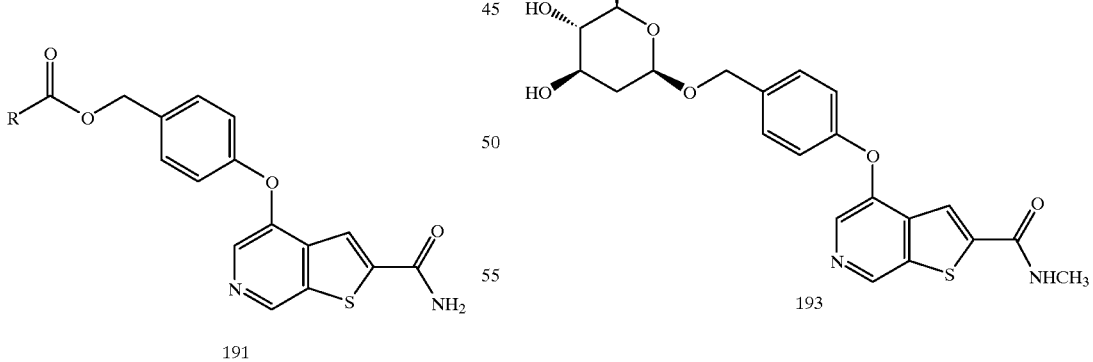

Glycosides of benzyl alcohol 187 may be produced using the procedure outlined in Scheme 48. Treatment of the alcohol 187 and tri-O-acetyl-D-glucal with stoichiometric scandium triflate afforded stereo-specifically protected glycoside 192, which was deprotected with methyl amine to give the free glycoside 193.

Scheme 49

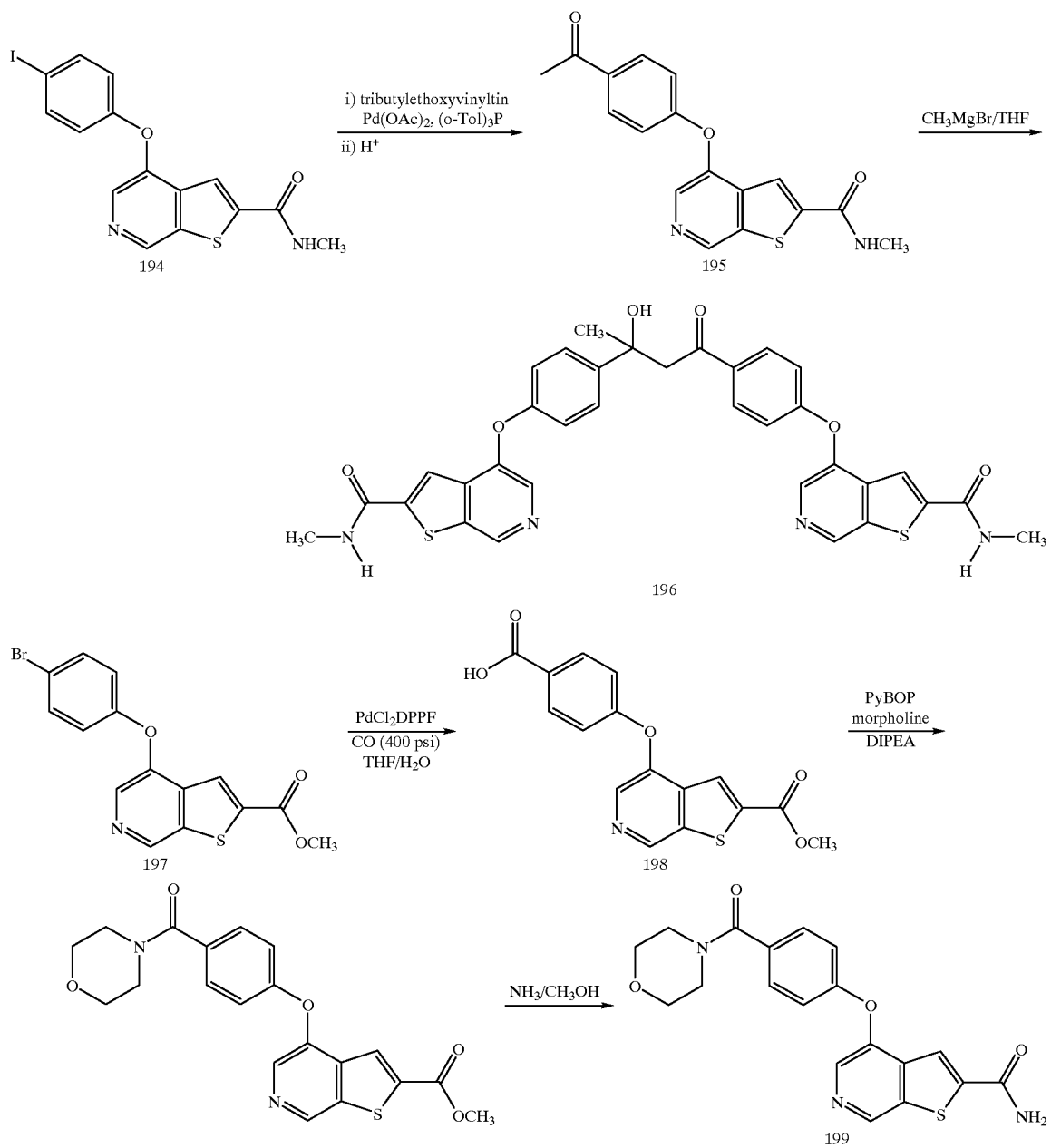

Stille coupling of iodophenyl derivative 194 (or the corresponding bromophenyl analogs) with tributylethoxyvinyltin allows for the introduction of an acetyl group onto the 4-position of the phenyl ether as shown in Scheme 49. The intermediate vinyl ether is hydrolyzed during the work up conditions, thus providing acetophenone derivative 195. Addition of methylmagnesium bromide to ketone 195 at −50° C. did not give the expected addition product, but rather aldol adduct 196 was isolated in 40% yield. The palladium catalyzed carbonylation of bromophenoxy methyl ester 197 in aqueous media afforded the acid 198 in modest yield. PyBOP- or EDC-mediated coupling with amines (illustrated above with morpholine), followed by amination of the 2-methyl ester, provided the diamides 199.

Scheme 50

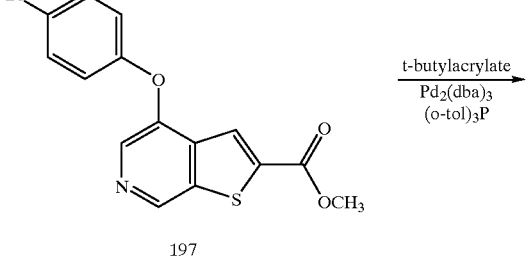

-continued

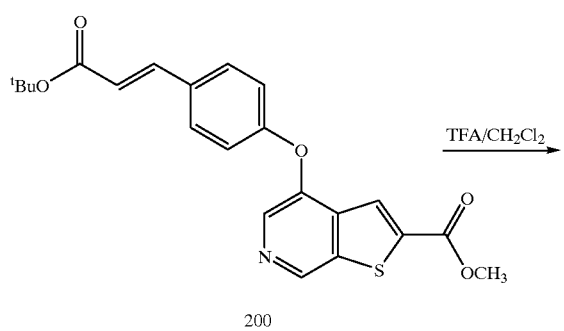

200

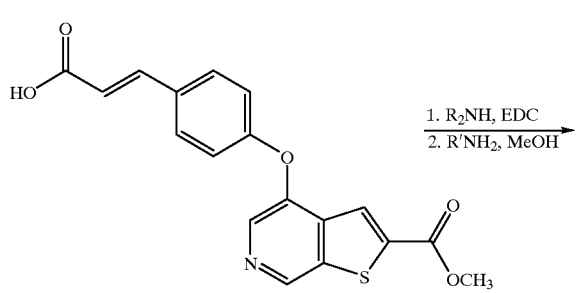

201

In Scheme 50 the preparation of cinnamide ethers is described. Heck reaction of the bromophenoxy methyl ester 197 with t-butyl acrylate using tritolylphosphine as ligand furnished cinnamate 200 in good yield. Hydrolysis of the t-butyl ester with trifluoroacetic acid, followed by PyBOP or EDC-mediated coupling with an amine, and then amination of the methyl ester, provided diamide 201.

Scheme 51

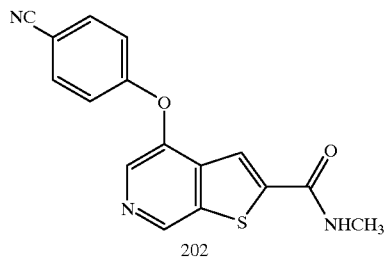

202

-continued

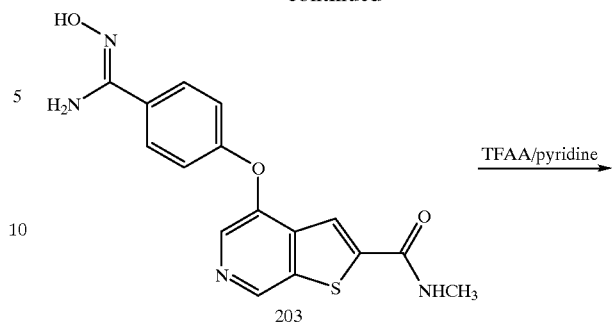

203

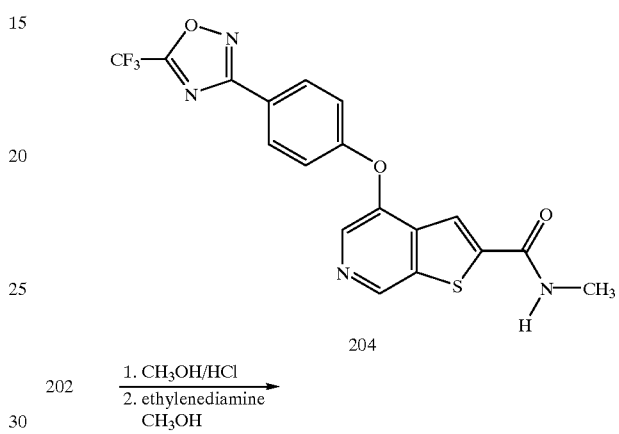

204

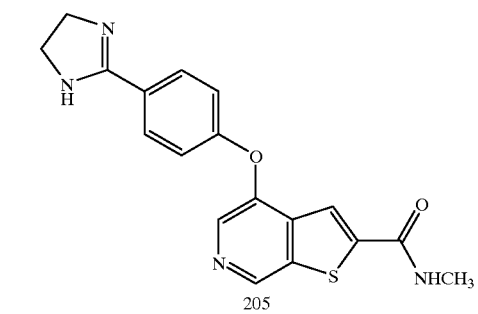

205

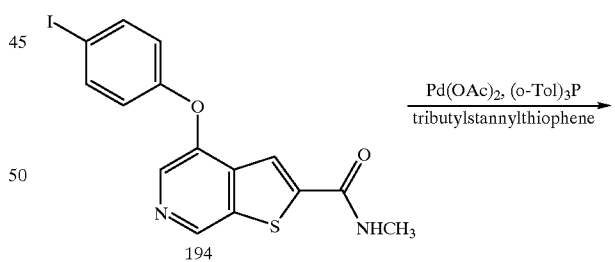

194

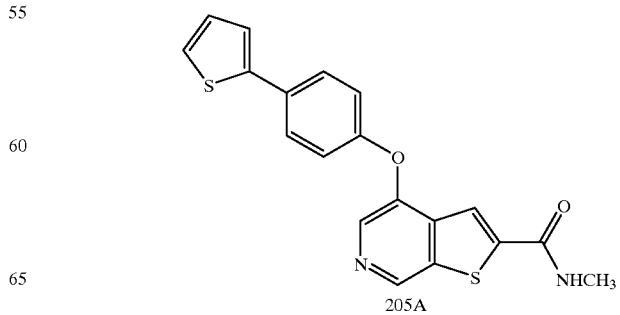

205A

Scheme 51 exemplifies the preparation of 4-heterocyclephenoxythienopyridines. Treatment of para-cyanophenyl derivative 202 with hydroxyamine in a mixture of DMF and ethanol smoothly gave hydroxyimidamide 203, which was heated with trifluoroacetic anhydride in pyridine to provide the oxadiazole 204. Cyano derivative 202 was transformed into imidazoline 205 under the conditions described above. Incorporation of other heterocycles was accomplished using known Stille, Suzuki, or Heck conditions as exemplified by the Stille coupling of iodo compound 194 and tributylstannylthiophene to provide compound 205A. The aryl coupling reactions described above may be applied to compounds with a variety of substituents at C-2 of the thienopyridine, in addition to the methyl amides exemplified in Scheme 51.

Scheme 52

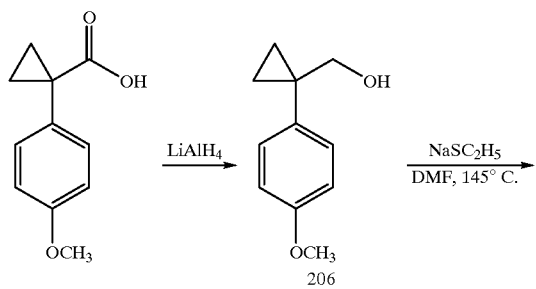

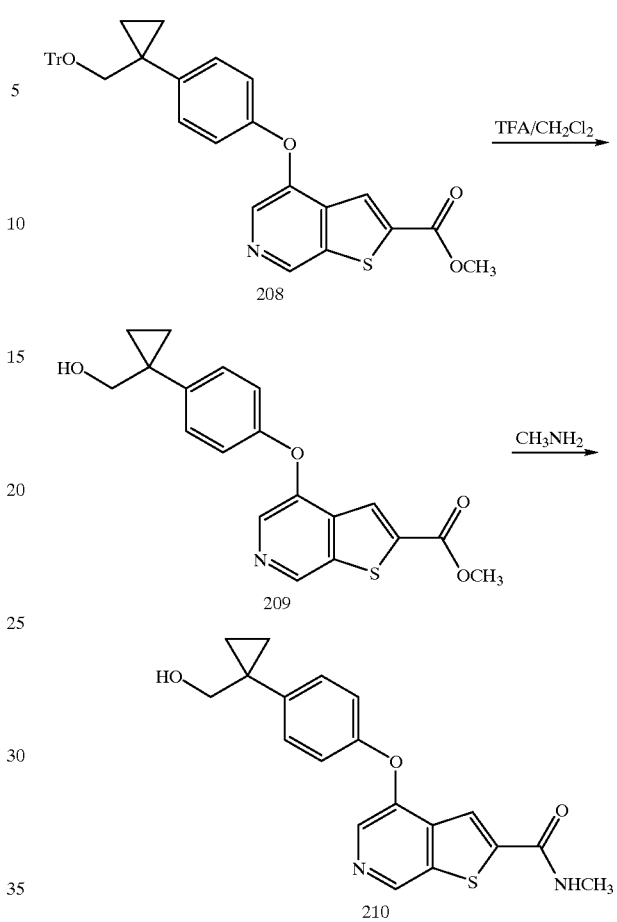

Cyclopropylcarbinyl alcohol derivatives of the 4-phenyl ethers may be prepared according to the procedure described in Schemes 52 and 53. Commercially available phenylcyclopropane carboxylic acid is converted to the corresponding alcohol 206 by LAH reduction, then demethylation and selective protection of the hydroxymethyl group affords phenol 207. Using the procedure of Scheme 7, phenol 207 was condensed with dichloroaldehyde 18 and then methyl thioglycolate, to produce thienopyridine 208. Standard transformations led to the desired compounds 209 and 210.

Scheme 53

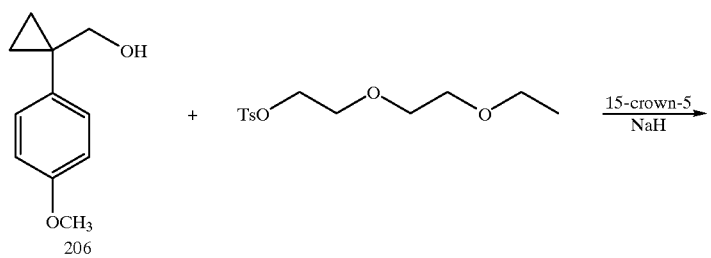

-continued
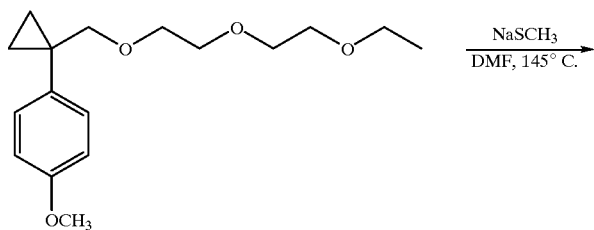
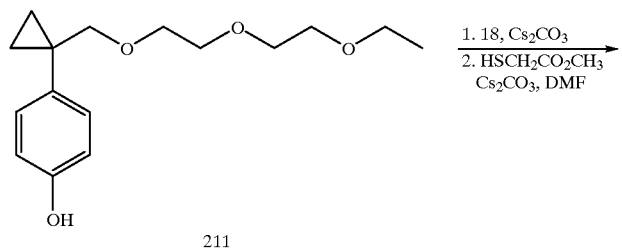
211
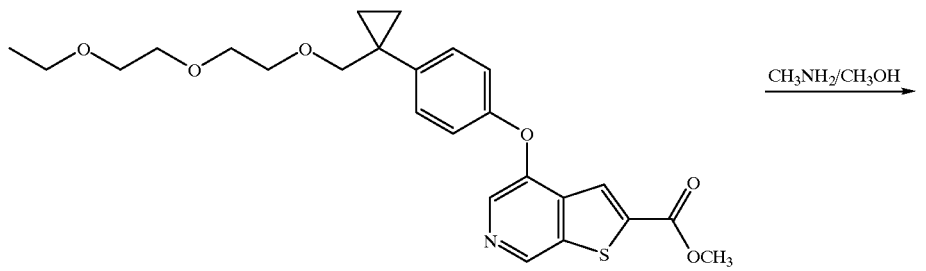
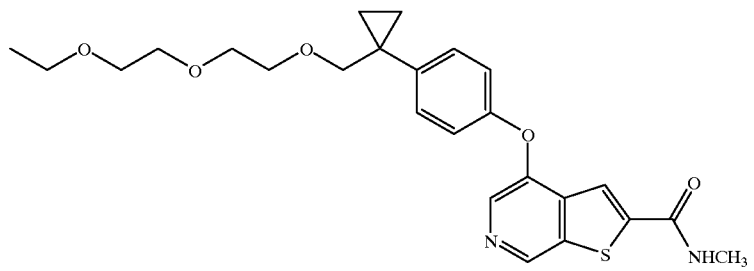
212
As shown in Scheme 53, alcohol 206 was alkylated to produce the polyether phenol 211 which was converted into cyclopropylcarbinyl polyether 212 using similar procedures described in Scheme 52. Such alkylation chemistry may be broadly applied by replacement of the diether tosylate shown with other alkyl halides or sulfonate esters.
Scheme 54
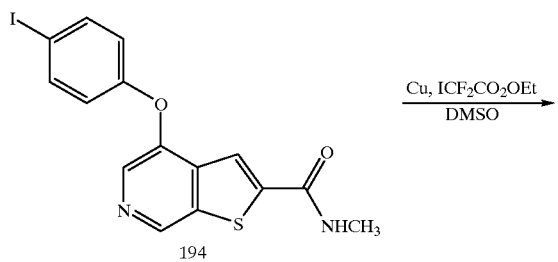
194

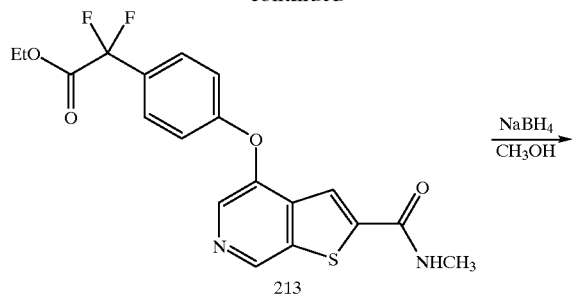

213

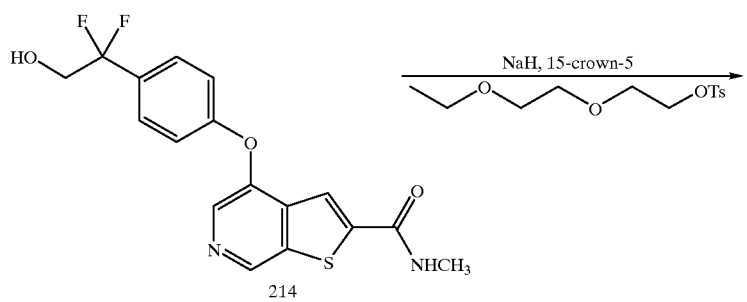

214

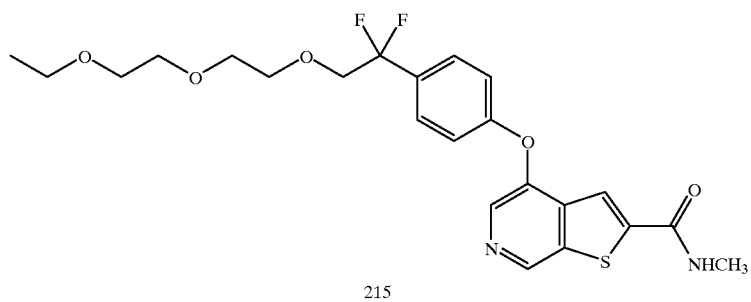

215

In Scheme 54, difluoroacetic acid derivative 213 was synthesized by a copper mediated coupling between iodide 194 and ethyl iododifluoroacetate in the presence of phenol, which was found to remarkably inhibit side reactions. Reduction of the ester 213 gave difluoroethyl alcohol 214. Alkylation of alcohol 214 with ethoxyethyl tosylate in the presence of sodium hydride and 15-crown-5 afforded polyether 215.

Scheme 55

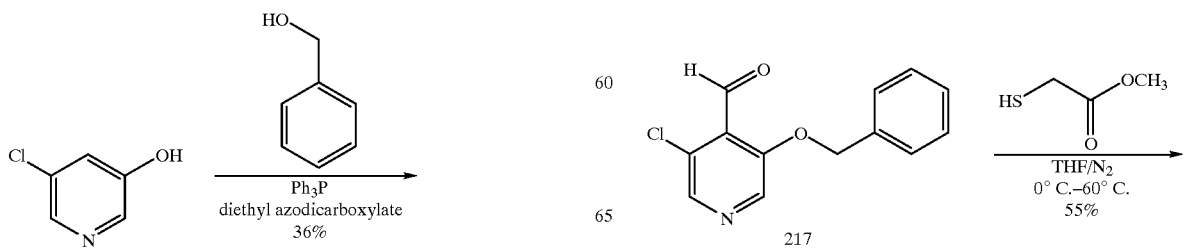

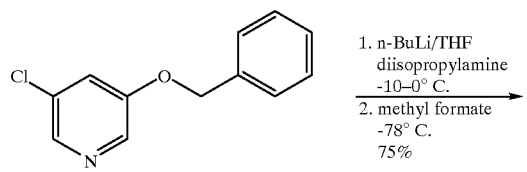

217

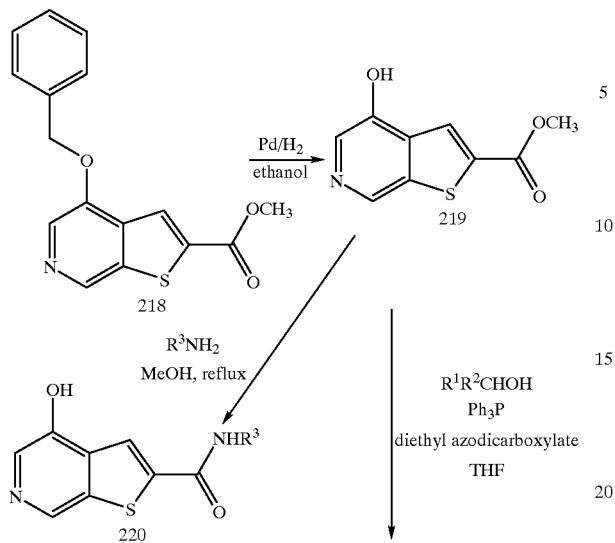

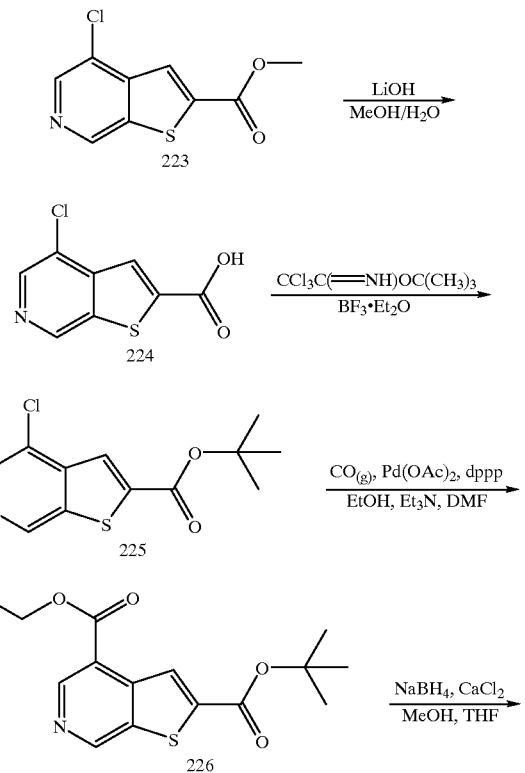

An alternative synthesis of 4-alkoxythieno[2,3-c] pyridines through a phenolic alkylation strategy is outlined in Scheme 55. Mitsunobu alkylation of 5-chloro-3-hydroxypyridine provided benzyl ether 216, which was deprotonated with alkyllithium base and the resulting anion was treated with methyl formate to produce the pyridine carboxaldehyde 217. Construction of the thienopyridine core is accomplished by condensation with methyl thioglycolate under previously described conditions, leading to ester 218. This method may be applied to other alkyl ethers analogous to 216 to provide a variety of 4-alkoxy derivatives related to 218. Esters 218 were then converted to other active derivatives such as amides using previously described procedures. Benzyl ether 218 was hydrogenolyzed to phenol 219, which was converted to the corresponding amide 220 by standard procedures. Phenol 219 also serves as a partner in Mitsunobu reactions with a variety of primary or secondary alcohols, to provide alkyl ethers of general formula 221 (Huang, F., et al. J. Med. Chem. 1998, 41, 4216–4223). Esters of general formula 221 were converted to amides of general formula 222 by treatment under the standard conditions of reflux with methanolic amine solutions.

Scheme 56

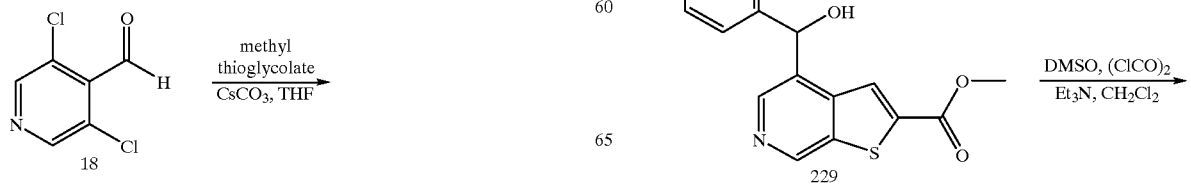

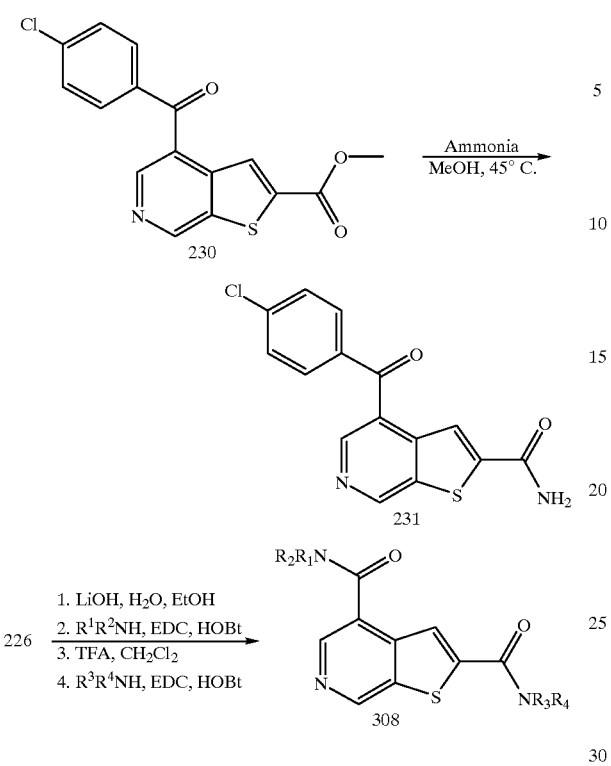

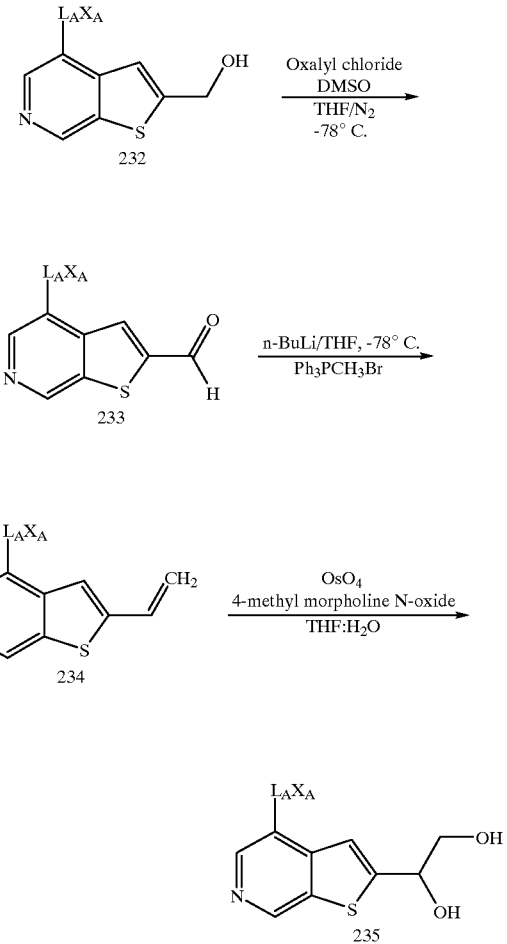

Thienopyridine analogs bearing a 4-carbonyl group may be prepared by the procedures described in Scheme 56. Dichloropyridine aldehyde 18 was treated with methyl thioglycolate under previously described conditions to produce the 4-chlorothienopyridine ester 223. Ester exchange was accomplished by base catalyzed hydrolysis to acid 224, and tert-butyl esterification to 225 was accomplished with O-t-butyl trichloroacetimidate under Lewis acid catalysis. Palladium-catalyzed carbethoxylation proceeded under previously described conditions to give diester 226. Reduction/oxidation reactions led to the aldehyde 227, which was then condensed with arylmagnesium halide reagents (exemplified above with 4-chlorophenyl magnesium chloride) to produce alcohol 228. The ester 228 may be transformed to various 2-substituted thienopyridine analogs directly, or oxidized to the corresponding 4-keto derivative 230. Standard transformation of ester 230 to amide 231 completes the synthesis. It should be noted that ester 226 may be selectively converted to amide derivatives by initial alkaline hydroysis of the ethyl ester, coupling to an amine, then acidic hydrolysis of the tert-butyl ester, and finally coupling to another amine to produce 308.

Scheme 57

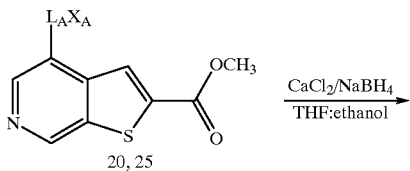

A variety of 2-substituted thieno[2,3-c]pyridines are accessible from 2-esters of general formula 20 and 25. Scheme 57 exemplifies products which may be obtained from hydroxymethyl derivatives of general formula 232. Calcium borohydride reduction of esters of general formula 20 or 25 provided alcohols of general formula 232. Swern oxidation cleanly provided aldehydes of general formula 233. This versatile intermediate may be converted to olefins by standard Wittig conditions, as exemplified by the preparation of 2-vinylthienopyridines of general formula 234 (Hibino, S. J. Org. Chem. 1984, 49, 5006–5008). Additional modification to dihydroxyethyl compound 235 was accomplished through the use of catalytic osmium tetroxide with 4-methylmorpholine N-oxide as stoichiometric oxidant.

Scheme 58

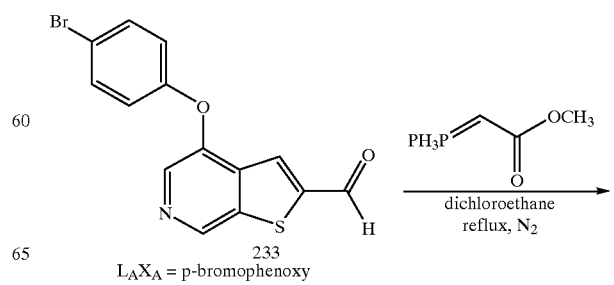

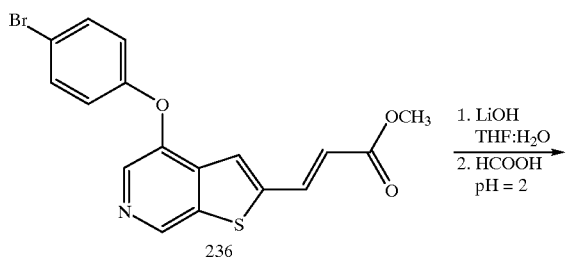

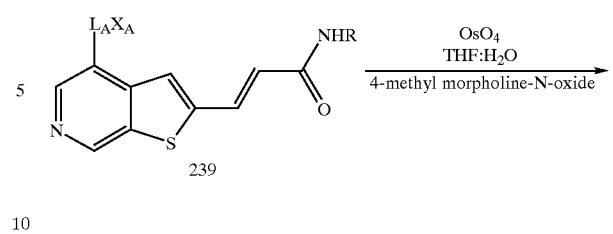

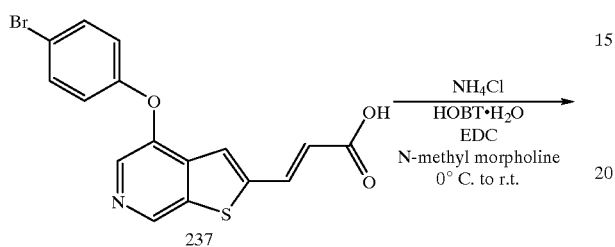

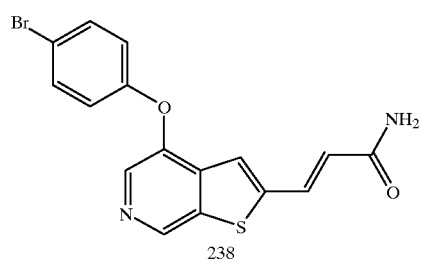

Scheme 58 illustrates the conversion of aldehyde 233 to the acrylate 236, which was accomplished by Horner-Emmons condensation with trimethyl phosphonoacetate (Jung, M. E. and Kiankarami, M. J. Org. Chem. 1998, 63, 2968–2974). The described methods may be extended to analogs bearing a wide variety of C-4 substituents, including aryloxy, alkoxy, arylamino, aryl, alkyl. The derived ester 236 was then subjected to hydrolysis to provide acid 237. Carboxylic acid 237 was subjected to standard coupling conditions to produce amide 238. The derived acrylates of general formula 239 may be oxidized to the corresponding diols of general formula 240 with catalytic osmium tetroxide in the presence of 4-methylmorpholine-N-oxide.

Scheme 59

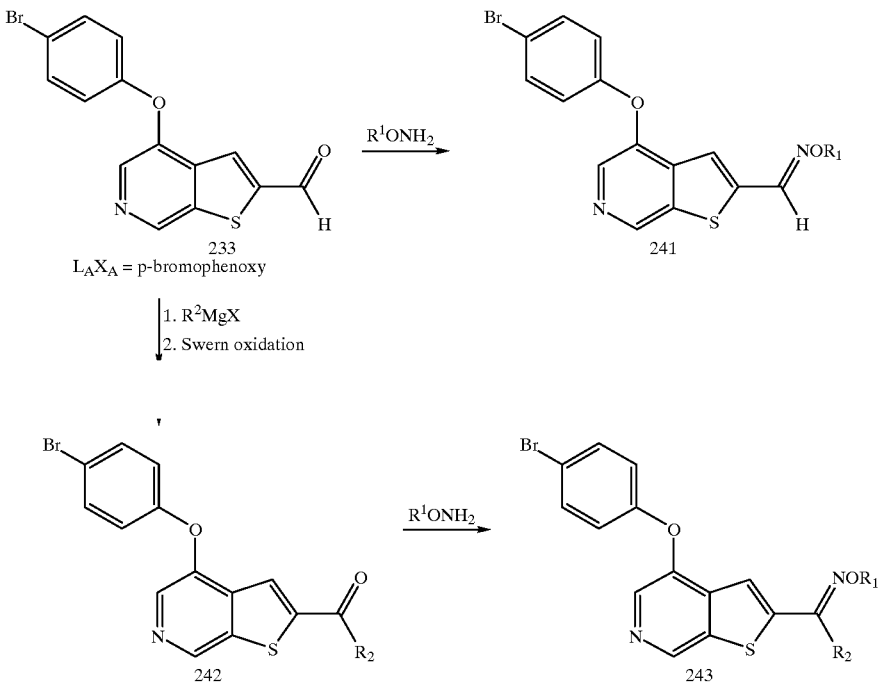

Sheme 59 illustrates the use of aldehyde 233, with $L_AX_A$= aryloxy, as starting material for the preparation of oxime derivatives of general formula 241. The strategy outlined is generally applicable to analogs with a variety of $L_AX_A$ substituents. Aldehydes of general formula 233 were also reacted with organomagnesium (or organolithium) reagents to produce secondary alcohols which were oxidized to the corresponding ketones of general formula 242. Oxidation is preferably accomplished by standard Swern conditions (DMSO and oxalyl chloride in $CH_2Cl_2$ solution at low temperature, followed by treatment with tertiary amines such as ethyldiisopropyl amine), but other conditions (tetra-n-propyl perruthenate, manganese dioxide) may be employed. The ketones were then converted to oximes of general formula 243 by previously described methods.

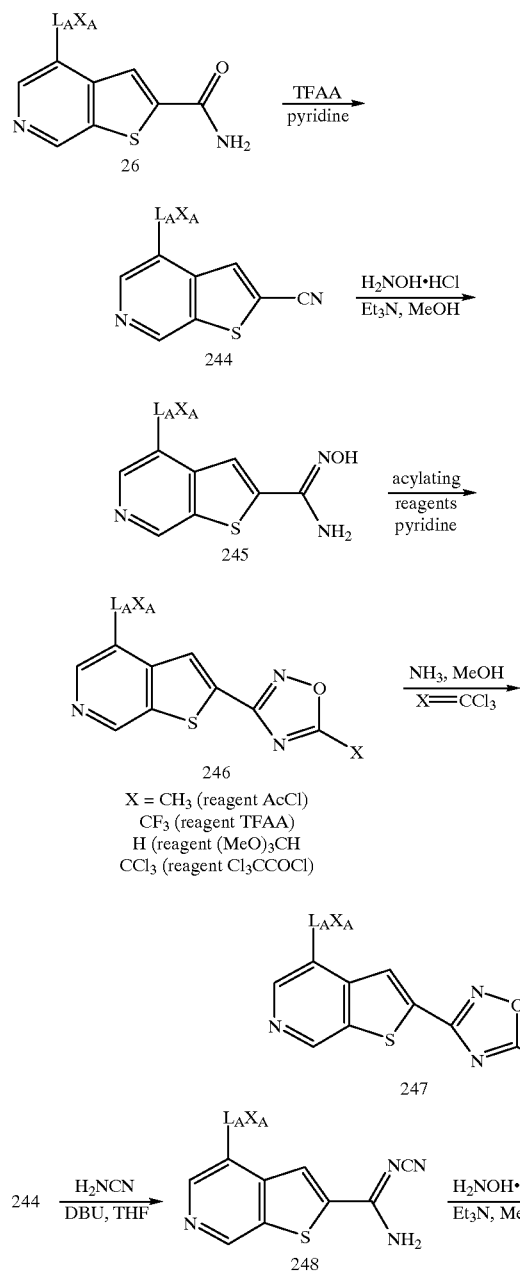

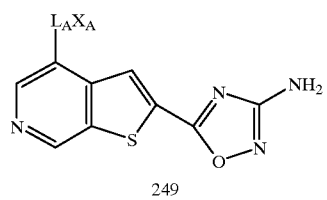

The preparation of 2-heterocyclic thienopyridines of general formula 249 is illustrated in Scheme 60. Primary amides of general formula 26 were treated with excess trifluoroacetic anhydride in pyridine to smoothly produce nitriles of general formula 244, which serves as a convenient intermediate for the preparation of amidine and azole derivatives. Thus, nitriles of general formula 244 were converted to the amidoximes of general formula 245 by treatment with hydroxylamine hydrochloride and triethylamine. Reaction of amidoximes of general formula 245 with acetyl chloride, trifluoroacetic anhydride, triethylorthoformate or trichloroacetyl chloride in pyridine produced the oxadiazoles of general formula 246 with variations in X dictated by the choice of acylating/dehydrating reagent. The trichloromethyl oxadiazoles of general formula 246 ($X=CCl_3$) were converted to the 5-amino-1,2,4-oxadiazoles of general formula 247 by heating with ammonia in a sealed tube. Nitriles of general formula 244 were also converted to cyanoamidines of general formula 248 when subjected to excess cyanamide in THF with DBU as the base. The 3-amino-1,2,4-oxadiazoles of general formula 249 were then generated by treatment of cyanoamidines of general formula 248 with hydroxylamine hydrochloride and triethyamine in methanol.

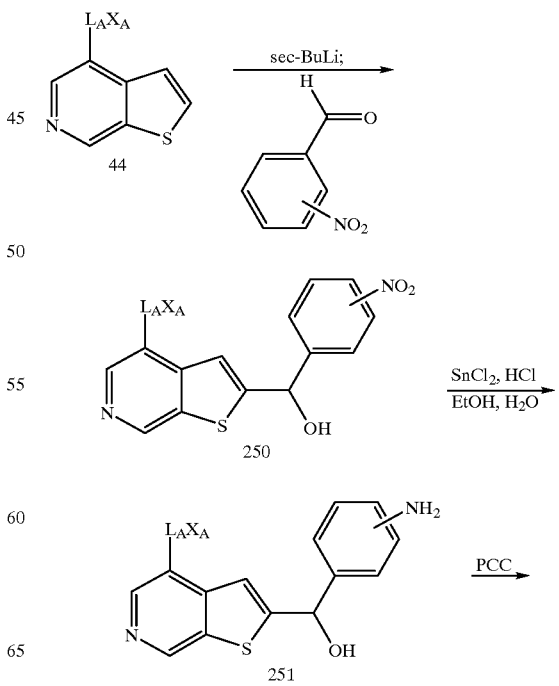

-continued

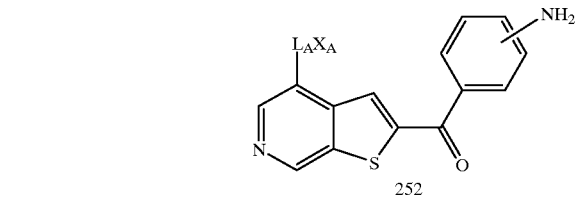

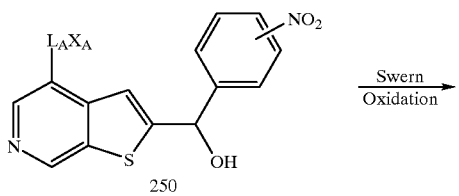

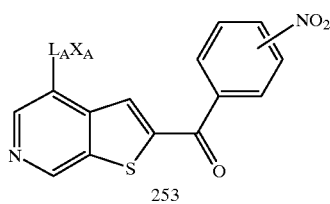

Scheme 61 depicts the preparation of 2-arylcarbonylthienopyridines. Thienopyridines of general formula 44 were deprotonated with alkyllithium base and condensed with nitrobenzaldehdyes to produce the benzyl alcohols of general formula 250. Tin(II)-induced reduction of the nitrophenyls to the anilines of general formula 251 were followed by selective alcohol oxidation with pyridinium chlorochromate. The nitro benzyl alcohols of general formula 250 were also converted to the corresponding ketones of general formula 253 under Swern conditions (for example, oxalyl chloride/DMSO/CH$_2$Cl$_2$ at low temperature, followed by treatment with amine bases).

Scheme 62 depicts the preparation of 2-carbamatethienopyridines and 2-ureathienopyridines. Alcohols of general formula 232 were converted to the amines of general formula 254 by Mitsunobu reaction with phthalimide, followed by deprotection with hydrazine. The amines of general formula 254 were converted to the corresponding ureas of general formula 255 by reaction with potassium isocyanate under acidic conditions. Similarly, the alcohols of general formula 232 were converted to the corresponding carbamates of general formula 256. This chemistry is generally applicable to the use of substituted isocyanates or carbamoyl chlorides, leading to mono or disubstituted carbamates or ureas.

Scheme 63

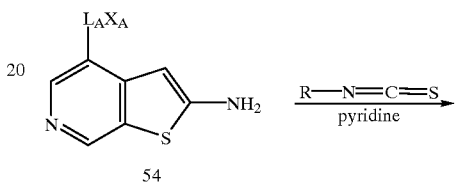

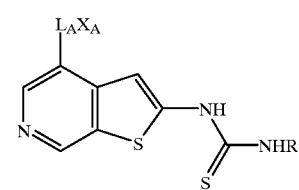

Scheme 63 illustrates the preparation of 2-thioureathienopyridines, starting from 2-aminothienpyridines of general formula 54. Reaction of 54 with substituted isothiocyanates in pyridine at reflux provided the thioureas of general formula 257.

Scheme 62

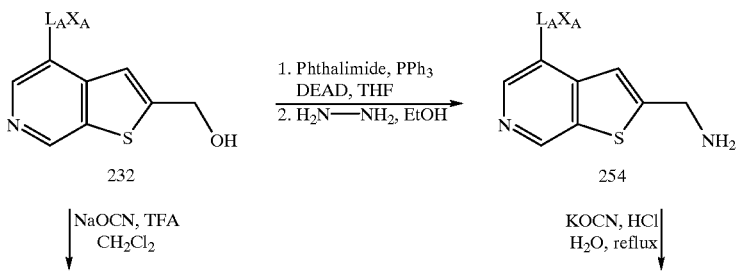

Scheme 64

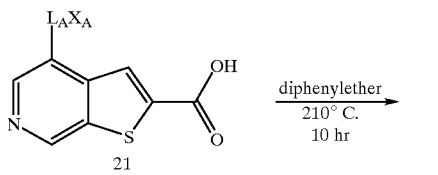

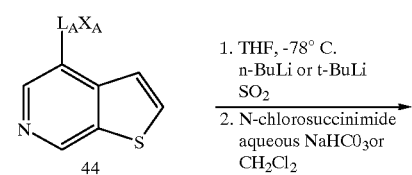

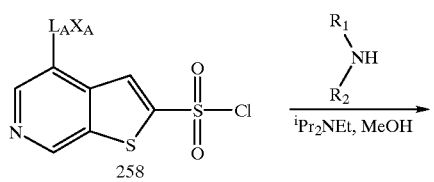

Scheme 65

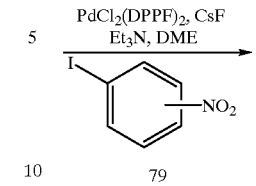

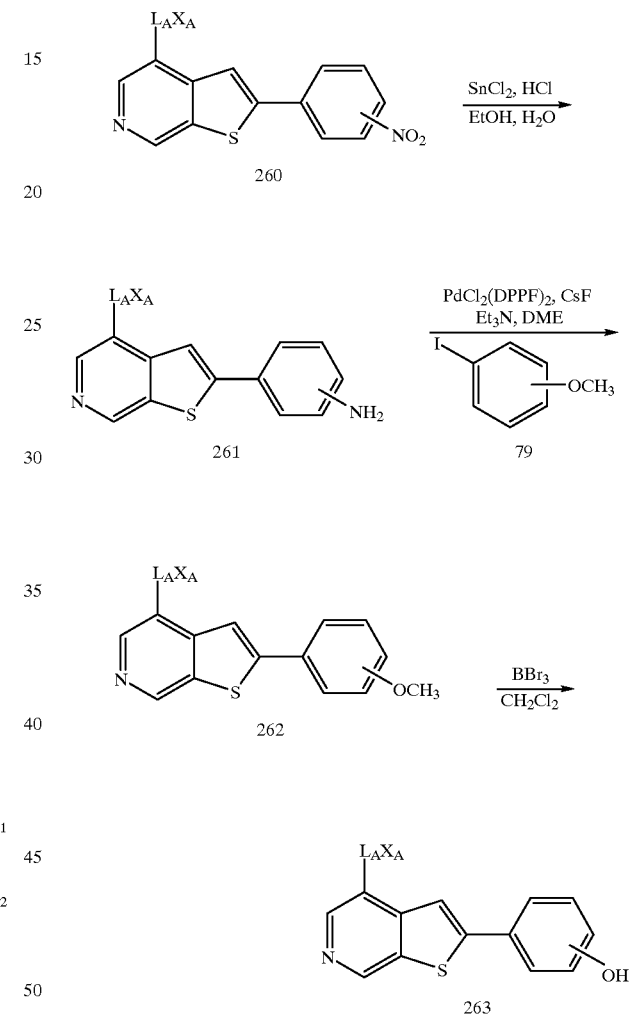

Scheme 64 exemplifies the synthesis of sulfonamides at the 2-position of the thienopyridines. An improved procedure for decarboxylation of thienopyridine-2-carboxylic acids is shown, wherein acids of general formula 21 were heated in diphenylether at 210° C. to provide thienopyridines of general formula 44 in high yield. Compounds 44 were deprotonated with strong base, then treated with sulfur dioxide to produce intermediate sulfinic acids. Addition of N-chlorosuccinimide produced sulfonyl chlorides of general formula 258, from which a variety of sulfonamides of general formula 259 were prepared by reaction with ammonia, primary or secondary amines in the presence of diisopropylethylamine in protic solvents such as methanol (Prugh, J. D., et al. J. Med. Chem. 1991, 34, 1805–1818; Davidsen, S. K., et al. J. Med. Chem. 1998, 41, 74–95).

Scheme 65 provides the outline of the synthesis of additional 2-arylthienopyridines with amino or hydroxy groups on the aryl ring. Using the method of Scheme 24, Suzuki coupling of boronic acids of general formula 79 with nitro-substituted aryl iodides produced biaryls of general formula 260. Biaryls of general formula 260 were reduced to the aminophenyl derivatives of general formula 261 with tin(II) chloride. Methyl ethers of general formula 262 were prepared from boronic acids 79 by coupling with methoxy iodobenzenes, and were converted to the hydroxy derivatives of general formula 263 through the use of boron tribromide to demethylate the methyl ethers.

Scheme 66

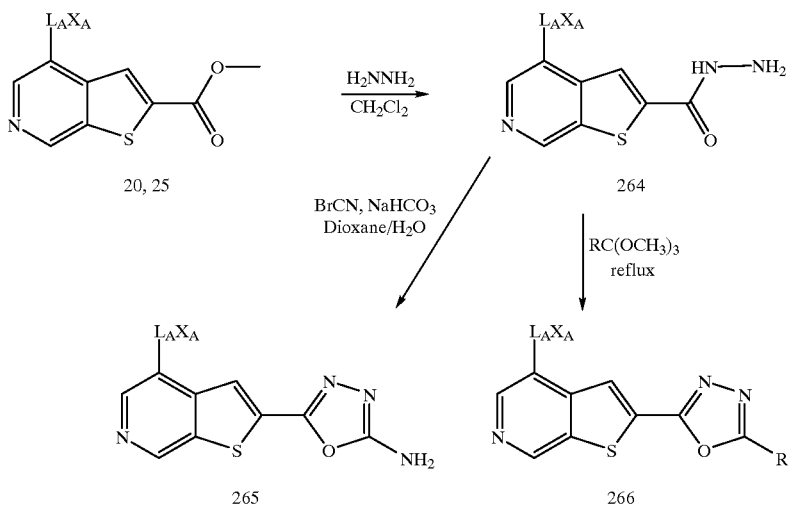

Schemes 66–71 illustrate syntheses for additional 5-membered heterocycles at the 2-position of the thienopyridines. Scheme 66 outlines a method for producing 1,3,4-oxadiazoles. Hydrazides of general formula 264 were prepared by treating esters of general formula 20 or 25 with hydrazine in methylene chloride. The hydrazides were converted to 5-amino-1,3,4-oxadiazoles of general formula 265 by reaction with cyanogen bromide. Hydrazides of general formula 264 may be converted to 5-unsubstituted or 5-alkyl-substituted-1,3,4-oxadiazoles of general formula 266 by condensation with orthoesters under reflux conditions.

Scheme 67

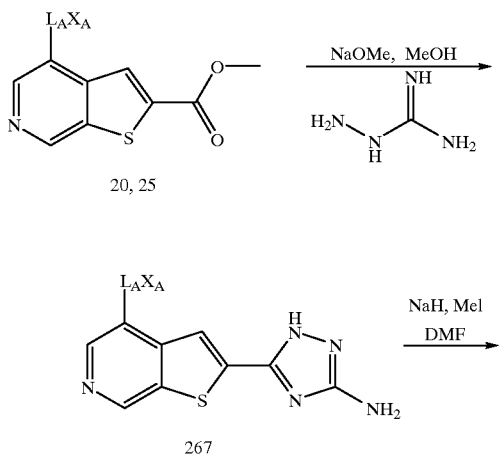

Scheme 67 indicates a method of preparing 1,3,4-triazoles from methyl esters of general formula 20 or 25. Condensation with aminoguanidine under basic conditions (for example sodium methoxide in methanol) produced the 2-amino-1,3,4-triazoles of general formula 267. Nonspecific methylation was performed on 1,3,4 triazoles of general formula 267 using sodium hydride and methyl iodide, which provided mono-methyl triazoles of general formula 268, dimethyl triazoles of general formula 269, and trimethyl triazoles of general formula 270, which were chromatographically separable.

Scheme 68

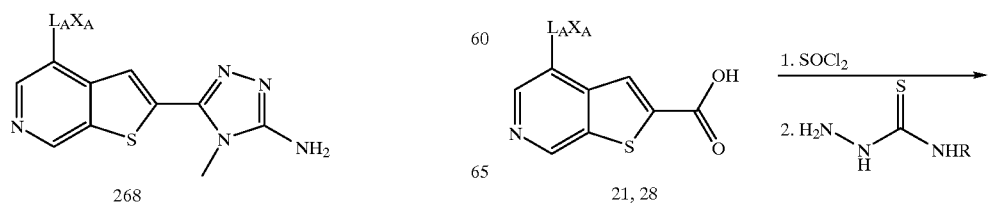

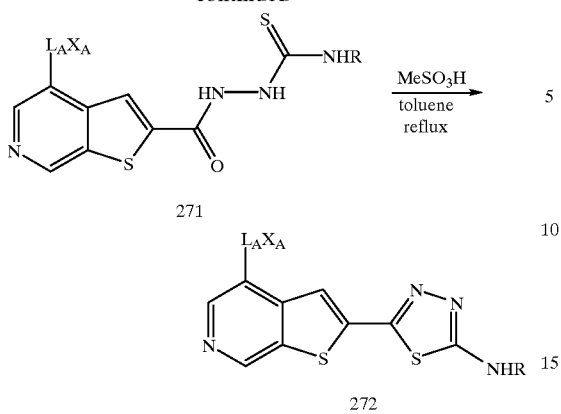

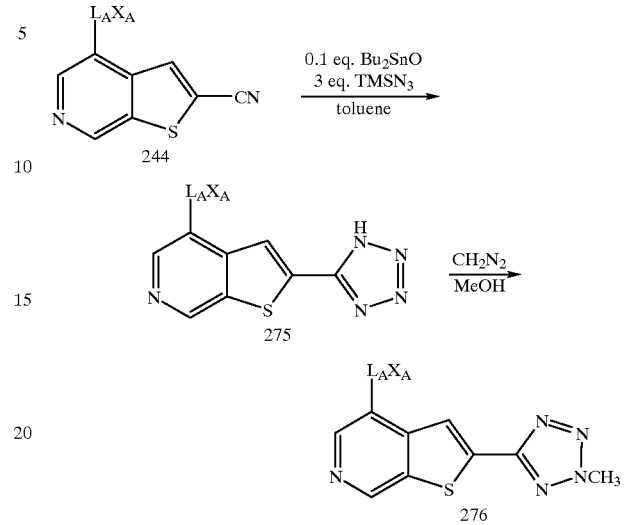

Scheme 68 indicates a method for the preparation of 1,3,4-thiadiazoles of general formula 272. The acid chlorides derived from acids of general formula 21 or 28 were reacted with thiosemicarbazide or substituted thiosemicarbazides to give intermediate acylated thiosemicarbazides of general formula 271, which were cyclized under acid catalysis (for example methanesulfonic acid in refluxing toluene) to provide thiadiazoles of general formula 272.

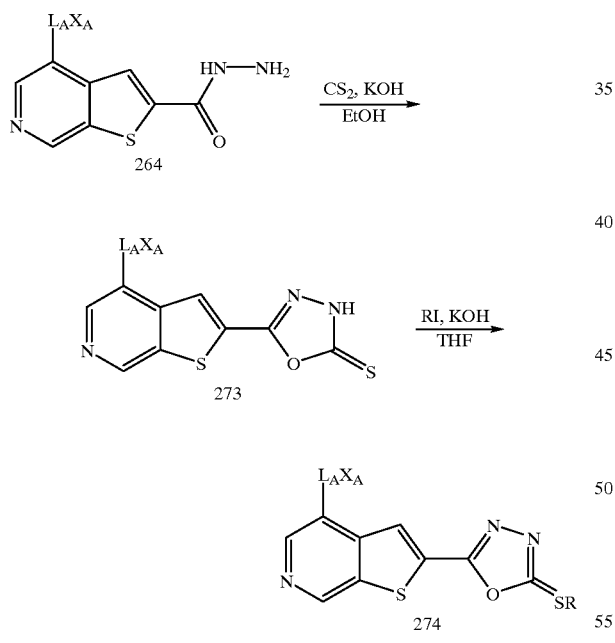

Scheme 70 shows the preparation of tetrazoles at the 2-position of thienopyridines. 2-Cyano derivatives of general formula 244 were converted to tetrazoles of general formula 275 using trimethylsilyl azide in the presence of catalytic dibutyltin oxide. The tetrazoles were converted to the N-methyl derivatives of general formula 276 by use of a solution of diazomethane in methanol.

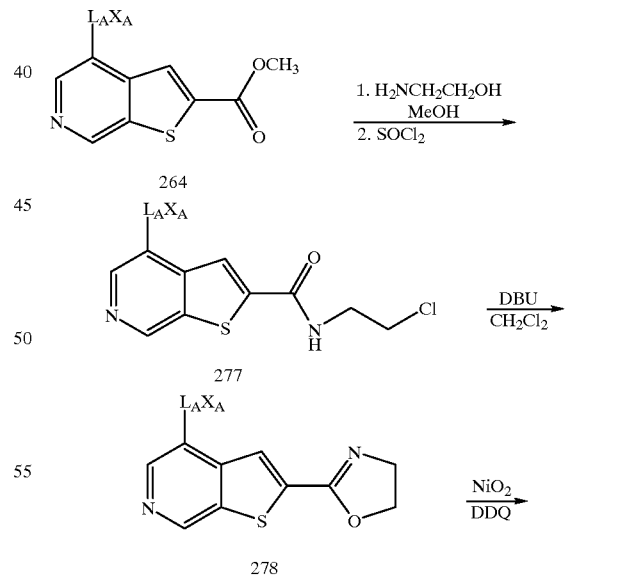

Scheme 69 provides a method for the preparation of 1,3,4-oxadiazol-2-thiones and the derived alkylthio-substituted oxadiazoles of general formula 274. Hydrazides of general formula 264 were treated with carbon disulfide in potassium hydroxide in aqueous ethanol solution to give the cyclic thiocarbamates of general formula 273. The thiocarbonyl group was alkylated in low yield with alkyl halides to give the alkylthio 1,3,4-oxadiazoles of general formula 274.

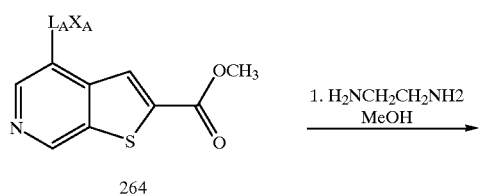

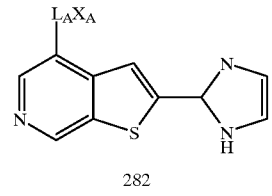

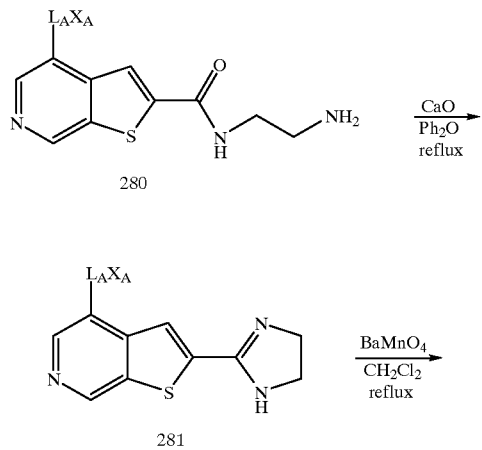

Scheme 71 illustrates the syntheses of 2-oxazole and 2-imidazole thienopyridines. Chloroethyl amides of general formula 277 were prepared by chlorination of the corresponding hydroxyethyl amides and then cyclized to oxazolines of general formula 278 under basic catalysis (for example, diazabicycloundecane in dichloromethane). The oxazolines of general formula 278 may be converted to the oxazoles of general formula 278 by dehydrogenation according to the procedure of Meyers (Meyers, A. I., et al. J. Amer. Chem. Soc. 1975, 97, 7383). Aminoethyl amides of general formula 280 were cyclized to the imidazolines of general formula 281 by treatment with calcium oxide at high temperature in diphenyl ether. Imidazolines of general formula 281 may be converted to imidazoles of general formula 282 by literature methods (Hughey, J. L., et al. Synthesis [SYNTBF] 1980, (6), 489).

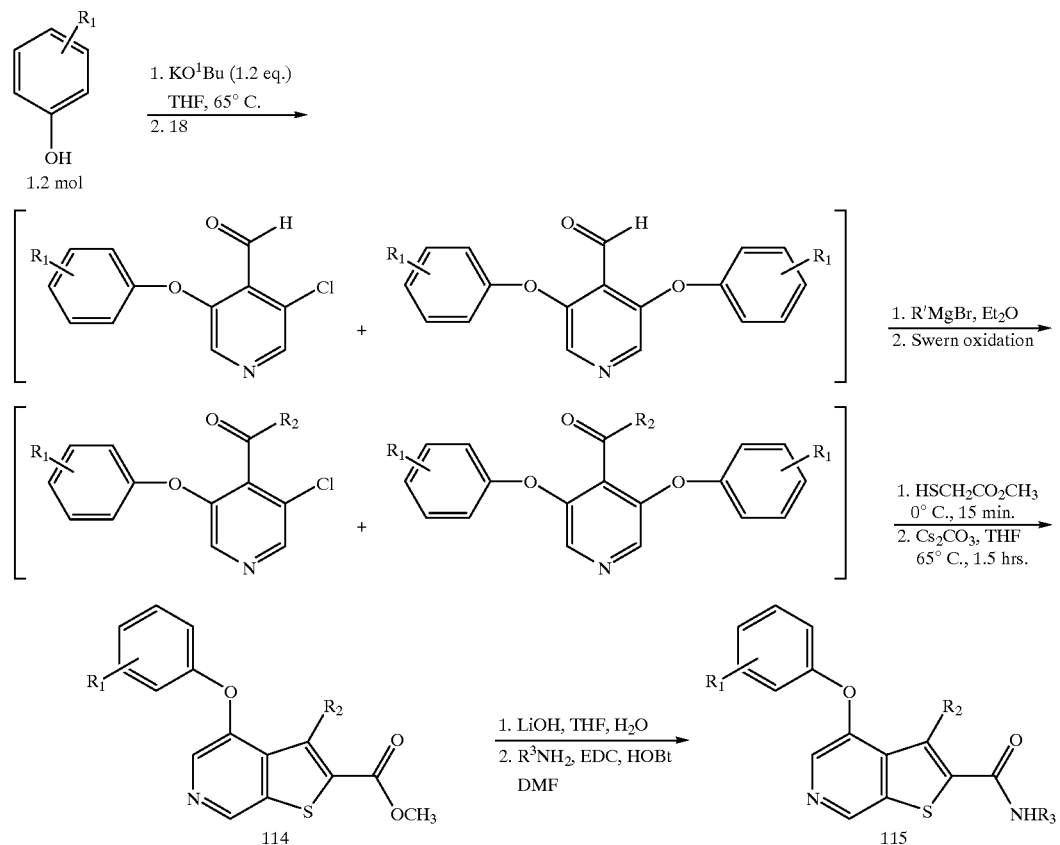

In Scheme 72, an improved preparation of 3-alkyl-substituted thienopyridines of general formula 115 is disclosed. Aldehyde 18 was condensed with preformed potassium phenoxides to produce a mixture of mono- and disubstituted aryloxyaldehydes. This mixture was then reacted with the desired Grignard reagent, followed by a Swern oxidation of the resultant mixture of secondary alcohols to give the desired aryloxy ketone compounds. The mixture of aryloxy ketones were further reacted with methyl thioglycolate in the presence of cesium carbonate to provide the 2,3,4-trisubstituted thieno[2,3-c]pyridine esters of general formula 114. These esters were converted to the corresponding acids by hydrolysis with lithium hydroxide, and then the acids were coupled with various amines, for example by carbodiimides, to give the desired amnides of general formula 115.

low temperature, followed by the addition of t-butyl chlorooxoacetate to provide the 4-tert-butyl-2-ketoester of 3,5-dichloropyridine 283. The ester 283 was then reacted with 1.25 equivalents of preformed potassium phenoxides at ambient temperature, to give the monoaryloxy derivatives as the main product. Without purification, the monoaryloxy esters were treated with methyl thioglycolate and base such as potassium t-butoxide or cesium carbonate to provide the desired thienopyridine diesters of general formula 284. The diesters of general formula 284 were then treated with methanolic amines to give the corresponding 3-tert-butyl ester amides of general formula 285. The tert-butyl ester amides of general formula 285 were converted to the corresponding acid amides of general formula 287 by solvolysis with trifluoroacetic acid. Diesters of general formula 284 may also be converted to the acids of general formula 286 by a similar solvolysis reaction.

Scheme 73

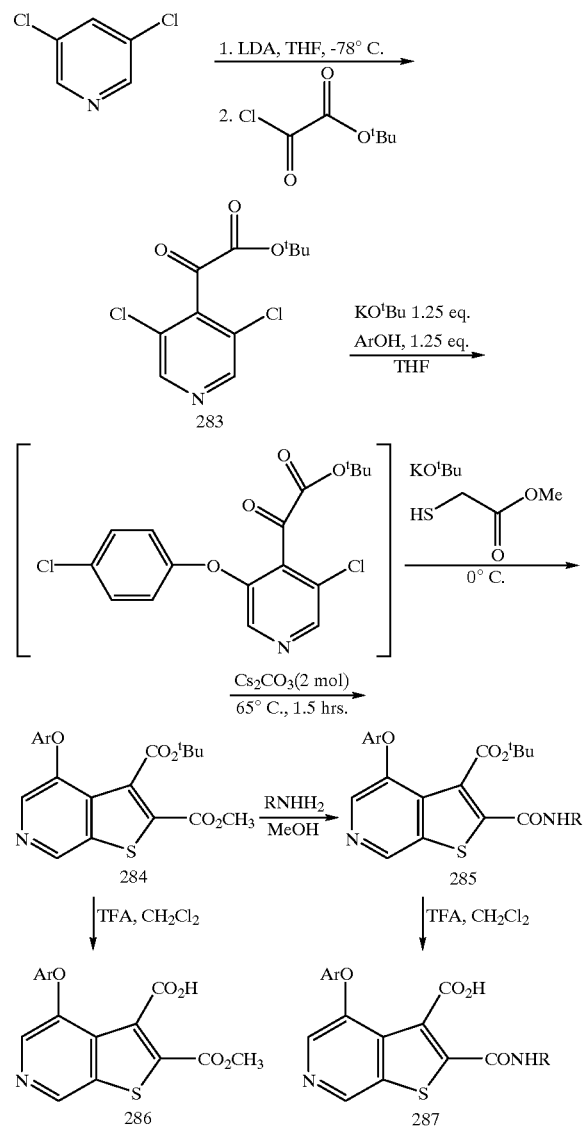

Scheme 74

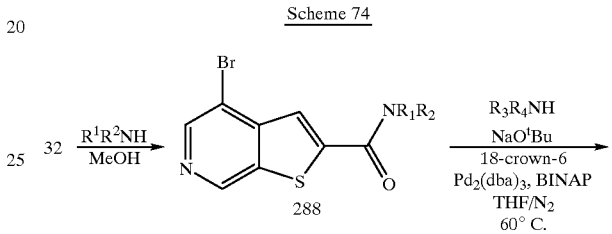

Scheme 74 describs the use of 4-bromothienopyridine 32 to prepare 4-amino substituted thienopyridine derivatives. Ester 32 was converted to amides of general formula 288 by standard procedures, and then coupled to a variety of amines using palladium(0) catalysis, as described by Buchwald (J. Org. Chem. 1997, 62, 6066–6068), producing 4-amino derivatives of general formula 289.

Scheme 75

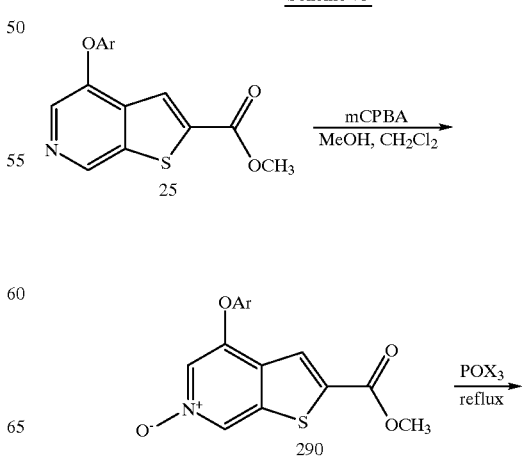

Scheme 73 provides a synthesis for 3-carboxythienopyridines. Using methodology analogous to that described for the preparation of 20 or 25, 3,5-dichloropyridine was treated with strong base such as lithium diisopropylamide in anhydrous ethereal solvent at

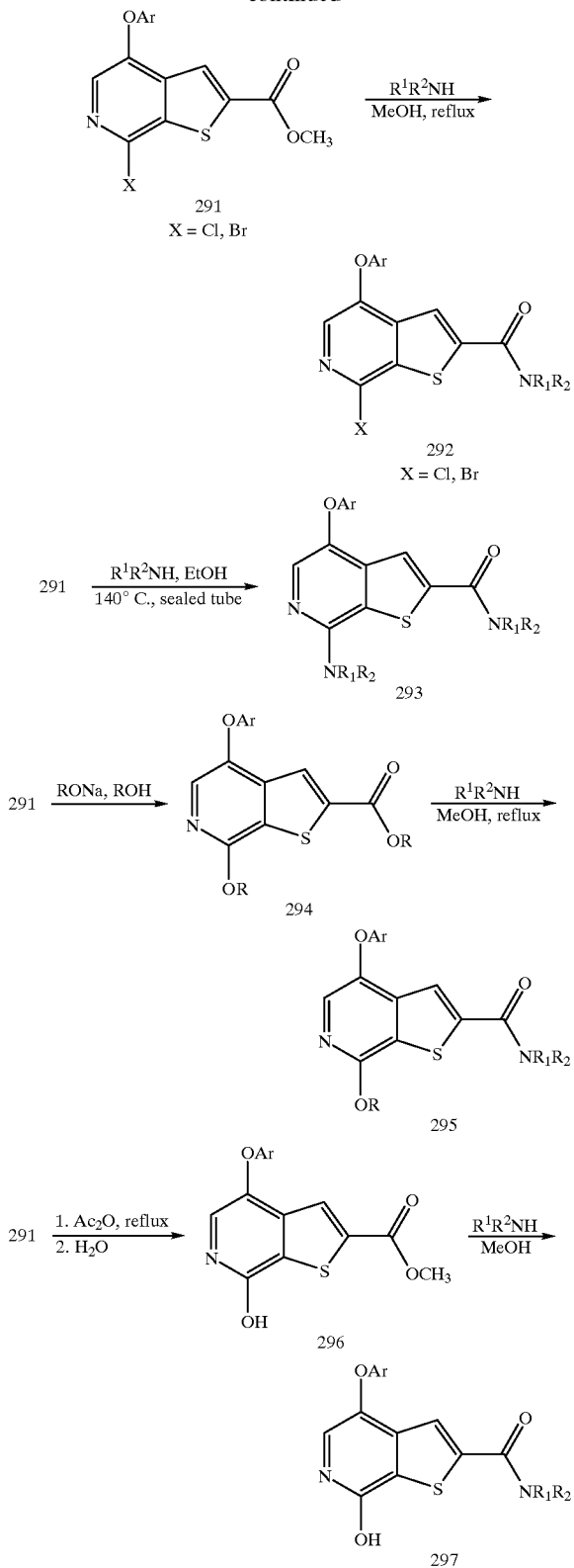
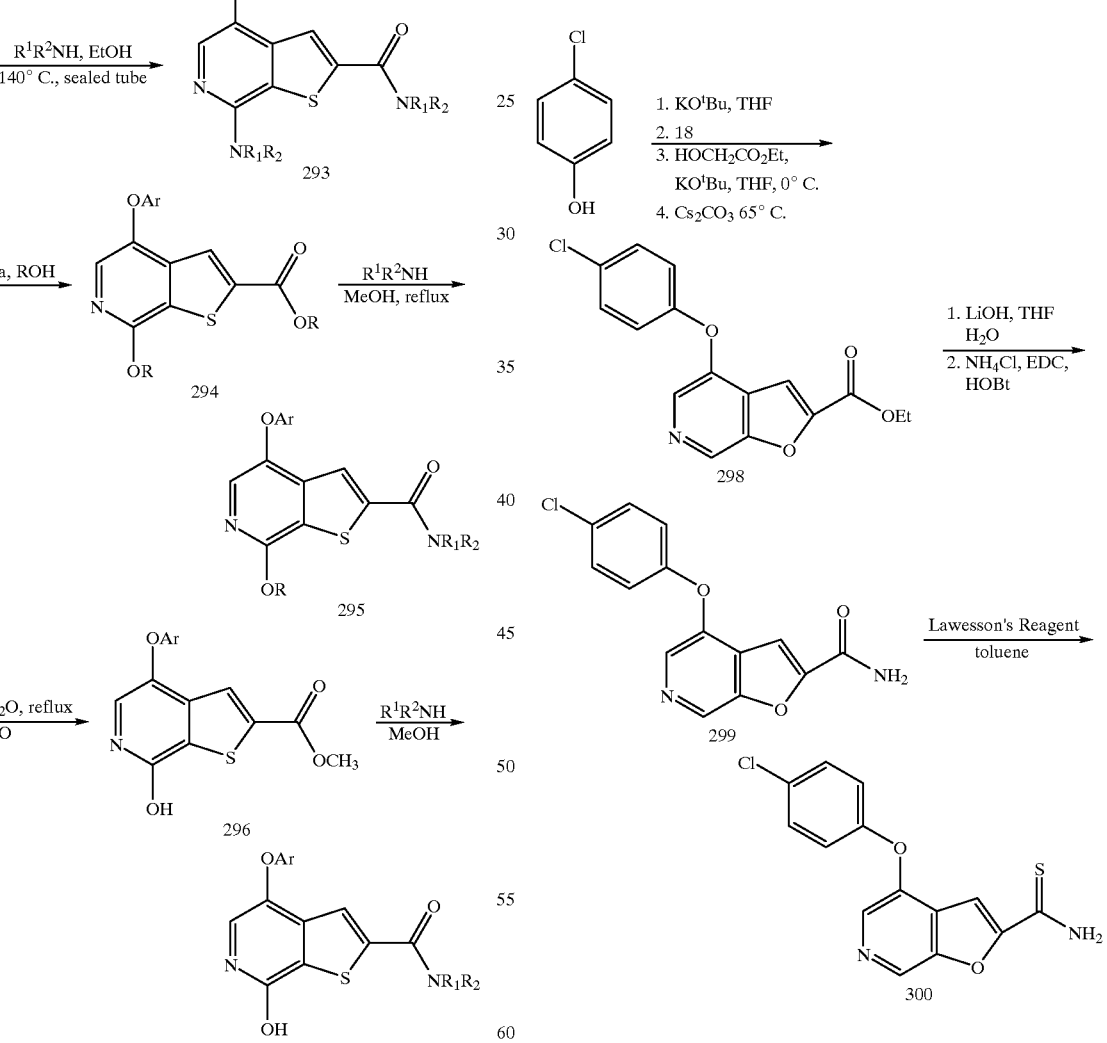

were oxidized to the pyridine-N-oxides of general formula 290 with meta-chloroperbenzoic acid. The N-oxides were rearranged to the 7-halo derivatives of general formula 291 by warming in phosphorous oxychloride or phosphorous oxybromide. The resultant 7-halides could be converted to the amide derivatives of general formula 292 by standard methods without reaction of the 7-chloro or 7-bromo moieties. However, under more forcing conditions, the chloro or bromo groups could be substituted with amines or alcohols to provide 7-amino derivatives of general formula 293 and 7-alkoxy derivatives of general formula 294 respectively. Esters of general formula 294 were converted to amides of general formula 295 using standard methods. 7-Hydroxy analogs of general formula 296 were prepared from 291 derivatives using acetic anhydride followed by hydrolysis with water. In addition, the 7-halo derivatives 291, in particular the 7-bromo derivatives, were effective educts in Suzuki reactions with aryl boronic acids, similar to those described in Scheme 19 and 65.

Scheme 76

Scheme 75 outlines the preparation and reactions of 7-chloro and 7-bromothienopyridine derivatives. The analogs are useful for preparing active derivatives as well as serving as synthetic intermediates for a variety of 7-substituted thienopyridines. Esters of general formula 25

Scheme 76 describes the preparation of furopyridine analogs such as 299 (Example 327). By a procedure analogous to that of the preparation of 20 or 25, dichloropyridinecarboxaldehyde 18 was reacted sequentially with a potassium phenoxide, then with ethyl glycolate, followed by cyclization under basic conditions, affording furopyridine ester 298 in low yield. Standard hydrolysis and coupling conditions afforded the amide 299. The amide was converted to the thioamide 300 by treatment with Lawesson's reagent in hot toluene.

Scheme 77

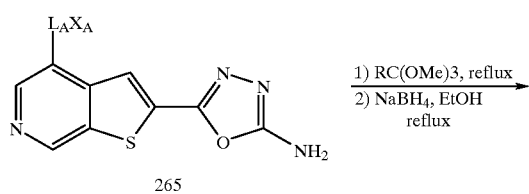

Scheme 77 illustrates the preparation N-alkyl 5-amino-1,3,4,-oxadiazoles. The treatment of 265 in refluxing trimethylorthoformate followed by reduction of the eneamine intermediate with sodium borohydride in refluxing ethanol provides the N-alkylated 5-amino-1,3,4,-oxadiazoles of general formula 301.

Scheme 78

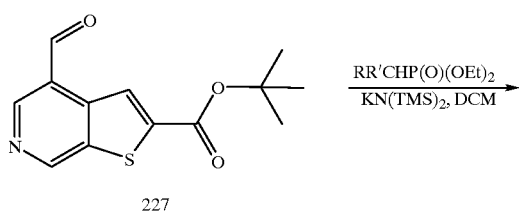

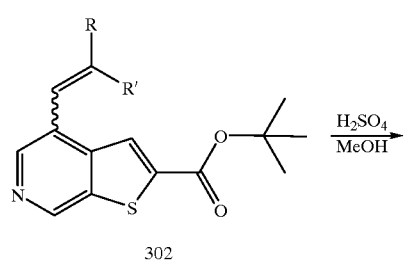

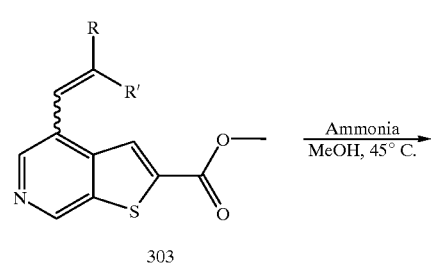

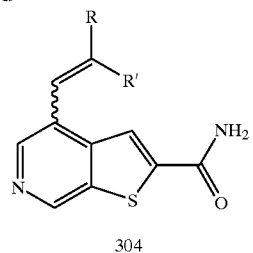

Scheme 78 exemplifies the synthesis of substituted vinyl moieties at the 4-position of thienopyridines. Treatment of aldehyde 227 with the appropriate diethylphosphonate in the presence of potassium bis(trimethylsilyl)amide provided 302. Compound 302 was then treated with sulfuric acid in methanol to yield the methyl ester 303, followed by standard amide formation with ammonia and methanol to produce 4-vinylsubstituted thienopyridines of general formula 304. Installation of a substituted vinyl can also be accomplished by using Wittig phosphorane chemistry.

Scheme 79

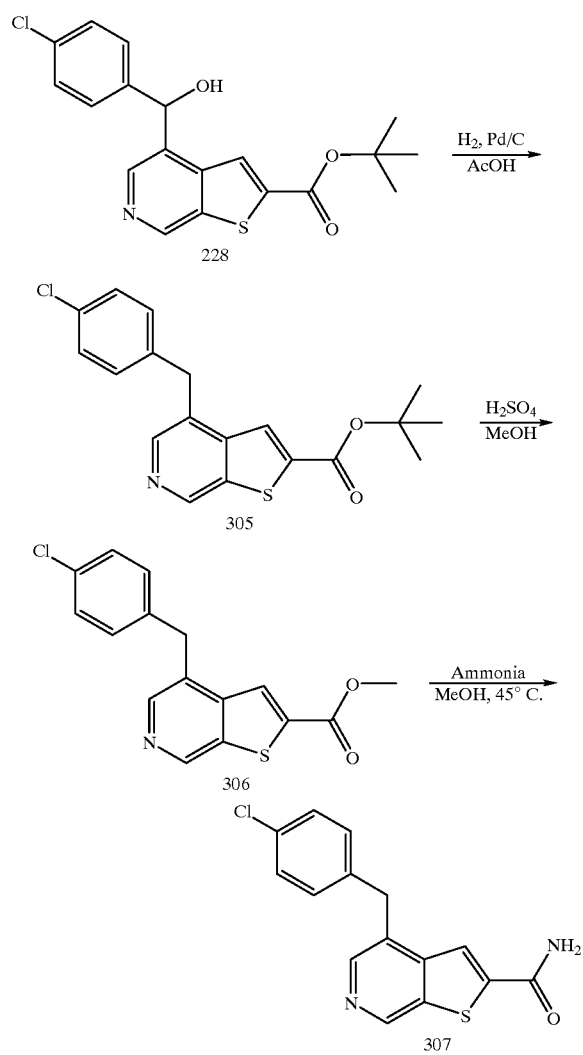

Scheme 79 demonstrates the preparation of 4-substituted alkyl thienopyridines. Alcohol 228 was subjected to palladium on carbon in acetic acid to generate the methylene derivative 305. Treatment of 305 with sulfuric acid in methanol yields 306. Formation of the amide is accomplished by treatment of 306 with ammonia in methanol to yield 307 of substituted amides. In addition, esters of general formula 310 may be converted to carbamates of general formula 312 through Curtius rearrangement of the intermediate acid. The tert-butyl carbamates of general formula 312 were converted to the primary amines of general formula 313 by the action of trifluoroacetic acid.

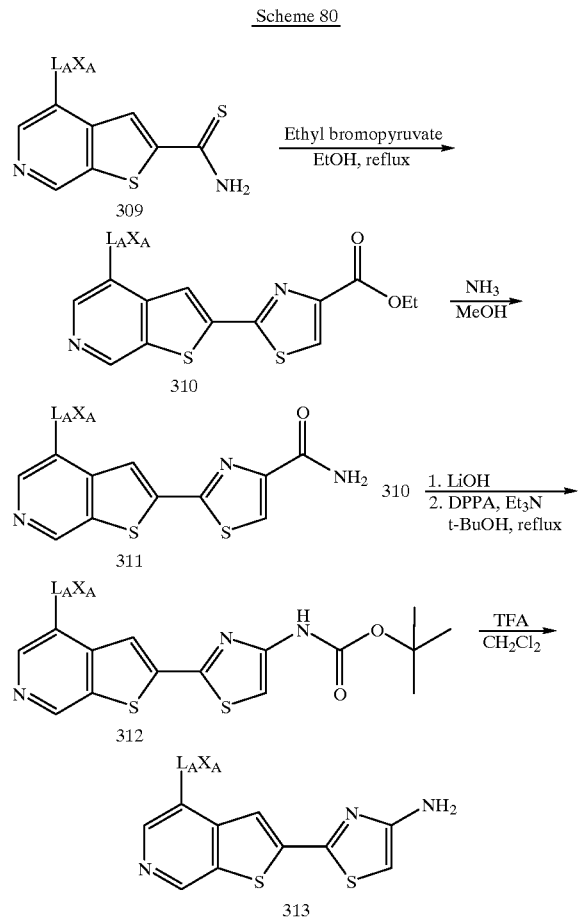

Scheme 80

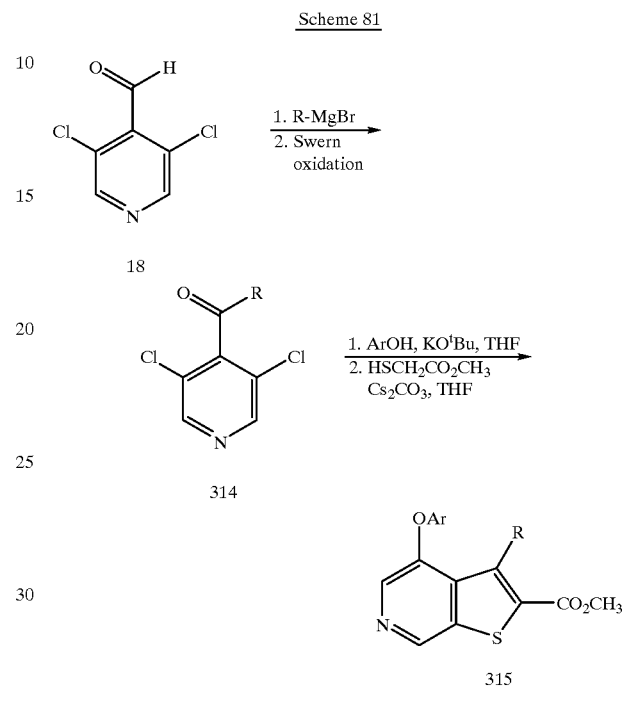

Scheme 81

Scheme 80 illustrates the preparation of thiazole derivatives at the 2-position of thienopyridines. Thioamides of general formula 309 were alkylated and cyclized with ethyl bromopyruvate, providing thiazole esters of general formula 310. Standard amide formation led to amides of general formula 311. Other amines may be used to produce a variety Scheme 81 outlines an alternative method for preparing 3-substituted thienopyridines, wherein Ar=unsubstituted or substituted aryl, or heterocycle, and R=alkyl, alkoxy, substituted alkyl, aryl, arylalkyl. Aldehyde 18 was reacted with the appropriate organomagnesium halide, to give an intermediate secondary alcohol, which was oxidized to the corresponding ketone 314. The method of oxidation was the Swern procedure, although other standard oxidations of this type may be employed (e.g PCC, TPAP). The procedure then follows that previously described for the 3-unsubstituted analogs, leading to ester 315. Ester 315 then served as starting material for the preparation of amides, or other heterocyclic derivatives at the 2-position of the thienopyridines.

Scheme 82

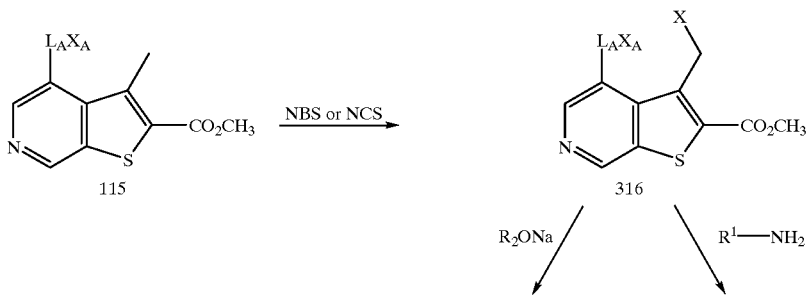

Scheme 82 describes a method for producing cyclic derivatives between the 2- and 3-positions of thienopyridines. 3-Methyl derivative 115 was treated with N-bromosuccinimide (or alternatively N-chlorosuccinimide) in carbon tetrachloride to give bromomethyl (or chloromethyl) compound 316 (X=Br, Cl). Compound 316 can then be reacted with a primary amine, through alkylation and acylation, leading to the tricyclic lactam 317. Compound 316 may also be treated with sodium alkoxides or aryloxides $R^2$=alkyl, aryl, or heterocycle) leading to the 3-position extended alkoxymethyl derivatives 318. These esters in turn can be reacted with substituted amines to yield the corresponding amides 319.

The compounds and processes of the present invention will be better understood in connection with the following examples which are intended as an illustration of and not a limitation upon the scope of the invention.

EXAMPLE 1 methyl 2-[(6-ethylthieno[2,3-d]pyrimidin-4-yl)thio]acetate

EXAMPLE 1A methyl 6-ethyl-3,4-dihydro-4-oxothieno[2,3-d]pyrimidine-2-carboxylate The desired compound was prepared as described in J. Heterocylic Chem. 1987, 24, 581–587.

EXAMPLE 1B 6-ethylthieno[2,3-d]pyrimidin-4(3H)-one

Example 1A (35 g, 140 mmol) and LiCl (6.5 g, 153 mmol) in DMSO (80 mL) and water (8 mL) was heated to 150° C. for 18 hours, cooled to room temperature, diluted with water, and extracted with ethyl acetate. The extract was dried ($MgSO_4$), filtered, and concentrated to provide the designated compound.

EXAMPLE 1C 4-chloro-6-ethylthieno[2,3-d]pyrimidine

Example 1B (3.97 g, 22.0 mmol) in $POCl_3$ (22 mL) was heated to reflux for 2 hours, cooled, poured onto ice, diluted with water, made basic with concentrated ammonium hydroxide, and extracted with ethyl acetate. The extract was dried ($MgSO_4$), filtered, and concentrated. The residue was purified by flash chromatography on silica gel with 10% ethyl acetate-hexane to provide the designated compound.

EXAMPLE 1D methyl 2-[(6-ethylthieno[2,3-d]pyrimidin-4-yl)thio)acetate

Example 1C (0.25 g, 1.26 mmol) in DMF (1.2 mL) was treated sequentially with methyl thioglycolate (0.134 g, 1.26 mmol) and potassium carbonate (0.174 g, 1.26 mmol), stirred at room temperature for 18 hours, cooled, poured into water, diluted with brine, and extracted with dicheoromethane. The extract was washed with wa ter and brine, dried ($MgSO_4$), filtered, and concentrated. The residue was triturated then washed with 10% ethyl acetate/hexanes to provide the title compound.

MP 36–58° C.; MS ($DCI/NH_3$) m/lz 269 $(M+H)^+$; $^1H$ NMR (300 MHz, DMSO-$d_6$) δ 1.33 (t, 3H), 2.99 (q, 2H), 3.75 (s, 2H), 4.26 (s, 3H), 7.23 (s, 1 H), 8.76 (s, 1H).

EXAMPLE 2

6-ethyl-4-[(4-methylphenyl)thio]thieno[2,3-d]pyrimidine

Example 1C was processed as in Example 1D but substituting thiocresol for methyl thioglycolate to provide the title compound.

mp 56–58° C.; MS ($DCI/NH_3$) m/z 286 $(M+H)^+$; $^1H$ NMR (300 MHz, DMSO-$d_6$) δ 1.32 (t, 3H), 2.38 (s, 3H), 2.99 (q, 2H), 7.20 (s, 1H), 7.33 (m, 2H), 7.52 (m, 2H), 8.63 (s, 1H); Anal. calcd for $C_{15}H_{14}N_2S_2$: C, 62.90; H, 4.93; N, 9.78. Found: C, 63.11; H, 4.82 N, 9.63.

EXAMPLE 3

6-ethyl-4-(2-pyridinylthio)thieno[2,3-d]pyrimidine

Example 1C was processed as in Example 1D but substituting 2-mercaptopyridine for methyl thioglycolate to provide the title compound.

mp 76.5–79° C.; MS ($DCI/NH_3$) m/z 274 $(M+H)^+$; $^1H$ NMR (300 MHz, DMSO-$d_6$) δ 1.31 (t, 3H), 2.99 (q, 2H), 7.18 (s, 1H), 7.46 (dt, 1H), 7.81 (d, 1H), 7.90 (dt, 1H), 8.60 (m, 1H), 8.74 (s, 1H).

EXAMPLE 4

6-ethyl-4-[(2-methylethyl)thio]thieno[2,3-d]pyrimidine

Example 1C was processed as in Example 1D but substituting isobutyl mercaptan for methyl thioglycolate to provide the title compound.

MS ($DCI/NH_3$) m/z 253 $(M+H)^+$; $^1H$ NMR (300 MHz, DMSO-$d_6$) δ 1.08 (d, 6H), 1.39 (t, 3H), 2.03 (hep, 1H), 2.95 (q, 2H), 3.28 (d, 2H), 7.01 (s, 1H), 8.71 (s, 1H); Anal. calcd for $C_{12}H_{16}N_2S_2$: C, 57.12; H, 6.38; N, 11.09. Found: C, 57.22; H, 6.29 N, 11.08.

EXAMPLE 5

6-ethyl-4-[(phenylmethyl)thio]thieno[2,3-d]pyrimidine

Example 1C was processed as in Example 1D but substituting benzyl mercaptan for methyl thioglycolate to provide the title compound.

mp 54–60° C.; MS (DCI/NH$_3$) m/z 287 (M+H)$^+$; $^1$H NMR (300 MHz, DMSO-d$_6$) δ 1.30 (t, 3H), 2.96 (q, 2H), 4.65 (s, 2H), 7.16 (s, 1H), 7.21–7.36 (m, 3H), 7.46 (m, 2H), 8.83 (s, 1H); Anal. calcd for C$_{15}$H$_{14}$N$_2$S$_2$: C, 62.90; H, 4.93; N, 9.78. Found: C, 62.11; H, 4.94 N, 9.71.

EXAMPLE 6

6-ethyl-4-[(5-methyl-1,3,4-thiadiazol-2-yl)thio] thieno[2,3-d]pyrimidine

Example 1C was processed as in Example 1D but substituting 5-methyl-1,3,4-thiadiazol-2-thiol for methyl thioglycolate to provide the title compound.

mp 132–135° C.; MS (DCI/NH$_3$) m/z 295 (M+H)$^+$; $^1$H NMR (300 MHz, DMSO-d$_6$) δ 1.35 (t, 3H), 2.82, (s, 3H), 3.05 (q, 2H), 7.42 (s, 1H), 8.88 (s, 1H); Anal. calcd for C$_{11}$H$_{10}$N$_4$S$_3$: C, 44.88; H, 3.42; N, 19.03. Found: C, 44.61; H, 3.47 N, 18.92.

EXAMPLE 7 ethyl 6-ethyl-4-[(4-methylphenyl)thio]thieno[2,3-d] pyrimidine-6-carboxylate

Example 1A was processed as in examples 1C and 2 to provide the title compound.

mp 87.5–90° C.; MS (DCI/NH$_3$) m/z 359 (M+H)$^+$; $^1$H NMR (300 MHz, DMSO-d$_6$) δ 1.26 (t, 3H), 1.31 (t, 3H), 2.39 (s, 3H), 3.02 (q, 2H), 4.27 (q, 2H), 7.17 (s, 1H), 7.33 (m, 2H), 7.57 (m, 2H); Anal. calcd for C$_{18}$H$_{18}$N$_2$O$_2$S$_2$: C, 60.31; H, 5.06; N, 7.81. Found: C, 60.44; H, 4.88 N, 7.65.

EXAMPLE 8

6-ethyl-N-(phenylmethyl)thieno[2,3-d]pyrimidin-4-amine

Example 1C (0.27 g, 1.37 mmol) in isopropanol (1.5 mL) was treated with benzylamine (0.19 mL, 1.71 mmol) and sodium carbonate (0.24 g, 2.3 mmol), stirred at room temperature overnight, filtered, and concentrated. The residue was purified by flash chromatography on silica gel with 25% ethyl acetate/hexanes to provide the title compound.

mp 128–131° C.; MS (DCI/NH$_3$) m/z 270 (M+H)$^+$; $^1$H NMR (300 MHz, DMSO-d$_6$) δ 1.30 (t, 3H), 2.88 (q, 2H), 4.72 (d, 2H), 7.20–7.40 (m, 6H), 8.26 (s, 1H), 8.34 (t, 2H); Anal. calcd for C$_{15}$H$_{15}$N$_3$S$_2$: C, 66.89; H, 5.61; N, 15.60. Found: C, 66.66; H, 5.43 N, 15.43.

EXAMPLE 9

6-ethyl-N-(5-methyl-1,3,4-thiadiazol-2-yl)thieno[2, 3-d]pyrimidin-4-amine

A solution of Example 1C (0.20 g, 1.01 mmol) in isopropanol (2 mL) was treated with 2-amino-5-methyl-1,3,4-thiadiazole (0.115 g, 1.726 mmol) and sodium carbonate (0.18 g, 1.7 mmol), stirred at room temperature for 48 hours, treated with cesium carbonate (0.55 g, 1.7 mmol), stirred at reflux for 24 hours, concentrated, treated with water, and extracted with dichloromethane. The extract was dried (MgSO$_4$), filtered, and concentrated. The residue was recrystallized with ethanol/water to provide the title compound.

mp 277–280° C.; MS (DCI/NH$_3$) m/z 278 (M+H)$^+$; $^1$H NMR (300 MHz, DMSO-d$_6$) δ 1.33 (t, 3H), 2.63 (s, 3H), 2.96 (q, 1H), 7.81 (br s, 1H), 8.65 (s, 1H); Anal. calcd for C$_{11}$H$_{11}$N$_5$S$_2$: C, 47.63; H, 4.00; N, 25.25. Found: C, 47.48; H, 3.68 N, 24.89.

EXAMPLE 10

4-[(5-amino-1,3,4-thiadiazol-2-yl)thio]-6-ethyl-2-(phenylmethyl)thieno[2,3-d]pyrimidine

EXAMPLE 10A 2-amino-5-ethylthiophene-3-carboxamide

The designated compound was prepared as described in J. Heterocylic Chem. 1987, 24, pp 581–587.

EXAMPLE 10B 5-ethyl-2-[(phenylacetyl)amino]-3-thiophenecarboxamide

Example 10A was processed as in Bull. Soc. Chim. France 1975, p 815 to provide the designated compound.

EXAMPLE 10C 6-ethyl-2-phenylmethylthieno[2,3-d]pyrimidin-4(3H)-one

Example 10B was stirred in dioxane/water in the presence of 10% Na$_2$CO$_3$ to provide the designated compound.

EXAMPLE 10D 4-chloro-6-ethyl-2-(phenylmethyl)thieno[2,3-d] pyrimidine

Example 10C was processed as in Example 1C to provide the designated compound.

EXAMPLE 10E

4-[(5-amino-1,3,4-thiadiazol-2-yl)thio]-6-ethyl-2-(phenylmethyl)thieno[2,3-d]pyrimidine Example 10D and 5-amino-1,3,4-thiadiazole-2-thiol were processed as in Example 1D to provide the title compound.

MS (DCI/NH$_3$) m/z 386 (M+H)$^+$; $^1$H NMR (300 MHz, DMSO-d$_6$) δ 1.31 (t, 3H), 2.97 (q, 2H), 4.17 (s, 2H), 7.17–7.30 (m, 6H), 7.70 (br s, 2H); Anal. calcd for C$_{17}$H$_{15}$N$_5$S$_3$: C, 52.96; H, 3.92; N, 18.17. Found: C, 53.10; H, 3.74 N, 18.03.

EXAMPLE 11

7-methyl-4-[(4-methylphenyl)thio]thieno[3,2-d] pyrimidine

3-Methyl-7-chlorothieno[3,2-d]pyrimidine was processed as in Example 1D but substituting p-thiocresol for methyl glycolate to provide the title compound.

mp 103–107° C.; MS (DCI/NH$_3$) m/z 273 (M+H)$^+$; $^1$H NMR (300 MHz, DMSO-d$_6$) δ 2.40 (s, 6H), 7.36 (m, 2H), 7.57 (m, 2H), 8.04 (s, 1H), 8.88 (s, 1H); Anal. calcd for C$_{15}$H$_{12}$N$_2$OS$_2$: C, 61.73; H, 4.44; N, 10.28. Found: C, 61.73; H, 4.50 N, 10.21.

EXAMPLE 12

7-methyl-4-[(5-methyl-1,3,4-thiadiazol-2-yl)thio] thieno[3,2-d]pyrimidine

3-Methyl-7-chlorothieno[3,2-d]pyrimidine and 5-methyl-1,3,4-thiadiazol-2-thiol were processed as in Example 1D to provide the title compound.

mp 144–147° C.; MS (DCI/NH$_3$) m/z 281 (M+H)$^+$; $^1$H NMR (300 MHz, DMSO-d$_6$) δ 2.44 (s, 3H), 2.83 (s, 3H), 8.20 (s, 1H), 9.08 (s, 1H); Anal. calcd for C$_{10}$H$_8$N$_4$S$_3$: C, 42.84; H, 2.88; N, 19.98. Found: C, 42.72; H, 2.83 N, 19.64.

EXAMPLE 13

7-methyl-4-[[5-(methylthio)-1,3,4-thiadiazol-2-yl]thio]thieno[3,2-d]pyrimidine

3-Methyl-7-chlorothieno[3,2-d]pyrimidine and 5-(methylthio)-1,3,4-thiadiazol-2-thiol were processed as in Example 1D to provide the title compound.

mp 163–166° C.; MS (DCI/NH$_3$) m/z 313 (M+H)$^+$; $^1$H NMR (300 MHz, DMSO-d$_6$) δ 2.45 (s, 3H), 2.83 (s, 3H), 8.22 (s, 1H), 9.11 (s, 1H); Anal. calcd for C$_{10}$H$_8$N$_4$S$_4$: C, 38.44; H, 2.58; N, 17.93. Found: C, 38.46; H, 2.63 N, 17.82.

EXAMPLE 14

4-[(5-amino-1,3,4-thiadiazol-2-yl)thio]-7-methylthieno[3,2-d]pyrimidine

3-Methyl-7-chlorothieno[3,2-d]pyrimidine and 5-amino-1,3,4-thiadiazole-2-thiol were processed as in Example 1D to provide the title compound.

mp 221–223° C.; MS (DCI/NH$_3$) m/z 282 (M+H)$^+$; $^1$H NMR (300 MHz, DMSO-d$_6$) δ 2.43 (s, 3H), 7.80 (br s, 2H), 8.15 (s, 1H), 9.02 (s, 1H); Anal. calcd for C$_9$H$_7$N$_5$S$_3$: C, 38.42; H, 2.51; N, 24.89. Found: C, 38.41; H, 2.42 N, 24.97.

EXAMPLE 15

7-methyl-N-[(4-(methylthio)phenyl]thieno[3,2-d]primidin-4-amine

A solution of 3-methyl-7-chlorothieno[3,2-d]pyrimidine in ethanol was treated with 4-(methylmercapto)aniline, stirred at reflux for 45 minutes, cooled to room temperature, and filtered. The precipitate was recrystallized from ethanol/water to provide the title compound.

mp 212–215° C.; MS (DCI/NH$_3$) mlz 288 (M+H)$^+$; $^1$H NMR (300 MHz, DMSO-d$_6$) δ 2.37 (s, 3H), 2.48 (s, 3H), 7.29 (m, 2H), 7.76 (m, 2H), 7.87 (br s, 1H), 8.60 (s, 1H), 9.63 (br s, 1H); Anal. calcd for C$_{14}$H$_{13}$N$_3$S$_2$: C, 58.51; H, 4.56; N, 14.62. Found: C, 58.31; H, 4.49 N, 14.47.

EXAMPLE 16

7-methyl-4-[(4-methylphenyl)thio]thieno[3,2-d]pyrimidine-6-carboxamide

EXAMPLE 16A 7-methyl-4-[(4-methylphenyl)thio]thieno[3,2-d]pyrimidine-2-carboxylic acid A solution of LDA (0.1M in THF, 9.6 mL) at −78° C. was treated with Example 11 (0.26 g, 0.96 mmol), warmed to 0° C. over 1 hour, poured onto dry ice with constant swirling, quenched with saturated NH$_4$Cl, and extracted with 3:1 chloroformlisopropanol. The extract was concentrated, and t he residue was purified by flash chromatograpy on silica gel with 7% methanol/dichloromethane to provide the designated compound.

EXAMPLE 16B 7-methyl-4-[(4-methylphenyl)thio]thieno[3,2-d]pyrimidine-2-carboxamide A suspension of Example 16A in dichloromethane (3.3 mL) was treated sequentially with oxalyl chloride (0.03 mL, 0.33 mmol) and DMF (1 drop), and concentrated after formation of the acid chloride. The residue was suspended in THF (10 mL), transferred to a vigorously stirred solution of 1:1 ammonium hydroxide/water (10 mL), and extracted with dichloromethane. The extract was dried (MgSO$_4$), filtered, and concentrated. The residue was recrystallized from ethyl acetate/hexanes to provide the title compound.

mp 243–246° C.; MS (DCI/NH$_3$) m/z 316 (M+H)$^+$; $^1$H NMR (300 MHz, DMSO-d$_6$) δ 2.40 (s, 3H), 2.58 (s, 3H), 7.35 (m, 2H), 7.57 (m, 2H), 8.01 (br s, 2H), 8.93 (s, 1H); Anal. calcd for C$_{15}$H$_{13}$N$_3$OS$_2$: C, 57.12; H, 4.15; N, 13.32. Found: C, 56.81; H, 4.06 N, 13.25.

EXAMPLE 17 methyl 4-[(4-methylphenyl)thio]thieno[2,3-c]pyridine-2-carboxylate

EXAMPLE 17A 3,5-dichloropyridine-4-carboxaldehyde

Diisopropyl amine (15.6 mL, 0.111 mol) in dry THF (25 mL) at 0° C. was treated with n-BuLi (44.6 mL, 2.5 M in hexane, 0.111 mol) over 35 minutes, stirred for 30 minutes, cooled to −78° C., diluted with THF (100 mL), and a solution of 3,5-dichloropyridine (15.0 g, 0.101 mol) in THF (175 mL) was added slowly over 3.5 hours in order to maintain an internal temperature <−74° C. The solution was stirred at −78° C. for 30 minutes, treated dropwise over 35 minutes with methyl formate (12.5 mL, 0.203 mmol) in THF (50 mL) maintaining an internal temperature of <−74° C., stirred at −78° C. for 1.4 hours, rapidly cannulated into a ice cold solution of saturated NaHCO$_3$ with vigorous stirring, partitioned with ethyl acetate (500 mL), extracted sequentially with saturated NaHCO$_3$ (2×100 mL), brine (3×150 mL), dried (MgSO$_4$), and concentrated. The residue was purified by flash chromatography on silica gel with 10% acetone/hexane.

MS (DCI/NH$_3$) m/z 176, 178, 180 (M+H)$^+$; $^1$H NMR (300 MHz, DMSO-d$_6$) δ 8.80 (s, 2H), 10.31 (s, 1H).

EXAMPLE 17B 3-(4-methylphenylthio)-5-chloro-4-pyridinecarboxaldehyde

Example 17A (5.05 g, 28.7 mmol) in DMF (70 mL) was treated with p-thiocresol (3.56 g, 28.7 mmol) and potassium carbonate (4.36 g, 31.6 mmol), stirred for 0.5 hours at 0° C. then for 1 hour at room temperature, poured into water, diluted with brine, and extracted with dichloromethane. The extract was washed sequentially with water and brine, dried (MgSO$_4$), filtered, and concentrated to provide the designated compound.

EXAMPLE 17C methyl 4-[(4-methylphenyl)thio]thieno[2,3-c]pyridine-2-carboxylate A solution of Example 17B was processed as in Example 1D to provide the title compound.

mp 116–119° C.; MS (DCI/NH$_3$) m/z 316 (M+H)$^+$; $^1$H NMR (300 MHz, DMSO-d$_6$) δ 2.28 (s, 3H), 3.91 (s, 3H), 7.20 (m, 2H), 7.29 (m, 2H), 8.00 (s, 1H), 8.44 (s, 1H), 9.36 (s, 1H); Anal. calcd for C$_{16}$H$_{13}$NO$_2$S$_2$.0.25 H$_2$O C, 60.07; H, 4.25; N, 4.37. Found: C, 60.04; H, 4.08 N, 4.27.

EXAMPLE 18

4-[(4-methylphenyl)thio]thieno[2,3-c]pyridine-2-carboxylic acid

A suspension of Example 17C (2.0 g, 6.35 mmol) and LiOH.H$_2$O (1.4 g, 32 mmol) in isopropanol (25 mL) and water (15 mL) was heated to 75° C. for 1 hour, cooled, treated with water, and washed with diethyl ether. The aqueous layer was cooled in an ice bath and adjusted to pH 2 with 10% HCl. The resulting solid was collected, washed with water, dried, and recrystallized from ethanol/water to provide the title compound.

mp 272–274° C.; MS (DCI/NH$_3$) m/z 302 (M+H)$^+$; $^1$H NMR (300 MHz, DMSO-d$_6$) δ 2.29 (s, 3H), 7.20 (m, 2H), 7.28 (m, 2H), 7.92 (s, 1H), 8.44 (s, 1H), 9.34 (s, 1H); Anal. calcd for C$_{15}$H$_{12}$N$_2$OS$_2$: C, 59.78; H, 3.67; N, 4.64. Found: C, 59.48; H, 3.58 N, 4.54.

EXAMPLE 19

4-[(4-methylphenyl)thio]thieno[2,3-c]pyridine-2-carboxamide

A suspension of Example 18 (0.535 g, 1.78 mmol) in dichloromethane (25 mL) at 0° C. was treated sequentially with oxalyl chloride (0.34 g, 2.67 mmol) and DMF (1 drop), stirred at room temperature for 0.5 hours, and concentrated. The residue was suspended in THF, treated with THF (60 mL), water (30 mL), and concentrated NH$_4$OH (30 mL), and stirred for 0.5 hours. The THF layer was separated, washed with brine, partially dried (MgSO$_4$), filtered, and concentrated. The residue was purified by flash chromatograpy on silica gel with 5% methanol/dichloromethane and recrystallized from 95% ethanol to provide the title compound.

mp 198–199° C.; MS (DCI/NH$_3$) m/z 301 (M+H)$^+$; $^1$H NMR (300 MHz, DMSO-d$_6$) δ 2.29 (s, 3H), 7.20 (m, 2H), 7.30 (m, 2H), 7.89 (br s, 1H), 8.26 (s, 1H), 8.35 (s, 1H), 8.54 (br s, 1H) 9.16 (s, 1H); Anal. calcd for C$_{15}$H$_{12}$N$_2$OS$_2$: C, 59.97; H, 4.02; N, 9.32. Found: C, 59.84; H, 4.12 N, 9.31.

EXAMPLE 20

4-(2-pyridinylthio)thieno[2,3-c]pyridine-2-carboxamide

Example 17A was processed as in examples 17B, 17C, 18, and 19 but substituting 2-mercaptopyridine for p-thiocresol in Example 17B to provide the title compound.

mp 239–242° C.; MS (DCI/NH$_3$) m/z 305 (M+NH$_4$)$^+$; $^1$H NMR (300 MHz, DMSO-d$_6$) δ 6.99 (d, 1H), 7.17 (dd, 1H), 7.65 (dt, 1H), 7.85 (br s, 1H), 8.18 (s, 1H), 8.36 (m, 1H), 8.49 (br s, 1H), 8.69 (s, 1H), 9.23 (s, 1H); Anal. calcd for C$_{13}$H$_9$N$_3$OS$_2$: C, 54.34; H, 3.16; N, 14.47. Found: C, 54.10; H, 3.14; N, 14.62.

EXAMPLE 21

4-[(4-chlorophenyl)thio]thieno[2,3-c]pyridine-2-carboxamide

Example 17A was processed as in examples 17B, 17C, 18, and 19 but substituting 4-chlorothiophenol for p-thiocresol in Example 17B to provide the title compound.

mp 239–241° C.; MS (DCI/NH$_3$) m/z 321 (M+H)$^+$; $^1$H NMR (300 MHz, DMSO-d$_6$) δ 7.31 (m, 2H), 7.43 (m, 2H), 7.89 (br s, 1H), 8.24 (s, 1H), 8.54 (br s, 1H), 8.56 (s, 1H), 9.38 (s, 1H); Anal. calcd for C$_{14}$H$_9$ClN$_2$OS$_2$: C, 52.42; H, 2.83; N, 8.73. Found: C, 52.33; H, 2.80; N, 8.63.

EXAMPLE 22

N-methoxy-N-methyl-4-[(4-methylphenyl)thio]thieno[2,3-c]pyridine-2-carboxamide A solution of Example 18 (0.66 g, 2.2 mmol) in dichloromethane was treated sequentially with oxalyl chloride (0.29 mL, 3.3 mmol) and DMF (1 drop), stirred for 30 minutes, and concentrated. The residue was suspended in THF, transferred to a solution of N,O-dimethylhydroxylamine hydrochloride (0.32 g, 3.3 mmol) and triethylamine (0.92 mL, 6.6 mmol) in 1:1 THF water, and stirred for 5 minutes. The THF layer was separated, dried (MgSO$_4$), filtered, and concentrated. The residue was purified by flash chromatography on silica gel with 20% ethyl acetate/hexanes to provide the title compound.

mp 103–107° C.; MS (DCI/NH$_3$) m/z 345 (M+H)$^+$; $^1$H NMR (300 MHz, DMSO-d$_6$) δ 2.27 (s, 3H), 3.34 (s, 3H), 3.74 (s, 3H), 7.19 (m, 2H), 7.27 (m, 2H), 8.02 (s, 1H), 8.46 (s, 1H); Anal. calcd for C$_{17}$H$_{16}$N$_2$O$_2$S$_2$: C, 59.28; H, 4.68; N, 8.13. Found; C, 58.76; H, 4.58; N, 8.06.

EXAMPLE 23

N-methoxy-4-[(4-methylphenyl)thio]thieno[2,3-c]pyridine-2-carboxamide

Example 18 was processed as in Example 22 but substituting O-methylhydroxylaminehydrochloride for N,O-dimethylhydroxylamine hydrochloride to provide the title compound.

mp 200–203° C.; MS (DCI/NH$_3$) m/z 331 (M+H)$^+$; $^1$H NMR (300 MHz, DMSO-d$_6$) δ 2.29 (s, 3H), 3.76 (s, 3H), 7.20 (m, 2H), 7.30 (m, 2H), 7.89 (br s, 1H), 8.15 (s, 1H), 8.4 (s, 1H), 9.3 (s, 1H); Anal. calcd for C$_{16}$H$_{14}$N$_2$O$_2$S$_2$.0.25.H$_2$OC, 58.16; H. 4.27; N, 8.48. Found: C, 57.46; H, 4.1 N, 8.01.

EXAMPLE 24

N-(4-chlorophenyl)-4-[(4-methyl]phenyl)thio]thieno[2,3-c]pyridine-2-carboxamide A solution of Example 18 (0.1 g, 0.33 mmol) in dichloromethane was treated with oxalyl chloride (0.03 mL, 0.33 mmol) and DMF (1 drop) stirred at reflux for 20 minutes, and concentrated. The residue was suspended in (3:1) benzene/dichloromethane (4 mL), treated with triethylamine (0.5 mL) and 4-chloroaniline (46 mg, 0.36 mmol), stirred at reflux overnight, and concentrated. The residue was treated with water and extracted with dichloromethane. The extract was dried (MgSO$_4$), filtered, and concentrated. The residue was purified by flash chromatography on silica gel with ethyl acetate/hexanes to provide the title compound.

mp 208–211° C.; MS (DCI/NH$_3$) m/z 411 (M+H)$^+$; $^1$H NMR (300 MHz, DMSO-d$_6$) δ 2.29 (s, 3H), 7.23 (m, 2H), 7.33 (m, 2H), 7.47 (m, 2H), 7.81 (m, 2H), 8.34 (s, 1H), 8.57 (s, 1H), 9.31 (s, 1H), 10.90 (br s, 1H); Anal. calcd for C$_{12}$H$_{15}$ClN$_2$OS$_2$: C, 61.38; H, 3.68; N, 6.82. Found: C, 61.22; H, 3.67; N, 6.79.

EXAMPLE 25

4-[(4-methylphenyl)thio]thieno[2,3-c]pyridine-2-carboxaldehyde

A solution of Example 22 (3.33 g, 9.6 mmol) in THF at −5° C. was treated dropwise with 1M DIBAl-H in THF (14.5 mL, 14.5 mmol), stirred for 45 minutes, poured into ice/HCl with constant stirring, and extracted with dichloromethane. The extract was dried (MgSO$_4$), filtered, and concentrated to provide the title compound.

MS (DCI/NH$_3$) m/z 303 (M+H)$^+$; $^1$H NMR (300 MHz, DMSO-d$_6$) δ 2.29 (s, 3H), 7.22 (m, 2H), 7.34 (m, 2H), 8.40 (s, 1H), 8.48 (s, 1H), 9.38 (s, 1H), 10.23 (s, 1H); Anal. calcd for $C_{15}H_{11}NOS_2$: C, 63.13; H, 3.33; N, 4.91. Found: C, 62.81; H, 3.97; N, 5.01.

EXAMPLE 26

4-[(4-methylphenyl)thio]thieno[2,3-c]pyridine-2-carboxaldehyde, O-methyloxime A solution of Example 25 (0.22 g, 0.76 mmol) in 1:1 pyridine:ethanol (8 mL) was treated with methoxylaminehydrochloride (0.51 mL, 1.52 mmol), stirred at room temperature for 3 hours, concentrated, treated with water and extracted with dichloromethane. The extract was washed with 1N HCl, dried ($MgSO_4$), filtered, and concentrated. The residue was purified by flash chromatography on silica gel with 20% ethyl acetate/hexanes to provide the title compound.

mp 95–98° C.; MS ($DCI/NH_3$) m/z 315 $(M+H)^+$; $^1$H NMR (300 MHz, DMSO-$d_6$) 2.28 (s, 3H), 3.95 (s, 1.8H), 4.08 (s, 1.2H), 7.18 (m, 2H), 7.25 (m, 2H), 7.79 (s, 0.6H), 7.95 (s, 0.4H), 8.27 (s, 0.4H), 8.36 (s, 0.6H), 8.38 (s, 0.4H), 8.68 (s, 0.6H), 9.20 (s, 0.6H), 9.30 (s, 0.4H); Anal. calcd for $C_{16}H_{14}N_2OS_2$: C, 61.12; H, 4.49; N, 8.91. Found: C, 60.93; H, 4.55; N, 8.98.

EXAMPLE 27

4-[(4-methylphenyl)thio]thieno[2,3-c]pyridine-2-carboxaldehyde, O-(phenylmethyl)oxime Example 25 and O-benzylhydroxylamine hydrochloride were processed as in Example 26 but for 18 hours instead of 3 hours to provide the title compound.

mp 127–133° C.; MS ($DCI/NH_3$) m/z 391 $(M+H)^+$; $^1$H NMR (300 MHz, DMSO-$d_6$) 2.27 (s, 3H), 5.22 (s, 1.2H), 5.38 (s, 0.8H), 7.15–7.26 (m, 4H), 7.31–7.47 (m, 5H), 7.78 (s, 0.6H), 7.96 (s, 0.4H), 8.31 (s, 0.4H), 8.36 (s, 0.6H), 8.39 (s, 0.4H), 8.74 (s, 0.6H), 9.20 (s, 0.6H), 9.30 (s, 0.4H); Anal. calcd for $C_{22}H_{18}N_2OS_2$: C, 67.66; H, 4.65; N, 7.17. Found: C, 67.45; H, 4.80; N, 7.13.

EXAMPLE 28

2-[[[4-[(4-methylphenyl)thio]thieno[2,3-c]pyridin-2-ylmethylene]amino]oxy]acetic acid Example 25 was processed as in Example 26 but substituting carboxymethoxylamine hemihydrochloride for methoxylaminehydrochloride to provide the title compound.

mp 227–230° C.; MS ($DCI/NH_3$) m/z 359 $(M+H)^+$; $^1$H NMR (300 MHz, DMSO-$d_6$) 2.28 (s, 3H), 4.71 (s, 2H), 7.19 (m, 2H), 7.25 (m, 2H), 7.84 (s, 1H), 8.36 (s, 1H), 8.79 (s, 1H), 9.20 (s, 1H); Anal. calcd for $C_{17}H_{14}N_2O_3S_2$: C, 56.97; H, 3.94; N 7.82. Found C, 56.90; H, 4.10; N, 7.97.

EXAMPLE 29

4-[(4-methylphenyl)thio]thieno[2,3-c]pyridine-2-carboxaldehyde, O-phenyloxime Example 25 was processed as in Example 26 but substituting O-phenylhydroxylamine hydrochloride for methoxylaminehydrochloride to provide the title compound.

mp 94–97° C.; MS ($DCI/NH_3$) m/z 377 $(M+H)^+$; $^1$H NMR (300 MHz, DMSO-$d_6$) 2.38 (s, 3H), 7.09–7.50 (m, 9H), 7.98 (s, 0.5H), 8.16 (s, 0.5H), 8.39 (s, 0.5H), 8.42 (s, 05H), 8.71 (s, 0.5H), 9.16 (s, 0.5H), 9.27 (s, 0.5H), 9.37 (s, 0.5); Anal. calcd for $C_{21}H_{16}N_2OS_2$: C, 67.00; H 4.28; N, 7.44. Found: C, 67.14; H, 4.50; N, 7.57.

EXAMPLE 30

4-[(4-methylphenyl)thio]thieno[2,3-c]pyridine-2-carboxaldehyde, oxime

Example 25 was processed as in Example 26 but substituting hydroxylamine hydrochloride for methoxylaminehydrochloride to provide the title compound. mp 209–210° C.; MS ($DCI/NH_3$) m/z 301 $(M+H)^+$; $^1$H NMR (300 MHz, DMSO-$d_6$) δ 2.28 (s, 3H), 7.18 (m, 2H), 7.70 (s, 0.3H), 7.87 (s, 0.7H), 8.19 (s, 0.7H), 8.35 (s, 0.3H), 8.38, (s, 0.7H), 8.56 (s, 0.3H), 9.17 (s, 0.3H), 9.27 (s, 0.7H); Anal. calcd for $C_{15}H_{12}N_2OS_2$: C, 59.98; H, 4.03; N, 9.33. Found: C, 59.80; H, 4.08, N, 9.30.

EXAMPLE 31

2-[[[4-[(4-methylphenyl)thio]thieno[2,3-c]pyridine-2-ylmethylene]amino]oxy]acetamide Example 28 was processed as in Example 19 to provide the title compound.

mp 152–156° C.; MS ($DCI/NH_3$) m/z 358 $(M+H)^+$; $^1$H NMR (300 MHz, DMSO-$d_6$) δ 2.27 (s, 3H), 4.52 (s, 0.6H), 4.66 (s, 0.4H), 7.19 (m, 2H), 7.25 (m, 2H), 7.32 (br s, 1H), 7.40 (br s, 1H), 7.84 (s, 0.6H), 7.97 (s, 0.4H), 8.32 (s, 0.4H), 8.37 (s, 0.6H), 8.40 (s, 0.4H), 8.75 (s, 0.6H), 9.21 (s, 0.6H), 9.32 (s, 0.4H); Anal. calcd for $C_{17}H_{15}N_3O_2S_2 \cdot (1.25 H_2O)$: C, 57.12; H, 4.23; N, 11.76. Found C, 56.19; H, 4.48; N, 10.94

EXAMPLE 32

(E)-3-[(4-methylphenyl)thio]thieno[2,3-c]pyridin-2-yl]-2-propenamide

Example 25 (0.23 g, 1.27 mmol) in chloroform (10 mL) was treated with carbamoylmethylenetriphenylphosphorane (0.41 g, 1.27 mmol), heated to reflux for 30 minutes, cooled, and concentrated. The residue was purified with flash chromatography on silica gel with 2% methanol/dichloromethane to provide the title compound.

mp 171–174° C.; MS ($DCI/NH_3$) m/z 327 $(M+H)^+$; $^1$H NMR (300 MHz, DMSO-$d_6$) δ 2.28 (s, 3H), 6.64 (d 1H), 7.19 (m, 2H), 7.25–7.37 (m, 3H), 7.68–7.82 (m, 3H), 8.35 (s, 1H), 9.19 (s, 1H); Anal. calcd for $C_{17}H_{14}N_2OS_2 \cdot H_2O$: C, 62.55; H, 4.32; N, 8.58. Found: C, 59.78; H, 4.50; N, 8.20.

EXAMPLE 33

1-[4-[(4-methyltphenyl)thio]thieno[2,3-c]pyridin-2-yl]ethanone

A solution of Example 22 in THF (25 mL) at 0° C. was treated with methyl magnesium bromide (1.4M in toluene/THF, 1.85 mL, 2.6 mmol), warmed to room temperature, stirred overnight, treated with methylmagnesiumbromide (1.4M in toluene/THF, 0.7 mL, 1.3 mmol) stirred for 1 hour, poured with constant swirling onto ice/$NH_4Cl$, and extracted with ethyl acetate. The extract was dried ($MgSO_4$), filtered, and concentrated. The residue was purified by flash chromatography on silica gel with 20% ethyl acetate/hexanes to provide the title compound.

mp 134–138° C.; MS ($DCI/NH_3$) m/z 317 $(M+NH_4)^+$; $^1$H NMR (300 MHz, DMSO-$d_6$) δ 2.33 (s, 3H), 2.71 (s, 3H), 7.24 (m, 2H), 7.38 (m, 2H), 8.28 (s, 1H), 8.31 (s, 1H), 9.29 (s, 1H); Anal. calcd for $C_{16}H_{13}NOS_2$: C, 64.19; H, 4.38; N, 4.68. Found C, 64.11; H, 4.41; N, 4.61.

EXAMPLE 34

2-benzoyl-4-[(4-methyl]phenyl)thio]thieno[2,3-c]pyridine

Example 22 and phenyl lithium were processed as in Example 33 to provide the title compound.

mp 103–107/° C.; MS (DCI/NH$_3$) m/z 362(M+H)$^+$; $^1$H NMR (300 MHz, DMSO d$_6$) δ 2.33 (2,3H), 7.26 (m, 4H), 7.57 (m, 2H), 7.71 (m, 4H), 8.49 (s, 1H), 9.40 (s, 1H); Anal. Calcd for C$_{21}$H$_{15}$NOS$_2$.1.25 H$_2$O: C, 65.68;, H, 4.59; N, 3.64. Found: C, 65.67; H, 4.09; N, 3.46.

EXAMPLE 35

2-ethyl-4-[(4-methylphenyl)thio]thieno[2,3-c]pyridine

A solution of Example 33 in ethylene glycol (10 mL) was treated with hydrazine hydrate (0.18 mL, 5.8 mmol), stirred at 160° C. for 30 minutes, cooled to room temperature, treated with potassium hydroxide, stirred at 150° C. for 45 minutes, cooled to room temperature, treated with water, and extracted with ethyl acetate. The extract was washed with water, dried (MgSO$_4$), filtered, and concentrated. The residue was purified by flash chromatography on silica gel with 10% ethyl acetate/hexanes to provide the title compound.

MS (DCI/NH$_3$) m/z 286 (M+H)$^+$; $^1$H NMR (300 MHz, DMSO-d$_6$) δ 1.28 (t, 3H), 2.26 (s, 3H), 2.99 (q, 2H), 7.14–7.27 (m, 5H), 8.34 (s, 1H), 9.11 (s, 1H); Anal. calcd. for C$_{16}$H$_{15}$NS$_2$.0.25 H$_2$O: C, 67.33; Hi, 5.30; N, 4.91. Found: C, 66.63; H, 5.38; N, 4.72.

EXAMPLE 36

1-[4-[(4-methylphenyl)thio]thieno[2,3-c]pyridin-2-yl]ethanone, oxime

Example 33 and hydroxylamine hydrochloride were processed as in Example 26 to provide the title compound.

mp 209–213° C.; MS (DCI/NH$_3$) m/z 315 (M+H)$^+$; $^1$H NMR (300 MHz, DMSO-d$_6$) δ 2.22 (s, 1.5H), 2.28 (s, 3H), 2.32 (s, 1.5H), 7.20 (m, 2H), 7.30 (m, 2H), 7.62 (s, 0.5H), 7.70 (s, 0.5H), 8.30 (s, 0.5H), 8.34 (s, 0.5H), 9.12 (s, 0.5H), 9.24 (s, 0.5H); Anal. calcd for C$_{16}$H$_{14}$N$_2$OS$_2$: C, 61.16; H, 4.49, N, 8.91. Found C, 60.83, H, 4.61; N, 9.03.

EXAMPLE 37

N-(2,3-dihydroxypropyl)-4-[(4-methylphenyl)thio]thieno[2,3-c]pyridine-2-carboxamide A solution of Example 18 (2.5 g, 8.3 mmol) and N-hydroxysuccinimide (0.95 g, 8.3 mmol) in dichloromethane (35 mL) was treated with DCC (1.882 g, 9.13 mmol) in methylene chloride (15 mL), stirred at room temperature for 18 hours, and concentrated. The residue was dissolved in ethyl acetate, washed with water, dried (MgSO$_4$), filtered, and concentrated. The residue was added to a solution of 3-amino-1,2-propane diol (0.144 g, 1.6 mmol) in 3:1 dioxane/methanol (20 mL), was stirred at room temperature for 18 hours, concentrated, dissolved in ethyl acetate, washed with water, dried (MgSO$_4$), filtered, and concentrated. The residue was purified by flash chromotograpy on silica gel with 6% methanol/dichloromethane to provide the title compound.

mp 120–122° C.; MS (DCI/NH$_3$) m/z 375 (M+H)$^+$; $^1$H NMR (300 MHz, DMSO-d$_6$) δ 2.29 (s, 3 H), 3.19 (m, 1H), 3.4 (m, 1H), 3.65 (m, 1 H), 4.62, (t, 1H), 4.88 (d, 1H) 7.20 (m, 2 H), 7.30 (m, 2 H), 8.38 (s, 1H), 9.1 (s, 1 H), 9.28 (s, 1H); Anal. calcd for C$_{18}$H$_{18}$N$_2$O$_3$S$_2$.0.75H$_2$O: C, 57.73; H, 4.84; N, 7.48. Found: C, 55.54, H, 5.23 N, 6.7.

EXAMPLE 38

4-[(4-methylphenyl)thio]thieno[2,3-c]pyridine-2-carboxylic acid, hydrazide

Example 18 was processed as in Example 37 but substituting hydrazine for 3-amino-1,2-propanediol to provide the title compound.

mp 176–178° C.; MS (DCI/NH$_3$) m/'z 316 (M+H)$^+$; $^1$H NMR (300 MHz, DMSO-d$_6$) δ 2.29 (s, 3 H), 4.68 (br s, 2H), 7.20 (m, 2 H), 7.30 (m, 2 H), 8.2 (s, 1 H), 8.4 (s, 1 H), 9.28 (s, 1 H) 10.4 (br s, 1 H); Anal. calcd for C$_{15}$H$_{13}$N$_3$OS$_2$.0.25.H$_2$O: C, 57.12; H, 4.15; N, 13.32. Found: C, 56.49; H, 4.19 N, 12.29.

EXAMPLE 39

N$^2$-4-[(4-methylphenyl)thio]thieno[2,3-c]pyridin-2-yl]carbonyl]-N$^6$-[(nitroamino)iminomethyl]-L-lysine, methyl ester N-ω-nitroarginine methyl ester hydrochloride and NaHCO$_3$ were processed as in Example 37. The residue was purified by flash chromatograpy on silica gel with 5% methanol/dichloromethane to provide the title compound.

mp 84–87° C.; MS (DCI/NH$_3$) mi/z 517 (M+H)$^+$; $^1$H NMR (300 MHz, DMSO-d$_6$) δ 1.60 (m, 2H), 1.85 (m, 2H), 2.29 (s, 3 H), 3.20, (m, 2H), 3.68, (s, 3H), 4.35, (t, 1H), 4.48, (m, 1H, 7.20 (m, 2 H), 7.30 (m, 2 H), 8.32 (s, 1 H), 8.48 (s, 1 H), 8.52, (br s, 1H), 9.30 (s, 1 H), 9.42 (d, 1H); Anal. calcd for C$_{22}$H$_{24}$N$_6$O$_5$S$_2$.0.25 H$_2$O: C, 51.15; H, 4.68; N, 16.27. Found: C, 50.95; H,4.89; N,15.73.

EXAMPLE 40

N-(aminoiminomethyl)-4-[(4-methylphenyl)thio]thieno[2,3-c]pyridine-2-carboxamide A solution of guanidine hydrochloride (0.095 g, 1 mmol) in methanol was treated with potassium t-butoxide (0.112 g, 1 mmol), stirred at room temperature for 30 minutes, treated with Example 17 (0.1 g, 0.3 mmol), warmed to room temperature for 16 hours and concentrated. The concentrate was dissolved in ethyl acetate (100 mL), washed with water, dried (MgSO$_4$), filtered, and concentrated. The residue was purified by flash chromotograpy on silica gel with 6% methanol/dichloromethane to provide the title compound.

mp 202–205° C.; MS (DCI/NH$_3$) m/z 343 (M+H)$^+$; $^1$H NMR (300 MHz, DMSO-d$_6$) δ 2.29 (s, 3H), 6.90 (br s, 2H), 7.20 (m, 4H), 7.80 (S, 1H), 8.00 (br s, 2H), 8.20 (s, 1H), 8.40 (s, 1H), 9.24 (s, 1H).

EXAMPLE 41

4-[(4-methylphenyl)thio]thieno[2,3-c]pyridine-2-carbothioamide

A solution of Example 19 (190 mg, 0.63 mmol) and Lawsesson's reagent (383 mg, 9.48 mmol) in toluene (15 mL) was heated to room temperature for 5 hours and concentrated. The residue purified by flash chromatograpy on silica gel with 4% methanol/dichloromethane to provide the title compound.

mp 181–183° C.; MS (DCI/NH$_3$) m/z 317 (M+H)$^+$; $^1$HNMR (300 MHz, DMSO-d$_6$) δ 2.29 (s, 3H), 7.20 (m, 2H), 7.30 (m, 2H), 8.18 (br s, 1H), 8.32 (s, 1H), 9.2 (s, 1H) 10.1 (br s, 1H) 10.2 (br s, 1H); Anal. calcd for C$_{15}$H$_{12}$N$_2$S$_3$.0.25 H2O: C, 56.93; H, 3.82; N, 8.85. Found: C, 55.89; H,3.83 N, 8.48.

EXAMPLE 42

4-[(4-methylphenyl)thio]thieno[2,3-c]pyridine

Boiling Dowtherm A (2 mL) was treated sequentially with Example 18 (0.6 g, 1.99 mmol) and copper powder (0.3 g), stirred for 5 minutes, cooled, diluted with hexanes, and purified by flash chromatography on silica gel with 15% ethyl acetate/hexanes. The product was then recrystallized from hexanes to provide the title compound.

mp 94–95° C.; MS (DCI/NH$_3$) m/z 258 (M+H)$^+$; $^1$H NMR (300 MHz, DMSO-d$_6$) δ 2.27 (s, 3H), 7.16 (m, 2H), 7.23 (m, 2H), 7.44 (d, 1H), 8.20 (d, 1H), 8.40 (s, 1H), 9.27 (s, 1H); Anal. calcd for C$_{14}$H$_{11}$NS$_2$: C, 65.33; H, 4.30; N, 5.44. Found: C, 65.44; H, 4.20, N, 5.26.

EXAMPLE 43 methyl 4-[(2-methoxy-2-oxoethyl)thio]thieno[2,3-c]pyridine-2-carboxylate

Example 93A was processed as in examples 17B and 17C, but substituting methyl thioglycolate for p-thiocresol in Example 17B to provide the title compound.

MS (DCI/NH$_3$) m/z 298 (M+H)$^+$; $^1$H NMR (500 MHz, DMSO-d$_6$) δ 3.59 (s, 3H), 3.94 (s, 3H), 4.04 (s, 2H), 8.14 (s, 1H), 8.55 (s, 1H), 9.27 (s, 1H).

EXAMPLE 44

4-[(2-amino-2-oxoethyl)thio]thieno[2,3-c]pyridine-2-carboxamide

Example 43 was dissolved in 2M methanolic ammonia and warmed to 45° C. in a sealed tube for 18 hours. The precipitate was filtered, washed with methanol-diethyl ether (1:1) and dried under vacuum to provide the title compound.

MS (APCI) m/z 268 (M+H)$^+$; $^1$H NMR (400 MHz, DMSO-d$_6$) δ 3.81 (s, 2H), 7.17 (br s, 1H), 7.59 (br s, 1H), 7.82 (br s, 1H), 8.29 (br s, 1H), 8.46 (s, 1H), 8.52 (br s, 1H), 9.14 (s, 1H).

EXAMPLE 45

4-[(4-bromophenyl)thio]thieno[2,3-c]pyridine-2-carboxamide

Example 17A was processed as in examples 17B and 17C, and 44, but substituting 4-bromothiophenol for p-thiocresol in Example 17B to provide the title compound.

MS (DCI/NH$_3$) m/z 365 (M+H)$^+$; $^1$H NMR (300 MHz, DMSO-d$_6$) δ 7.20 (dt, 2H), 7.53 (dt, 2H), 7.87 (br s, 1H), 8.21 (s, 1H), 8.51 (br s, 1H), 8.54 (s, 1H), 9.36 (s, 1H); Anal. calcd for C$_{14}$H$_9$BrN$_2$OS$_2$: C, 46.04; H, 2.48; N, 7.67. Found: C,45.86; H,2.30; N, 7.51.

EXAMPLE 46

4-(phenylthio)thieno[2,3-c]pyridine-2-carboxamide

Example 17A was processed as in examples 17B, 17C, and 44 but substituting thiophenol for p-thiocresol in Example 17B to provide the title compound.

MS (DCI/NH$_3$) m/z 287 (M+H)$^+$; $^1$H NMR (300 MHz, DMSO-d$_6$) δ 7.29–7.40 (m, 5H), 7.86 (br s, 1H), 8.25 (s, 1H), 8.46 (s, 1H), 8.52 (br s, 1H), 9.31 (s, 1H); Anal. calcd for C$_{14}$H$_{10}$N$_2$OS$_2$: C, 58.72; H, 3.52; N, 9.28. Found: C, 58.62; H, 3.42; N, 9.48.

EXAMPLE 47

4-[[4-(trifluoromethyl)phenyl]thio]thieno[2,3-c]pyridine-2-carboxamide

Example 17A was processed as in examples 17B, 17C, and 44 but substituting α,α,α-trifluorothiocresol for p-thiocresol in Example 17B to provide the title compound.

MS (DCI/NH$_3$) m/z 355 (M+H)$^+$; $^1$H NMR (300 MHz, DMSO-d$_6$) δ 7.31 (d, 2H), 7.65 (d, 2H), 7.85 (br s, 1H), 8.19 (s, 1H), 8.50 (br s, 1H), 8.68 (s, 1H), 9.44 (s 1H); Anal. calcd for C$_{15}$H$_9$F$_3$N$_2$OS$_2$: C,50.84; H, 2.56; N, 7.91. Found: C, 50.63; H, 2.44; N, 7.82.

EXAMPLE 48

4-[(2-methylphenyl)thio]thieno[2,3-c]pyridine-2-carboxamide

Example 17A was processed as in examples 17B and 17C, and 44, but substituting 2-methylthiophenol for p-thiocresol in Example 17B. The residue was purified by column chromatography, eluting with 5% methanol in dichloromethane to provide the title compound.

mp 170–172° C.; MS (DCI/NH$_3$) m/z 301 (M+H)$^+$; $^1$H NMR (300 MHz, DMSO-d$_6$) δ 2.41 (s, 3H), 7.04 (dd, 1H), 7.15 (dt, 1H), 7.27 (dt, 1H), 7.38 (br d, 1H), 7.86 (br s, 1H), 8.20 (s, 1H), 8.23 (s, 1H), 8.53 (br s, 1H), 9.28 (s, 1H); Anal. calcd for C$_{15}$H$_{12}$N$_2$OS$_2$: C, 59.97; H, 4.03; N, 9.33. Found: C, 59.86; H, 4.16; N, 9.11.

EXAMPLE 49

4-[(3-methylphenyl)thio]thieno[2,3-c]pyridine-2-carboxamide

Example 17A was processed as in examples 17B and 17C, and 44, but substituting 3-methylthiophenol for p-thiocresol in Example 17B. The residue was purified by flash chromatography with 5% methanol/dichloromethane to provide the title compound.

mp 171–173° C.; MS (DCI/NH$_3$) m/z 301 (M+H)$^+$; $^1$H NMR (300 MHz, DMSO-d$_6$) δ 2.27 (s, 3H), 7.06–713 (m, 2H), 7.21–7.27 (m, 2H), 7.89 (br s, 1H), 8.26 (s, 1H), 8.42 (s, 1H), 8.55 (br s, 1H), 9.30 (s, 1H); Anal. calcd for C$_{15}$H$_{12}$N$_2$OS$_2$.0.25H$_2$O: C, 59.08; H, 4.13; N, 9.19. Found: C, 59.10; H, 4.16; N, 9.11.

EXAMPLE 50

4-[(3,4-dimethylphenyl)thio]thieno[2,3-c]pyridine-2-carboxamide

Example 17A was processed as in examples 17B and 17C, and 44, but substituting 3,4-dimethylthiophenol for p-thiocresol in Example 17B. The residue was purified by flash chromatography with 5% methanol/dichloromethane to provide the title compound.

mp 192–194° C.; MS (APCI) m/z 315 (M+H)$^+$; $^1$H NMR (300 MHz, DMSO-d$_6$) δ 2.09 (s, 3H), 2.11 (s, 3H), 7.05 (m, 2H), 7.19 (s, 7.81 (br s, 1H), 8.12 (d, 2H), 8.49 (br s, 1H), 9.15 (s, 1H); Anal. calcd for C$_{16}$H$_{14}$N$_2$OS$_2$.0.25H$_2$O: C, 60.25; H, 4.58; N, 8.78. Found: C, 60.34; H, 4.52; N, 8.75.

EXAMPLE 51

4-[(3,5-dimethylphenyl)thio]thieno[2,3-c]pyridine-2-carboxamide

Example 17A was processed as in examples 17B and 17C, and 44, but substituting 3,5-dimethylthiophenol for p-thiocresol in Example 17B. The residue was purified by flash chromatography with 5% methanol/dichloromethane to provide the title compound.

mp 177–179° C.; MS (DCI/NH3) m/z 315 (M+H)$^+$; $^1$H NMR (300 MHz, DMSO-d$_6$) δ 2.13 (s, 6H), 6.83 (s, 3H), 6.92 (s, 1H), 7.81 (br s, 1H), 8.21 (s, 1H), 8.30 (s, 1H), 8.50

(br s, 1H), 9.19 (s, 1H); Anal. calcd for $C_{16}H_{14}N_2OS_2$: C, 61.12; H, 4.49; N, 8.91. Found: C, 60.82; H, 4.48; N, 8.75.

EXAMPLE 52

4-[(2,4-dimethylphenyl)thio]thieno[2,3-c]pyridine-2-carboxamide

Example 17A was processed as in examples 17B and 17C, and 44, but substituting 2,4-dimethylthiophenol for p-thiocresol in Example 17B. The residue was purified by flash chromatography with 5% methanol/dichloromethane to provide the title compound.

mp 193–195° C.; MS (APCI) m/z 315 (M+H)$^+$; $^1$H NMR (300 MHz, DMSO-d$_6$) δ 2.28 (s, 3H), 2.38 (s, 3H), 7.02 (d, 1H), 7.13 (d, 1H), 7.20 (s, 1H), 7.91 (br s, 1H), 8.05 (s, 2H), 8.58 (br s, 1H), 9.22 (s, 1H); Anal. calcd for $C_{16}H_{14}N_2OS_2 \cdot 0.25H_2O$: C, 60.25; H, 4.58; N, 8.78. Found: C, 60.40; H, 4.52; N, 8.72.

EXAMPLE 53

4-[(2-methyl-3-furanyl)thio]thieno[2,3-c]pyridine-2-carboxamide

Example 17A was processed as in examples 17B and 17C, and 44, but substituting 2-methyl-3-furanthiol for p-thiocresol in Example 17B. The residue was purified by flash chromatography with 5% methanol/dichloromethane to provide the title compound.

mp 236–239° C. (decomposes); MS (ESI) m/z 291 (M+H)$^+$; $^1$H NMR (300 MHz, DMSO-d$_6$) δ 2.41 (s, 3H), 6.68 (d, 1H), 7.74 (d, 1H), 7.93 (br s, 1H), 8.19 (s, 1H), 8.38 (s, 1H), 8.60 (br s, 1H), 9.15 (s, 1H); Anal. calcd for $C_{13}H_{10}N_2O_2S_2 \cdot 0.25H_2O$: C, 52.95; H, 3.59; N, 9.50. Found: C, 52.57; H, 3.41; N, 9.30.

EXAMPLE 54

4-[[(4-chlorophenyl)methyl]thio]thieno[2,3-c]pyridine-2-carboxamide

Example 17A was processed as in examples 17B and 17C, and 44, but substituting 4-chlorobenzylmercaptan for p-thiocresol in Example 17B. The residue was purified by flash chromatography with 5% methanol/dichloromethane to provide the title compound.

mp 198–199° C.; MS (APCI) m/z 335 (M+H)$^+$; $^1$H NMR (300 MHz, DMSO-d$_6$) δ 4.40 (s, 2H), 7.31 (s, 4H), 7.86 (br s, 1H), 8.26 (s, 1H), 8.41 (s, 1H), 8.52 (br s, 1H), 9.15 (s, 1H); Anal. calcd for $C_{15}H_{11}ClN_2OS_2$: C, 53.80; H, 3.31; N, 8.37. Found: C, 53.52; H, 3.18; N, 8.31.

EXAMPLE 55

4-[(3,4-dichlorophenyl)thio]thieno[2,3-c]pyridine-2-carboxamide

Example 17A was processed as in examples 17B and 17C, and 44, but substituting 3,4-dichlorothiophenol for p-thiocresol in Example 17B. The residue was purified by flash chromatography with 5% methanol/dichloromethane to provide the title compound.

MS (ESI) m/z 355 (M+H)$^+$; $^1$H NMR (300 MHz, DMSO-d$_6$) δ 7.10 (dd, 1H), 7.55 (d, 1H), 7.59 (d, 1H), 7.91 (br s, 1H), 8.21 (s, 1H), 8.53 (br s, 1H), 8.62 (s, 1H), 9.41 (s, 1H); Anal. calcd for $C_{14}H_8Cl_2N_2OS_2$: C, 47.33; H, 2.27; N, 7.89. Found: C, 47.34; H, 2.52; N, 8.05.

EXAMPLE 56

4-[(4-methoxyphenyl)thio]thieno[2,3-c]pyridine-2-carboxamide

Example 17A was processed as in examples 17B and 17C, and 44, but substituting 4-methoxythiophenol for p-thiocresol in Example 17B. The residue was purified by flash chromatography with 5% methanol/dichloromethane to provide the title compound.

mp 219–221° C.; MS (ESI) m/z 317 (M+H)$^+$; $^1$H NMR (300 MHz, DMSO-d$_6$) δ 3.76 (s, 3H), 6.99 (d, 2H), 7.46 (d, 2H), 7.89 (br s, 1H), 8.17 (s, 1H), 8.30 (s, 1H), 8.54 (br s, 1H), 9.18 (s, 1H); Anal. calcd for $C_{15}H_{12}N_2O_2S_2$: C, 56.94; H, 3.82; N, 8.85. Found: C, 56.80; H, 3.78; N, 8.79.

EXAMPLE 57

4-(cyclohexylthio)thieno[2,3-c]pyridine-2-carboxamide

Example 17A was processed as in examples 17B and 17C, and 44, but substituting cyclohexylmercaptan for p-thiocresol in Example 17B. The residue was purified by flash chromatography with 5% methanol/dichloromethane to provide the title compound.

mp 205–207° C.; MS (ESI) m/z 293 (M+H)$^+$; $^1$H NMR (300 MHz, DMSO-d$_6$) δ 1.14–1.43 (br m, 6H), 1.51–1.61 (br m, 1H), 1.66–1.78 (br m, 2H), 1.83–1.98 (br m, 2H), 7.90 (br s, 1H), 8.33 (s, 1H), 8.52 (s, 1H), 8.57 (br s, 1H), 9.22 (s, 1H); Anal. calcd for $C_{14}H_{16}N_2OS_2$: C, 57.50; H, 5.51; N, 9.58. Found: C, 57.53; H, 5.39; N, 9.51.

EXAMPLE 58

4-[(4-methlphenyl)thio]-N-[3-(4-morpholinyl)propyl]thieno[2,3-c]pyridine-2-carboxamide, trifluoromethylacetate (salt)

Example 17C (200 mg, 0.635 mmol) in 9:1 4-(3-aminopropyl)morpholine/acetic acid (2 mL) was warmed at 70° C. for 4 hours, diluted with acetonitrile (6 mL), and purified by C-18 reverse phase HPLC with a gradient of 20% acetonitrile/water to 100% CH$_3$CN containing 0.1% trifluoroacetic acid to provide the title compound.

MS (APCI) m/z 428 (M+H)$^+$; $^1$H NMR (400 MHz, DMSO-d$_6$) δ 1.95 (m, 2H), 3.08 (m, 2H), 3.18 (m, 2H), 3.36 (m, 2H), 3.43 (m, 2H), 3.68 (m, 4H), 7.20 (d, 2H), 7.28 (d, 2H), 8.0 (br s, 1H), 8.27 (s, 1H), 8.34 (m, 1H), 9.27 (m, 1H).

EXAMPLE 59

4-[(4-methylphenyl)sulfinyl]thieno[2,3-c]pyridine-2-carboxamide

EXAMPLE 59A

Methyl 4-[(4-methylphenyl)sulfinyl]thieno[2,3-c]pyridine-2-carboxylate

A solution of Example 17C (144 mg, 0.46 mmol) in dichloromethane (10 mL) at 0° C. was treated with 3-chloroperoxybenzoic acid (57–86%, 82 mg), warmed to room temperature over 4 hours, treated with dichloromethane (50 mL), washed sequentially with 1N NaOH, water, and brine, dried (MgSO$_4$), filtered, and concentrated. The residue was purified by flash chromatography on silica gel with 50% ethyl acetate/hexane to provide the title compound.

MS (DCI/NH$_3$) m/z 332 (M+H)$^+$; $^1$H NMR (300 MHz, DMSO-d$_6$) δ 2.25 (s, 3H), 3.84 (s, 3H), 7.38 (d, 2H), 7.65 (d, 2H), 8.41 (s, 1H), 9.0 (s, 1H), 9.58 (s, 1H).

EXAMPLE 59B

4-[(4-methylphenyl)sulfinyl]thieno[2,3-c]pyridine-2-carboxamide

Example 59A was processed as in Example 44 to provide the title compound.

MS (DCI/NH$_3$) m/z 317 (M+H)$^+$; $^1$H NMR (300 MHz, DMSO-d$_6$) δ 2.31 (s, 3H), 7.38 (d, 2H), 7.79 (d, 2H), 7.94 (br s, 1H), 8.43 (s, 1H), 8.62 (br s, 1H), 8.85 (s, 1H), 9.43 (s, 1H).

EXAMPLE 60

4-(4-methylphenoxy)thieno[2,3-c]pyridine-2-carboxamide

EXAMPLE 60A methyl 4-(4-methylphenoxy)thieno[2,3-c]pyridine-2-carboxylate

Example 17A was processed as in examples 17B and 17C, but substituting p-cresol for p-thiocresol in Example 17B to provide the title compound.

mp 96–98° C.; MS (DCI/NH$_3$) m/z 317 (M+NH$_4$)$^+$, 300 (M+H)$^+$; $^1$H NMR (300 MHz, DMSO-d$_6$) δ 2.32 (s, 3 H), 3.91 (s, 3 H), 7.05 (m, 2 H), 7.24 (m, 2 H), 7.95 (s, 1 H), 8.12 (s, 1 H), 9.17 (s, 1 H); Anal. calcd for C$_{16}$H$_{13}$NO$_3$S: C, 64.19; H, 4.37; N, 4.67. Found: C, 64.05; H, 4.34 N, 4.52.

EXAMPLE 60B 4-(4-methylphenoxy)thieno[2,3-c]pyridine-2-carboxamide

Example 60A was processed as in examples 18 and 19 to provide the title compound.

mp 196–197° C.; MS (DCI/NH$_3$) m/z 285 (M+H)$^+$, 302 (M+NH$_4$)$^+$; $^1$H NMR (300 MHz, DMSO-d$_6$) δ 2.31 (s, 3H), 7.04 (m, 2 H), 7.25 (m, 2 H), 7.82 (br s, 1 H), 8.00 (s, 1 H), 8.21 (s, 1 H), 8.42 (br s, 1 H) 9.07 (s, 1 H); Anal. calcd for C$_{15}$H$_{12}$N$_2$O$_2$S. C, 63.36; H, 4.25; N, 9.85. Found: C, 63.29; H, 4.28 N, 9.68.

EXAMPLE 61

4-(4-chlorophenoxy)thieno[2,3-c]pyridine-2-carboxamide

EXAMPLE 61A methyl 4-(4-chlorophenoxy)thieno[2,3-c]pyridine-2-carboxylate

A solution of 4-chlorophenol (2.63 g, 20.5 mmol) in THF (20 mL) at 0° C. was treated dropwise with a solution of potassium tert-butoxide (1.0 M solution in THF, 20.4 mL, 20.5 mmol), stirred at 25° C. for 1 hour, cooled to 0° C., treated with a solution of Example 17A (3.54 g, 20.23 mmol) in THF (40 mL), warmed at 60° C. for 0.5 hours, cooled to 0° C., treated with methylthioglycolate (1.989 mL, 22.25 mmol) and Cs$_2$CO$_3$ (6.59 g, 20.23 mmol), warmed at 60° C. for 0.25 hours, cooled to room temperature and filtered. The filtrate was diluted with ethyl acetate, washed sequentially with water and brine, dried (MgSO$_4$), filtered, and concentrated. Purification of the residue by flash chromatography on silica gel with 4% acetone/hexane provided the title compound.

mp 99–100° C.; MS (APCI) m/z 320 (M+H)$^+$; $^1$H NMR (300 MHz, DMSO-d$_6$) δ 3.91 (s, 3H, OCH$_3$), 7.14 (d, 2H), 7.48 (d, 2H), 7.95 (s, 1H), 8.23 (s,1H), 9.23 (s, 1H); $^{13}$C NMR (100 MHz, DMSO-d$_6$) δ 56.45 (OCH$_3$), 120.19 (CH), 123.06 (Ar—CH), 128.04 (Ar—CH), 131.34 (C), 132.37 (Ar—CH), 133.38 (Ar—CH), 136.40 (Ar—CH), 139.38 (C), 141.75 (C), 142.09 (C), 144.89 (Ar—CH), 150.91 (C), 158.64 (C), 164.95 (CO); Anal. calcd for C$_{15}$H$_{10}$ClNO$_3$S: C, 56.34; H, 3.15; N, 4.38. Found: C, 56.23; H, 3.16; N, 4.38.

EXAMPLE 61B 4-(4-chlorophenoxy)thieno[2,3-c]pyridine-2-carboxamide

Example 61A was processed as in Example 44 to provide the title compound.

mp 176–177° C.; MS (DCI/NH$_3$) m/z 305 (M+H)$^+$; $^1$H NMR (300 MHz, DMSO-d$_6$) δ 7.15 (m, 2H), 7.50 (m, 2H), 7.95 (b, 2H), 8.25 (d, 2H), 8.45 (b, 1H), 9.15 (s, 1H); Anal. calcd for C$_{14}$H$_9$ClN$_2$O$_2$S.0.25H$_2$O: C, 54.37; H, 3.10; N, 9.06. Found: C, 54.44; H, 2.74; N, 9.06.

EXAMPLE 62

4-[4-(trifluoromethyl)phenoxy]thieno[2,3-c]pyridine-2-carboxamide

Example 17A was processed as in Example 61 but substituting 4-(trifluoromethyl)phenol for 4-chlorophenol to provide the title compound.

MS (DCI/NH$_3$) m/z 339 (M+H)$^+$; $^1$H NMR (300 MHz, DMSO-d$_6$) δ 7.24 (d, 2H), 7.77 (d, 2H), 7.88 (br s, 1H), 8.10 (s, 1H), 8.33 (s, 1H), 8.45 (br s, 1H), 9.24 (s, 1H); Anal. calcd for C$_{15}$H$_9$F$_3$N$_2$O$_2$S: C,53.26; H, 2.68; N, 8.28. Found: C, 53.06; H, 2.55; N, 8.19.

EXAMPLE 63

4-(4-octylphenoxy)thieno[2,3-c]pyridine-2-carboxamide

Example 17A and 4-octylphenol were processed as in Example 61 to provide the title compound.

MS (DCI/NH$_3$) m/z 383 (M+H)$^+$; $^1$H NMR (300 MHz, CDCl$_3$) δ 0.88 (t, 3H), 1.22–1.38 (m, 10H), 1.62 (m, 2H), 2.61 (t, 2H), 6.05 (br s, 2H), 6.99 (d, 2H), 7.20 (d, 2H), 7.87 (s, 1H), 8.07 (br s, 1H), 8.92 (br s, 1H); Anal. calcd for C$_{22}$H$_{26}$N$_2$O$_2$S: C, 69.08; H, 6.85; N, 7.32. Found: C, 69.04; H, 6.82; N, 7.22.

EXAMPLE 64

4-[4-(1-methylethyl)phenoxy]thieno[2,3-c]pyridine-2-carboxamide

Example 17A and 4-(1-methylethyl)phenol were processed as in Example 61 to provide the tide compound.

MS (DCI/NH$_3$) m/z 313 (M+H)$^+$; $^1$H NMR (300 MHz, DMSO-d$_6$) δ 1.21 (d, 6H), 2.92 (septet, 1H), 7.05 (d, 2H), 7.30 (d, 2H), 7.82 (br s, 2H), 8.03 (s, 2H), 8.21 (s, 2H), 8.44 (br s, 1H), 9.09 (s, 1H).

EXAMPLE 65

4-(2-bromo-4-chlorophenoxy)thieno[2,3-c]pyridine-2-carboxamide

Example 17A and 2-bromo-4-chlorophenol were processed as in Example 61 to provide the title compound.

MS (DCI/NH$_3$) m/z 383 (M+H)$^+$; $^1$H NMR (300 MHz, DMSO-d$_6$) δ 7.18 (d, 1H), 7.49 (dd, 1H), 7.90 (br s, 1H), 7.98 (s 2H), 8.23 (s, 1H), 8.49 (br s, 1H), 9.14 (s, 1H); Anal. calcd for C$_{14}$H$_8$BrClN$_2$O$_2$S: C, 43.83; H, 2.10; N, 7.30. Found: C, 43.53; H, 1.97; N, 6.99.

EXAMPLE 66

4-(4-ethylphenoxy)thieno[2,3-c]pyridine-2-carboxamide

Example 17A and 4-ethylphenol were processed as in Example 61 to provide the title compound.

MS (DCI/NH$_3$) m/z 299 (M+H)$^+$; $^1$H NMR (300 MHz, DMSO-d$_6$) δ 1.19 (t, 3H), 2.62 (q, 2H), 7.05 (dt, 2H), 7.26 (dt, 2H), 7.81 (br s, 1H), 8.07 (s, 1H), 8.21 (s, 1H), 8.43 (br s, 1H), 9.08 (s, 1H); Anal. calcd for C$_{16}$H$_{14}$N$_2$O$_2$S.CH$_3$OH: C, 63.71; H, 4.69; N, 9.14. Found: C, 63.34; H, 4.51; N, 9.51.

EXAMPLE 67

4-(4-ethenylphenoxy)thieno[2,3-c]pyridine-2-carboxamide

EXAMPLE 67A

4-Vinylphenol

A solution of 4-vinylphenol in propylene glycol was treated with water and extracted with diethyl ether in order to remove the propylene glycol and provide the designated compound in diethyl ether.

EXAMPLE 67B

4-(4-ethenylphenoxy)thieno[2,3-c]pyridine-2-carboxamide

Example 17A and Example 67A were processed as in Example 61 to provide the title compound.

MS (DCI/NH$_3$) m/z 297 (M+H)$^+$; $^1$H NMR (300 MHz, DMSO-d$_6$) δ 5.24 (d, 1H), 5.79 (d, 1H), 6.75 (dd, 1H), 7.10 (d, 2H), 7.54 (d, 2H), 7.87 (br s, 1H), 8.12 (s, 1H), 8.18 (s, 1H), 8.45 (br s, 1H), 9.13 (s, 1H); Anal. calcd for C$_{16}$H$_{12}$N$_2$O$_2$S.0.25CH$_3$OH: C, 64.13; H, 4.06; N, 9.20. Found: C, 64.40; H, 4.12; N, 9.27.

EXAMPLE 68

4-[4-(1,2-dihydroxyethyl)phenoxy]thieno[2,3-c]pyridine-2-carboxamide

A solution of Example 67B (35 mg, 0.118 mmol) in pyridine (5 mL) was treated with OsO$_4$ (90 mg, 0.354 mmol), stirred for 5 hours, treated with 10% aqueous NaHSO$_3$, stirred for 5 hours, treated with brine, and extracted with ethyl acetate. The extract was dried (MgSO$_4$), filtered, and concentrated. The residue was purified by flash chromatography on silica gel with 1:10 methanol/dichloromethane to provide the title compound.

MS (DCI/NH$_3$) m/z 331 (M+H)$^+$; $^1$H NMR (300 MHz, DMSO-d$_6$) δ 3.44 (t, 2H), 4.55 (q, 1H), 4.73 (t, 2H), 5.27 (d, 1H), 7.08 (d, 2H), 7.39 (d, 2H), 7.85 (br d, 1H), 8.03 (s, 1H), 8.21 (s, 1H), 8.47 (br s, 1H), 9.10 (s, 1H); Anal. calcd for C$_{16}$H$_{14}$N$_2$O$_4$S.0.25CH$_3$OH: C, 57.68; H, 4.24; N, 8.28. Found: C, 57.92; H, 4.35; N, 8.24.

EXAMPLE 69

4-[2-(2-propyenyl)phenoxy]thieno[2,3-c]pyridine-2-carboxamide

Example 17A and 2-allylphenol were processed as in Example 61 to provide the title compound.

MS (DCI/NH$_3$) m/z 311 (M+H)$^+$; $^1$H NMR (300 MHz, DMSO-d$_6$) δ 3.43 (d, 2H), 5.01 (m, 1H), 5.05 (m, 1H), 5.98 (m, 1H), 7.00 (dd, 1H), 7.27 (m, 2H), 7.39 (dd, 1H), 7.82 (s, 1H), 7.88 (br s, 1H), 8.27 (s, 1H), 8.49 (br s, 1H), 9.05 (s, 1H); Anal. calcd for C$_{17}$H$_{14}$N$_2$O$_2$S: C, 65.79; H, 4.55; N, 9.03. Found: C, 65.53; H, 4.37; N, 8.95.

EXAMPLE 70

4-[2-(2,3-dihydroxypropyl)phenoxy]thieno[2,3-c]pyridine-2-carboxamide

Example 69 was processed as in Example 68 to provide the title compound.

MS (DCI/NH$_3$) m/z 345 (M+H)$^+$; $^1$H NMR (300 MHz, DMSO-d$_6$) δ 2.60 (dd, 1H), 2.88 (dd, 1H), 3.29 (t, 2H), 3.76 (m, 1H), 4.55 (t, 1H), 4.63 (d, 1H), 6.94 (dd, 1H), 7.22 (m, 2H), 7.45 (dd, 1H), 7.84 (s, 1H), 7.88 (br s, 1H), 8.26 (s, 1H), 8.46 (br s, 1H), 9.04 (s, 1H); Anal. calcd for C$_{17}$H$_{16}$N$_2$O$_4$S: C, 59.29; H, 4.68; N, 8.13. Found: C, 59.16; H, 4.51; N, 8.06.

EXAMPLE 71

4-[4-(trifluoromethyl)phenoxy]thieno[2,3-c]pyridine-2-carboxamide, 1-oxide

A solution of Example 62 (26 mg, 0.077 mmol) in (1 mL) and dichloromethane (5 mL), at 0° C. was treated with m-CPBA (80–85%, 30 mg, 0.14 mmol), stirred at 0° C. for 1 hour, and at room temperature for 10 hours. The precipitate that formed was collected by filtration and washed with dichloromethane. HPLC analysis of the material (C-18, reverse phase) showed a mixture of desired sulfoxide and starting thiephene in a 8:1 ratio. The mixture was recrystallized from DMF/methanol/dichloromethane to provide the title compound (97.5% pure by HPLC analysis).

MS (HPCI/NH$_3$) m/z 355 (M+H)$^+$; $^1$H NMR (300 MHz, DMSO-d$_6$) δ 7.39 (d, 2H), 7.79 (br s, 1H), 7.81 (d, 2H), 8.02 (s, 1H), 8.05 (d, 1H), 8.36 (br s, 1H), 9.02 (s, 1H); Anal. calcd for C$_{15}$H$_9$F$_3$NO$_3$S.0.25CH$_3$OH: C,50.55; H, 2.57; N, 7.73. Found: C, 50.55; H, 2.59; N, 7.69.

EXAMPLE 72

4-[3-(pentadecyl)phenoxy]thieno[2,3-c]pyridine-2-carboxamide

Example 17A and 3-pentadecylphenol were processed as in Example 61 to provide the title compound.

MS (DCI/NH$_3$) m/z 481 (M+H)$^+$; $^1$H NMR (300 MHz, DMSO-d$_6$) δ 0.84 (t, 3H), 1.20–1.28 (m, 24H), 1.54 (m, 2H), 2.57 (t, 2H), 6.92 (m, 1H), 6.97 (t, 1H), 7.03 (d, 1H), 7.33 (t, 1H), 7.85 (br s, 1H), 8.03 (s, 1H), 8.23 (s, 1H), 8.44 (br s, 1H), 9.09 (s, 1H); Anal. calcd for C$_{29}$H$_{40}$N$_2$O$_2$S: C, 72.46; H, 8.39; N, 5.83. Found: C, 72.69; H, 8.18; N, 5.47.

EXAMPLE 73

Methyl 4-(4-Bromophenoxy)thieno[2,3-c]pyridine-2-carboxylate

To a solution of 4-bromophenol (4.94 g., 28.55 mmol) in anhydrous tetrahydrofuran (10 mL) under nitrogen atmosphere was added dropwise a solution of potassium t-butoxide (1 M solution in THF, 28.6 mL, 28.6 mmol). The reaction mixture was stirred at ambient temperature for 30 minutes, then a solution of Example 17A (2 g, 11.4 mmol) in anhydrous tetrahydrofuran (20 mL) was added and refluxed for 8 hours. The reaction mixture was allowed to cool to 25° C., methyl thioglycolate (1.23 mL, 13.7 mmol) was added and refluxed for 15 minutes. The cooled reaction mixture was diluted with ethyl acetate (300 mL) and partitioned with an ice cold solution of 1 N NaOH (3×75 mL). The organic layer was washed with brine (3×100 mL), dried (MgSO$_4$) and solvents were removed under reduced pressure to obtain the crude product (4.2 g). This was purified by flash chromatography on silica gel eluting with 10% acetone-hexane to obtain the title compound (1.81 g) in 44% yield.

$^1$H NMR (300 MHz, DMSO-d$_6$) δ 3.91 (s, 3H), 7.10 (d, J=9 Hz, 2H), 7.59 (d, J=9 Hz, 2H), 7.94 (s, 1H), 8.25 (s, 1H), 9.24 (s, 1H); MS (APCI) m/e 364;366 (M+H)$^+$.

EXAMPLE 74

4-(3-chlorophenoxy)thieno[2,3-c]pyridine-2-carboxamide

Example 17A and 3-chlorophenol were processed as in Example 61 to provide the title compound.

MS (DCI/NH$_3$) m/z 305 (M+H)$^+$; $^1$H NMR (300 MHz, DMSO-d$_6$) δ 7.10 (m, 1H), 7.30 (m, 2H), 7.45 (b, 1H), 7.95 (b, 1H), 8.20 (d, 1H), 8.30 (s, 1H), 8.6 (b, 1H), 9.30 (s, 1H).

EXAMPLE 75

4-(4-t-butylphenoxy)thieno[2,3-c]pyridine-2-carboxamide

Example 17A and 4-tert-butylphenol were processed as in Example 61 to provide the title compound.

MS (DCI-NH$_3$) m/z 327 (M+H)$^+$; $^1$H NMR (300 MHz, DMSO-d$_6$) δ 1.3 (s, 9H), 7.10 (d, 2H), 7.45 (d, 2H), 7.85 (br s, 1H), 8.05 (s, 1H), 8.20 (s, 1H), 8.45 (br s, 1H), 9.1 (s, 1H).

EXAMPLE 76

4-(4-chloro-3-methylphenoxy)thieno[2,3-c]pyridine-2-carboxamide

Example 17A and 4-chloro-3-methylphenol were processed as in Example 61 to provide the title compound.

MS (DCI/NH$_3$) m/z 319 (M+H)$^+$; $^1$H NMR (300 MHz, DMSO-d$_6$) δ 2.30 (s, 3H), 6.95 (dd, 1H), 7.20 (d, 1H), 7.45 (d, 1H), 7.85 (br s, 1H), 8.15 (s, 1H), 8.19 (s, 1H), 8.45 (br s, 1H), 9.15 (s, 1H).

EXAMPLE 77

4-(4-chloro-2-methylphenoxy)thieno[2,3-c]pyridine-2-carboxamide

Example 17A and 4-chloro-2-methylphenol were processed as in Example 61 to provide the title compound.

MS (DCI/NH$_3$) m/z 319 (M+H)$^+$; $^1$H NMR (300 MHz, DMSO-d$_6$) δ 2.30 (s, 3H), 6.95 (dd, 1H), 7.30 (d, 1H), 7.50 (d, 1H), 7.85 (br s, 1H), 7.95 (s, 1H), 8.25 (s, 1H), 8.45 (br s, 1H), 9.15 (s, 1H).

EXAMPLE 78

4-(4-methoxyphenoxy)thieno[2,3-c]pyridine-2-carboxamide

Example 17A and 4-methoxyphenol were processed as in Example 61 to provide the title compound.

MS (DCI/NH$_3$) m/z 301 (M+H)$^+$; $^1$H NMR (300 MHz, DMSO-d$_6$) δ 3.78 (s, 3H), 7.00 (dd, 2H), 7.15 (d, 2H), 7.85 (b, 1H), 7.90 (s, 1H), 8.30 (s, 1H), 8.45 (b, 1H), 9.05 (s, 1H).

EXAMPLE 79 ethyl 3-[[2-(aminocarbonyl)thieno[2,3-c]pyridin-4-yl]oxy]benzoate

Example 17A and ethyl 3-hydroxybenzoate were processed as in Example 61 to provide the title compound.

MS (DCI/NH$_3$) m/z 343 (M+H)$^+$; $^1$H NMR (300 MHz, DMSO-d$_6$) δ 1.30 (t, 3 H), 4.30 (s, 3 H), 7.40 (dd, 1 H), 7.60 (m, 2 H), 7.80 (dd, 1H), 7.85 (b,1H), 8.15 (s, 1 H), 8.20 (s, 1 H), 8.42 (b,1H), 9.17 (s,1H).

EXAMPLE 80

4-phenoxythieno[2,3-c]pyridine-2-carboxamide

Example 17A and phenol were processed as in Example 61 to provide the title compound.

MS (DCI/NH$_3$) m/z 271 (M+H)$^+$; $^1$H NMR (300 MHz, DMSO-d$_6$) δ 7.15 (dd, 2H), 7.20 (t, 1H), 7.45 (t, 2H), 7.85 (b, 1H), 8.10 (s, 1H), 8.20 (s, 1H), 8.45 (b, 1H), 9.15 (s, 1H).

EXAMPLE 81

4-(3-bromophenoxy)thieno[2,3-c]pyridine-2-carboxamide

Example 17A and 3-bromophenol were processed as in Example 61 to provide the title compound.

MS (DCI/NH$_3$) m/z 349, 351 (M+H)$^+$; $^1$H NMR (300 MHz, DMSO-d$_6$) δ 7.07 (dt, 2 Hz, 1H), 7.36–7.39 (m, 3H), 7.87 (br s, 1H), 8.15 (s, 1H), 8.20 (s, 1H), 8.45 (br s, 1H), 9.17 (s, 1H); Anal calcd for C$_{14}$H$_9$N$_2$O$_2$S.CH$_3$OH: C, 47.26; H, 2.64; N, 7.35. Found: C, 47.26; H, 3.21; N, 7.29.

EXAMPLE 82

4-(4-fluorophenoxy)thieno[2,3-c]pyridine-2-carboxamide

Example 17A and 4-fluorophenol were processed as in Example 61 to provide the title compound.

MS (DCI/NH$_3$) m/z 289 (M+H)$^+$; $^1$H NMR (300 MHz, DMSO-d$_6$) δ 7.25 (m, 4 H), 7.85 (b, 1H), 8.05 (s, 1H), 8.20 (s, 1 H), 8.42 (b, 1H), 9.10 (s, 1H).

EXAMPLE 83

4-(3,5-dimethylphenoxy)thieno[2,3-c]pyridine-2-carboxamide

Example 17A and 3,5-dimethylphenol were processed as in Example 61 to provide the title compound.

MS (DCI/NH$_3$) m/z 299 (M+H)$^+$; $^1$H NMR (300 MHz, DMSO-d$_6$) δ 3.30 (s, 6H), 6.75 (s, 2H), 6.85 (s, 1H), 7.80 (b, 1H), 8.05 (s, 1H), 8.18 (s, 1H), 8.45 (b, 1H), 9.10 (s,1H).

EXAMPLE 84

4-(3-chloro-4-methylphenoxy)thieno[2,3-c]pyridine-2-carboxamide

Example 17A and 3-chloro-4-methylphenol were processed as in Example 61 to provide the title compound.

MS (DCI-NH$_3$) m/z 319 (M+H)$^+$; $^1$H NMR (300 MHz, DMSO-d$_6$) δ 2.35 (s, 3H), 7.00 (dd, 1H), 7.25 (d, 1H), 7.45 (d, 1H); 7.85 (b, 1H), 8.15 (s, 1H), 8.20 (s, 1H), 8.45 (b, 1H), 9.15 (s, 1H).

EXAMPLE 85

4-(4-iodophenoxy)thieno[2,3-c]pyridine-2-carboxamide

Example 17A and 4-iodophenol were processed as in Example 61 to provide the title compound.

MS (DCI/NH$_3$) m/z 397 (M+H)$^+$; $^1$H NMR (300 MHz, DMSO-d$_6$) δ 6.94 (d, 2H), 7.74 (d, 2H), 7.86 (br s, 1H), 8.13 (s, 1H), 8.17 (s, 1H), 8.44 (br s, 1H), 9.16 (s, 1H); Anal calcd for C$_{14}$H$_9$IN$_2$O$_2$S: C, 42.44; H, 2.29; N, 7.07. Found: C, 42.58; H, 2.27; N, 7.08.

EXAMPLE 86

4-(4-(methoxymethyl)phenoxy)thieno[2,3-c]pyridine-2-carboxamide

Example 17A and 4-(methoxymethyl)phenol were processed as in Example 61 to provide the title compound.

mp 168–168.5° C. MS (DCI/NH$_3$) m/z 315 (M+H)$^+$; $^1$H NMR (300 MHz, DMSO-d$_6$) δ 3.30 (s, 3H), 4.41 (s, 2H), 7.10 (d, 2H), 7.37 (d, 2H), 7.86 (s, 1H), 8.08 (s, 1H), 8.19 (s, 1H), 8.45 (br s, 1H), 9.12 (s, 1H).

EXAMPLE 87

2-(aminocarbonyl)-4-(4-chlorophenoxy)thieno[2,3-c]pyridinium, iodide

Example 61 (0.11 g, 0.0033 mole) was treated with methyl iodide (0.2 mL, 0.0033 mmol) at reflux for 2 hours and filtered. The precipitate was washed with ether, dried, and recrystallized from acetonitrile to provide the title compound.

MS (DCI/NH$_3$) m/z 305 (M+H)$^+$; $^1$H NMR (300 MHz, DMSO-d$_6$) δ 4.40 (s, 3H), 7.40 (dd, 2H), 7.65 (dd, 2H), 8.25 (br 1H), 8.55 (s, 1H), 8.65 (s, 1H), 8.70 (br s, 1H), 9.70 (s, 1H).

EXAMPLE 88

4-(4-chlorophenoxy)thieno[2,3-c]pyridine-2-carboxylic acid

Example 61A (354 mg, 1.11 mmol), lithium hydroxide monohydrate (98 mg, 2,33 mmol) in 3:1 methanol/water (4 mL) was stirred at room temperature for 20 hours, acidified with 90% formic acid (0.13 mL), and filtered to provide the title compound.

MS (DCI/NH$_3$) m/z 306, 308 (M+H)$^+$; $^1$H NMR (300 MHz, DMSO-d$_6$) δ 7.26 (m, 2H), 7.47 (m, 2H), 7.83 (s, 1H), 8.23 (s, 1H), 9.21 (s, 1H); Anal. calcd for C$_{14}$H$_8$ClNO$_3$S: C, 55.00; H, 2.64; N, 4.58. Found: C, 54.77; H, 2.60; N, 4.44.

EXAMPLE 89

N-(4-(4-chlorotphenoxy)thieno[2,3-c]pyridin-2-yl)-O-(3-tetrahydrofuranyl)carbamate A suspension of Example 88 (100 mg, 0.327 mmol) in toluene (2 mL) was treated with ethyldiisopropylamine (63 mg, 0.49 mmol) and diphenylphosphorylazide (109 mg, 0.394 mmol) at 63° C., stirred for 1, treated with (±)-3-hydroxytetrahydrofuran (130 mg, 1.47 mmol) at 110° C., stirred for 18 hours, and concentrated. The residue was purified by flash chromatography on silica gel with 30% ethyl acetate/hexane and recrystallized from ethyl acetate to provide the title compound.

mp 194–201; MS (APCI) m/z 391 (M+H)$^+$; $^1$H NMR (300 MHz, DMSO-d$_6$) δ 1.93–2.04 (m, 1H), 2.13–2.28 (m, 1H), 3.29–3.34 (m, 1H plus HOD), 3.70–3.86 (m, 4H), 5.33 (m, 1H), 6.56 (s, 1H), 7.02 (dt, 2H), 7.43 (dt, 2H), 8.14 (s, 1H), 8.91 (s, 1H); Anal. calcd for C$_{18}$H$_{15}$ClN$_2$O$_4$S: C, 55.32; H, 3.87; N, 7.17. Found: C, 55.08; H, 3.69; N, 7.05.

EXAMPLE 90

4-(4-chlorolphenoxy)thieno[2,3-c]pyridine-2-methanol

A solution of Example 61A (254 mg, 0.793 mmol) in absolute ethanol (4 mL) was treated with anhydrous CaCl$_2$ (177 mg, 1.59 mmol), stirred for 1 hour, cooled to 0° C., treated with NaBH$_4$ (123 mg, 3.25 mmol), stirred at 0° C. for 4 hours and at room temperature for 18 hours, treated with water and extracted with dichloromethane. The extract was washed with brine, dried (Na$_2$SO$_4$), filtered and concentrated. The residue was purified on silica gel with 30% ethyl acetate/hexane to provided the title compound.

mp 90–91° C.; MS (APCI) m/z 292, 294 (M+H)$^+$; $^1$H NMR (300 MHz, CDCl$_3$) δ 2.2–2.65 (vbr s, 1H), 4.97 (d, 2H), 6.95 (dt, 2H), 7.43 (m, 1H), 7.31 (dt, 2H), 8.13 (s, 1H), 8.89 (s, 1H); Anal. calcd for C$_{14}$H$_{10}$ClNO$_2$S: C, 57.64; H, 3.45; N, 4.80. Found: C, 57.50; H, 3.58; N, 4.66.

EXAMPLE 91

(E)-3-[4-(4-chlorophenoxy)thieno[2,3-c]pyridin-2-yl]-2-propenoic acid

EXAMPLE 91A 4-(4-chlorophenoxy)thieno[2,3-c]pyridine-2-carboxaldehyde

A solution of DMSO (77 mg, 0.99 mmol) in 1.7 mL dichloromethane at −78° C. was treated dropwise with oxalyl chloride (109 mg, 0.86 mmol), stirred for 5 minutes, treated dropwise with Example 90 (123 mg, 0.420 mmol) in 2 mL dichloromethane, stirred at −78° C. for 1 hour, treated with ethyldiisopropylamine (326 mg, 2.53 mmol) warmed to −20° C., stiffed 1.5 hours and partitioned between 10 mL dichloromethane and 5 mL water, and extracted. The extract was washed with water (5 mL) and brine (5 mL), dried (Na$_2$SO$_4$), and filtered. The residue was rotoevaporated and dried under high vacuum to provide the title compound.

MS (APCI) m/z 290, 292 (M+H)$^+$.

EXAMPLE 91B (E)-methyl 3-[4-(4-chlorolphenoxy)thieno[2,3-c]pyridin-2-yl]-2-propenoate Example 91A (138 mg, 0.42 mmol) and methyl triphenylphosphoranylidene acetate (210 mg, 0.628 mmol) in dichloroethane (2 mL) was stirred at 65° C. for 3 hours and concentrated. The residue was purified by flash chromatography on silica gel with 25% ethyl acetate/hexane to provide the title compound.

MS (APCI) m/z 346, 348 (M+H)$^+$; $^1$H NMR (300 MHz, CDCl$_3$) δ 3.83 (s, 3H), 6.43 (d, 1H), 7.00 (dt, 2H), 7.35 (dt, 2H), 7.48 (s, 1H), 7.84 (d, 1H), 8.11 (s, 1H), 8.88 (s, 1H); Anal. calcd for C$_{17}$H$_{17}$ClNO$_3$S: C, 59.05; H, 3.50; N, 4.05. Found: C, 58.82; H, 3.46; N, 3.86.

EXAMPLE 91C (E)-3-[4-(4-chlorophenoxy)thieno[2,3-c]pyridin-2-yl]-2- propenoic acid Example 91B was processed as in Example 88 to provide the title compound.

MS (ESI−) m/z 330, 332 (M−H)$^-$; $^1$H NMR (300 MHz, DMSO-d$_6$) δ 6.46 (d, 3 H), 7.14 (dt, 2H), 7.46 (dt, 2H), 7.83 (s, 1H), 7.92 (d, 1 H), 8.15 (s, 1H), 9.10 (s, 1 H); Anal. calcd for C$_{17}$H$_{17}$ClNO$_3$S: C, 59.05; H, 3.50; N, 4.05. Found: C, 58.82; H, 3.46; N, 3.86.

EXAMPLE 92

(E)-3-[4-(4-chlorophenoxy)thieno[2,3-c]pyridin-2-yl]-2-propenamide

A solution of Example 91C (51.5 mg, 0.155 mmol), N-hydroxybenzotriazole monohydrate (34.5 mg, 0.225 mmol), 4-methylmorpholine (47 mg, 0.464 mmol) and NH$_4$CN (31.6 mg, 0.591 mmol) in DMF (1 mL) at 0° C. was treated with EDC (45.0 mg, 0.235 mmol), stirred at 0° C. for 4 hours and at room temperature for 10 hours, treated with chloroform (5 mL), washed sequentially with 1M NaHCO$_3$ and brine, dried (Na$_2$SO$_4$), filtered, and concentrated. The residue was purified by flash chromatography on silica gel with 5% methanol/dichloromethane to provide the title compound.

mp 176–178° C.; MS (ESI) m/z 331, 333 (M+H)$^+$; $^1$H NMR (300 MHz, CDCl$_3$) δ 5.60 (br s, 2H), 6.46 (d, 1H), 7.01 (m, 2H), 7.35 (m, 2H), 7.46 (s, 1H), 7.84 (d, 1H), 8.11 (s, 1H), 8.88 (s, 1H); Anal. calcd for C$_{16}$H$_{11}$ClN$_2$O$_2$S: C, 58.10; H, 3.35; N, 8.47. Found: C, 57.98; H, 3.24; N, 8.45.

EXAMPLE 93

4-bromothieno[2,3-c]pyridine-2-carboxamide

EXAMPLE 93A 3,5-dibromopyridine-4-carboxaldehyde

A solution of diisopropylamine (6.6 mL, 46.43 mmol) in THF (40 mL) at 0° C. was treated with n-butyllithium in hexanes (2.50 M solution, 18.6 miL, 46.43 mmol) over 15 minutes, stirred at 0° C. for 30 minutes, diluted with THF (200 mL), cooled to –78° C., treated with 3,5-dibromopyridine (10 g, 42.21 mmol) in THF (110 mL) over 95 minutes, stirred at –78° C. for 30 minutes, treated dropwise with methylformate (5.2 mL, 84.42 mmol), stirred at –78° C. for 2 hours, transferred to ice-cold saturated NaHCO$_3$ solution, stirred for 15 minutes, and extracted with diethyl ether. The extract was washed with brine, dried (MgSO$_4$), filtered, and concentrated. The residue was purified by flash chromatography on silica gel with 10% acetone/hexane to provide the title compound. MS (DCI/NH$_3$) m/z 266 (M+H)$^+$; $^1$H NMR (300 MHz, DMSO-d$_6$) δ 8.91 (s, 2H), 10.09 (s, 1H).

EXAMPLE 93B methyl 4-bromothieno[2,3-c]pyridine-2-carboxylate

Example 93A was processed as in Example 17C except at 0–25° C. to provide the title compound.

MS (DCI/NH$_3$) m/z 274 (M+H)$^+$; $^1$H NMR (500 MHz, DMSO-d$_6$) δ 3.95 (s, 3H), 7.99 (s, 1H), 8.67 (s, 1H), 9.31 (s, 1H).

EXAMPLE 93C 4-bromothieno[2,3-c]pyridine-2-carboxamide

Example 93B was processed as in Example 44 to provide the title compound.

MS (DCI/NH$_3$) m/z 257 (M+H)$^+$; $^1$H NMR (400 MHz, DMSO-d$_6$) δ 7.97 (br s, 1H), 8.11 (s, 1H), 8.33 (br s, 1H), 8.43 (s, 1H), 9.24 (s, 1H).

EXAMPLE 94

4-chlorothieno[2,3-c]pyridine-2-carboxamide 3,5-Dichloropyridine was processed as in Example 93 to provide the title compound.

MS (DCI/NH$_3$) m/z 213 (M+H)$^+$; $^1$H NMR (300 MHz, DMSO-d$_6$) δ 7.93 (br s, 1H, NH), 8.28 (s, 1H), 8.55 (br s, 1H, NH), 8.58 (s, 1H), 9.28 (s, 1H).

EXAMPLE 95

4-[4-(trifluoromethyl)phenyl]thieno[2,3-c]pyridine-2-carboxamide

EXAMPLE 95A methyl 4-f4-(trifluoromethyl)phenyl]thieno[2,3-c]pyridine-2-carboxylate A solution of Example 93B (272 mg, 1 mmol), 4-(trifluoromethyl)phenyl boronic acid (209 mg, 1.1 mmol) and cesium fluoride (347 mg, 2.1 mmol) in DME (5 mL) was degassed for 15 minutes, treated with tetrakis (triphenylphosphine)palladium(0) (35 mg, 0.03 mmol), warmed at 80° C. for 6 hours, stirred at room temperature for 12 hours, filtered through Celite®, and concentrated. The residue was purified by flash chromatography on silica gel with 5% acetone/hexane to provide the title compound.

MS (DCI/NH$_3$) m/z 338 (M+H)$^+$; $^1$H NMR (300 MHz, DMSO-d$_6$) δ 3.92 (s, 3H), 7.94 (m, 4H), 8.06 (s, 1H), 8.66 (s, 1H), 9.47 (s, 1H).

EXAMPLE 95B

4-[4-(trifluoromethyl)phenyl]thieno[2,3-c]pyridine-2-carboxamide

Example 95A was processed as in Example 44 to provide the title compound.

MS (APCI) m/z 323 (M+H)$^+$, 321 (M–H)$^-$, and 357 (M+Cl)$^-$; $^1$H NMR (400 MHz, DMSO-d$_6$) δ 7.81 (br s, 1H), 7.93 (m, 4H), 8.24 (s, 3H), 8.45 (br s, 1H), 8.59 (br s, 1H), 9.37 (br s, 1H).

EXAMPLE 96

N-methyl-4-[4-(trifluoromethyl)phenyl]thieno[2,3-c]pyridine-2-carboxamide

Example 95A was processed as in Example 44 but substituting methylamine (2.0 M in methanol) for methanolic ammonia to provide the title compound.

MS (APCI) m/z 337 (M+H)$^+$, 335 (M–H)$^-$, and 371 (M+Cl)$^-$; $^1$H NMR (400 MHz, DMSO-d$_6$) δ 2.82 (d, 3H), 7.90 (d, 2H), 7.94 (d, 2H), 8.17 (s, 1H), 8.58 (s, 1H), 8.93 (br d, 1H), 9.36 (s, 1H); $^{13}$C NMR (100 MHz, DMSO-d$_6$) δ: 26.1 (CH$_3$), 121.6 (Ar—CH), 123.1, 125.3 (C), 125.7 (CH), 125.8 (CH), 128.3, 128.6, 128.8, 129.1 (CF$_3$), 129.9 (2×Ar—CH), 136.6 (C), 140.6 (C), 142.4 (C), 142.5 (CH), 145.0 (2×CH), 146.6 (C), 161.1 (C).

EXAMPLE 97

4-phenylthieno[2,3-c]pyridine-2-carboxamide

EXAMPLE 97A methyl 4-phenylthieno[2,3-c]pyridine-2-carboxylate

Example 93B and phenylboronic acid were processed as in Example 95 to provide the designated compound.

MS (DCI/NH$_3$) m/z 338 (M+H)$^+$; $^1$H NMR (300 MHz, DMSO-d$_6$) δ 3.92 (s, 3H), 7.94 (m, 4H), 8.06 (s, 1H), 8.66 (s, 1H), 9.47 (s, 1H).

EXAMPLE 97B 4-phenylthieno[2,3-c]pyridine-2-carboxamide

Example 97A was processed as in Example 44 to provide the title compound.

MS (DCI/NH$_3$) m/z 255 (M+H)$^+$; $^1$H NMR (300 MHz, DMSO-d$_6$) δ 7.52–7.69 (m, 5H), 7.78 (br s, 1H), 8.23 (s, 1H), 8.44 (br s, 1H), 8.52 (s, 1H), 9.30 (s, 1H); Anal. calcd for C$_{14}$H$_{10}$N$_2$OS: C, 66.12; H, 3.96; N, 11.02. Found: C, 66.02; H, 3.94; N, 11.00.

EXAMPLE 98

4-([1,1'-biphenyl]-4-ylthio)thieno[2,3-c]pyridine-2-carboxamide

Example 73 and phenylboronic acid were processed and purified as in Example 95 then repurified by HPLC (C18 reverse phase, 0–90% acetonitrile gradient in water containing 0.1% TFA) to provide the title compound.

MS (DCI/NH$_3$) m/z 363 (M+H)$^+$; $^1$H NMR (300 MHz, DMSO-d$_6$) δ 7.36–7.48 (m, 5H), 7.63–7.68 (m, 4H), 7.91 (br s, 1H), 8.30 (s, 1H), 8.54 (s, 1H), 8.57 (br s, 1H), 9.36 (s, 1H).

EXAMPLE 99

Methyl 4-[3-(2,3,4,5-Tetrahydrofuranyl)oxy]thieno[2,3-c]pyridine-2-carboxamide

EXAMPLE 99A

Methyl 4-[3-(2,3,4,5-Tetrahydrofuranyl)oxy]thieno[2,3-c]pyridine-2-carboxylate

To a solution of Example 236E (110 mg, 0.53 mmol) in anhydrous tetrahydrofuran (10 mL) at room temperature under nitrogen atmosphere was added 3-hydroxy tetrahydrofuran (0.043 mL, 0.53 mmol), triphenylphosphene (138 mg, 0.53 mmol) and diethyl azodicarboxylate (0.083 mL, 0.53 mmol). After 22 hr the reaction mixture was diluted with ethyl acetate (100 mL), filtered and the filtrate was concentrated under reduced pressure. The residue obtained was purified by flash chromatography on silica gel (Biotage Flash 40 S) eluting with 10% acetone-hexane to obtain the title compound in 22% yield.

$^1$H NMR (400 MHz, DMSO-d$_6$) δ 2.05–2.18 (m, 1H), 2.26–2.49 (m, 1H), 3.61–3.77 (m, 2H), 3.93 (s, 2H), 4.25–4.31 (m, 2H), 5.32–5.39 (m, 1H), 8.10 9s, 1H), 8.26 (s, 1H), 8.99 (s, 1H); MS (APCI) m/e 280 (M+H)$^+$.

EXAMPLE 99B

Methyl 4-[3-(2,3,4,5-Tetrahydrofuranyl)oxy]thieno[2,3-c]pyridine-2-carboxamide

The title compound (5.7 mg, 19%) was prepared from Example 99A (30 mg, 0.108 mmol) as described in Example 171. The product was isolated by C-18 reverse phase HPLC eluting with a gradient of 20% CH$_3$CN-H$_2$0 containing 0.1% trifluoroacetic acid.

$^1$H NMR (400 MHz, DMSO-d$_6$) δ 2.05–22.13 (m, 1H), 2.30–2.40 (m, 1H), 2.81 (d, J=5 Hz, 3H), 3.78–3.84 (m, 1H), 3.90–4.01 (m, 3H), 5.32–5.37 (m, 1H), 8.13 (s, 1H), 8.90 (s, 1H), 8.85 (d, J=5 Hz, 1H); $^{13}$C NMR (75 MHz, DMSO-d$_6$) δ 26.2 (CH$_3$), 32.5 (CH$_2$), 66.4 (CH$_2$), 72.3 (CH$_2$), 78.5 (CH),119.6 (CH), 126.7 (CH), 135.6 (C),137.3 (C), 137.8 (CH),144.3 (C), 148.6 (C), 161.1 (CO); MS (APCI) m/e 279 (M+H)$^+$, 313 (M+Cl)$^-$.

EXAMPLE 100 ethyl 4-[[2-(aminocarbonyl)thieno[2,3-c]pyridin-4-yl]oxy]benzoate

A solution of Example 73 (120 mg, 0.33 mmol), palladium(II)acetate (11 mg, 0.05 mmol), 1,3-bis(diphenylphosphino)propane (20.6 mg, 0.05 mmol), and triethylamine (100 mg, 0.99 mmol) in DMF (6 mL) and ethanol (3 mL) were purged with carbon monoxide, heated at 105° C. under a carbon monoxide atmosphere (balloon) for 12 hours, treated with ether, washed sequentially with brine and water, dried (Na$_2$SO$_4$), filtered, and concentrated. The residue was purified by flash chromatography (20% ethyl acetate/hexane) to provide the title compound. MS (DCI/NH$_3$) m/z 358 (M+H)$^+$.

EXAMPLE 101

4-[[2-(amnocarbonyl)thieno[2,3-c]pyridin-4-yl]oxy]benzoic acid

A solution of Example 100 (50 mg) in DMF (5 mL) and methanol (10 mL) was treated with a solution of NAOH (200 mg) in water (0.5 mL), stirred for 13 hours, treated sequentially with acetic acid (500 mg) and water, and filtered. The residue was recrystallized from DMF/water to provide the title compound.

MS (DCI/NH$_3$) m/z 315 (M+H)$^+$; $^1$H NMR (300 MHz, DMSO-d$_6$) δ 7.13 (dt, 1.8 Hz, 2H), 7.86 (br s, 1H), 7.98 (dt, 2H), 8.09 (s, 1H), 8.31 (s, 1H), 8.44 (br s, 1H), 9.22 (s, 1H); Anal. calcd for C$_{15}$H$_{10}$N$_2$O$_4$S: C, 57.32; H, 3.21; N, 8.91. Found: C,57.32; H, 3.30; N, 8.92.

EXAMPLE 102

4-(1-phenylethenyl)thieno[2,3-c]pyridine-2-carboxamide

EXAMPLE 102A styrene α-boronic acid

A solution of (x-bromo styrene (5.5 g, 30 mmol) in diethyl ether (30 mL) at −78° C. was treated with a solution of tert-BuLi (1.7 M solution, 21.2 mL, 36 mmol), stirred at −78° C. for 0.5 hours, treated with triisopropyl borate (8.31 mL, 36 mmol) over 48 minutes, stirred for 1 hour, warmed to room temperature over 18 hours, diluted with diethyl ether (100 mL), treated with 1M HCl (100 mL), stirred at room temperature for 5 hours, concentrated to remove the THF, adjusted pH 14 with 1N NaOH, washed with hexane, adjusted to pH 1 with 1M HCl, and extracted with ethyl acetate. The extract was dried (Na$_2$SO$_4$), filtered and concentrated to provide the title compound.

$^1$H NMR (300 MHz, DMSO-d$_6$) δ 5.75 (d, 1H), 5.83 (d, 1H), 7.2–7.39 (m, 5H, Ar—CH).

EXAMPLE 102B methyl 4-(1phenylethenyl)thieno[2,3-c]pyridine-2-carboxalate

Example 93B and styrene-α-boronic acid were processed as in Example 95 to provide the title compound.

MS (APCI) m/z 296(M+H)$^+$; $^1$H NMR (400 MHz, DMSO-d$_6$) δ 3.84 (s, 3H), 5.56 (s, 1H), 5.95 (s, 1H), 7.31 (m, 2H), 7.36 (m, 3H), 7.47 (s, 1H), 8.5 (s, 1H), 9,40 (s, 1H); $^{13}$C NMR (100 MHz, DMSO-d$_6$) δ 53.03 (OCH$_3$), 118.37 (vinylic CH$_2$), 126.79 (Ar—CH), 127.60 (Ar—CH), 128.38 (Ar—CH), 128.75 (Ar—CH), 132.55 (Ar—CH), 137.20 (C), 138.10 (C), 139.59 (C), 141.88 (C), 142.97 (3-CH), 144.03 (C), 145.39 (CH), 161.69 (CO).

EXAMPLE 102C 4-(1-phenylethenyl)thieno[2,3-c]pyridine-2-carboxamide

Example 102B was processed as in Example 44 to provide the title compound.

MS (DCI) m/z 281 (M+H)$^+$; $^1$H NMR (400 MHz, DMSO-d$_6$) δ 5.53 (S, 1H), 6.04 (S, 1H), 7.31 (m, 2H), 7.35 (m, 3H), 7.72 (br s, 1H), 7.82 (s, 1H), 8.33 (s, 1H), 8.37 (br s, 1H), 9.29 (s, 1H); $^{13}$C NMR (100 MHz, DMSO-d$_6$) δ 118.0 (CH$_2$), 123.10 (CH), 126.73 (Ar—CH), 128.22 (CH), 128.60 (Ar—CH), 132.41 (C), 136.59 (C), 139.42 (C), 142.73 (3-CH), 143.41 (C), 144.01 (C), 144.66 (5-CH), 146.0 (C), 162.5 (CO).

EXAMPLE 103

4-[(4-methylphenyl)thio]thieno[2,3-c]pyridine-2-methanol

A suspension of NaBH$_4$ (28 mg, 0.743 mmol) in 2:3 THF/ethanol (2 mL) was stirred at 0° C. for 10 minutes, treated with CaCl₂ (41.2 mg, 0.37 mmol), stirred for 15 minutes, treated with a solution of Example 17C (117 mg, 0.37 mmol) in 2:3 THF/ethanol (3 mL), stirred at 0° C. for 4 hours, treated with 20% aqueous acetic acid (5 mL), and concentrated to remove the lower boiling solvents. The resulting mixture was adjusted to pH 7 with saturated NaHCO₃ and extracted with ethyl acetate. The extract was dried (MgSO₄), filtered, and concentrated. The residue was purified by column chromatography on silica gel eluting with 15% acetone/hexane to provide the title compound.

MS (DCI/NH₃) m/z 288 (M+H)⁺; ¹H NMR (500 MHz, DMSO-d₆) δ 2.25 (s, 3H), 4.80 (s, 2H), 5.90 (br s, 1H), 7.14 (d, 2H), 7.18 (d, 2H), 7.32 (s, 1H), 8.36 (s, 1H), 9.15 (s, 1H).

EXAMPLE 103A 4-(4-chlorophenoxy)-N-methylthieno[2,3-c]pyridine-2-carboxamide A solution of Example 61A (100 mg, 0.3135 mmol) and methylamine (2M solution in THF, 0.467 mL, 0.941 mmol) in THF (2 mL) at 0° C. was treated with NaH (12 mg, 0.47 mmol), stirred at room temperature for 1 hour, treated with water (0.1 mL), and concentrated. The residue was purified by flash chromatography on silica gel with 20% acetone/hexane to provide the title compound.

MS (APCI) m/z 319 (M+H)⁺; ¹H NMR (300 MHz, DMSO-d₆) δ 2.80 (d, 3H), 7.13 (d, 2H), 7.45 (d, 2H), 8.06 (s, 1H), 8.19 (s, 1H), 8.94 (d, 1H), 9.16 (s, 1H).

EXAMPLE 104

4-(4-chlorophenoxy)-N,N-dimethylthieno[2,3-c]pyridine-2-carboxamide

Example 61A and dimethylamine were processed as in Example 103A to provide the title compound.

MS (APCI) m/z 333 (M+H)⁺; ¹H NMR (300 MHz, DMSO-d₆) δ 3.03 (br s, 3H), 3.12 (br s, 3H), 7.17 (d, 2H), 7.46 (d, 2H), 7.62 (s, 1H), 8.18 (s, 1H), 9.15 (s, 1H).

EXAMPLE 105

4-(4-chlorophenoxy)-N,N-diethylthieno[2,3-c]pyridine-2-carboxamide

Example 61A and diethylamine were processed as in Example 103A to provide the title compound.

MS (APCI) m/z 361 (M+H)⁺; ¹H NMR (300 MHz, DMSO-d₆) δ 1.09 (m, 6H), 3.42 (m, 4H), 7.15 (d, 2H), 7.45 (d, 2H), 7.49 (s, 1H), 8.74 (s, 1H), 9.17 (s, 1H).

EXAMPLE 106

4-(4-chlorophenoxy)-N-cyclopropylthieno[2,3-c]pyridine-2-carboxamide

Example 61A and cyclopropylamine were processed as in Example 103A to provide the title compound.

MS (APCI) m/z 345 (M+H)⁺; ¹H NMR (500 MHz, DMSO-d₆) δ 2.85 (m, 1H), 7.12 (d, 2H), 7.46 (d, 2H), 8.11 (s, 1H), 8.13 (s, 1H), 8.93 (d, 1H), 9.12 (s, 1H).

EXAMPLE 107

1-[[4-(4-chlorophenoxy)thieno[2,3-c]pyridin-2-yl]carbonyl]pyrrolidine

Example 61A and pyrrolidine were processed as in Example 103A to provide the title compound.

MS (APCI) m/z 359 (M+H)⁺; ¹H NMR (400 MHz, DMSO-d₆) δ 1.83–1.93 (m, 4H), 3.53 (t, 2H), 3.71 (t, 2H), 7.17 (d, 2H), 7.47 (d, 2H), 7.70 (s, 1H), 8.16 (s, 1H), 9.12 (s, 1H).

EXAMPLE 108

1-[[4-(4-chlorophenoxy)thieno[2,3-c]pyridin-2-yl]carbonyl]piperidine

Example 61A and piperidine were processed as in Example 103A to provide the title compound.

MS (APCI) m/z 373 (M+H)⁺; ¹H NMR (400 MHz, DMSO-d₆) δ 1.52 (m, 3H), 1.62 (m, 2H), 3.53 (m, 5H), 7.14 (d, 2H), 7.46 (d, 2H), 7.47 (s, 1H), 8.20 (s, 1H), 9.14 (s, 1H).

EXAMPLE 109

4-[[4-(4-chlorophenoxy)thieno[2,3-c]pyridin-2-yl]carbonyl]morpholine

Example 61A and morpholine were processed as in Example 103A to provide the title compound.

MS (APCI) m/z 375 (M+H)⁺; ¹H NMR (500 MHz, DMSO-d₆) δ 3.6 (m, 8H), 7.14 (d, 2H), 7.45 (d, 2H), 7.55 (s, 1H), 8.17 (s, 1H), 9.14 (s, 1H).

EXAMPLE 110

1-[[4-(4-chlorolphenoxyy)thieno[2,3-c]pyridin-2-yl]carbonyl]-4-methylpiperazine

Example 61A and methylpiperazine were processed as in Example 103A to provide the title compound.

MS (APCI) m/z 388 (M+H)⁺; ¹H NMR (400 MHz, DMSO-d₆) δ 2.2 (s, 3H), 2,32 (br s, 4H), 8.58 (br s, 4H), 7.15 (dd, 1H), 7.47 (dd, 1H), 7.49 (s, 1H), 8.2 (d, 1H), 9.15 (s, 1H).

EXAMPLE 111

1-[[4-(4-chlorophenoxy)thieno[2,3-c]pyridin-2-yl]carbonyl]-4-phenyllpiperazine

Example 61A and phenylpiperazine were processed as in Example 103A to provide the title compound.

MS (APCI) m/z 450 (M+H)⁺; ¹H NMR (500 MHz, DMSO-d₆) δ 3.18 (br s, 4H), 3.73 (br s, 4H), 6.81 (t, 1H), 6.95 (d, 2H), 7.15 (d, 2H), 7.24 (d, 2H), 7.46 (d, 2H), 7.57 (s, 1H), 8.20 (s, 1H), 9.17 (s, 1H).

EXAMPLE 112

1-[[4-(4-chlorophenoxy)thieno[2,3-c]pyridin-2-yl]carbonyl]-4-(phenylmethyl)piperazine Example 61A and benzylpiperazine were processed as in Example 103A to provide the title compound.

MS (APCI) m/z 464 (M+H)⁺; ¹H NMR (500 MHz, DMSO-d₆) δ 2.38 (br s, 4H), 3.51 (s, 2H), 3.58 (br s, 4H), 7.13 (d, 2H), 7.32 (m, 5H), 7.45 (d, 2H), 7.47 (s, 1H), 8.91 (s, 1H), 9.13 (s, 1H).

EXAMPLE 113

1-[[4-(4-chlorophenoxy)thieno[2,3-c]pyridin-2-yl]carbonyl]4-(2-pyridinyl)piperazine Example 61A and 2-pyridylpiperazine were processed as in Example 103A to provide the title compound.

MS (APCI) m/z 451 (M+H)+; 1H NMR (500 MHz, CDCl3-d) δ 3.65 (br s, 4H), 3.85 (br s, 4H), 6.70 (m, 2H), 7.07 (d, 2H), 7.34 (d, 2H), 7.50 (s, 1H), 7.54 (m, 1H), 8.15 (s, 1H), 8.29 (m, 1H), 8.96 (s, 1H).

EXAMPLE 114

4-(4-chlorolphenoxcy)-N-(2-hydroxyethyl)lthieno[2,3-c]pyridine-2-carboxamide

Example 61A and ethanolamine were processed as in Example 103A to provide the title compound.

MS (DCI/NH3) m/z 349 (M+H)+; 1H NMR (400 MHz, DMSO-d6) δ 3.33 (m, 2H), 3.51 (m, 2H), 5.76 (t, 1H), 7.12 (d, 2H), 7.26 (d, 2H), 8.17 (s, 2H), 8.98 (br.t, 1H), 9.14 (s, 1H); 13C NMR (100 MHz, DMSO-d6) δ 42.3 (N—CH2), 59.4 (O—CH2), 119.2 (CH), 119.3 (Ar—CH), 127.6 (C), 130.0 (Ar—CH), 133.2 (CH), 137.5 (C), 137.9 (C), 141.4 (CH), 146.4 (C), 147.1 (C), 155.6 (C), 160.6 (CO).

EXAMPLE 115

4-[[4-(4-chlorophenoxy)thieno[2,3-c]pyridin-2-yl]carbonyl]-N-(1-methylethyl)-1-piperazineacetamide, trifluoroacetate (salt)

Example 61A and N-isopropylpiperazine acetamide were processed as in Example 103A to provide the title compound. The residue was purified by C-18 reverse phase HPLC with a gradient of 20% $CH_3CN$/water and 100% $CH_3CN$ containing 0.1% trifluoroacetic acid to provide the title compound.

MS (APCI) m/z 473 (M+H)+; 1H NMR (400 MHz, DMSO-d6) δ 1.09 (m, 6H), 3.05 (br s, 4H), 3.43 (s, 2H), 3.87 (br s, 4H), 7.16 (d, 2H), 7.67 (d, 2H), 7.68 (s, 1H), 8.20 (s, 1H), 9.18 (s, 1H).

EXAMPLE 116

4-(4-chlorophenoxy)-N-[1-(hydroxymethyl)ethyl]thieno[2,3-c]pyridine-2-carboxamide Example 61A and DL-2-amino-1-propanol were processed as in Example 103A to provide the title compound.

MS (APCI) m/z 363 (M+H)+, 361 (M−H)−, 397 (M+Cl)−; 1H NMR (400 MHz, DMSO-d6) δ 1.14 (d, 3H), 3.36–3.40 (m, 1H), 3.43–3.5 (m, 1H), 3.97–4.04 (m, 1H), 4.77 (t, 1H), 7.15 (d, 2H), 7.48 (d, 2H), 8.14 (s, 1H), 8.26 (s, 1H), 8.67 (d, 1H), 9.14 (s, 1H); 13C NMR (100 MHz, DMSO-d6) δ 16.87 (CH3), 47.74 (CH), 64.06 CH2OH), 119.16 (3-CH), 119.46 (2×Ar—CH), 127.72 (C), 130.08 (2×Ar—CH), 132.84 (5-CH), 137.51 (C), 137.91 (C), 141.20 (7-CH), 146.62 (C), 147.28 (C), 155.53 (C), 160.01 (CO).

EXAMPLE 117

4-(4-chlorophenoxy)-N-[1,1-bis(hydroxymethyl)ethyl]thieno[2,3-c]pyridine-2-carboxamide Example 61A and 2-amino-2-methyl-1,3-propanediol were processed as in Example 103A to provide the title compound.

MS (APCI) m/z 393 (M+H)+, 391 (M−H)−, 393 (M+Cl)−; 1H NMR (400 MHz, DMSO-d6) δ 1.28 (s, 3H), 3.56–3.66 (m, 4H), 4.71 (t, 2H), 7.16 (d, 2H), 7.48 (d, 2H), 7.92 (s, 1H), 8.11 (s, 1H), 8.31 (s, 1H), 9.12 (s, 1H); 13C NMR (100 MHz, DMSO-d6) δ 18.45 (CH3), 59.80 (C), 63.08 (CH2), 119.46 (CH), 119.74 (2×Ar—CH), 127.83 (C), 130.09 (2×Ar—CH), 132.53 (CH), 137.43 (C), 137.84 (C), 140.99 (CH), 147.38 (C), 147.50 (C), 155.40 (C), 160.59 (CO);

EXAMPLE 118

(D,L)-4-(4-chloroohenoxy)-N-(2-hydroxypropyl)thieno[2,3-c]pyridine-2-carboxamide Example 61A and DL-1-amino-2-propanol were processed as in Example 103A to provide the title compound.

MS (APCI) m/z 363 (M+H)+ and 397 (M+Cl)−; 1H NMR (400 MHz, DMSO-d6) δ 1.08 (d, 3H), 3.21 (m, 2H), 3.75–3.84 (m, 1H), 4.8 (br s, 1H), 7.14 (d, 2H), 7.48 (d, 2H), 8.17 (s, 1H), 8.22 (s, 1H), 8.98 (br s, 1H), 9.15 (s, 1H); 13C NMR (100 MHz, DMSO-d6) δ 21.13 (CH3), 47.24 (CH2), 64.84 (CH), 119.30 (3-CH), 119.42 (2×Ar—CH), 127.66 (C), 130.04 (2×Ar—CH), 133.05 (CH), 137.48 (C), 137.92 (C), 141.30 (CH), 146.37 (C), 147.16 (C), 155.58 (C), 160.59 (CO).

EXAMPLE 119

4-(4-chlorophenoxU)-N-[2-(4-morpholinyl)ethyl]thieno[2,3-c]pyridine-2-carboxamide Example 61A and 4-(2-aminoethyl)morpholine were processed as in Example 103A to provide the title compound.

MS (APCI) m/z 418 (M+H)+, 452 (M+Cl)−; 1H NMR (400 MHz, DMSO-d6) δ 2.41 (t, 4H), 2.48 (m, 2H), 3.40 (m, 2H), 3.56 (t, 4H), 7.15 (d, 2H), 7.47 (d, 2H), 8.13 (s, 1H), 8.17 (s, 1H), 8.94 (t, 1H), 9.04 (s, 1H); 13C NMR (100 MHz, DMSO-d6) δ 36.73 (N—CH2), 53.21 (morpholine ring 2×N—CH2), 57.07 (N—CH2), 66.12 (morphline ring 2×—OCH2), 119.14 (3-CH), 119.50 (2×Ar—CH), 127.73 (C), 130.06 (2×Ar—CH), 132.96 (pyridyl ring CH), 137.35 (C), 137.91 (C), 141.29 (pyridyl ring CH), 146.20 (C), 147.20 (C), 155.40 (C), 160.45 (CO).

EXAMPLE 120

4-(4-Chlorophenoxy)thieno[2,3-c]pyridine-2-sulfonamide

To a solution of Example 124A (261 mg, 1 mmol) in anhydrous THF (5 mL) at −78° C. was added tert-BuLi (1.7 M solution in hexanes, 0.647 mL, 1.1 mmol) under nitrogen atmosphere. The reaction mixture was stirred at −78° C. for 15 minutes and $SO_2$ gas was bubbled into the solution for 15 minutes. Then this was stirred at −72° C. for 2.5 hours and at 0° C. for 4 hours. The reaction mixture was diluted with hexane (10 mL) and evaporated, and the residue obtained was suspended in $CH_2Cl_2$ (5 mL) and treated with N-chlorosuccinimide (214 mg, 1.6 mmol) at 0° C. After 2 hours at ambient temperature the reaction mixture was diluted with $CH_2Cl_2$, washed with 10% aqueous $NaHSO_3$ solution (3×25 mL) followed by brine (3×25 mL). The dried ($MgSO_4$) organic layer was evaporated to dryness under reduced pressure to obtain the crude sulfonyl chloride as an oil. This was dissolved in acetone (5 mL) and treated with ice cold solution of NH4OH (5 mL) at 0° C. After 2 hr at 0° C. reaction mixture was evaporated from toluene to obtain the crude product as an oil. The title compound (57 g, 16%) was obtained by flash chromatography on silica gel eluting with 20% acetone-hexane followed by 40% acetone-hexane.

1H NMR (400 MHz, DMSO-d6) δ 7.21 (d, J=9 Hz, 2H), 7.51 (d, J=9 Hz, 2H), 7.79 (s, 1H), 8.14 (br.s, 2H), 8.30 (s, 1H), 9.27 (s, 1H); 13C NMR (100 MHz, DMSO-d6) δ 119.65 (CH), 120.88 (CH), 127.94 (C), 130.12 (CH), 133.67 (CH), 135.61 (C), 141.65 (CH)152.11 (C), 155.41 (C); MS (APCI) m/e 341 (M+H)+, 339 M−H)−, 375 (M+Cl)−.

EXAMPLE 121

4-[(4-methylphenyl)methyl]thieno[2,3-c]pyridine-2-carboxamide

EXAMPLE 121A methyl 4-[(4-methylphenyl)methyl]thieno[2,3-c]pyridine-2-carboxylate Example 121A is processed as in J. Org. Chem, 1988, 53, pp. 2392–2394. For example, a suspension of Zn dust (92 mg, 1.4 mM) in THF (2 ml) containing 1,2-dibromoethane (0.05 ml, 0.054 mmol) is heated at 65° C. for 2 minutes, cooled to 25° C., treated with trimethylsilyl chloride (0.009 ml, 0.043 mM), stirred at room temperature for 25 minutes, cooled to 0° C., slowly treated with a solution of 4-methylbenzyl bromide (0.248 mL, 1.0 mmol) in THF (5 mL), warmed to 40° C. for 3 hours, cooled to −10° C., treated with CuCN (106 mg, 1.18 mM) and LiCl (100 mg, 2.35 mM) in THF (10 mL), stirred at 0° C. for 30 minutes, treated slowly with a solution of Example 93B (272 mg, 1 mmol) in THF (5 mL), stirred at 0° C. for 3 hours, warmed to 25° C. over 18 hours, treated with ethyl acetate, washed sequentially with saturated $NH_4Cl$ and brine, dried ($MgSO_4$), filtered and concentrated. The residue is purified by flash chromatography on silica gel to provide the title compound.

EXAMPLE 121B

4-[(4-methylphenyl)methyl]thieno[2,3-c]pyridine-2-carboxamide

Example 121A is processed as in Example 44 to provide the title compound.

EXAMPLE 122

Methyl 4-(Morpholino)thieno[2,3-c]pyridine-2-carboxamide

Example 122 (241 mg, 72%) was prepared as described in Example 308, substituting 1,4-dioxo-8-azaspiro[4,5]decane (0.256 mL, 2 mmol) for 4-methylaniline.

$^1$H NMR (400 MHz, DMSO-$d_6$) δ 1.91 (m, 4H), 2.85 (d, J=4 Hz, 3H), 3.25 (m, 4H), 3.96 (s, 4H), 8.10 (s, 1H), 8.12 (s, 1H), 8.87 (s, 1H), 8.96 (d, J=4 Hz, 1H); $^{13}$C NMR (100 MHz, DMSO-$d_6$) δ 26.1 ($CH_3$), 35.0 ($CH_2$), 49.7 ($CH_2$), 63.8 ($CH_2$), 69.8 ($CH_2$), 106.1 (C), 121.3 (CH), 132.0 (CH), 136.9 (C), 138.3 (C), 138.7 (CH), 143.6 (C), 143.8 (C), 161.3 (C); MS (APCI) m/e 334 (M+H)$^+$, 368 (M+Cl)$^-$.

EXAMPLE 123

4-(4-chlorophenoxy)thieno[2,3-c]pyridine-2-carboxamide, N-oxide

EXAMPLE 123A methyl (4-chlorophenoxy)thieno[2,3-c]pyridine-2-carboxylic acid, N-oxide A solution of methyl 4-(4-chlorophenoxy)thieno[2,3-c] pyridine-2-carboxylate (319 mg, 1 mmol) in dichloromethane (15 mL) at 0° C. was treated with 3-chloroperoxybenzoic acid (302 mg, 1.75 mmol), stirred 0.5 hours at 0° C. and 4 hours at room temperature washed sequentially with water, saturated sodium bicarbonate, water, and brine, dried ($Na_2SO_4$), filtered and concentrated to provide the title compound.

MS (DCI/$NH_3$) m/z 336 (M+H)$^+$; $^1$H NMR (300 MHz, DMSO-$d_6$) δ 3.89 (s, 3H), 7.30 (m, 2H), 7.52 (m, 2H), 7.84 (s, 1H), 7.88 (s, 1H), 9.02 (s, 1H).

EXAMPLE 123B 4-(4-chlorophenoxy)thieno[2,3-c]pyridine-2-carboxamide, N-oxide Example 123A was processed as in Example 44 to provide the title compound.

$^1$H NMR (300 MHz, DMSO-$d_6$) δ 7.30 (m, 2H), 7.52 (m, 2H), 7.74 (d, 1H), 7.81 (br s, 1H), 8.10 (s, 1H), 8.34 (br s, 1H), 8.93 (s, 1H).

EXAMPLE 124

4-(4-chlorophenoxy)-2-(2-methoxyphenyl)thieno[2,3-c]pyridine

EXAMPLE 124A 4-(4-Chlorophenoxy)thieno[2,3-c]pyridine

Example 88 (4.5 g, 14.75 mmol) was added to a solution of diphenyl ether (55 ml) at 210° C. and kept at this temperature for 10 hours. The cooled reaction mixture was directly purified by flash chromatography on silica gel eluting with hexane followed by 10% acetone-hexane to obtain the title compound (3.83 g, 99.5%).

mp 87–89° C.; MS (DCI/$NH_3$) m/e 262 (M+H)$^+$; $^1$H NMR (300 MHz, DMSO-$d_6$) δ 7.09 (d, J=9 Hz, 2H), 7.35 (d, J=6 Hz, 1H), 7.45 (d, J=9 Hz, 2H), 8.13 (d, J=6 Hz, 1H), 8.18 (s, 1H), 9.15 (s, 1H); Anal. calcd for $C_{13}H_8Cl_1N_1O_1S_1$: C, 59.66; H, 3.08; N, 5.35. Found: C, 59.52; H, 3.08; N, 5.15.

EXAMPLE 124B 4-(4-chlorophenoxy)thieno[2,3-c]pyridine-2-boronic acid

A solution of sec-butyllithium (0.92 mmol) in THF (2 mL) at −78° C. was treated dropwise with Example 124A in THF (1 mL), stirred at −78° C. for 30 minutes, treated dropwise with tributylborate, stirred for 5 minutes at −78° C., stirred at room temperature for 45 minutes, treated with 2M NaOH (3 mL), stirred for 5 minutes, washed with hexanes, and acidified to pH 2 with 6M HCl. The precipitate that formed was collected and dried under vacuum to provide the title compound.

MS (APCI) m/z 262, 264 (M+H−B(OH)$_2$)$^+$, 340, and 342 (M+Cl−)$^-$; $^1$H NMR (300 MHz, $CD_3OD$) δ 7.29 (d, 2H), 7.53 (d, 2H), 8.08 (s, 1H), 8.11 (s, 1H), 9.40 (s, 1H).

EXAMPLE 124C 4-(4-chloroihenoxy)-2-(2-methoxyphenyl)thieno[2,3-c]pyridine

Example 124B is processed as in Example 95 but substituting of 2-iodoanisole for Example 93B and Example 124B for 4-(trifluoromethyl)phenylboronic acid to provide the title compound.

Example 125 4-(4-Chlorophenoxy)-3-methylthienol [2,3-c]yridine-2-carboxamide

EXAMPLE 125A

Methyl 4-(4-Chlorophenoxy)-3-methylthienol[2,3-c] pyridine-2-carboxylate

4-Chlorophenol was dissolved in THF (20 mnL) and treated with 1 M potassium t-butoxide (13 mL, 13 mmol) and stirred at room temperature for 1 hour. To this solution was added Example 17A (1.76 g, 10 mmol) in THF (5 mL). The reaction was heated at 70° C. for 4 hours, and cooled to room temperature. Poured into water diluted with brine and extracted with ethyl acetate. The ethyl acetate was then washed (3×20 mL), dried and evaporated. The residue was dissolved in THF (20 mL) and cooled in an ice bath, to which 3 M methyl magnesium bromide in ethyl ether (4 mL, 12 mmol) was added. The reaction was stirred at room temperature overnight. The excess Grignard reagent was decomposed with a saturated ammonia chloride solution (25 mL) and then extracted with ethyl acetate (3×25 mL). The ethyl acetate was washed with brine (3×25 mL), dried and evaporated to give the desired phenoxy alcohol. This alcohol was then subjected to an Swern oxidation, using the following conditions. To a solution of oxalyl chloride (1.1 mL, 12 mmol) in anhydrous methylene chloride (20 ml) cooled to −78° C. was added dimethylsulfoxide (1.85 mL, 24 mmol) over 30 minutes. Then a solution of the above phenoxy alcohol in methylene chloride (20 mL) was added over 15 minutes. Triethylamine (7.5 mL) was added and the reaction allowed to come to room temperature over 2 hours. Ice water was then added and the mixture was extracted with ethyl acetate. The ethyl acetate was washed with brine (3×20 mL), dried and evaporated. To a 0° C. solution of this residue in THF (20 mL) was added methyl thioglycolate (0.88 mL, 10 mmol) and cesium carbonate (3.2 g, 10 mmol). The reaction was then heated at 70° C. for 1 hour, cooled, poured into water, diluted with brine and extracted with ethyl acetate. The ethyl acetate was then washed with 1 N NaOH (2×20 mL), brine (3×20 mL), dried and evaporated to give an oil. This oil was triturated with methanol to give the desired compound.

mp 140–141° C.; MS (DCI/NH$_3$) m/e 334 (M+H)$^+$; $^1$H NMR (300 MHz, DMSO-d$_6$) δ 2.80 (s, 3H), 3.90 (s, 3H), 7.22 (d, 2H), 7.45 (d, 2H) 8.12 (s, 1H), 9.15 (s, 1H); Anal. Calcd for C$_{16}$H$_{12}$ClNO$_3$S.0.5 H$_2$O: C, 56.06; H, 3.82; N, 4.09. Found: C, 56.03; H, 3.43; N, 3.71.

EXAMPLE 125B 4-(4-chlorophenoxy)-3-methylthieno[2,3-c]pyridine-2-carboxylic acid A solution of Example 125A (1.1 g, 3.3 mmol) and LiOH.H$_2$O (0.30 g, 6.9 mmol) in THF (20 mIL) and H$_2$O (10 mL) was heated at 50° C. for 1 hour, then cooled, acidified with formic acid, and extracted with ethyl acetate. The ethyl acetate extract was washed with brine (3×15 mL), then dried and evaporated to give the desired product as white solid.

mp 315–317° C.; MS (DCI/NH$_3$) m/e 320 (M+H)$^+$; $^1$H NMR (300 MHz, DMSO-d$_6$) δ 2.76 (s, 3H), 3.30 (m, 1H), 7.10 (d, 2H), 7.45 (d, 2H), 8.12 (s, 1H), 9.15 (s, 1H);

EXAMPLE 125C 4-(4-chlorophenoxy)-3-methylthieno[2,3-c]pyridine-2-carboxamide Example 125B was processed as in Example 92 to provide the title compound.

mp 174–175° C.; MS (DCI/NH$_3$) m/e 319 (M+H)$^+$; $^1$H NMR (300 MHz, DMSO-d$_6$) δ 2.55 (s, 3H), 7.05 (d, 2H), 7.45 (d, 2H), 7.90 (m, 1H), 7.95 (m, 1H), 8.15 (s, 1H), 9.12 (s, 1H); Anal. calcd for C$_{15}$H$_{11}$ClN$_2$O$_2$S: C, 56.52; H, 3.48; N, 8.79. Found: C, 56.36; H, 3.50; N, 8.69.

EXAMPLE 126

4-(4-chlorophenoxy)-3-hydroxythieno[2,3-c]pyridine-2-carboxamide

EXAMPLE 126A ethyl 3,5-dichlorpyridine-4-carboxylate

To a stirred solution of lithium diisopropylamide (45 mL, 1.5 M in THF, 67.6 mmol) in 150 mL THF at −78° C. is treated with 3,5-dichloropyridine (10 g, 67.6 mmol) in 40 mL THF over 1.5 hours, stirred for 1 hour at −78° C., treated with ethyl chloroformate (9.5 mL, 100 mmol), stirred for 2 hours, transferred into saturated sodium bicarbonate (200 ml) at 0° C., treated with diethyl ether (200 ml), and extracted with ethyl ether (2×100 mL). The extract is washed sequentially with saturated sodium bicarbonate solution (2×100 mL), brine (2×100 mL), dried (MgSO$_4$), and concentrated. The residue is purified by flash chromatography on silica gel with hexane/ethyl acetate to provide the title compound.

EXAMPLE 126B methyl 4-(4-chlorophenoxy)-3-hydroxythieno[2,3-c]pyridine-2-carboxylate Example 126A is treated as in Example 61A to provide the title compound.

EXAMPLE 126C 4-(4-chlorophenoxy)-3-hydroxythieno[2,3-c]pyridine-2-carboxamide Example 126B is treated as in Example 61B to provide the title compound.

EXAMPLE 127

4-(4-chlorophenoxy)-3-(1-methylethoxy)thieno[2,3-c]pyridine-2-carboxamide

Example 127 is processed as in J. Medicinal. Chem. 1992, 35, p. 958. Example 126C (0.10 g, 0.3 mmol) in 50 ml of THF and cesium carbonate (1.0 g, 0.1 mmol) are treated with 2-bromopropane (0.37 g, 0.3 mmol), heated for 2 hours, poured on ice, extracted with ethyl ether, washed sequentially with 1 N aqueous sodium hydroxide and brine, and concentrated. The residue is purified by flash chromatorgraphy on silica gel with hexane-acetone (7:3) to provide the title compound.

EXAMPLE 128

3-bromo-4-(4-chlorophenoxy)thieno[2,3-c]pyridine

The method described in (Arkiv For Kemi (1970–74), 32, p. 249) may be adapted. Example 124A in thionyl chloride is treated with bromine at 90° C. for 4 hours to provide the title compound.

EXAMPLE 129

4-(4-chlorophenoxy)thieno[2,3-c]pyridine-3-carboxylic acid

The method described in (Arkiv For Kemi (1970–74), 32, p. 249) may be adapted. Example 128 cooled to −78° C. is treated with ethyllithium followed by reaction with carbon dioxide to provide the title compound.

EXAMPLE 130

4-(4-chlorophenoxy)thieno[2,3-c]pyridine-3-carboxamide

Example 129 may be treated as in Example 19 to provide the title compound.

EXAMPLE 131

3-amino-4-(4-chlorophenoxy)thieno[2,3-c]pyridine-2-carboxamide

EXAMPLE 131A 3,5-Dichloropyridine-4-carbonitrile

Example 17A (2.0 g, 11.4 mmol) in formic acid (10 mL) is treated with hydroxylamine hydrochloride (1.04 g, 11.4 mmol) and concentrated sulfuric acid (0.05 mL), stirred at reflux for 18 hours and concentrated. The residue was partitioned between 1:1 ethyl acetate-water, and washed sequentially with saturated sodium bicarbonate, water, brine, dried ($Na_2SO_4$), and concentrated. The residue is recrystallized from hexanes to provide the title compound.

mp 117–118° C.; $^1$H NMR (300 MHz, $CDCl_3$) δ 8.70 (s); IR (KBr, ν $cm^{-1}$) 1710, 1525, 1400, 1250, 1190, 1100, 920, 820, 800, 750.

EXAMPLE 131B methyl 3-amino-4-(4-chlorophenoxy)thieno[2,3-c]pyridine-2-carboxylate A solution of 4-chlorophenol (1.12 g, 8.72 mmol) in THF (20 mL) at 0° C. is treated with a solution of potassium t-butoxide (8.72 mL, 8.72 mmol, 1 M in THF), stirred at 0° C. for 1 hour, treated with Example 131A (1.5 g, 8.72 mmol) in THF (10 mL) at 0° C., warmed to room temperature, stirred overnight, concentrated, partitioned between 1:1 ethyl acetate-water, and extracted. The extract is washed with brine, dried ($Na_2SO_4$), and concentrated. A solution of concentrate in DMF (50 mL) at 0° C. was treated with potassium carbonate (2.42 g, 17.51 mmol) and methyl thioglycolate (778 μL, 8.72 mmol), warmed to room temperature, stirred overnight, and poured into ether (400 mL). The organic layer was washed with brine, dried ($Na_2SO_4$), and concentrated. The residue was purified by flash chromatography on silica gel with 0–5% acetone-hexane to provide the title compound.

mp 194–196° C.; MS (APCI) m/z 335 $(M+H)^+$; $^1$H NMR (300 MHz, DMSO-$d_6$) δ 3.81 (s, 3H), 6.86 (br s, 2H), 7.22–7.32 (m, 2H), 7.45–7.56 (m, 2H), 7.88 (s, 1H), 8.89 (s,1H); Anal. Calcd for $C_{15}H_{11}ClN_2O_3S$: C, 53.81; H, 3.31; N, 8.36. Found: C, 53.80; H, 3.27; N, 8.27.

EXAMPLE 131C

3-Amino-4-(4-chlorophenoxy)thieno[2,3-c]pyridine-2-carboxylic acid

The title compound was prepared from Example 131B using the procedure of Example 18.

mp 173–176° C. (dec); $^1$H NMR (300 MHz, DMSO-$d_6$) δ 7.29 (m, 2H), 7.52 (m, 2H), 7.88 (s, 1H), 8.89 (s, 1H); MS (ESI) m/e 321 $(M+H)^+$; Anal. Calcd for $C_{14}H_9ClN_2O_3S \cdot 0.25H_2O$: C, 51.70; H, 2.94; N, 8.61. Found??

EXAMPLE 131D 3-amino-4-(4-chlorophenoxy)thieno[2,3-c]pyridine-2-carboxamide

A solution of Example 131C (96 mg, 0.3 mmol) in DMF (2 mL) is treated with 1-hydroxybenzotriazole hydrate (67 mg, 0.44 mmol), $NH_4Cl$ (61 mg, 1.14 mmol) and 4-methylmorpholine (100 μL, 0.9 mmol), cooled to 0° C., treated with 1-[3-(dimethylamino)propyl]-3-ethylcarbodiimide hydrochloride (86 mg, 0.45 mmol), warmed to room temperature, stirred overnight, poured into saturated $NaHCO_3$, collected, washed with water and dried. The residue is recrystallized from methanol/toluene/hexanes to provide the title compound.

mp 202–204° C.; MS (APCI) m/z 320 $(M+H)^+$; $^1$H NMR (300 MHz, DMSO-$d_6$) δ 6.84 (br s, 2H), 7.21–7.30 (m, 2H), 7.39 (br s, 2H), 7.47–7.56 (m, 2H), 7.88 (s, 1H), 8.90 (s,1H); Anal. Calcd for $C_{14}H_{10}ClN_3O_2S$: C, 52.58; H, 3.15; N, 13.14. Found: C, 52.63; H, 3.18; N, 13.12.

EXAMPLE 132A ethyl 4-chlorothieno[2,3-b]pyridine-5-carboxylate

Example 132A was processed as in J. Heterocyclic Chem. 1977, 14, pp. 807–812 to provide the title compound.

mp 71–72° C.; MS (DCI/$NH_3$) m/z 259 $(M+H)^+$; 242 $(M+NH_4)^+$; $^1$H NMR (300 MHz, DMSO-$d_6$) δ 1.37 (t, 3 H), 4.41 (q, 2 H), 7.64 (d, 1 H), 8.17 (d, 1 H), 8.95 (s, 1 H); Anal. calcd for $C_{10}H_8ClNO_2S$: C, 49.69; H, 3.33; N, 5.79; S, 13.26. Found: C, 49.46; H, 3.13; N, 5.62; S, 13.42.

EXAMPLE 132B ethyl 4-[(4-methylphenyl)thio]thieno[2,3-b]pyridine-5-carboxylate Example 132A and thiocresol were processed as in Example 2 to provide the title compound.

mp 60–63° C.; MS (DCI/$NH_3$) m/z 347 $(M+NH_4)^+$ and 330 $(M+H)^+$; $^1$H NMR (300 MHz, DMSO-$d_6$) 1.30 (t, 3H), 2.28 (s, 3H), 4.26 (q, 2H), 7.00 (d, 1H), 7.17 (m, 2H), 7.24 (m, 2H), 7.91 (d, 1H), 8.81 (s, 1H); Anal. calcd for $C_{17}H_{15}NO_2S_2$: C, 61.98, H, 4.59; N, 4.25. Found C, 61.92, H, 4.53, N, 4.21.

EXAMPLE 132C

4-[(4-methylphenyl)thio]thieno[2,3-b]pyridine

Example 132B was processed as in Example 18 and 42 to provide the title compound.

mp 90–92° C.; MS (DCI/$NH_3$) m/z 275 $(M+NH_4)^+$ and 258 $(M+H)^+$; $^1$H NMR (300 MHz, DMSO-$d_6$) δ 2.39 (s, 3 H), 6.66 (d, 1 H), 7.38 (m, 2 H), 7.46 (d, 1 H), 7.53 (m, 2 H), 7.46 (d, 1 H), 7.53 (m, 2 H), 7.95 (d, 1 H), 8.12 (d, 1 H); Anal. calcd for $C_{14}H_{11}NS_2$: C, 65.33; H, 4.30; N, 5.44. Found: C, 65.40; H, 4.26, N, 5.26.

EXAMPLE 132D

4-[(4-methylphenyl)thio]thieno[2,3-b]pyridine-2-carboxamide

Diisopropylamine (0.056 g, 0.56 mmol) in THF (10 mL) at −78° C. was treated with n-butyllithium (0.22 mL, 0.56 mmol, 2.5 M in hexanes), stirred for 15 minutes, treated with Example 132C (0.13 g, 0.51 mmol) in THF (5 mL), stirred for 0.5 hours, warmed to 0° C. for 1 minutes, recooled to −78° C., poured onto solid $CO_2$, stirred for 0.5 hours, diluted with saturated $NH_4Cl$, and extracted with ethyl acetate. The extract was washed with brine, dried ($MgSO_4$) and concentrated to provide the title compound.

mp 280–282° C.; MS (DCI/$NH_3$) m/z 318 $(M+NH_4)^+$ and 301 $(M+H)^+$; $^1$H NMR (300 MHz, DMSO-$d_6$) δ 2.41 (s, 3 H), 6.62 (d, 1H), 7.40 (m, 2 H), 7.57 (m, 2 H), 7.77 (br s, 1 H), 8.26 (s, 1 H), 8.36 (d, 1H), 8.43 (br s, 1 H); Anal. calcd for $C_{15}H_{12}N_2OS_2$: C, 59.97; H, 4.02; N, 9.32. Found: C, 59.83; H, 4.03 N, 9.11.

EXAMPLE 133

4-chloro-N-(4-chlophenyl)thieno[2,3-b]pyridine-5-carboxamide

Example 132A was processed as in examples 18 and 19 but substituting 4-chloroaniline for concentrated $NH_4OH$ in Example 19 to provide the title compound.

mp 199–202° C.; MS (DCI/NH$_3$) m/z 340 (M+NH$_4$)$^+$, 342 (M+NH$_4$)$^+$, 323 (M+H)$^+$, 325 (M+H)$^+$; $^1$H NMR (300 MHz, DMSO-d$_6$) δ 7.6 (m, 2H), 7.62 (d, 1H), 7.77 (m, 2H), 8.19 (d, 1H), 8.79 (s, 1H); Anal. calcd for C$_{14}$H$_8$Cl$_2$N$_2$OS$_2$: C, 52.03; H, 2.49; N, 8.67. Found: C, 52.02; H, 2.15; N, 8.50.

EXAMPLE 134 ethyl 4-[(5-methyl-1,3,4-thiadiazol-2-yl)thio]thieno [2,3-b]pyridine-5-carboxylate Example 132A and 5-methyl-1,3,4-thiadiazol-2-thiol were processed as in Example 17B to provide the title compound.

mp 93–94° C.; MS (DCI/NH$_3$) m/z 355 (M+NH$_4$)$^+$ and 238 (M+H)$^+$; $^1$H NMR (300 MHz, DMSO-d$_6$) δ 1.32 (t, 3 H), 2.66 (s, 3H), 4.36 (q, 2 H), 7.34 (d, 1H), 8.13 (d, 1H), 9.00 (s, 1H); Anal. calcd for C$_{13}$H$_{11}$N$_3$O$_2$S$_3$: C, 46.27; H, 3.28; N, 12.45; S, 28.50. Found: C, 46.04; H, 3.20; N, 12,32; S, 28.39.

EXAMPLE 135

7-[(4-methylphenyl)thio]thieno[3,2-b]pyridine-2-carboxamide

Ethyl 7-chlorothieno[3,2-b]pyridine-6-carboxylate was processed as in Example 17B, 18, and 19 to provide the title compound.

MS (DCI/NH$_3$) m/z 301 (M+H)$^+$; $^1$H NMR (300 MHz, DMSO-d$_6$) δ 2.38 (s, 3H), 6.83 (d, 1H), 7.37 (m, 2H), 7.56 (m, 2H), 7.83 (br s, 1H), 8.25 (s, 1H), 8.41 (br s, 1H), 8.53 (d, 1H); Anal. calcd for C$_{15}$H$_{12}$N$_2$OS$_2$: C, 59.98; H, 4.03; N, 9.33. Found: C, 59.79; H, 4.01; N, 9.16.

EXAMPLE 136 methyl 6-[(4-methylphenyl)thio]thieno[2,3-b] pyridine-2-carboxylate

EXAMPLE 136A 2,6, dichloro-3-pyridinecarbonitrile

EXAMPLE 136B methyl 3-amino-6-chlorothieno[2,3-b]pyridine-2-carboxylate

Example 136A and methyl thiogycolate were processed as in Example 1D to provide the designated compound.

EXAMPLE 136C methyl 6-[(4-methylphenyl)thio]thieno[2,3-b] pyridine-2-carboxylate Example 136B (32 g, 1.34 mmol) in 75% H$_2$SO$_4$ (7.4 mL) at 0° C. was treated dropwise with aqueous NaNO$_2$ (0.24 g/1.5 mL, 3.5 mmol), stirred for 30 minutes, poured into cold 50% H$_2$PO$_3$ (11.8 mL), stirred for 30 minutes, stored at 0° C. for 60 hours, warmed to room temperature, treated with NaHCO$_3$, and extracted with ether. The extract was dried (MgSO$_4$), filtered, and concentrated. The residue was dissolved in methanol (7 mL), heated to 50° C., treated sequentially with NaOCH$_3$ (0.08 g, 1.45 mmol) and p-thiocresol (0.18 g, 1.45 mmol), stirred at room temperature for 18 hours, and concentrated. The residue was treated with 10% citric acid and extracted with dichloromethane. The extract was dried (MgSO$_4$), filtered, and concentrated. The residue was purified by flash chromatography on silica gel with 25% ethyl acetate/hexanes to provide the title compound.

mp 127–130° C.; MS (DCI/NH$_3$) m/z 316 (M+H)$^+$; $^1$HNMR (300 MHz, DMSO-d$_6$) 2,39 (s, 3H), 3.89 (s, 3H) 7.02 (d, 7.36 (m, 2H), 7.57 (m, 2H), 8.13 (s, 1H), 8.23 (d, 1H); Anal. calcd for C$_{16}$H$_{13}$NO$_2$S$_2$: C, 60.93; H, 4.15; N, 4.44. Found: C, 60.79; H, 4.18; N, 4.35.

EXAMPLE 137

6-[(4-methylphenyl)thio]thieno[2,3-b]pyridine-2-carboxamide

The title compound can be prepared from Example 136C using the procedure of Example 44.

EXAMPLE 138

2-bromo-4-[(4-methyllhenyl)thio]thieno[3,2-c] pyridine

Para-thiocresol (500 mg, 4 mmol) in DMF (10 mL) was treated with potassium t-butoxide (451 mg, 4 mmol) at room temperature, after 15 minutes cooled to 0° C., treated with 2-bromo-4-chlorothieno[3,2-c]pyridine (prepared in 6 steps according to the method of F. Eloy and A. Deryckere (Bull. Soc. Chim. Belg. 1970, 79, 301) (1.0 g, 4.0 mmol), stirred at 0° C. for 2 hours and at room temperature for 12 hours, poured into water and extracted with diethyl ether. The extract was washed with water, dried (Na$_2$SO$_4$), and concentrated under vacuum. The residue was purified by flash chromatography on silica gel with 1:20 ethyl acetate-hexane to provide the title compound.

MS (DCI/NH$_3$) m/z 336, 338 (M+H)$^+$; $^1$H NMR (300 Hz, CDCl$_3$) δ 2.36 (s, 3H), 7.18(d, 2H), 7.40 (d, 2H), 7.48 (br s, 1H), 7.52 (br d, 1H), 8.16 (d, 1H).

EXAMPLE 139

4-[(4-methylphenyl)thio]thieno[3,2-c]pyridine-2-carboxamide

EXAMPLE 139A 4-chlorothieno[3,2-c]pyridine-2-carbonitrile

A solution of 4-oxo-4,5-dihydrothieno[3,2-c]pyridine-2-nitrile (500 mg, 2.84 mmol) prepared as in F. Eloy and A. Deryckere, Bull. Soc. Chim. Belg. 1970, 79, 301) and phosphoryl chloride (5 mL) was heated at reflux for 1 hour. The formed red solution was poured onto ice and extracted with methylene chloride (2×150 mL). The dichloromethane solution was dried over anhydrous Na$_2$SO$_4$, filtered, and concentrated. The residue was purified by flash chromatography with 1:10 EtOAc/hexanes to provide the title compound.

MS (DCI/NH$_3$) m/z 195 (M+H)$^+$; $^1$H NMR (300 MHz, CDCl$_3$) δ 7.74 (d, 1H), 8.10 (s, 1H), 8.41 (d, 1H).

EXAMPLE 139B

4-[(4-methylphenyl)thio]thieno[3,2-c]pyridine-2-carbonitrile

Para-thiocresol (192 mg, 1.54 mmol) in DMF (5 mL) at room temperature was treated with potassium tert-butoxide (173 mg, 1.54 mmol), stirred for 15 minutes, cooled to 0° C., treated with Example 139A (200 mg, 1.03 mmol), stirred first at 0° C. and then at room temperature for 48 hours, treated with water, and extracted with dicholomethane. The extract was dried (MgSO$_4$), filtered, and concentrated. The residue was purified by flash chromatography on silca gel with 1:7 ethyl acetate-hexane to provide the title compound.

IR (KBr, cm$^{-1}$) 2200 (w, CN), 1550 (s), 1520 (s) cm$^{-1}$; MS (DCI/NH$_3$) m/z 283 (M+H)$^+$; $^1$H NMR (300 MHz, CDCl$_3$) δ 2.40 (s, 3H), 7.25 (d, 2H), 7.47 (d, 2H), 7.49 (d, 1H), 8.07 (s, 1H), 8.33 (d, 1H); Anal. calcd for C$_{15}$H$_{10}$N$_2$S$_2$: C, 63.80; H, 3.57; N, 9.92. Found: C, 63.80; H, 3.52; N, 9.98.

EXAMPLE 139C

4-[(4-methylphenyl)thio]thieno[3,2-c]pyridine-2-carboxamide

Example 139B (198 mg, 0.7 mmol) in polyphosphoric acid (5 mL) was heated at 110° C. for 3 hours, cooled, treated with water, and extracted with dichloromethane. The extract was dried (MgSO$_4$), filtered, and concentrated. The residue was purified by flash chromatography on silca gel with 4:5 ethyl acetate-hexane to provide the title compound.

IR(KBr) 3300 (m), 3130 (s), 1660 (s), 1600 (s); MS (DCI/NH$_3$) m/z 301 (M+H)$^+$; $^1$H NMR (300 MHz, DMSO-d$_6$) δ 2.36 (s, 3H), 7.28 (d, 2H), 7.47 (d, 2H), 7.78 (br s, 1H), 7.84 (d, 1H), 8.19 (d, 1H), 8.34 (s, 1H), 8.46 (br s, 1H); Anal. calcd for C$_{15}$H$_{12}$N$_2$OS$_2$: C, 59.98; H, 4.03; N, 9.33. Found: C, 59.77; H, 3.88; N, 9.15.

EXAMPLE 140

4-(4-methylphenoxy)thieno[3,2-c]pyridine-2-carboxamide

EXAMPLE 140A 4-(4-methylphenoxy)thieno[3,2-c]pyridine-2-carbonitrile

Example 139A and 4-methylphenol were processed as in Example 139B to provide the title compound.

IR (KBr) 2200 (w), 1580 (s), 1540 (s), 1500 (s), 1440 (s) cm$^{-1}$; MS (DCI/NH$_3$) m/z 267 (M+H)$^+$; $^1$H NMR (300 MHz, CDCl$_3$) δ 2.39 (s, 3H), 7.09 (dt, 2H), 7.25 (br d, 2H), 7.43 (dd, 1H), 8.10 (d, 1H), 8.21 (s, 1H); Anal. calcd for C$_{15}$H$_{10}$N$_2$OS: C, 67.65; H, 3.78; N, 10.52. Found: C, 67.60; H, 3.66; N, 10.48.

EXAMPLE 140B 4-(4-methylphenoxy)thieno[3,2-c]pyridine-2-carboxamide

Example 140A was processed as in Example 139C to provide the title compound.

IR (KBr) 3400 (m), 1680 (m), 1650 (s), 1600 (s), 1500 (s) cm$^{-1}$; MS (DCI/NH$_3$) m/z 285 (M+H)$^+$; $^1$H NMR (300 MHz, DMSO-d$_6$) δ 2.34 (s, 3H), 7.13 (d, 2H), 7.25 (d, 2H), 7.75 (d, 1H), 7.76 (br s, 1H), 7.95 (d, 1H), 8.38 (br s, 1H), 8.41 (s, 1H); Anal. calcd for C$_{15}$H$_{12}$N$_2$O$_2$S: C, 63.36; H, 4.25; N, 9.85. Found: C, 63.16; H, 4.18; N, 9.77.

EXAMPLE 141

7-(4-methylphenoxy)oxazolo[5,4-c]pyridine-2-carboxamide

EXAMPLE 141A 3-chloropyridine-N-oxide

Example 141A was processed as in Caldwell and Martin (J. Heterocyclic Chem., 1980, 17, 989). A solution of 3-chloropyridine (15.0 g, 132 mmol) in acetic anhydride (75 mL) with cooling to maintain an internal temperature below 30° C. was treated with hydrogen peroxide (75 mL of 30% aqueous solution), stirred at room temperature for 3 hours, heated at 60° C. for 18 hours, diluted with water (200 mL), concentrated, and solid sodium bisulfite added in portions until peroxides could no longer be detected (by enzymatic peroxide test), and the remaining solvent was removed under reduced pressure. The residue was triturated with ethyl acetate. The washes were filtered and concentrated to provide the designated compound.

EXAMPLE 141B 4-nitro-3-chloropyridine-N-oxide

Example 141B was processed as in Caldwell and Martin (J. Heterocyclic Chem., 1980, 17, 989). Example 141A (16.8 g, 130 mmol) in sulfuric acid (25 mL, 98%), fuming sulfuric acid (30% SO$_3$, 10 mL), and nitric acid (60 mL, 90%) was heated at 120° C. for 2 hours, cooled to room temperature, poured into ice water (200 mL), solid ammonium carbonate was added to bring the solution to pH=9, and extracted with methylene chloride (4×100 mL). The extracts were dried (Na$_2$SO$_4$) and concentrated. The residue was recrystallized from ethyl acetate-hexanes to provide a clean first crop of the title compound. Second crop recrystallizations provided mixtures of title compound and side products.

MS (DCI/NH$_3$) m/z 194 ($^{37}$Cl)/192 ($^{35}$Cl), (M+NH$_4$)$^+$; 177 ($^{37}$Cl)/175 ($^{35}$Cl), (M+H)$^+$; $^1$H NMR (CDCl$_3$, 300 MHz) δ 8.01 (d, 1H), 8.14 (dd, 1H), 8.32 (d, 1H).

EXAMPLE 141C 4-nitro-3-(4-methylphenoxy)pyridine-N-oxide

NaH (834 mg, 34.8 mmol) in DMF (20 mL) at room temperature was treated sequentially with p-Cresol (3.57 g, 33.0 mmol) Example 141B (5.75 g, 32.9 mmol), stirred for 10 minutes at room temperature and partitioned between ethyl acetate and 1 N aqueous HCl. The aqueous phase was separated and washed with ethyl acetate. The organic phases were washed with 1 N aqueous HCl, dried (Na$_2$SO$_4$), and concentrated. Recrystallization from diethyl ether provided the title compound.

MS (DCI/NH$_3$) m/z 264 (M+NH$_4$)$^+$, 247 (M+H)$^+$; $^1$H NMR (CDCl$_3$, 300 MHz) δ 2.39 (s, 3H), 7.02 (d, 2H), 7.26 (d, 2H), 7.78 (d, 1H), 7.89 (dd, 1H), 7.98 (d, 1H).

EXAMPLE 141D 3-(4-methylphenoxy)-4-pyridinamine

Example 141C (3.65 g, 14.8 mmol) was dissolved in methanol (100 mL), treated with raney nickel (1.00 g), flushed with hydrogen, pressurized to 4 atm., at 37° C. for 2.5 hours, and filtered. The filtrate was concentrated to provide the title compound.

MS (DCI/NH$_3$) m/z 201 (M+H)$^+$; $^1$H NMR (CDCl$_3$, 300 MHz) δ 2.32 (s, 3H), 4.40 (br s, 2H), 6.68 (br s, 1H), 6.88 (d, 2H), 7.12 (d, 2H), 8.01 (m, 2H).

EXAMPLE 141E 2,2-dimethyl-N-[3-(4-methylphenoxy)-4-pyridinyl]propanamide

Example 141D (2.80 g, 14.0 mmol) was dissolved in methylene chloride (50 mL), cooled to 0° C., treated sequentially with triethylamine (1.78 g, 17.6 mmol) and trimethylacetyl chloride (1.86 g, 15.4 mmol), stirred at room temperature for 15 hours, and poured into water (100 mL) containing a trace of sodium chloride. The organic layer was separated, treated with activated charcoal, filtered through Celite®, washed with saturated sodium bicarbonate, dried (Na$_2$SO$_4$), and concentrated to provide the title compound.

MS (DCI/NH$_3$) m/z 285 (M+H)$^+$; $^1$H NMR (CDCl$_3$, 300 MHz) δ 1.24 (s, 9H), 2,35 (s, 3H), 6.93 (d, 2H), 7.18 (d, 2H), 8.14 (br s, 1H), 8.15 (s, 1H), 8.32 (d, 1H), 8.42 (d, 1H).

EXAMPLE 141F

5-Hydroxy-4-(N-trimethylacetyl)amino-3-(4-methylphenoxy)pyridine

The procedure of Chu-Moyer and Berger (*J. Org. Chem.* 1995, 60, 5721) was adapted. Example 141E (5.50 g, 19.3 mmol) was dissolved in diethyl ether and cooled to –78° C. tert-Butyllithium (24.0 mL of 1.7 M soluton in pentane, 40.8 mmol) was added dropwise and let stir 2 h at –78° C. Trimethylborate (5.01 g, 48.3 mmol) was added, and the reaction was slowly warmed to room temperature and stirred for 18 h. Glacial acetic acid (3.9 mL) was added, followed by the addition of 30% aqueous hydrogen peroxide (5.8 mL). The reaction was stirred 2 h at room temperature and then poured into water. The resulting mixture was washed twice with CH$_2$Cl$_2$, and the organic layers were treated with activated charcoal and filtered through celite. The filtrate was washed once with water, once with brine, dried (Na$_2$SO$_4$), and concentrated under reduced pressure to give a mixture of two compounds, the higher R$_f$ being desired. The mixture was purified by flash silica chromatography using a 40M Biotage cartridge, 1.5% methanol in CH$_2$Cl$_2$ eluent, to give 0.15 mmol (15% yield) of the desired product and 0.73 mmol (73%) of the title compound.

MS (DCI/NH$_3$) m/e 301 (M+H)$^+$; $^1$H NMR (CDCl$_3$, 300 MHz) δ 1.20 (s, 9H), 2.27 (s, 3H), 6.84 (d, 2H), 7.09 (d, 2H), 7.65 (br s, 1H), 8.08 (s, 1H), 8.14 (br s, 1H), 10.26 (br s, 1H).

EXAMPLE 141G

5-Hydroxy-4-amino-3-(4-methylphenoxy)pyridine

Example 141F (850 mg, 2.83 mmol) was suspended in 3 N aqueous HCl and stirred at 90° C. for 18 h. The reaction was then cooled to 0° C., neutralized with 6 N aqueous NaOH, and extracted with CH$_2$Cl$_2$. The organic layers were combined, dried (Na$_2$SO$_4$), and concentrated under reduced pressure to give the desired product (612 mg, 100% yield).

MS (DCI/NH$_3$) m/e 217 (M+H)$^+$; $^1$H NMR (300 MHz, DMSO-d$_6$) δ 2.25 (s, 3H), 5.16 (s, 2H), 6.81 (d, 2H), 7.12 (d, 2H) 7.50 (s, 1H), 7.71 (s, 1H), 8.14 (s, 1H), 9.55 (br s, 1H).

EXAMPLE 141H

Methyl Oxazolo[5,4-c]-4-(4-methylphenoxy)pyridine-2-carboxylate

To Example 141G (1.00 mmol) in DMF is added pyridine (1.10 mmol) and methyl oxalyl chloride (1.10 mmol), and the resulting solution is stirred at room temperature overnight. The reaction is then partitioned between methylene chloride and 1 N aqueous HCl, and the organic phase is separated, dried (Na$_2$SO$_4$), and concentrated under reduced pressure to give the title compound.

EXAMPLE 141I

Oxazolo[5,4-c]-4-(4-methylphenoxy)pyridine-2-carboxamide

Example 141H may be treated according to the procedure of Example 44 to give the title compound.

EXAMPLE 142

7-(4-Methylphenoxy)[1,3]thiazolo[5,4-c]pyridine-2-carboxamide

EXAMPLE 142A 5-(N,N-Dimethylthiuram)sulfide-4-(N-trimethylacetyl)amnino-3-(4-methylphenoxy)pyridine Example 141E (284 mg, 1.00 mmol) in diethylether (12 mL) at –78° C. was treated dropwise with tert-butyllithium (1.3 mL of 1.7 M solution in pentanes, 2.21 mmol, Aldrich) followed by stirring for 3 h at –78° C. Tetramethyl thiuram disulfide (529 mg, 2.20 mmol) was added to the resultant dianion, and stirring and temperature elevation was continued for 18 h. The reaction was quenched with water and extracted with CH$_2$Cl$_2$. The organic phase is dried (Na$_2$SO$_4$) and concentrated under reduced pressure. The title compound (50 mg, 12% yield) was isolated by flash silica gel column chromatography.

MS (DCI/NH$_3$) m/e 404 (M+H)$^+$; $^1$H NMR (CDCl$_3$, 300 MHz) δ 2.32 (s, 3H), 3.55 (s, 3H), 3.58 (s, 3H), 6.92 (d, 2H), 7.12 (d, 2H), 7.93 (s, 1H), 8.43 (s, 1H), 8.45 (s, 1H).

EXAMPLE 142B 5-(N,N-Dimethylthiuram)sulfide-4-amino-3-(4-methylphenoxy)pyridine Example 142A (270 mg, 0.67 mmol) was combined with formic acid (20 mL of 96%, Aldrich) and stirred at 90° C. for 72 hr. The reaction is then cooled to room temperature, and the formic acid is removed under reduced pressure. The resulting residue is purified by flash silica gel chromatography (70% EtOAc in hexane) to provide the title compound (96 mg, 45% yield).

MS (DCI/NH$_3$) m/e 320 (M+H)$^+$; $^1$H NMR (CDCl$_3$, 300 MHz) δ 2.33 (s, 3H), 3.56 (s, 3H), 3.58 (s, 3H), 4.93 (br s, 2H), 6.94 (d, 2H), 7.15 (d, 2H), 8.04 (s, 1H), 8.12 (s, 1H).

EXAMPLE 142C 5-(N,N-Dimethylthiuram)sulfide-4-methyloxamate-3-(4-methylphenoxy)pyridine Example 142B (90 mg, 0.28 mmol) was combined with CH$_2$Cl$_2$ (7.0 mL). Triethyl amine (0.39 mL, 2.2 mmol) was added, followed by the addition of methyl oxalyl chloride (120 mL, 1.30 mmol, Aldrich). After 6 h, the mixture was combined with saturated aqueous sodium bicarbonate and extracted thrice with CH$_2$Cl$_2$. The organic layers were combined, dried (Na$_2$SO$_4$), filtered, and concentrated under reduced pressure.

MS (DCI/NH$_3$) m/e 406 (M+H)$^+$; $^1$H NMR (CDCl$_3$, 300 MHz) δ 2.33 (s, 3H), 3.54 (s, 3H), 3.58 (s, 3H), 3.90 (s, 3H), 7.00 (d, 2H), 7.15 (d, 2H), 8.37 (s, 1H), 8.41 (s, 1H), 9.20 (br s, 1H).

EXAMPLE 142D

Methyl 4-(4-Methylphenoxy)thiazolo[5,4-c]-pyridine-2-carboxylate

Example 142C (50 mg, 0.12 mmol) was dissolved in formic acid (14 mL, 96%, Aldrich), and heated to reflux. After 4 h, the reaction was cooled, and volatiles were removed. Flash silica gel column chromatography (60%

EtOAc in hexane) provided the title compound (15 mg, 39% yield) as a white solid.

MS (DCI/NH$_3$) m/e 301 (M+H)$^+$, 318 (M+NH$_3$)$^+$; $^1$H NMR (CDCl$_3$, 300 MHz) δ 2.39 (s, 3H), 4.10 (s, 3H), 7.08 (d, J=8.5 Hz, 2H), 7.22 (d, J=8.5 Hz, 2H), 8.14 (s, 1H), 9.00 (s, 1H).

EXAMPLE 142E 4-(4-Methylphenoxy)thiazolo[5,4-c]-pyridine-2-carboxamide

Example 142D (2.0 mg, 6.7 mmol) was treated according to the procedure of Example 44 to give the title compound (1.5 mg, 75%) as a white solid.

MS (DCI/NH$_3$) m/e 286 (M+H)$^+$, 303 (M+NH$_3$)$^+$; $^1$H NMR (CDCl$_3$, 300 MHz) δ 2.39 (s, 3H), 5.66 (br s, 1H), 7.06 (d, J=8.2 Hz, 2H), 7.22 (d, J=7.8 Hz, 2H), 7.32 (br s, 1H), 8.20 (s, 1H), 9.04 (s, 1H).

EXAMPLE 143

7-(4-methylphenoxy)-3H-imidazo[4,5-c]pyridine-2-carboxamide

EXAMPLE 143A

N-[3-amino-5-(4-methylphenoxy)-4-pyridinyl]-2,2-dimethylpropanamide

Example 141F (1.00 mmol) is suspended in ammonium hydroxide (28%), saturated with sulfur dioxide, heated to 150° C. in a pressure vessel for 27 hours, and cooled, and extracted with ethyl acetate. The extract is concentrated to provide the title compound.

EXAMPLE 143B 5-(4-methylphenoxy)-3,4-pyridinediamine

Example 143A (1.00 mmol) is suspended in HCl (3N aqueous) and stirred at 90° C. for 18 hours, cooled to 0° C., neutralized with 6 N aqueous NaOH, and the water removed. The resulting residue is triturated with methanol. The washes are concentrated to provide the title compound.

EXAMPLE 143C methyl 7-(4-methylphenoxy)-3H-imidazo[4,5-c]pyridine-2-carboxylate Example 143B (1.00 mmol) in DMF is treated with pyridine (1.10 mmol) and methyl oxalyl chloride (1.10 mmol), stirred at room temperature overnight, and partitioned between methylene chloride and 1 N aqueous HCl. The organic phase is separated, dried (Na$_2$SO$_4$), and concentrated to provide the title compound.

EXAMPLE 143D 7-(4-methylphenoxy)-3H-imidazo[4,5-c]pyridine-2-carboxamide

Example 143C can be treated as in Example 44 to give the title compound.

EXAMPLE 144

4-(4-chlorophenoxy)thieno[2,3-d]pyridazine-2-carboxamide

EXAMPLE 144A

3-Bromothiophene-2-carboxaldehyde

Example 144A can be processed as in Prugh, et. al. (J. Med. Chem. 1991, 34, 1805). A solution of dibromothiophene (14 g, 58 mmol) in THF (100 mL) at −78° C. was treated with n-butyllithium (24 mL, 59 mmol), stirred for 15 minutes, treated with dry DMF (6.8 mL, 87 mmol), stirred at −78° C. for 10 minutes, slowly warmed to 0° C. over a period of 15 minutes, poured into cold 1 N aqueous HCl, and extracted with diethyl ether. The extract was washed with 1 N aqueous HCl, water, and saturated sodium bicarbonate. The washes were extracted with diethyl ether. The organic layers were combined, dried (MgSO$_4$), filtered, and concentrated under reduced pressure. The residue was purified by flash chromatography on silica gel with 5% ethyl acetate/hexanes to provide the title compound.

$^1$H NMR (CDCl$_3$, 300 MHz) δ 7.16 (d, 1H), 7.74 (d, 1H), 10.0 (s, 1H).

EXAMPLE 144B 3-bromo-2-(2-dioxolanyl)thiophene

Example 144B can be processed as in Prugh, et. al. (J. Med. Chem. 1991, 34, 1805). A three-necked flask equipped with a Dean-Stark trap is charged with Example 144A (5.24 g, 27.4 mmol), ethylene glycol (6.2 mL, 110 mmol), pyridinium tosylate (276 mg, 1.10 mmol), and toluene (30 mL), heated at reflux for 14 hours, cooled to room temperature, poured into water, and extracted with diethyl ether. The organic layer is washed with water and saturated sodium bicarbonate, dried (MgSO$_4$), filtered, and concentrated. The residue is purified by flash chromatography on silica gel with 5% ethyl acetate/hexanes to provide the title compound.

MS (DCI/NH$_3$) m/z 252 ($^{79}$Br)/254 ($^{81}$Br), (M+NH$_4$)$^+$; 235 ($^{79}$Br)/237 ($^{81}$Br), (M+H)$^+$; $^1$H NMR (CDCl$_3$, 300 MHz) δ 4.11–4.02 (m, 4H), 6.14 (s, 1H), 6.97 (d, 1H), 7.30 (d, 2H).

EXAMPLE 144C ethyl-2-(2-dioxylanyl)thiophene-3-carboxylate

Example 144C can be processed as in Prugh et al. (J. Med. Chem., 1991, 34, 1805). Example 144B (1.00 g, 4.25 mmol) in THF (12 mL) is treated with n-butyllithium (1.7 mL, 4.25 mmol) while maintaining temperature between −105 and −95° C., treated with diethyl carbonate (0.57 mL, 4.68 mmol), and warmed to room temperature. The solution is poured into water and extracted with diethyl ether. The extract is washed with brine, dried (MgSO$_4$), filtered, and concentrated under reduced pressure. The residue is purified by flash chromatography on silica gel 5% ethyl acetate/hexanes to provide the title compound.

EXAMPLE 144D 2-formylthiophene-3-carboxylic acid

Example 144C (1.0 mmol) and ethanol (1.0 mL) are treated with 1 N aqueous sodium hydroxide solution (100 mmol), stirred for 1 hour, brought to pH=5 by the addition of glacial acetic acid, stirred for 1 hour, diluted with water, and extracted with ethyl acetate. The extracts are combined, washed with brine, washed with saturated sodium bicarbonate, dried (MgSO$_4$), filtered, and concentrated. The designated compound is used without further purification.

EXAMPLE 144E 4-oxothieno[2,3-d]pyridazine

Example 144D is processed as in Bull. Soc. Chim. Fr. 1967, 2495.

EXAMPLE 144F

4-chlorothieno[2,3-d]pyridazine

Example 144E is processed as in Bull. Soc. Chim. Fr. 1967, 2495.

EXAMPLE 144G

4-(4-Chlorophenoxy)thieno[2,3-d]pyridazine

Adapting the method of Robba and others (Bull. Soc. Chim. Fr., 1967, 4220), Example 144F (100 mg, 0.59 mmol) was combined with 4-chlorophenol (1.0 mL, 10.0 mmol) and sodium metal (21 mg, 0.90 mmol). The mixture was heated at 100° C. for 14 h. After cooling to room temperature, the residue was diluted with chloroform and washed once with 2 N aqueous sodium hydroxide and once with brine. The organic layer was dried (MgSO$_4$), filtered, and concentrated under reduced pressure. Recrystallization from diethyl ether gave the title compound (124 mg, 85%) as a white solid.

MS (DCI/NH$_3$) m/e: 363 (M+H)$^+$; $^1$H NMR (CDCl$_3$, 300 MHz) d 7.27 (d, J=8.9 Hz, 2H), 7.42 (d, J=8.9 Hz, 2H), 7.72 (d, J=5.5 Hz, 1H), 7.88 (d, J=5.2 Hz, 1H), 9.41 (s, 1H).

EXAMPLE 144H

4-(4-chlorophenoxy)thieno[2,3-d]pyridazine-2-carboxylic acid

Example 144G (1.0 mmol) in THF (1.0 mL) at −78° C. is treated with n-Butyllithium (1.0 mmol), stirred for 15 minutes, saturated with CO$_2$, slowly warmed to room temperature, partitioned between 1 N aqueous sodium hydroxide and diethyl ether, separated, and glacial acetic acid added to the aqueous layer until pH=5. The acidic solution is extracted thrice with methylene chloride. The extracts are combined, washed with dilute sodium bicarbonate, dried (MgSO$_4$), filtered, and concentrated to provide the title compound.

EXAMPLE 144I

4-(4-chlorophenoxy)thieno[2,3-d]pyridazine-2-carbamide

Example 144I can be processed as in Desai and Stramiello (Tetrahedron Lett, 1993, 34, 7685). Example 144H (1.0 mmol), 1-hydroxybenzotriazol (1.4 mmol), N-methylmorpholine (12 mmol), and DMF (1.0 mL) are combined and cooled to 0° C., treated with 1-(3-Dimethylaminopropyl)-3-ethylcarbodiimide hydrochloride (1.4 mmol), stirred at 0° C. for 1 hour, and partitioned between methylene chloride, saturated sodium bicarbonate, and separated. The extract is dried (MgSO$_4$), filtered, and concentrated. Recrystallization from hot methanol will provide the title compound.

EXAMPLE 145

7-(4-chlorophenoxy)thieno[3,2-c]pyridine-2-carbamide

EXAMPLE 145A

2,5-dibromo-3-thioiphenecarboxaldehyde

A solution of 3-thiophenecarboxaldehyde is processed as in Bull. Soc. Chim. Fr., 1974, 3040 to provide the title compound.

EXAMPLE 145B dimethylacetyl-(2,5-dibromo-3-thienyl)carboximino ethane

Example 145A is processed as in Bull. Soc. Chim. Fr., 1974, 3040 to provide the title compound.

EXAMPLE 145C

6,7-dihydro-7-oxothieno[3,2-c]pyridine

Example 145B is processed as in Bull. Soc. Chim. Fr., 1974, 3040 to provide the title compound.

EXAMPLE 145D

7-(4-chlorophenoxy)thieno[3,2-c]pyridine

Example 145D can be processed as in Lindley (Tetrahedron, 1983, 1433). A solution of Example 145C (1.0 mmol) and DMF (2.0 mL) is treated at 0° C. with sodium hydride (1.0 mmol), slowly warmed to room temperature, treated with 1-chloro-4-iodobenzene (1.0 mmol) and copper iodide (0.1 mmol), heated at 80° C. overnight, and cooled. The solution is poured into water and extracted with diethyl ether. The extracts are combined, dried (MgSO$_4$), filtered, and concentrated. Recrystallization from ethyl acetate/hexanes provides the title compound.

EXAMPLE 145E

7-(4-chlorophenoxy)thieno[3,2-c]pyridine-2-carboxylic acid

The designated compound is processed in the manner described for Example 144H.

EXAMPLE 145F

7-(4-chlorophenoxy)thieno[3,2-c]pyridine-2-carboxamide

The designated compound is processed in the manner described for Example 144I.

EXAMPLE 146

4-(4-Chlorophenoxy)thieno[2,3-c]pyridine-2-carbothioamide

A solution of Example 61 (50 mg, 0.16 mmol) and Lawesson's reagent (73 mg, (0.18 mmol) in toluene (2 mL) was heated at reflux for 4 hours. The solvent was removed under reduced pressure to obtain the crude product (150 mg) as a yellow residue. The purified title compound (24 mg, 47%) was obtained by flash chromatography on silica gel eluting with 10% methanol in dichloromethane.

MS (DCI/NH$_3$) m/e 321 (M+H)$^+$; $^1$H NMR (300 MHz, DMSO-d$_6$) δ 7.14 (m, 2H), 7.47 (m, 2H), 8.18 (s, 1H), 8.21 (s, 1H), 9.14 (s, 1H); 9.86 (s, 1H);10.15 (s, 1H).

EXAMPLE 147

4-(4-Chlorophenoxy)-N-ethylthieno[2,3-c]pyridine-2-carboxamide

Example 61A (200 mg, 0.627 mmol) was prepared as in Example 171 but substituting ethylamine (1 ml, 17.65 mmol) for methylamine to provide the title compound (209 mg, 100%).

MS (DCI/NH$_3$) m/e 333 (M+H)$^+$, 303; $^1$H NMR (400 MHz, DMSO-d$_6$) δ 1.14 (t, J=8 Hz, 3H), 3.30 (m, 2H), 7.14 (d, J=9 Hz, 2H), 7.47 (d, J=9 Hz, 2H, 8.13 (s, 1H), 8.17 (s, 1H), 8.91 (t, J=6 Hz, 1H), 9.15 (s, 1H).

EXAMPLE 148

4-(4-Chlorophenoxy)-N-(2,3-dihydroxypropyl)thieno[2,3-c]pyridine-2-carboxamide

Example 148 was prepared in a similar manner as Example 103A, by combining 3-amino-1,2-propanediol (60 mL, 0.782 mmol) with Example 61A (250 mg, 0.782 mmol) to provide the title compound (133 mg, 45% yield) as a white solid.

mp 106–115° C.; MS (DCI/NH$_3$) m/e: 379 (M+H)$^+$; $^1$H NMR (300 MHz, DMSO-d$_6$) δ 3.16 (m, 2H), 3.38 (m, 2H), 3.63 (m, 1H), 4.56 (t, J=5.7 Hz, 1H), 4.81 (d, J=5.1 Hz, 1H), 7.13 (d, J=9.2, 2H), 7.47 (d, J=9.2 Hz, 2H), 8.18 (s, 1H), 8.21 (s, 1H), 8.95 (t, J=5.7 Hz, 1H), 9.16 (s, 1H); Anal. calcd for C$_{17}$H$_{15}$ClN$_2$O$_4$S.0.25 H$_2$O: C, 53.27; H, 4.08; N, 7.31. Found: C, 53.19; H, 4.22; N, 6.22.

EXAMPLE 149

4-(4-Bromophenoxy)-N-(2,3-dihydroxypropyl)thieno[2,3-c]pyridine-2-carboxamide

Example 149 was prepared according to the procedure of Example 114, with the substitution of methyl 4-(4-bromophenoxy)-thieno[2,3-c]pyridine-2-carboxylate for Example 61A.

mp 76–77° C.; MS (DCI/NH$_3$) m/e: 423,425 (M+H)$^+$; $^1$H NMR (300 MHz, DMSO-d$_6$) δ 3.12 (m, 2H), 3.41 (m, 3H), 3.63 (m, 2H), 7.06 (d, 2H, J=8.8 Hz), 7.59 (d, 2H, J=8.8 Hz), 8.20 (s, 1H), 8.22 (s, 1H), 8.99 (t, 1H, J=5.5 Hz), 9.18 (s, 1H).

EXAMPLE 150

N-(2-Chloroethyl)-4-(4-chlorophenoxy)thieno[2,3-c]pyridine-2-carboxamide

To a solution of Example 114 (0.32 g, 0.92 mmol) in anhydrous THF (5 mL) was slowly added thionyl chloride (0.34 mL, 4.60 mmol). The reaction was heated to 50° C. for 18 hr, cooled to room temperature, and neutralized with sat. NaHCO$_3$. The aqueous suspension was extracted with dichloromethane (100 mL) and the organic layer washed with dilute NaHCO$_3$ (2×100 mL), brine (50 mL), partially dried (Na$_2$SO$_4$), and concentrated to a solid. The crude product was purified by flash chromatography on silica gel using EtOAc/hexane as eluent to yield the title compound as a solid (0.27 g, 80%).

mp 60–62° C. (dec); MS (DCI-NH$_3$) m/e 367 (M+H)$^+$; $^1$H NMR (300 MHz, DMSO-d$_6$) δ 3.60 (m, 2H), 3.75 (t, J=6.1 Hz, 2H), 7.15 (m, 2H), 7.48 (m, 2H), 8.18 (s, 1H), 8.18 (s, 1H), 9.17 (s, 1H), 9.26 (m, 1H); Anal. calcd for C$_{16}$H$_{12}$Cl$_2$N$_2$O$_2$S: C, 52.33; H, 3.29; N, 7.63. Found: C, 52.22; H, 3.47; N, 7.35.

EXAMPLE 151

4-(4-Bromophenoxy)-N-(2-hydroxyethyl)thieno[2,3-c]pyridine-2-carboxamide

Example 151 was prepared according to the procedure of Example 114, with the substitution of methyl 4-(4-bromophenoxy)-thieno[2,3-c]pyridine-2-carboxylate for Example 61A.

mp 158–159° C.; MS (DCI/NH$_3$) m/e: 393,395 (M+H)$^+$; $^1$H NMR (300 MHz, DMSO-d$_6$) δ 3.32 (m, 2H), 3.51 (m, 3H), 4.79 (t, 1H, J=5.9 Hz), 7.06 (d, 2H, J=8.8 Hz), 7.59 (d, 2H, J=8.8 Hz), 8.17 (s, 1H), 8.20 (s, 1H), 9.02 (t, 1H, J=5.5 Hz), 9.17 (s, 1H).

EXAMPLE 152

4-(2-Bromo-4-chlorophenoxy)-N-(2-hydroxyethyl)thieno[2,3-c]pyridine-2-carboxamide Example 152 was prepared according to the procedure of Example 114, with the substitution of 2-bromo-4-chlorophenol for 4-chlorophenol.

MS (DCI/NH$_3$) m/e: 428 (M+H)$^+$; $^1$H NMR (300 MHz, DMSO-d$_6$) δ 2.86 (q, 1H, J=5.4 Hz), 3.34 (m, 2H), 3.55 (m, 2H); 7.15 (d, 1H, J=8.8 Hz), 7.48 (dd, 1H, J=2.4, 8.8 Hz), 7.97 (d, 1H, J=2.7 Hz), 8.02 (s, 1H), 8.25 (s, 1H), 9.05 (t, 1H, J=5.4 Hz), 9.16 (s, 1H).

EXAMPLE 153

N-(2-Hydroxyethyl)-4-[4-(trifluoromethyl)phenoxy]thieno[2,3-c]pyridine-2-carboxamide A solution of Example 62A (322 mg, 0.912 mmol) in 10 mL of dichloromethane was treated with 226 mg (3.65 mmol) of ethanolamine. The solution was heated to reflux for 4 hours. Upon cooling crystals formed. Recrystallization from ethyl acetate afforded 170 mg (48.8%) of white crystals.

mp 181–182° C.; MS (DCI/NH$_3$) m/e: 383 (M+H)$^+$; $^1$H NMR (300 MHz, DMSO-d$_6$) δ 3.3–3.4 (m, 2H), 3.5–3.6 (m, 2H), 4.80 (t, 1H), 7.21 (d, 2H), 7.79 (d, 2H), 8.15 (s, 1H), 8.38 (s, 1H), 9.01 (t, 1H), 9.25 (s, 1H); Anal. calcd for C$_{17}$H$_{13}$F$_3$N$_2$O$_3$S: C, 53.40; H, 3.43; N, 7.33. Found: C, 53.41; H, 3.62; N, 7.30.

EXAMPLE 154

N-(2-Aminoethyl)-4-(4-chlorophenoxy)thieno[2,3-c]pyridine-2-carboxamide

To a suspension of Example 88 (0.50 g, 1.64 mmol) in anhydrous methylene chloride (15 mL) was added N,N-diisopropylethylamine (0.57 mL, 3.28 mmol). The reaction was cooled in an ice bath and pivaloyl chloride (0.24 mL, 1.97 mmol) was slowly added. After 10 minutes, the ice bath was removed and reaction stirred at ambient temperature for 1.5 hr. The reaction contents were slowly transferred via cannula into an anhydrous solution of ethylenediamine (0.33 mL, 4.92 mmol) in methylene chloride (5 mL) at 0° C. over a period of 5 minutes. The reaction was stirred 15 minutes and the cold bath was removed. The reaction was stirred 1 hr and then partitioned between CHCl$_3$/Sat.NaHCO$_3$. The organic layer was washed with dilute aqueous NaHCO$_3$, brine, dried (Na$_2$SO$_4$), and concentrated to yield a light yellow foam. The crude product was purified by preparative HPLC using a gradient of 25%–65% acetonitrile/water +0.1% TFA over 40 minutes. The product was neutralized with saturated aqueous NaHCO$_3$, precipitate collected by filtration, and dried in a desiccator to yield the title compound as a white solid (0.45 g, 79%).

mp 111–114° C.; MS (APCI) m/e 348 (M+H)$^+$; $^1$H NMR (300 MHz, DMSO-d$_6$) δ 2.69 (t, J=6.4 Hz, 2H), 3.25 (t, J=6.4 Hz, 2H), 7.14 (m, 2H), 7.47 (m, 2H), 8.16 (s, 1H), 8.18 (s, 1H), 9.15 (s, 1H).

EXAMPLE 155

4-(4-Chlorophenoxy)-N-hydroxythieno[2,3-c]pyridine-2-carboxamide

Example 155 was prepared as in Example 92 by combining Example 88 (161 mg, 0.527 mmol) with hydroxylamine hydrochloride (37.0 mg, 0.527 mmol) to provide the title product (40 mg, 24% yield) as a white solid.

mp 145° C. (decomposes); MS (DCI/NH$_3$) m/e: 321 (M+H)$^+$; $^1$H NMR (300 MHz, CD$_3$OD) δ 7.11 (d, J=9.2 Hz, 2H), 7.42 (d, J=9.2 Hz, 2H), 7.90 (s, 1H), 8.05 (s, 1H), 9.01 (s, 1H); IR (KBr) 3200–2800 (m), 1660 (s), 1640 (s), 1560 (m), 1485 (s), 1420 (s) cm−1; Anal. calcd for C$_{14}$H$_9$ClN$_2$O$_3$S+0.25 H$_2$O: C, 51.70; H, 2.94; N, 8.61. Found: C, 51.64; H, 2.71; N, 8.80.

EXAMPLE 156

4-(4-Chlorophenoxy)thieno[2,3-c]pyridine-2-carbohydrazide

Example 61A (0.50 g, 1.56 mmol) was dissolved in dichloromethane (10 mL) and anhydrous hydrazine (1 mL) was added. After 24 hours, the precipitate was collected by filtration and washed with dichloromethane (2×25 mL) and water (2×50 mL). The product was dried in a desiccator to yield the title compound as a white solid (0.35 g, 70%).

mp 197–199° C.; MS (APCI) m/e: 320 (M+H)$^+$; $^1$H NMR (300 MHz, DMSO-d$_6$) δ 4.62 (broad s, 2H), 7.12 (m, 2H), 7.46 (m, 2H), 8.03 (s, 1H), 8.19 (s, 1H), 9.15 (s, 1H), 10.24 (br s, 1H); Anal. calcd for C$_{14}$H$_{10}$ClN$_3$O$_2$S: C, 52.59; H, 3.15; N, 13.14. Found: C, 52.59; H, 3.12; N, 13.18.

EXAMPLE 157

4-(4-Bromophenoxy)thieno[2,3-c]pyridine-2-carbohydrazide

Example 73A (0.21 g, 0.58 mmol) was dissolved in dichloromethane (2 mL) and anhydrous hydrazine (1 mL) added. After 18 hours, the precipitate was collected by filtration and washed with dichloromethane (2×5 mL), water (2×5 mL), acetonitrile (2×5 mL) to yield white solid. The washes were combined, diluted with sat. NaHCO$_3$ (100 mL) and extracted with dichloromethane (4×25 mL). Organic extracts were combined, partially dried (Na$_2$SO$_4$), and concentrated to yield a white solid which was combined with the collected precipitate and dried in a desiccator (0.21 g, 99%).

mp 176–178° C.; MS (APCI) m/e: 364 (M+H)$^+$; $^1$H NMR (300 MHz, DMSO-d$_6$) δ 4.62 (br s, 2H), 7.06 (m, 2H), 7.58 (m, 2H), 8.02 (s, 1H), 8.21 (s, 1H), 9.16 (s, 1H), 10.24 (br s, 1H); Anal calcd for C$_{14}$H$_{10}$BrN$_3$O$_2$S: C, 46.17; H, 2.77; N, 11.54. Found: C, 46.08; H, 2.90; N, 11.41.

EXAMPLE 158

4-[4-(Trifluoromethyl)phenoxy]thieno[2,3-c]pyridine-2-carbohydrazide

Example 62A was treated according to the procedure of Example 157 to provide the title compound.

mp 146–147° C.; MS (ESI) m/e: 353.9 (M+H)$^+$; $^1$H NMR (300 MHz, DMSO-d$_6$) δ 3.18 (d, 2H), 4.11 (t, 1H), 7.19 (d, 2H), 7.77 (d, 2H), 7.78 (s, 1H), 8.36 (s, 1H), 9.21 (s, 1H).

EXAMPLE 159

2-({[4-(4-Chlorophenoxy)thieno[2,3-c]pyridin-2-yl]carbonyl}amino)acetic acid Example 159A 4-(4-Chlorophenoxy)thieno[2,3-c]pyridin-2-carboxylic acid A suspension of Example 61A (354 mg, 1.11 mmol) in 3 mL methanol and 1 mL water was treated with lithium hydroxide monohydrate (98 mg, 2.33 mmol) and the resulting mixture was stirred at room temperature (under N$_2$) for 20 hours. The reaction was acidified with 0.13 mL of 90% formic acid, and the white suspension was stirred for 5 minutes, then the solid was isolated by suction filtration. The solid was washed sequentially with 15 mL water and 5 mL diethyl ether, then dried under vacuum to provide 302 mg (89%) of the title compound.

MS (DCI-NH$_3$) m)/e: 306, 308 (M+H)$^+$; $^1$H NMR (300 MHz, DMSO-d$_6$) δ 7.15 (m, 2H), 7.47 (m, 2H), 7.82 (s, 1H), 8.23 (s, 1H), 9.21 (s, 1H), 13–15 (vbr s, 1H); Anal. calcd for C$_{17}$H$_8$ClNO$_3$S: C, 55.00; H, 2.64; N, 4.58. Found: C, 54.77; H, 2.60; N, 4.44.

EXAMPLE 159B

Methyl 2-({[4-(4-Chlorophenoxy)thieno[2,3-c]pyridin-2-yl]carbonyl}amino)acetate The title compound was prepared from Example 159A in analogy to Example 92, with the substitution of glycine methyl ester hydrochloride for ammonium chloride.

HPLC: Supelco C-18 column, eluent gradient of water-:acetonitrile 0:90–90:0 over 30 minutes, detection at 254 nm, flow rate of 0.8 mL/min, RT 19.04 minutes; MS (APCI) m/e: 377 (M+H)$^+$; $^1$H NMR (300 MHz, DMSO-d$_6$) δ 3.68 (s, 3H), 4.05 (d, J=6 Hz, 2H), 7.13 (m, 2H), 7.49 (m, 2H), 8.19 (s, 1H), 8.21 (s, 1H), 9.19 (s, 1H), 9.50 (br t, J=6 Hz, 1H); Anal. calcd for C$_{17}$H$_{13}$ClN$_2$O$_4$S: C, 54.19; H, 3.48; N, 7.43. Found: C, 53.92; H, 3.61; N, 7.52.

EXAMPLE 159C

2-({[4-(4-Chlorophenoxy)thieno[2,3-c]pyridin-2-yl]carbonyl}amino)acetic acid The title compound was prepared from Example 159B using the procedure of Example 18 to provide the title compound.

MS (APCI) m/e: 363 (M+H)$^+$; $^1$H NMR (300 MHz, DMSO-d$_6$) δ 3.95 (d, J=6 Hz, 2H), 7.13 (m, 2H), 7.48 (m, 2H), 8.19 (s, 1H), 8.21 (s, 1H), 9.19 (s, 1H), 9.41 (br t, J=6 Hz, 1H), 12.77 (br s, 1H); Anal. calcd for C$_{16}$H$_{11}$ClN$_2$O$_4$S.1 H$_2$O: C, 50.46; H, 3.44; N, 7.36. Found: C, 50.33; H, 3.38; N, 7.29.

EXAMPLE 160

N-(2-Amino-2-oxoethyl)-4-(4-chlorophenoxy)thieno[2,3-c]pyridine-2-carboxamide The title compound was prepared from Example 159C in analogy to Example 92.

mp 222–225° C.; MS (APCI) m/e: 362 (M+H)$^+$; $^1$H NMR (300 MHz, DMSO-d$_6$) δ 3.82 (br s, 2H), 7.12 (m, 2H), 7.49 (m, 2H), 8.19 (s, 1H), 8.21 (s,1H), 9.20 (s,1H), 9.29 (br s, 1H); Anal. calcd for C$_{16}$H$_{12}$ClN$_3$O$_3$S.1.35 H$_2$O: C, 49.77; H, 3.84; N, 10.88. Found: C, 49.86; H, 3.79; N, 10.59.

EXAMPLE 161

N-(2-Amino-2-oxoethyl)-4-(4-bromophenoxy)thieno[2,3-c]pyridine-2-carboxamide

EXAMPLE 161A

Methyl N-(2-amino-2-oxoethyl)-4-(4-bromophenoxy)thieno[2,3-c]pyridine-2-carbocylate Example 73A was hydrolyzed according to the procedure of Example 18. The derived carboxylic acid was coupled to glycine methyl ester hydrochloride in analogy to Example 92.

MS (DCI/NH$_3$) m/e: 421 (M+H)$^+$; $^1$H NMR (300 MHz, DMSO-d$_6$) δ 370 (s, 3H), 4.11 (br d, 2H), 7.11 (br d, 2H), 7.61 (br d, 2H), 8.22 (br d, 2H), 9.19 (s, 1H), 9.51 (br t, 1H); $^{13}$C NMR (100 MHz, DMSO-d$_6$) δ 41.15, 51.84, 104.95, 115.57, 119.74, 119.97, 132.93, 133.32, 137.36, 138.04, 141.45, 145.06, 147.03, 156.10, 161.09, 169.80; Anal. calcd for C$_{17}$H$_{13}$BrN$_2$O$_4$S: C, 48.47; H, 3.11; N, 6.65. Found: C, 48.16; H, 3.27; N, 6.65.

EXAMPLE 161B 2-({[4-(4-Bromophenoxy)thieno[2,3-c]pyridin-2-yl]carbonyl}amino)acetic acid The title compound was prepared from Example 161A using the procedure of Example 18 to provide the title compound.

MS (DCI/NH$_3$) m/e: 407 (M+H)$^+$; $^1$H NMR (300 MHz, DMSO-d$_6$) δ 4.11 (br d, 2H), 7.10 (br d, 2H), 7.60 (br d, 2H), 8.21 (br d, 2H), 9.19 (s, 1H), 9.40 (br t, 1H); $^{13}$C NMR (100 MHz, DMSO-d$_6$) δ 41.50, 115.85, 120.00, 120.09, 133.25, 133.67, 137.76, 138.34, 141.79, 145.74, 147.29, 156.46, 161.28, 171.05; Anal. calcd for C$_{16}$H$_{11}$BrN$_2$O$_4$S.H$_2$O: C, 45.19; H, 3.08; N, 6.59. Found: C, 45.20; H, 3.15; N, 6.45.

EXAMPLE 161C

N-(2-Amino-2-oxoethyl)-4-(4-bromophenoxy)thieno[2,3-c]pyridine-2-carboxamide

The title compound was prepared from Example 161B in analogy to Example 92.

MS (APCI) m/e: 406 (M+H)$^+$; $^1$H NMR (300 MHz, DMSO-d$_6$) δ 3.81 (br d, J=6 Hz, 2H), 7.08 (m, 2H), 7.10 (br s, 1H), 7.60 (m, 2H), 8.19 (s, 1H), 8.22 (s, 1H), 9.20 (s, 1H), 9.28 (br t, J=6 Hz, 1H); Anal. calcd for C$_{16}$H$_{12}$BrN$_3$O$_3$S.0.3 H$_2$O: C, 46.68; H, 3.09; N, 10.21. Found: C, 46.68; H, 3.30; N, 10.16.

EXAMPLE 162

N-[(1S)-2-Amino-1-(hydroxymethyl)-2-oxoethyl]-4-(4-chlorophenoxy)thieno[2,3-c]pyridine-2-carboxamide

EXAMPLE 162A (2S)-2-({[4-(4-Chlorophenoxy)thieno[2,3-c]pyridin-2-yl]carbonyl}amino)-3-hydroxypropanoic acid Example 162A was prepared in analogy to Example 92, with the substitution of L-serine ethyl ester hydrochloride for ammonium chloride. The intermediate ester was then hydrolyzed according to the procedure of Example 18 to provide the title compound. HPLC: Supelco C-18 column, eluent gradient of water:acetonitrile 0:90–90:0 over 30 minutes, detection at 254 nm, flow rate of 0.8 mL/min, RT 15.93 minutes;

MS (APCI) m/e: 392 (M+H)$^+$; $^1$H NMR (300 MHz, DMSO-d$_6$) δ 3.70 (m, 2H), 4.43 (br t, 2H), 5.04 (br s, 1H), 7.13 (m, 3H), 7.49 (m, 3H), 8.18 (s, 1H), 8.37 (s, 1H), 8.98 (br s, 1H), 9.18 (s, 1H).

EXAMPLE 162B

N-[(1S)-2-Amino-1-(hydroxymethyl)-2-oxoethyl]-4-(4-chlorophenoxy)thieno[2,3-c]pyridine-2-carboxamide Example 162B was prepared from Example 162A in analogy to Example 92.

HPLC: Supelco C-18 column, eluent gradient of water:acetonitrile 0:90–90:0 over 30 minutes, detection at 254 nm, flow rate of 0.8 mL/min, RT 15.93 minutes; MS (APCI) m/e: 392 (M+H)$^+$; $^1$H NMR (300 MHz, DMSO-d$_6$) δ 3.70 (m, 2H), 4.43 (br t, 2H), 5.04 (br s, 1H), 7.13 (m, 3H), 7.49 (m, 3H), 8.18 (s, 1H), 8.37 (s, 1H), 8.98 (br s, 1H), 9.18 (s, 1H).

EXAMPLE 163

(2R)-2-({[4-(4-Chlorophenoxy)thieno[2,3-c]pyridin-2-yl]carbonyl}amino)-3-hydroxypropanoic acid Example 163 was prepared in analogy to Example 92, using D-serine methyl ester hydrochloride in place of ammonium chloride. The derived ester was hydrolyzed according to the procedure of Example 18 to give the title compound. HPLC: Supelco C-18 column, eluent gradient of water:acetonitrile 0:90–90:0 over 30 minutes, detection at 254 nm, flow rate of 0.8 mL/min, RT 16.47 minutes; MS (ESI) m/e: 393 (M+H)$^+$; $^1$H NMR (300 MHz, DMSO-d$_6$) δ 3.78 (br d, 2H), 4.49 (m, 1H), 5.02 (br s, 1H), 7.13 (m, 2H), 7.48 (m, 2H), 8.18 (s, 1H), 8.39 (s, 1H), 9.14 (d, 1H), 9.18 (s, 1H), 12.81 (br s, 1H).

EXAMPLE 164

4-(4-Chlorophenoxy)-N-[(1R)-1-methyl-2-(methylamino)-2-oxoethyl]thieno[2,3-c]pyridine-2-carboxamide

EXAMPLE 164A (2R)-2-({[4-(4-Chlorophenoxy)thieno[2,3-c]pyridin-2-yl]carbonyl}amino)propanoic acid Example 164A was prepared in analogy to Example 92, using D-alanine methyl ester hydrochloride in place of ammonium chloride. The derived ester was hydrolyzed according to the procedure of Example 18 to give the title compound. HPLC: Supelco C-18 column, eluent gradient of water:acetonitrile 0:90–90:0 over 30 minutes, detection at 254 nm, flow rate of 0.8 mL/min, RT 18.36 minutes; MS (DCI/NH$_3$) m/e: 377 (M+H)$^+$; $^1$H NMR (300 MHz, DMSO-d$_6$) δ 1.40 (d, J=7 Hz, 3H), 4.41 (q, J=7 Hz, 1H), 7.15 (m, 2H), 7.49 (m, 2H), 8.19 (s, 1H), 8.32 (s, 1H), 9.17 (s, 1H), 9.23 (d, J=7 Hz, 1H), 12.71 (br s, 1H).

EXAMPLE 164B 4-(4-Chlorophenoxy)-N-[(1R)-1-methyl-2-(methylamino)-2-oxoethyl]thieno[2,3-c]pyridine-2-carboxamide Example 164 was prepared in analogy to Example 92, using D-alanine methyl ester hydrochloride in place of ammonium chloride. The derived ester was treated according to the procedure of Example 171 to give the title compound. HPLC: Supelco C-18 column, eluent gradient of water:acetonitrile 0:90–90:0 over 30 minutes, detection at 254 nm, flow rate of 0.8 mL/min, RT 17.46 minutes;

MS (DCI/NH$_3$) m/e: 390 (M+H)$^+$; $^1$H NMR (300 MHz, DMSO-d$_6$) δ 1.32 (d, 3H), 2.60 (d, 3H), 4.41 (m, 1H), 7.13 (m, 2H), 7.49 (m, 2H), 7.96 (br d, 1H), 8.19 (s, 1H), 8.38 (s, 1H), 9.13 (br d, 1H), 9.19 (s, 1H).

EXAMPLE 165

4-(4-Chlorophenoxy)-N-[(1S)-1-methyl-2-(methylamino)-2-oxoethyl]thieno[2,3-c]pyridine-2-carboxamide

EXAMPLE 165A (2S)-2-({[4-(4-Chlorophenoxy)thieno[2,3-c]pyridin-2-yl]carbonyl}amino)propanoic acid Example 165A was prepared in analogy to Example 92, using L-alanine methyl ester hydrochloride in place of ammonium chloride. The derived ester was hydrolyzed according to the procedure of Example 18 to give the title compound. HPLC: Supelco C-18 column, eluent gradient of water:acetonitrile 0:90–90:0 over 30 minutes, detection at 254 nm, flow rate of 0.8 mL/min, RT 18.40 minutes;

MS (DCI/NH$_3$) m/e: 377 (M+H)$^+$; $^1$H NMR (300 MHz, DMSO-d$_6$) δ 1.40 (d, J=7 Hz, 3H), 4.41 (q, J=7 Hz, 1H), 7.15 (m, 2H), 7.48 (m, 2H), 8.18 (s, 1H), 8.31 (s, 1H), 9.16 (s, 1H), 9.21 (d, J=7 Hz, 1H), 12.71 (br s, 1H); $^{13}$C NMR (100 MHz, DMSO-d$_6$) δ 16.78, 48.46, 119.52, 119.80, 119.97, 127.84, 130.13, 132.97, 137.54, 137.60, 138.09, 141.30, 145.59, 147.38, 155.59, 160.54, 173.68.

EXAMPLE 165B 4-(4-Chlorophenoxy)-N-[(1S)-1-methyl-2-(methylamino)-2-oxoethyl]thieno[2,3-c]pyridine-2-carboxamide Example 165B was prepared from Example 165A in analogy to Example 92, with the substitution of L-alanine methyl ester for ammonium chloride. The intermediate ester was converted to the title compound according to the procedure or Example 171, using methanolic methylamine.

HPLC: Supelco C-18 column, eluent gradient of water:acetonitrile 0:90–90:0 over 30 minutes, detection at 254 nm, flow rate of 0.8 mL/nmin, RT 17.48 minutes; MS (DCI/NH$_3$) m/e: 390 (M+H)$^+$; $^1$H NMR (300 MHz, DMSO-d$_6$) δ 1.32 (d, 3H), 2.59 (d, 3H), 4.41 (m, 1H), 7.13 (m, 2H), 7.49 (m, 2H), 7.94 (br d, 1H), 8.18 (s, 1H), 8.36 (s, 1H), 9.12 (br d, 1H), 9.19 (s, 1H).

EXAMPLE 166

4-(4-Chlorophenoxy)-N-[(1R)-1-(hydroxymethyl)-2-(methylamino)-2-oxoethyl]thieno[2,3-c]pyridine-2-carboxamide The title compound was made in analogy to the procedure of Example 164B, using D-serine methyl ester.

HPLC: Supelco C-18 column, eluent gradient of water:acetonitrile 0:90–90:0 over 30 minutes, detection at 254 nm, flow rate of 0.8 mL/min, RT 16.10 minutes; MS (APCI) m/e: 404 (M–H)$^-$; $^1$H NMR (300 MHz, DMSO-d$_6$) δ 2.59 (d, 2H), 3.69 (m, 2H), 4.45 (m, 1H), 4.96, (t, 1H), 7.14 (m, 2H), 7.49 (m, 2H), 7.97 (m, 1H), 8.18 (s, 1H), 8.49 (s, 1H), 9.01 (br d, 1H), 9.19 (s, 1H).

EXAMPLE 167

4-(4-Chlorophenoxy)-N-[(1S)-1-(hydroxymethyl)-2-(methylamino)-2-oxoethyl]thieno[2,3-c]pyridine-2-carboxamide The title compound was made in analogy to the procedure of Example 164B, using L-serine methyl ester.

HPLC: Supelco C-18 column, eluent gradient of water:acetonitrile 0:90–90:0 over 30 minutes, detection at 254 nm, flow rate of 0.8 mL/imin, RT 16.18; MS (APCI) m/e: 404 (M–H)$^-$; $^1$H NMR (300 MHz, DMSO-d$_6$) δ 2.59 (d, 2H), 3.69 (m, 2H), 4.45 (m, 1H), 4.96, (t, 1H), 7.14 (m, 2H), 7.49 (m, 2H), 7.97 (br d, 1H), 8.18 (s, 1H), 8.49 (s, 1H), 9.01 (br d, 1H), 9.19 (s, 1H).

EXAMPLE 170

4-(3-Pyridinyloxy)thieno[2,3-c]pyridine-2-carboxamide

Example 17A and 3-Hydroxypyridine were processed as in Example 61 to provide the title compound.

MS (DCI1NH$_3$) m/e: 272 (M+H)$^+$; $^1$H NMR (300 MHz, DMSO-d$_6$) δ 7.50 (m, 2H), 7.85 (m, 1H), 8.20 (s, 2H), 8.45 (dd, 2H), 8.55 (d, 1H), 9.20 (s, 1H); Anal. Calcd for C$_{13}$H$_9$N$_3$O$_2$S.0.25 H$_2$O: C, 56.61; H, 3.47; N, 15.24. Found: C, 57.01; H, 3.50; N, 15.16.

EXAMPLE 171

4-(4-bromophenoxy)-N-methylthieno[2,3-c]pyridine-2-carboxamide

Example 73A (2 g, 5.5 mmol) was suspended in a solution of methylamine in methanol (2 M solution, 15 mL) and refluxed for 1 hour under nitrogen atmosphere. Then the solvent was removed and the residue was purified by flash chromatography on silica gel eluting with 30% acetone in hexane to obtain the title compound (1.96 g, 98%).

mp 78–80° C.; MS (DCI/NH$_3$) m/e: 363,365 (M+H)$^+$; $^1$H NMR (300 MHz, DMSO-d$_6$) δ 2.79 (d, 3H, J=4.8 Hz), 7.06 (d, 2H, J=8.8 Hz), 7.59 (d, 2H, J=8.8 Hz), 8.06 (s, 1H), 8.20 (s, 1H), 8.96 (q, 1H, J=4.8 Hz), 9.17 (s, 1H).

EXAMPLE 172

4-(4-Bromophenoxy)-N,N-dimethylthieno[2,3-c]pyridine-2-carboxamide

Example 172 was prepared according to the procedure of Example 104, with the substitution of methyl 4-(4-bromophenoxy)-thieno[2,3-c]pyridine-2-carboxylate for Example 61A.

mp 93–95° C.; MS (DCI/NH$_3$) m/e: 377, 379 (M+H)$^+$; $^1$H NMR (300 MHz, DMSO-d$_6$) δ 3.02 (br s, 3H), 3.13 (br s, 3H), 7.09 (d, 2H, J=8.8 Hz), 7.5 d, 2H, J=8.8 Hz), 7.60 (s, 1H), 8.19 (s, 1H), 9.15 (s, 1H)ppm.

EXAMPLE 173

N,N-Dimethyl-4-[4-(trifluoromethyl)phenoxy]thieno[2,3-c]pyridine-2-carboxamide

Example 173 was prepared according to the procedure of Example 104, with the substitution of methyl 4-(4-trifluoromethylphenoxy)-thieno[2,3-c]pyridine-2-carboxylate for Example 61A.

mp 74–76° C.; MS (DCI/NH$_3$) m/e: 367 (M+H)$^+$; $^1$H NMR (300 MHz, CDCl$_3$) δ 3.17 (br s, 6H), 7.11 (d, 2H, J=8.0 Hz), 7.45 (s, 1H), 7.63 (d, 2H, J=8.0 Hz), 8.24 (br s, 1H), 9.01 (br s, 1H).

EXAMPLE 174

4-(4-Chloro-3-fluorolphenoxy)-N-methylthieno[2,3-c]pyridine-2-carboxamide

Example 174 was prepared as in Example 103 but substituting 4-chloro-3-fluorophenol for 4-chlorophenol to provide the title compound.

mp 62–64° C.; MS (DCI/NH$_3$) m/e: 337 (M+H)$^+$; $^1$H NMR (300 MHz, DMSO-d$_6$) δ 3.05 (d, 3H, J=4.7 Hz), 6.24 (br s, 1H), 6.77 (d,1H, J=9.8 Hz), 6.84 (dd, 1H, J=2.4, 9.5 Hz), 7.26 (s,2H), 7.37 (t, 1H, J=8.5 Hz), 7.69 (s,1H), 8.21 (s, 1H), 9.00 (s, 1H); Anal. calcd for C$_{15}$H$_{10}$N$_2$ClFO$_2$S: C, 53.50; H, 2.99; N, 8.32. Found: C, 53.78; H, 3.26; N, 8.02.

EXAMPLE 175

4-(4-Chloro-3-fluorophenoxy)thieno[2,3-c]pyridine-2-carboxamide

Example 175 was prepared as in Example 61 but substituting 4-chloro-3-fluorophenol for 4-chlorophenol to provide the title compound.

mp 227–228° C.; MS (DCI/NH$_3$) m/e: 323 (M+H)$^+$; $^1$H NMR (300 MHz, DMSO-d$_6$) δ 6.94 (m,1H), 7.34 (dd, 1H, J=3.0, 10.5 Hz), 7.60 (t, 1H, J=8.7 Hz), 7.87 (s,1H), 8.11 (s, 1H), 8.26 (s, 1H), 8.44 (s, 1H), 9.19 (s, 1H); Anal. calcd for C$_{14}$H$_8$N$_2$ClFO$_2$S: C, 52.10; H, 2.50; N, 8.68. Found: C, 52.06; H, 2.49; N, 8.52.

EXAMPLE 176

4-(4-Chloro-3-ethylphenoxy)thieno[2,3-c]pyridine-2-carboxamide

Example 17A and 4-Chloro-3-ethylphenol were processed as in Example 61 to provide the title compound.

mp 185–187° C.; MS (DCI/NH$_3$) m/e: 333 (M+H)$^+$; $^1$H NMR (300 MHz, DMSO-d$_6$) δ 1.15 (t, 3H), 2.70 (q, 2H), 6.95 (dd, 1H), 7.20 (d, 1H), 7.45 (d, 1H), 7.85 (br s, 1H), 8.15 (s, 1H), 8.45 (m, 1H), 9.15 (s, 1H).

EXAMPLE 177

4-(3-Fluorophenoxy)thieno[2,3-c]pyridine-2-carboxamide

Example 177 was prepared according to the procedure of Example 61, with the substitution 3-fluorophenol for 4-chlorophenol.

mp 215–216° C.; MS (DCI/NH$_3$) m/e: 289 (M+H)$^+$; $^1$H NMR (300 MHz, DMSO-d$_6$) δ 6.90 (m, 1H), 7.05 (m, 2H), 7.43 (q, 1H, J=8.6 Hz), 7.86 (br s, 1H), 8.14 (s, 1H), 8.20 (s, 1H), 8.45 (br s, 1H), 9.17 (s, 1H).

EXAMPLE 178

4-(2,3-Difluorophenoxy)thieno[2,3-c]pyridine-2-carboxamide

Example 178 was prepared according to the procedure of Example 61, with the substitution 2,3-difluorophenol for 4-chlorophenol.

mp 207–209° C.; MS (DCI/NH$_3$) m/e: 307 (M+H)$^+$; $^1$H NMR (300 MHz, DMSO-d$_6$) δ 6.97 (t, 1H, J=8.5 Hz), 7.22 (q, 1H, J=8.5 Hz), 7.32 (q, 1H, J=8.5 Hz), 7.87 (br s, 1H), 8.18 (s, 1H), 8.21 (s, 1H), 8.43 (br s, 1H), 9.17 (s, 1H).

EXAMPLE 179

4-(2,3-Difluorophenoxy)-N-methylthieno[2,3-c]pyridine-2-carboxamide

Example 179 was prepared according to the procedure of Example 103, with the substitution 2,3-difluorophenol for 4-chlorophenol.

mp 169–171° C.; MS (DCI/NH$_3$) m/e: 321 (M+H)$^+$; $^1$H NMR (300 MHz, DMSO-d$_6$) δ 2.88 (d, 3H, J=4.4 Hz), 6.94 (t, 1H, J=8.5 Hz), 7.21 (q, 1H, J=8.5 Hz), 7.31 (q, 1H, J=8.5 Hz), 8.14 (s, 1H), 8.21 (s, 1H), 8.95 (q, 1H, J=4.5 Hz), 9.17 (s, 1H).

EXAMPLE 180

4-(3-Fluorophenoxy)-N-methylthieno[2,3-c]pyridine-2-carboxamide

Example 180 was prepared according to the procedure of Example 103, with the substitution 3-fluorophenol for 4-chlorophenol.

mp 194–195° C.; MS (DCI/NH$_3$) m/e: 303 (M+H)$^+$; $^1$H NMR (300 MHz, DMSO-d$_6$) δ 2.79 (d, 3H, J=4.4 Hz), 6.87 (d, 1H, J=8.5 Hz), 7.05 (m, 2H), 7.42 (q, 1H, J=8.5 Hz), 8.05 (s, 1H), 8.23 (s, 1H), 8.95 (q, 1H, J=4.4 Hz), 9.17 (s, 1H).

EXAMPLE 181

N-Methyl-4-(2,3,4-trifluorophenoxy)thieno[2,3-c]pyridine-2-carboxamide

Example 181 was prepared according to the procedure of Example 103, with the substitution 2,3,4-trifluorophenol for 4-chlorophenol.

mp 170–171° C.; MS (DCI/NH$_3$) m/e: 339 (M+H)$^+$; $^1$H NMR (300 MHz, DMSO-d$_6$) δ 2.82 (d, 3H, J=4.4 Hz), 7.13 (m, 1H), 7.35 (q, 1H, J=8.5 Hz), 8.16 (s, 1H), 8.17 (s, 1H), 8.97 (q, 1H, J=4.5 Hz), 9.16 (s, 1H).

EXAMPLE 182

4-(2,3,4-Trifluorophenoxy)thieno[2,3-c]pyridine-2-carboxamide

Example 182 was prepared according to the procedure of Example 61, with the substitution 2,3,4-trifluorophenol for 4-chlorophenol.

mp 218–219° C.; MS (DCI/NH$_3$) m/e: 325 (M+H)$^+$; $^1$H NMR (300 MHz, DMSO-d$_6$) δ 7.15 (m, 1H), 7.38 (q, 1H, J=8.5 Hz), 7.89 (br s, 1H), 8.15 (s, 1H), 8.23 (s, 1H), 8.45 (br s, 1H), 9.15 (s, 1H).

EXAMPLE 183

N-Methyl-4-[4-(trifluoromethyl)phenoxy]thieno[2,3-c]pyridine-2-carboxamide

Example 183 was prepared according to the procedure of Example 103, with the substitution 4-trifluoromethylphenol for 4-chlorophenol.

mp 157–158° C.; MS (DCI/NH$_3$) m/e: 353 (M+H)$^+$; $^1$H NMR (300 MHz, DMSO-d$_6$) δ 2.78 (d, 3H, J=4.4 Hz), 7.22 (d, 2H, J=8.5 Hz), 7.76 (d, 2H, J=8.5 Hz), 8.01 (s, 1H), 8.34 (s, 1H), 8.92 (q, 1H, J=4.4 Hz), 9.24 (s, 1H).

EXAMPLE 184

4-[3-(Trifluoromethyl)phenoxy]thieno[2,3-c]pyridine-2-carboxamide

Example 17A and 3-trifluoromethylphenol were processed as in Example 183 to provide the title compound.

mp 175–176° C.; MS (DCI/NH$_3$) m/e: 353 (M+H)$^+$; $^1$H NMR (300 MHz, DMSO-d$_6$) δ 2.80 (d, 3H), 7.35 (d, 1H), 7.20 (d, 1H), 7.60 (m, 3H), 8.10 (s, 1H), 8.30 (s, 1H), 9.00 (b, 2H), 9.25 (s, 1H); Anal. Calcd for C$_{16}$H$_{11}$F$_3$N$_2$O$_2$S.0.25 H$_2$O: C, 53.86; H, 3.25; N, 7.85. Found: C, 53.60; H, 3.06; N, 7.78.

EXAMPLE 185

N,N-Dimethyl-4-(4-vinylphenoxy)thieno[2,3-c]pyridine-2-carboxamide

Example 185 was prepared according to the procedure of Example 104, with the substitution 4-vinylphenol for 4-chlorophenol.

mp 80–81° C.; MS (DCI/NH$_3$) mle: 325 (M+H)$^+$; H NMR (300 MHz, DMSO-d$_6$) δ 3.02 (br s, 3H), 3.13 (br s, 3H), 5.24 (d, 1H, J=11.4 Hz) 5.78 (d, 1H, J=17.3 Hz), 6.74 (dd, 1H, J=11.4, 17.3 Hz), 7.09 (d, 2H, J=8.5 Hz), 7.53 (d, 2H, J=8.5 Hz), 7.61 (s, 1H), 8.16 (s, 1H), 9.13 (s, 1H).

EXAMPLE 186

4-(4-Cyanophenoxy)-N-methylthieno[2,3-c]
pyridine-2-carboxamide

Example 186 was prepared as in Example 103 but substituting 4-cyanophenol for 4-chlorophenol to provide the title compound.

MS (ESI/NH$_3$) m/e: 310 (M+H)$^+$; $^1$H NMR (300 MHz, DMSO-d$_6$) δ 2.78 (d, 3H, J=4.4 Hz), 7.20 (d, 2H, J=8.8 Hz), 7.89 (d, 2H, J=8.8 Hz), 7.97 (s, 1H), 8.37 (s, 1H), 8.94 (q, 1H, J=4.4 Hz), 9.26 (s, 1H); Anal. calcd for C$_{16}$H$_{11}$N$_3$O$_2$S.0.05 CH$_2$Cl$_2$: C, 61.46; H, 3.56; N, 13.30. Found: C, 61.29; H, 3.53; N, 13.23.

EXAMPLE 187

4-(4-Cyanophenoxy)thieno[2,3-c]pyridine-2-
carboxamide

Example 187 was prepared as in Example 61 but substituting 4-cyanophenol for 4-chlorophenol to provide the title compound.

mp 255–257° C.; MS (ESI/NH$_3$) m/e: 296 (M+H)$^+$; $^1$H NMR (300 MHz, DMSO-d$_6$) δ 7.20 (d, 2H, J=8.8 Hz), 7.84 (s, 1H), 7.89 (d, 2H, J=8.8 Hz), 8.05 (s, 1H), 8.36 (s, 1H), 8.41 (q, 1H, J=4.4 Hz), 9.26 (s, 1H); Anal. calcd for C$_{15}$H$_9$N$_3$O$_2$S.1.5CH$_3$OH: C, 57.71; H, 3.08; N, 12.24. Found: C, 57.45; H, 3.28; N, 12.43.

EXAMPLE 188

4-(4-Aminophenoxy)thieno[2,3-c]pyridine-2-
carboxamide

EXAMPLE 188A

3-Chloro-5-(4-(tert-butyloxycarbonyl)amino)
phenoxy-4-pyridinecarboxaldehyde

A solution of Example 17A (2.0 g, 11.4nmrol) and tert-butyl N-(4-hydroxyphenyl)carbamate (2.38 g, 11.4 mmol) which was prepared according to literature method (A. Vigroux, M. Bergon, C. Zedde; J. Med. Chem. 1995, 38, 3983) in DMF (30 mL) was treated with CsCO$_3$ (3.70 g, 11.4 mmol) at room temperature for 1 hour, and at 70° C. for 30 minutes. Brine (150 mL) was added, and the mixture was extracted with ether/ethyl acetate (2×200 mL). The combined organic phases were dried (MgSO$_4$), and concentrated. Flash chromatography of the residue on silica gel with 1:6 ethyl acetate/hexane provided the designated compound (2.65 g, 67%).

MS (ESI/NH$_3$) m/e: 349 (M+H)$^+$.

EXAMPLE 188B

Methyl 4-((4-tert-butyloxycarbonylamino)phenoxy)
thieno[2,3-c]pyridine-2-carboxylate A solution of Example 188A (2.64 g, 7.58 mmol) in THF (30 mL) was treated with methyl thioglycolate (804 mg, 7.58 rnmol) at 0° C. for 0.5 hour, and at room temperature for 1 hour, after which Cs$_2$CO$_3$ (2.47 g, 7.58 mmol) was added. The reaction mixture was stirred at room temperature for 1 hour, and at 70° C. for 0.5 hour. Brine (150 mL) was added and the mixture was extracted with ethyl acetate (2×150 mL). The combined organic phases were dried (MgSO$_4$) and concentrated. The residue was flash chromatographed on silica gel with 20% ethyl acetate in hexane to provide designated compound (1.29 g, 43%).

MS (ESI/NH$_3$) m/e: 401 (M+H)$^+$.

EXAMPLE 188C

4-[(4-tert-Butyloxycarbonylamino)phenoxy]thieno
[2,3-c]pyridine-2-carboxamide

Example 188C was prepared as in Example 44 but substituting Example 188B for Example 43 to provide the title compound.

MS (ESI/NH$_3$) m/e: 386 (M+H)$^+$.

EXAMPLE 188D 4-(4-Aminophenoxy)thieno[2,3-c]pyridine-2-
carboxamide

Example 188C was dissolved in trifluoroacetic acid (20 mL), and the solution was kept at room temperature for 1 hour before TFA was removed. The residual oil was treated with a mixture of ethyl acetate and aqueous NaHCO$_3$ solution. The formed solid was collected by filtration, washed successively with ethyl acetate, aqueous NaHCO$_3$ solution, water, methanol and ethyl acetate, and dried to provide the title compound (492 mg, 86% from Example 188B) as a yellow solid.

mp>250° C.; MS (DCI/NH$_3$) m/e: 286 (M+H)$^+$; $^1$H NMR (300 MHz, DMSO-d$_6$) δ 5.62 (br s, 2H), 6.65 (d, 2H, J=8.8 Hz), 6.93 (d, 2H, J=8.8 Hz), 7.86 (s, 1H), 8.30 (s, 1H), 8.44 (s, 1H), 9.00 (br s, 1H); Anal. calcd for C$_{14}$H$_{11}$N$_3$O$_2$S.0.5 CH$_3$OH: C, 57.79; H, 3.85; N, 13.94. Found: C, 57.69; H, 3.95; N, 13.57.

EXAMPLE 189

4-[4-(Acetylamino)phenoxy]thieno[2,3-c]pyridine-2-
carboxamide

Example 189 was prepared as in Example 188C but substituting 4-(acetylamino)phenol for t-butyl N-(4-hydroxyphenyl)carbamate to provide the title compound.

MS (DCI/NH$_3$) m/e: 328 (M+H)$^+$; $^1$H NMR (300 MHz, DMSO-d$_6$) δ 2.04 (s, 3H), 7.10 (d, 2H, J=8.8 Hz), 7.65 (d, 2H, J=8.8 Hz), 7.82 (br s, 1H), 7.99 (s, 1H), 8.20 (s, 1H), 8.43 (br s, 1H), 9.06 (s, 1H), 9.99 (s, 1H); Anal. calcd for C$_{16}$H$_{13}$N$_3$O$_3$S'1.0 CH$_3$OH: C, 56.81; H, 3.93; N, 11.69. Found: C, 56.51; H, 3.93; N, 11.57.

EXAMPLE 190

N-Methyl-4-[4-(4-morpholinyl)phenoxy]thieno[2,3-
c]pyridine-2-carboxamide

EXAMPLE 190A

Methyl-4-[4-(4-iodophenoxy]thieno[2,3-c]pyridine-
2-carboxylate

Example 190A was prepared as in Example 61A but substituting 4-iodophenol for 4-chlorophenol to provide the designated compound.

MS (DCI/NH$_3$) m/e: 412 (M+H)$^+$.

EXAMPLE 190B

N-Methyl-4-[4-(4-iodolphenoxy)]thieno[2,3-c]
pyridine-2-carboxamide

A solution of Example 190A (1.4 g, 3.4 mmol) in methylamine/methanol (2.0 M solution, 70 mL) was stirred at 45° C. for 15 hours, and concentrated under vacuum. The residue was flash chromatographed on silica gel with EtOAc/hexane (1.5/1) to provide the designated compound (1.3 g, 93%).

MS (DCI/NH$_3$) m/e: 411 (M+H)$^+$.

EXAMPLE 190C

N-Methyl-4-[4-(4-morpholinyl)phenoxy]thieno[2,3-c]pyridine-2-carboxamide

A two necked flask was charged with Example 190B (150 mg, 0.37 mmol), NaOBu-t (71 mg, 0.74 mmol), Pd$_2$(dba)$_3$ (14 mg, 0.014 mmol), BINAP (27 mg, 0.044 nmmol) and 18-crown-6 (196 mg, 0.74 mmol), and purged with nitrogen. Anhydrous degassed THF (10 mL) and morpholine (64 mg, 0.74 mmol) were added successively. The clear dark red solution was heated at 60° C. for 70 hours, and quenched with brine. The mixture was extracted with methylene chloride. The organic layer was dried (MgSO$_4$) and concentrated. The crude was flash chromatographed on silica gel (EtOAc/hexane) and was further purified on HPLC (C-18, CH$_3$CN/H$_2$O) to provide the title compound (26 mg).

MS (DCI/NH$_3$) m/e: 370 (M+H)$^+$; $^1$H NMR (300 MHz, DMSO-d$_6$) δ 2.81 (d, 3H, J=4.5 Hz), 3.1 (m, 2H), 3.74 (m, 2H), 6.99 (d, 2H, J=8.8 Hz), 7.05 (d, 2H, J=8.8 Hz), 7.92 (s, 1H), 8.20 (s, 1H), 8.98 (q, 1H, J=4.8 Hz), 9.04 (s, 1H).

EXAMPLE 191

4-[4-(Hydroxymethyl)phenoxy]thieno[2,3-c]pyridine-2-carboxamide

EXAMPLE 191A

Methyl 4-{4-[(trityloxy)methyl]phenoxy}thieno[2,3-c]pyridine-2-carboxylate

Example 191A was prepared as in Example 61A but substituting 4-trityloxymethylphenol which was prepared according to literature method (Frank, R.; Doring, R. Tetrahedron 1988, 44, 6031) for 4-chlorophenol to provide the title compound.

MS (DCI/NH$_3$) m/e: 558 (M+H)$^+$.

EXAMPLE 191B

4-{4-[(Tritloxy)methyl]phenoxy}thieno[2,3-c]pyridine-2-carboxamide

Example 191A was prepared as in Example 61 but substituting 4-trityloxymethylphenol for 4-chlorophenol to provide the title compound.

MS (DCI/NH$_3$) m/e: 543 (M+H)$^+$; $^1$H NMR (300 MHz, DMSO-d$_6$) δ 4.10 (s, 2H), 7.11 (d, 2H, J=8.5 Hz), 7.26–7.46 (m, 17H), 7.87 (brs, 1H), 8.09 (s, 1H), 8.21 (s, 1H), 8.46 (brs, 1H), 9.12 (s, 1H)ppm. Anal. calcd for C$_{34}$H$_{26}$N$_2$O$_3$S: C, 75.25; H, 4.83; N, 5.16. Found: C, 75.17; H, 4.76; N, 5.15.

EXAMPLE 191C

Methyl 4-[4-(hydroxymethyl)phenoxy]thieno[2,3-c]pyridine-2-carboxylate

A solution of Example 191A (5.05 g, 9 mmol) in a mixture of chloroform (20 mL) and methanol (8 mL) was treated with trifluoroacetic acid (10 mL) at 0° C. for 6 hours, and was then poured into a mixture of ice and saturated NaHCO$_3$. The mixture was extracted with methylene chloride (2×200 mL). The combined organic layers were dried (MgSO$_4$), and concentrated. The residue was flash chromatographed on silica gel with 66% EtOAc/hexane to give the designated compound (2.11 g, 74%).

MS (DCI/NH$_3$) mte: 316 (M+H)$^+$.

EXAMPLE 191D

4-[4-(Hydroxymethyl)phenoxy]thieno[2,3-c]pyridine-2-carboxamide

Example 191D was prepared as in Example 61 but substituting Example 191C for Example 61A to provide the title compound.

MS (DCI/NH$_3$) m/e: 301 (M+H)$^+$; $^1$H NMR (300 MHz, DMSO-d$_6$) δ 4.50 (d, 2H, J=5.8 Hz), 5.19 (t, 1H, J=5.8 Hz), 7.10 (d, 2H, J=8.5 Hz), 7.37 (d, 2H, J=8.5 Hz), 7.82 (br s, 1H), 8.03 (s, 1H), 8.20 (s, 1H), 8.43 (br s, 1H), 9.09 (s, 1H); Anal. calcd for C$_{15}$H$_{12}$N$_2$O$_3$S: C, 59.99; H, 4.03; N, 9.33. Found: C, 59.82; H, 3.93; N, 8.82.

EXAMPLE 192

4-[4-(Hydroxymethyl)phenoxy]-N-methylthieno[2,3-c]pyridine-2-carboxamide

Example 192 was prepared as in Example 103 but substituting Example 191C for Example 61A to provide the title compound.

mp 195–196° C.; MS (DCI/NH$_3$) m/e: 315 (M+H)$^+$; $^1$H NMR (300 MHz, DMSO-d$_6$) δ 2.80 (d, 3H, J=4.5 Hz), 4.49 (d, 2H, J=4.5 Hz), 5.19 (t, 1H, J=4.5 Hz), 7.08 (d, 2H, J=8.5 Hz), 7.37 (d, 2H, J=8.5 Hz), 8.07 (s, 1H), 8.11 (s, 1H), 8.94 (q, 1H, J=4.5 Hz), 9.10 (s, 1H); Anal. calcd for C$_{16}$H$_{14}$N$_2$O$_3$S.0.75 CH$_3$OH: C, 59.45; H, 4.39; N, 8.28. Found: C, 59.31; H, 4.35; N, 8.49.

EXAMPLE 193

4-[4-(Methoxymethyl)phenoxyl-N-methylthieno[2,3-c]pyridine-2-carboxamide

Example 193 was prepared as in Example 188C but substituting 4-methoxymethylphenol for 4-tert-butyloxycarbonylaminophenol and substituting methylamine for ammonia to provide the title compound.

mp 163–164° C.; MS (DCI/NH$_3$) m/e: 329 (M+H)$^+$; $^1$H NMR (300 MHz, DMSO-d$_6$) δ 2.79 (d, 3H, J=4.4 Hz), 3.29 (s, 3H), 4.40 (s, 2H), 7.08 (d, 2H, J=8.5 Hz), 7.37 (d, 2H, J=8.5 Hz), 8.09 (s, 1H), 8.12 (s, 1H), 8.94 (q, 1H, J=4.4 Hz), 9.12 (s, 1H); Anal. calcd for C$_{17}$H$_{16}$N$_2$O$_3$S: C, 62.18; H, 4.91; N, 8.53. Found: C, 61.86; H, 4.79; N, 8.40.

EXAMPLE 194

4-{4-[(2-Methoxyethoxy)methyl]phenoxy}thieno[2,3-c]pyridine-2-carboxamide

Example 194 was prepared as in Example 188C but substituting 4-(2-methoxyethoxymethyl)phenol for 4-tert-butyloxycarbonylaminophenol to provide the title compound.

MS (DCI/NH$_3$) m/e: 359 (M+H)$^+$; $^1$H NMR (300 MHz, CDCl$_3$) δ 3.40 (s, 3H), 3.60 (m, 2H), 3.65 (m, 2H), 4.56 (s, 2H), 7.02 (d, 2H, J=8.5 Hz), 7.36 (d, 2H, J=8.5 Hz), 7.80 (s, 1H), 8.13 (s, 1H), 8.94 (s, 1H); Anal. calcd for C$_{18}$H$_{18}$N$_2$O$_4$S: C, 60.32; H, 5.06; N, 7.82. Found: C, 60.33; H, 5.03; N, 7.63.

EXAMPLE 195

4-{4-[(2-Methoxyethoxy)methyl]phenoxy}-N-methylthieno[2,3-c]pyridine-2-carboxamide Example 195 was prepared as in Example 188C but substituting 4-(2-methoxyethoxymethyl)phenol for 4-tert-butyloxycarbonylaminophenol and substituting methylamine for ammonia to provide the title compound.

mp 133–134° C.; MS (DCI/NH$_3$) m/e: 373 (M+H)$^+$; $^1$H NMR (300 MHz, CDCl$_3$) δ 3.01 (d, 3H, J=5.1 Hz), 3.40 (s, 3H), 3.60 (m, 2H), 3.65 (m, 2H), 4.54 (s, 2H), 6.51 (q, 1H, J=5.1 Hz), 7.00 (d, 2H, J=8.5 Hz), 7.34 (d, 2H, J=8.5 Hz), 7.73 (s, 1H), 8.14 (s, 1H), 8.94 (s, 1H); Anal. calcd for C$_{19}$H$_{20}$N$_2$O$_4$S: C, 61.27; H, 5.41; N, 7.52. Found: C, 61.28; H, 5.35; N, 7.46.

EXAMPLE 196

4-(4-{[2-(2-Methoxyethoxy)ethoxyl]methyl}phenoxy)thieno[2,3-c]pyridine-2-carboxamide Example 196 was prepared as in Example 188C but substituting 4-{2-(2-methoxyethoxy)ethoxymethyl}phenol for 4-tert-butyloxycarbonylaminophenol to provide the title compound.

MS (DCI/NH$_3$) m/e: 403 (M+H)$^+$; $^1$H NMR (300 MHz, CDCl$_3$) δ 3.38 (s, 3H), 3.57 (m, 2H), 3.63–3.70 (m, 6H), 4.55 (s, 2H), 7.02 (d, 2H, J=8.5 Hz), 7.36 (d, 2H, J=8.5 Hz), 7.71 (s, 1H), 8.15 (s, 1H), 8.95 (s, 1H).

EXAMPLE 197

4-(4-{[2-(2-Methoxyethoxy)ethoxy]methyl}phenoxy)-N-methylthieno[2,3-c]pyridine-2-carboxamide Example 197 was prepared as in Example 188C but substituting 4-{2-(2-methoxyethoxy)ethoxymethyl}phenol for 4-tert-butyloxycarbonylaminophenol and substituting methylamine for ammonia to provide the title compound.

MS (DCI/NH$_3$) m/e: 417 (M+H)$^+$; $^1$H NMR (300 MHz, CDCl$_3$) δ 3.02 (d, 3H, J=4.8 Hz), 3.38 (s, 3H), 3.57 (m, 2H), 3.63–3.70 (m, 6H), 4.54 (s, 2H), 6.45 (m, 1H), 7.00 (d, 2H, J=8.5 Hz), 7.34 (d, 2H, J=8.5 Hz), 7.72 (s, 1H), 8.15 (s, 1H), 8.94 (s, 1H).

EXAMPLE 198

4-{4-[(2,3,4,5-Tetrahydro-2H-pyran-2-yloxy)methyl]phenoxy}thieno[2,3-c]pyridine-2-carboxamide

EXAMPLE 198A

Methyl 4-{4-{[(2,3,4,5-tetrahydro-2H-pyran-2-yl)oxy]methyl}phenoxy}thieno[2,3-c]pyridine-2-carboxylate Example 198A was prepared as in Example 188B but substituting 4-[(2,3,4,5-tetrahydro-2H-pyran-2-yl)oxy]methylphenol (P. A. Grieco, et al, J. Org. Chem. 1977, 42, 3772) for 4-tert-butyloxycarbonylaminophenol to provide the designated compound.

MS (DCI/NH$_3$) m/e: 400 (M+H)$^+$.

EXAMPLE 198B

4-{4-[(2,3,4,5-Tetrahydro-2H-pyran-2-yloxy)methyl]phenoxy}thieno[2,3-c]pyridine-2-carboxamide Example 198B was prepared as in Example 61 but substituting Example 198A for Example 61A to provide the designated compound.

mp 95–96° C.; MS (DCI/NH$_3$) m/e: 385 (M+H)$^+$; $^1$H NMR (300 MHz, DMSO-d$_6$) δ 1.49 (m, 4H), 1.69 (m, 2H), 3.49 (m, 1H), 3.80 (m, 1H), 4.44 (d, 1H, J=12.1 Hz), 4.67 (d, 1H, J=12.1 Hz), 4.70 (m, 1H), 7.10 (d, 2H, J=8.8 Hz), 7.41 (d, 2H, J=8.8 Hz), 7.87 (s, 1H), 8.08 (s, 1H), 8.20 (s, 1H), 8.46 (s, 1H), 9.12 (s, 1H); Anal. calcd for C$_{20}$H$_{20}$N$_2$O$_4$S.CH$_3$OH: C, 60.56; H, 5.08; N, 6.73. Found: C, 60.51; H, 5.07; N, 6.59.

EXAMPLE 199

N-Methyl-4-{4-[(tetrahydro-2H-pyran-2-yloxy)methyl]phenoxy}thieno[2,3-c]pyridine-2-carboxamide Example 199 was prepared as in Example 103 but substituting Example 198A for Example 61A to provide the designated compound.

mp 195–196° C.; MS (DCI/NH$_3$) m/e: 399 (M+H)$^+$; $^1$H NMR (300 MHz, DMSO-d$_6$) δ 1.49 (m, 4H), 1.69 (m, 2H), 2.79 (d, 3H, J=4.8 Hz), 3.50 (m, 1H), 3.80 (m, 1H), 4.44 (d, 1H, J=12.1 Hz), 4.67 (d, 1H, J=12.1 Hz), 4.70 (m, 1H), 7.09 (d, 2H, J=8.8 Hz), 7.40 (d, 2H, J=8.8 Hz), 8.11 (s, 1H), 8.12 (s, 1H), 8.97 (q, 1H, J=4.8 Hz), 9.13 (s, 1H); Anal. calcd for C$_{21}$H$_{22}$N$_2$O$_4$S: C, 63.30; H, 5.56; N, 7.03. Found: C, 63.22; H, 5.58; N, 6.93.

EXAMPLE 200

4-{[2-(Aminocarbonyl)thieno[2,3-c]pyridin-4-yl]oxy}benzyl 2-furoate

A solution of Example 191D (40 mg, 0.133 mmol) in DMF (5 mL) was treated with 2-furoic acid (45 mg, 0.4 mmol), HOBt (54 mg, 0.4 mmol), EDC (77 mg, 0.4 mmol) and 2 drops of triethylamine at room temperature for 48 hours. Brine was added and the mixture was extracted with EtOAc. The combined organic phases were washed with water, dried (MgSO$_4$) and concentrated. The residue was flash chromatographed on silica gel with 65% EtOAc/hexane to provide the designated compound.

mp 180–182° C.; MS (DCI/NH$_3$) m/e: 395 (M+H)$^+$; $^1$H NMR (300 MHz, DMSO-d$_6$) δ 5.31 (s, 2H), 6.70 (dd, 1H, J=1.7, 3.4 Hz), 7.14 (d, 2H, J=8.5 Hz), 7.36 (d, 1H, J=3.4 Hz), 7.50 (d, 2H, J=8.5 Hz), 7.84 (s, 1H), 8.00 (dd, 1H, J=1.1, 3.7 Hz), 8.13 (s, 1H), 8.17 (s, 1H), 8.44 (s, 1H), 9.14 (s, 1H).

EXAMPLE 201

4-[4-({[(2R, 4R, 5S, 6R)-4,5-Dihydroxy-6-(hydroxymethyl)tetrahydro-2H-pyran-2-yl]oxy}methyl)phenoxy]-N-methylthieno[2,3-c]pyridine-2-carboxamide

EXAMPLE 201A

Methyl 4-[4-({[(2R, 4R, 5S, 6R)-4,5-Diacetoxy-6-(acetoxymethyl)tetrahydro-2H-pyran-2-yl]oxy}methyl)phenoxy]thieno[2,3-c]pyridine-2-carboxylate A solution of Example 191C (200 mg, 0.63 mmol) and tri-O-acetyl-D-glycal (520 mg, 1.92 mmol) in dry CH$_2$Cl$_2$ (10 mL) was treated with Sc(OTf)$_3$ (380 mg, 0.75 mmol) at room temperature for 12 hours, and was directly flash chromatographed on silica gel with 40% EtOAc/hexane to provide the designated compound.

MS (DCI/NH$_3$) mne: 528 (M-OAc)$^+$.

EXAMPLE 201B

4-[4-({[(2R, 4R, 5S, 6R)-4,5-Dihydroxy-6-(hydroxnmethyl)tetrahydro-2H-pyran-2-yl]oxy}methyl)phenoxy]-N-methylthieno[2,3-c]pyridine-2-carboxamide A solution of Example 201A (167 mg) in a 2M solution of methylamine in methanol (10 mL) was heated at 45° C. for 12 hours, and was concentrated. The residual oil was chromatographed on silica gel with 8% MeOH/CH$_2$Cl$_2$ to give the designated compound (120 mg, 91%).

MS (ESI/NH$_3$) m/e: 443 (M−OH)$^+$; $^1$H NMR (300 MHz, DMSO-d$_6$) δ 2.79 (d, 3H, J=4.8 Hz), 3.53 (m, 3H), 3.67 (m, 1H), 3.87 (m, 1H), 4.50 (d, 1H, J=11.5 Hz), 4.64 (t, 1H, J=5.4 Hz), 4.76 (d, 1H, J=11.5 Hz), 5.06 (m, 2H), 5.70 (dt, 1H, J=10.2, 2.4 Hz), 5.86 (d, 1H, J=10.2 Hz), 7.08 (d, 2H, J=8.5 Hz), 7.40 (d, 2H, J=8.5 Hz), 8.10 (s, 1H), 8.11 (s, 1H), 8.95 (q, 1H, J=4.8 Hz), 9.12 (s, 1H).

EXAMPLE 202

4-(4-Acetylphenoxy)-N-methylthieno[2,3-c]pyridine-2-carboxamide

A flask, purged with nitrogen, was charged with Example 190B (500 mg, 1.2 mmol), Pd(OAc)$_2$ (27 mg, 0.12 mmol), (Tol)$_3$P (110 mg, 0.36 mmol), dry degassed DMF (20 mL), tributylethoxyvinyltin (810 mL, 2.4 mmol), and triethylamine (835 mL, 6 mmol). This suspension was stirred at 80° C. for 14 hours. After diluting with ethyl acetate, the reaction mixture was washed with 1% HCl aqeous solution, water, dried (MgSO$_4$), and concentrated. The residue was separated by HPLC (C-18, CH$_3$CN/H$_2$O containing 0.1% TFA) to provide the title compound (476 mg, 89%).

MS (DCI/NH$_3$) m/e: 327 (M+H)$^+$; $^1$H NMR (300 MHz, DMSO-d$_6$) 62.56 (s, 3H), 2.78 (d, 3H, J=4.8 Hz), 7.15 (d, 2H, J=8.8 Hz), 8.00 (d, 2H, J=8.8 Hz), 8.03 (s, 1H), 8.36 (s, 1H), 8.98 (q, 1H, J=4.8 Hz), 9.28 (s, 1H); Anal. calcd for C$_{17}$H$_{14}$N$_2$O$_3$S. 1.35 CF$_3$CO$_2$H: C, 49.25; H, 3.45; N, 5.83. Found: C, 49.31; H, 3.60; N, 5.93.

EXAMPLE 203

4-[4-(4-Morpholinylcarbonyl)phenoxy]thieno[2,3-c]pyridine-2-carboxamide

EXAMPLE 203A

Methyl 4-[4-(4-carboxy)phenoxy]thieno[2,3-c]pyridine-2-carboxylate

A suspension of methyl 4-bromophenoxythieno[2,3-c]pyridine-2-carboxylate (1.0 g, 2.74 mmol), PdCl$_2$DPPFCH$_2$Cl$_2$ (0.284 g), and triethylamine (0.55 g) in a mixture of THF(15 mL) and H$_2$O (15 mL) was heated at 130° C. under CO atmosphere (400 psi) for 19 hours. EtOAc (200 mL) was added, and the mixture was washed with brine, dried (MgSO$_4$), and concentrated. The residue was flash chromatographed on silica gel with 5% CH$_3$OH/CH$_2$Cl$_2$ to provide the designated compound (311 mg, 34%).

MS (DCI/NH$_3$) m/e: 330 (M+H)$^+$.

EXAMPLE 203B

Methyl 4-[4-(4-morpholinylcarbonyl)phenoxy]thieno[2,3-c]pyridine-2-carboxylate

A solution of Example 203A (200 mg, 0.61 mmol) in a mixture DMF (5 mL) and CH$_2$Cl$_2$ (15 mL) was treated with morpholine (80 mg, 0.91 mmol), PyBOP (474 mg, 0.91 mmol) and DIPEA (296 mg, 2.28 mmol) at room temperature for 2 hours. After diluting with CH$_2$Cl$_2$, the solution was washed with brine, dried (MgSO$_4$), and concentrated. The residue was flash chromatographed on silica gel with 90% EtOAc/hexane to give the designated compound (277 mg, 100%).

MS (DCI/NH$_3$) m/e: 399 (M+H)$^+$.

EXAMPLE 203C

4-[4-(4-morpholinylcarbonyl)phenoxy]thieno[2,3-c]pyridine-2-carboxamide

Example 203C was prepared as in Example 61 but substituting Example 203B for Example 61A to provide the title compound.

mp>260° C.;

MS (DCI/NH$_3$) m/e: 401 (M+NH$_4$)$^+$; $^1$H NMR (300 MHz, DMSO-d$_6$) δ 3.50 (m, 4H), 3.60 (m, 4H), 7.14 (d, 2H, J=8.5 Hz), 7.48 (d, 2H, J=8.5 Hz), 7.86 (s, 1H), 8.15 (s, 1H), 8.22 (s, 1H), 8.45 (s, 1H), 9.17 (s, 1H); Anal. calcd for C$_{19}$H$_{17}$N$_3$O$_4$S: C, 59.52; H, 4.47; N, 10.96. Found: C, 59.64; H, 4.52; N, 10.90.

EXAMPLE 204

N-Methyl-4-[4-(4-morpholinylcarbonyl)phenoxy]thieno[2,3-c]pyridine-2-carboxamide Example 204 was prepared as in Example 103 but substituting Example 203B for Example 61A to provide the title compound.

mp 173–175° C.; MS (DCI/NH$_3$) m/e: 415 (M+NH$_4$)$^+$; $^1$H NMR (300 MHz, DMSO-d$_6$) δ 2.79 (d, 3H, J=4.4 Hz), 3.50 (m, 4H), 3.60 (m, 4H), 7.12 (d, 2H, J=8.5 Hz), 7.48 (d, 2H, J=8.5 Hz), 8.07 (s, 1H), 8.24 (s, 1H), 8.96 (q, 1H, J=4.4 Hz), 9.18 (s, 1H); Anal. calcd for C$_{20}$H$_{19}$N$_3$O$_4$S. 1.5 CH$_3$OH: C, 57.96; H, 4.64; N, 9.43. Found: C, 57.99; H, 4.86; N, 9.63.

EXAMPLE 206

4-[4-({[2-(4-Morpholinyl)ethyl]amino}carbonyl)phenoxy]thieno[2,3-c]pyridine-2-carboxamide

EXAMPLE 206A

Methyl 4-[4-({[2-(4-morpholinyl)ethyl]amino}carbonyl)phenoxy]thieno[2,3-c]pyridine-2-carboxylate A solution of Example 203A (200 mg, 0.61 mmol) in DMF (11 mL) was treated with 4-(2-aminoethyl)morpholine (158 mg, 1.21 mmol), EDC (232 mg, 1.21 mmol), HOBt (164 mg, 1.21 mmol) and triethylamine (122 mg, 1.21 mmol) at room temperature for 18 hours. After diluting with EtOAc, the reaction mixture was washed with brine, dried (MgSO$_4$) and concentrated. The residue was flash chromatographed on silica gel with 10% MeOH/EtOAc to provide the designated compound (239 mg, 89%).

MS (DCI/NH$_3$) m/e: 442 (M+H)$^+$.

EXAMPLE 206B

4-[4-({[2-(4-Morpholinyl)ethyl]amino}carbonyl)phenoxy]thieno[2,3-c]pyridine-2-carboxamide Example 206B was prepared as in Example 61 but substituting Example 206A for Example 61A to provide the title compound.

mp 214–216° C.; MS (DCI/NH$_3$) m/e: 427 (M+H)$^+$; $^1$H NMR (300 MHz, DMSO-d$_6$) δ 2.41 (t, 4H, J=4.8 Hz), 3.37 (q, 2H, J=6.1 Hz), 3.56 (t, 4H, J=4.8 Hz), 7.14 (d, 2H, J=8.8 Hz), 7.84 (s, 1H), 7.87 (d, 2H, J=8.8 Hz), 8.11 (s, 1H), 8.22 (s, 1H), 8.39 (t, 1H, J=6.0 Hz), 8.43 (s, 1H), 9.17 (s, 1H).

EXAMPLE 207

N-Methyl-4-[4-({[2-(4-morpholinyl)ethyl]amino}carbonyl)phenoxy]thieno[2,3-c]pyridine-2-carboxamide Example 207 was prepared as in Example 103 but substituting Example 206A for Example 61A to provide the title compound.

mp 226–228° C.; MS (DCI/NH$_3$) m/e: 441 (M+H)$^+$; $^1$H NMR (300 MHz, DMSO-d$_6$) δ 2.42 (m, 4H), 2.78 (d, 3H, J=4.4 Hz), 3.36 (q, 2H, J=6.1 Hz), 3.56 (t, 4H, J=4.8 Hz), 7.12 (d, 2H, J=8.5 Hz), 7.89 (d, 2H, J=8.5 Hz), 8.03 (s, 1H), 8.26 (s, 1H), 8.41 (t, 1H, J=6.0 Hz), 8.95 (q, 1H, J=4.4 Hz), 9.20 (s, 1H).

EXAMPLE 208

4-{4-[(E)-3-(4-Morpholinyl)-3-oxo-1-propenyl]phenoxy}thieno[2,3-c]pyridine-2-carboxamide

EXAMPLE 208A

Methyl 4-{4-[(E)-3-(tert-butyloxy)-3-oxo-1-propenyl]phenoxy}thieno[2,3-c]pyridine-2-carboxylate A flask, purged with nitrogen, was charged with Example 73 (50 mg, 1.37 mmol), Pd$_2$(dba)$_3$ (63 mg, 0.069 mmol), tri-o-tolylphosphine (64 mg, 0.21 mmol), dry degassed DMF (20 mL), t-butyl acrylate (602 mL, 4.11 mmol), and triethylamine (575 mL, 4.11 mmol). This suspension was stirred at 100° C. under nitrogen for 12 hours. After diluting with ethyl acetate, the reaction mixture was washed with brine, water, dried (MgSO$_4$), and concentrated. The residue was flash chromatographed on silica gel with 20% EtOAc/hexane to provide the title compound (323 mg, 57%).

MS (DCI/NH$_3$) m/e: 412 (M+H)$^+$.

EXAMPLE 208B

Methyl 4-{4-[(E)-propenoic acid-1-yl]phenoxy}thieno[2,3-c]pyridine-2-carboxylate A solution of Example 208A (1.76 g, 4.2 mmol) in chloroform (50 mL) was treated with trifluoroacetic acid (10 mL) at room temperature for 4 hours, and was then poured into ice-cold aqeous NaHCO$_3$. The formed white solid was collected by filtration, washed with water, MeOH, CH$_2$Cl$_2$, and dried to provide the designated compound (1.38 g, 100%).

MS (DCI/NH$_3$) m/e: 356 (M+H)$^+$.

EXAMPLE 208C

Methyl 4-{4-[(E)-3-(4-morpholinyl)-3-oxo-1-propenyl]phenoxy}thieno[2,3-c]pyridine-2-carboxylate A solution of Example 208B (260 mg, 0.73 mmol) in a mixture of DMF (5 mL) and CH$_2$Cl$_2$ (10 mL) was treated with morpholine (127 mg, 1.46 mmol), PyBOP (760 mg, 1.46 mmol) and DIPEA (380 mg, 2.92 mmol) at room temperature for 12 hours. After diluting with CH$_2$Cl$_2$, the solution was washed with brine, dried (MgSO$_4$), and concentrated. The residue was flash chromatographed on silica gel with 90% EtOAc/hexane to give the designated compound.

MS (DCI/NH$_3$) m/e: 425 (M+H)$^+$.

EXAMPLE 208D

4-{4-[(E)-3-(4-morpholinyl)-3-oxo-1-propenyl]phenoxy}thieno[2,3-c]pyridine-2-carboxamide Example 208D was prepared as in Example 61 but substituting Example 208C for Example 61A to provide the title compound.

MS (DCI/NH$_3$) m/e: 410 (M+H)$^+$; $^1$H NMR (300 MHz, DMSO-d$_6$) δ 3.59 (m, 6H), 3.70 (m, 2H), 7.13 (d, 2H, J=8.5 Hz), 7.20 (d, 1H, J=15.5 Hz), 7.52 (d, 1H, J=15.5 Hz), 7.79 (d, 2H, J=8.5 Hz), 7.86 (s, 1H), 8.16 (s, 1H), 8.18 (s, 1H), 8.45 (s, 1H), 9.17 (s, 1H).

EXAMPLE 209

4-[4-((E)-3-{[2-(4-morpholinyl)ethyl]amino}-3-oxo-1-propenyl)phenoxy]thieno[2,3-c]pyridine-2-carboxamide

EXAMPLE 209A

Methyl 4-[4-((E)-3-{[2-(4-morpholinyl)ethyl]amino}-3-oxo-1-propenyl)phenoxy]thieno[2,3-c]pyridine-2-carboxylate Example 209A was prepared as in Example 208C but substituting 4-(2-aminoethyl)morpholine for morpholine to provide the designated compound.

MS (DCI/NH$_3$) m/e: 468 (M+H)$^+$.

EXAMPLE 209B

4-[4-((E)-3-{[2-(4-morpholinyl)ethyl]amino}-3-oxo-1-propenyl)phenoxy]thieno[2,3-c]pyridine-2-carboxamide Example 209B was prepared as in Example 61 but substituting Example 209A for Example 61A to provide the title compound.

MS (DCI/NH$_3$) m/e: 453 (M+H)$^+$; $^1$H NMR (300 MHz, DMSO-d$_6$) δ 2.44 (m, 4H), 3.30 (m, 4H), 3.59 (t, 4H, J=4.8 Hz), 6.60 (d, 1H, J=15.8 Hz), 7.13 (d, 2H, J=8.8 Hz), 7.42 (d, 1H, J=15.8 Hz), 7.61 (d, 2H, J=8.8 Hz), 7.87 (s, 1H), 8.06 (t, 1H, J=4.8 Hz), 8.16 (s, 1H), 8.21 (s, 1H), 8.45 (s, 1H), 9.17 (s, H).

EXAMPLE 210

N-methyl-4-[4-((E)-3-{[2-(4-morpholinyl)ethyl]amino}-3-oxo-1-propenyl)phenoxy]thieno[2,3-c]pyridine-2-carboxamide Example 210 was prepared as in Example 103 but substituting Example 209A for Example 61A to provide the title compound.

MS (DCI/NH$_3$) m/e: 467 (M+H)$^+$; $^1$H NMR (300 MHz, DMSO-d$_6$) δ 2.38 (m, 4H), 2.79 (d, 3H, J=4.4 Hz), 3.59 (m, 8H), 6.58 (d, 1H, J=15.8 Hz), 7.11 (d, 2H, J=8.8 Hz), 7.42 (d, 1H, J=15.8 Hz), 7.61 (d, 2H, J=8.8 Hz), 8.05 (s, 1H), 8.23 (s, 1H), 8.95 (q, 1H, J=4.4 Hz), 9.17 (s, 1H).

EXAMPLE 211

4-(4-{(E)-3-[(2,3-Dihydroxypropyl)amino]-3-oxo-1-propenyl}phenoxy)thieno[2,3-c]pyridine-2-carboxamide

EXAMPLE 211A

Methyl 4-(4-{(E)-3-[(2,3-Dihydroxypropyl)amino]-3-oxo-1-propenyl}phenoxy)thieno[2,3-c]pyridine-2-carboxylate A solution of Example 208B (250 mg, 0.71 mmol)) in DMF (10 mL) was treated with 3-amino-1,2-propanediol (128 mg, 1.41 mmol), EDC (270 mg, 1.41 mmol), HOBt (191 mg, 1.41 mmol) and triethylamine (142 mg, 1.41 mmol) at room temperature for 18 hours. After diluting with EtOAc, the reaction mixture was washed with brine, dried ($MgSO_4$) and concentrated. The residue was flash chromatographed on silica gel to provide the designated compound (189 mg, 63%).

MS ($DCI/NH_3$) m/e: 429 (M+H)$^+$.

EXAMPLE 211B 4-(4-{(E)-3-[(2,3-Dihydroxyprooyl)amino]-3-oxo-1-propenyl}phenoxy)thieno[2,3-c]pyridine-2-carboxamide Example 211B was prepared as in Example 61 but substituting Example 211A for Example 61A to provide the title compound.

mp 185–187° C.; MS ($DCI/NH_3$) m/e: 414 (M+H)$^+$; $^1$H NMR (300 MHz, DMSO-$d_6$) δ 3.10 (m, 1H), 3.30 (m, 2H), 3.54 (m, 1H), 4.60 (t, 1H, J=5.9 Hz), 4.84 (d, 1H, J=4.8 Hz), 6.66 (d, 1H, J=15.8 Hz), 7.13 (d, 2H, J=8.8 Hz), 7.42 (d, 1H, J=15.8 Hz), 7.61 (d, 2H, J=8.8 Hz), 7.86 (s, 1H), 8.08 (t, 1H, J=5.5 Hz), 8.16 (s, 1H), 8.21 (s, 1H), 8.45 (s, 1H), 9.17 (s, 1H); Anal. calcd for $C_{20}H_{19}N_3O_5S$: C, 58.10; H, 4.63; N, 10.16. Found: C, 57.99; H, 4.54; N, 10.08.

EXAMPLE 212

4-(4-{(E)-3-[(2,3-Dihydroxypropyl)amino]-3-oxo-1-propenyl}phenoxy)-N-methylthieno[2,3-c]pyridine-2-carboxamide Example 212 was prepared as in Example 103 but substituting Example 211A for Example 61A to provide the title compound.

mp 225–226° C.; MS ($DCI/NH_3$) m/e: 428 (M+H)$^+$; $^1$H NMR (300 MHz, DMSO-$d_6$) δ 2.79 (d, 3H, J=4.8 Hz), 3.10 (m, 1H), 3.30 (m, 2H), 3.54 (m, 1H), 4.60 (t, 1H, J=5.5 Hz), 4.84 (d, 1H, J=4.8 Hz), 6.66 (d, 1H, J=15.8 Hz), 7.11 (d, 2H, J=8.8 Hz), 7.42 (d, 1H, J=15.8 Hz), 7.61 (d, 2H, J=8.8 Hz), 8.06 (s, 1H), 8.08 (t, 1H, J=5.5 Hz), 8.23 (s, 1H), 8.97 (q, 1H, J=4.8 Hz), 9.18 (s, 1H); Anal. calcd for $C_{21}H_{21}N_3O_5S$: C, 59.00; H, 4.95; N, 9.83. Found: C, 58.85; H, 4.90; N, 9.58.

EXAMPLE 213

4-[4-((E)-3-{[2-(1H-Imidazol-4-yl)ethyl]amino}-3-oxo-1-propenyl)phenoxy]-N-methylthieno[2,3-c]pyridine-2-carboxamide Example 213 was prepared as in Example 212 but substituting 2-(1H-imidazol-5-yl)ethylamine for 3-amino-1,2-propanediol to provide the title compound.

MS ($DCI/NH_3$) m/e: 448 (M+H)$^+$; $^1$H NMR (300 MHz, DMSO-$d_6$) δ 2.79 (d, 3H, J=4.5 Hz), 2.85 (t, 2H, J=6.6 Hz), 3.49 (q, 2H, J=6.0 Hz), 6.53 (d, 1H, J=15.8 Hz), 7.11 (d, 2H, J=8.5 Hz), 7.42 (d, 1H, J=15.8 Hz), 7.47 (s, 1H), 7.61 (d, 2H, J=8.5 Hz), 8.07 (s, 1H), 8.24 (s, 1H), 8.27 (t, 1H, J=5.5 Hz), 8.97 (q, 1H, J=4.8 Hz), 9.01 (s, !H), 9.21 (s, 1H).

EXAMPLE 214

4-{4-[(E)-3-({2-[bis(2-Hydroxyethyl)amino] ethyl}amino)-3-oxo-1-propenyl]phenoxy}-N-methylthieno[2,3-c]pyridine-2-carboxamide Example 214 was prepared as in Example 212 but substituting 2-[bis(2-hydroxyethyl)amino]ethylamine for 3-amino-1,2-propanediol to provide the title compound.

MS ($DCI/NH_3$) m/e: 485 (M+H)$^+$; $^1$H NMR (300 MHz, DMSO-$d_6$) δ 2.79 (d, 3H, J=4.8 Hz), 3.34 (m, 6H), 3.58 (q, 2H, J=6.1 Hz), 3.77 (t, 4H, J=5.1 Hz), 6.55 (d, 1H, J=15.6 Hz), 7.13 (d, 2H, J=8.5 Hz), 7.48 (d, 1H, J=15.6 Hz), 7.64 (d, 2H, J=8.5 Hz), 8.07 (s, 1H), 8.24 (s, 1H), 8.43 (t, 1H, J=4.8 Hz), 8.97 (q, 1H, J=4.8 Hz), 9.20 (s, 1H).

EXAMPLE 215

4-{4-[(E)-3-({2-[Bis(2-hydroxyethyl)amino] ethyl}amino)-3-oxo-1-propenyl]phenoxy}thieno[2,3-c]pyridine-2-carboxamide Example 215 was prepared as in Example 211 but substituting bis(2-hydroxyethyl)aminoethylamine for 3-amino-1,2-propanediol to provide the title compound.

MS ($DCI/NH_3$) m/e: 471 (M+H)$^+$; $^1$H NMR (300 MHz, DMSO-$d_6$) δ 2.56 (m, 4H), 3.21 (m, 2H), 3.41 (m, 4H), 4.37 (t, 2H, J=5.6 Hz), 6.56 (d, 1H, J=15.4 Hz), 7.13 (d, 2H, J=8.8 Hz), 7.42 (d, 1H, J=15.4 Hz), 7.61 (d, 2H, J=8.8 Hz), 7.86 (s, 1H), 8.00 (t, 1H, J=5.5 Hz), 8.15 (s, 1H), 8.21 (s, 1H), 8.45 (s, 1H), 9.17 (s, 1H); Anal. calcd for $C_{23}H_{26}N_4O_5S \cdot CH_3OH$: C, 56.36; H, 5.41; N, 11.15. Found: C, 56.40; H, 5.76; N, 11.40.

EXAMPLE 216

4-(4-{3-Hydroxy-3-[4-({2-[(methylamino)carbonyl] thieno[2,3-c]pyridin-4-yl}oxy)phenyl] butanoyl}phenoxy)-N-methylthieno[2,3-c]pyridine-2-carboxamide A solution of Example 202 (200 mg, 0.45 mmol) in THF (5 mL) was treated with methylmagnesium bromide (3 M solution in ether, 0.18 mL, 0.55 mmol) at −50° C. for 30 minutes, and slowly warmed up to room temperature for 10 minutes. An aqueous $NH_4Cl$ solution was added, and the mixture was extracted with ether. The combined organic phases were washed with brine, water, dried ($MgSO_4$), and concentrated. The residue was flash chromatographed on silica gel with 5% MeOH/EtOAc to provide the title compound (60 mg, 40%).

MS ($ESI/NH_3$) m/e: 653 (M+H)$^+$; $^1$H NMR (300 MHz, DMSO-$d_6$) δ 1.58 (s, 3H), 2.77 (d, 3H, J=4.8 Hz), 2.80 (d, 3H, J=4.8 Hz), 3.35 (d, 1H, J=13.0 Hz), 3.49 (d, 1H, J=13.0 Hz), 5.27 (s, 1H), 7.02 (d, 2H, J=8.8 Hz), 7.08 (d, 2H, J=8.8 Hz), 7.53 (d, 2H, J=8.8 Hz), 7.96 (d, 2H, J=8.8 Hz), 7.99 (s, 2H), 8.13 (s, 1H), 8.30 (s, 1H), 8.94 (m, 2H), 9.08 (s, 1H), 9.21 (s, 1H); Anal. calcd for $C_{34}H_{28}N_4O_6S_2 \cdot CH_3OH$: C, 61.39; H, 4.27; N, 8.18. Found: C, 61.26; H, 4.29; N, 7.95.

EXAMPLE 217

4-[4-(1H-Imidazol-1-yl)phenoxy]thieno[2,3-c] pyridine-2-carboxamide

EXAMPLE 217A

Methyl 4-[4-(1H-imidazol-1-yl)phenoxy]thieno[2,3-c]pyridine-2-carboxylate

Example 17A (0.88 g, 5 mmol) in THF (15 mL) and DMF (5 mL) was treated with 4-(1-imidazolyl)phenol and potassium t-butoxide (1 N in THF, 5.0 mL, 5 mmol) at 70° C. for 4 hours, then cooled to 0° C., added methyl thioglycolate (0.4 mL, 5 mmol) and cesium carbonate (1.62 g, 5 mmol) then refluxed for 1 hour. The reaction was poured into water, diluted with brine and extracted with ethyl acetate. The ethyl acetate was then washed with 1 N NaOH (2×20 mL), then brine (3×20 mL), dried ($MgSO_4$) to give the titled compound.

MS (DCI/NH$_3$) m/e: 352 (M+H)$^+$; $^1$H NMR (300 MHz, DMSO-d$_6$) δ 3.90 (s, 3H), 7.10 (s, 1H), 7.30 (d, 2H), 7.70 (s, 1H), 7.25 (d, 2H), 8.00 (s, 1H), 8.25 (d, 2H), 9.25 (s, 1H).

EXAMPLE 217B

4-[4-(1H-Imidazol-1-yl)phenoxy]thieno[2,3-c] pyridine-2-carboxamide

Example 217A was dissolved in 2 M methanolic ammonia and warmed at 50° C. in a sealed tube for 24 hours. The reaction was then evaporated and crystallized from methanol to give the titled compound.

mp 310–312° C.; MS (DCI/NH$_3$) m/e: 337 (M+H)$^+$; $^1$H NMR (300 MHz, DMSO-d$_6$) δ 7.10 (s, 1H), 7.28 (m, 2H), 7.68 (t, 1H), 7.25 (dd, 2H), 7.85 (br s, 1H), 8.15 (s, 1H), 8.20 (d, 2H), 8.45 (br s, 1H), 9.15 (s, 1H); Anal. Calcd for C$_{17}$H$_{12}$N$_4$O$_2$S 0.50 H$_2$O: C, 59.12; H, 3.79; N, 16.22. Found: C, 59.40; H, 3.63; N, 16.30.

EXAMPLE 218

N-Methyl-4-[4-(1H-pyrazol-1-yl)phenoxy]thieno[2,3-c]pyridine-2-carboxamide

EXAMPLE 218A

Methyl-4-(4-(1H-pyrazol-1-yl)phenoxy)thienol[2,3-c]pyridine-2-carboxylate

Example 17A (0.8 g, 5 mmol) in THF (15 mL) was treated with 4-(1H-pyrazol-1-yl)phenol and cesium carbonate (1.6 g, 5 mmol) under reflux for 4 hours, then cooled to 0° C., then methyl thioglycolate (0.4 mL, 5 mmol) and cesium carbonate (1.62 g, 5 mmol) were added, then the mixture was refluxed for 1 hour. The mixture was poured into water, diluted with brine and extracted with ethyl acetate. The ethyl acetate was then washed with 1 N NaOH (2×20 mL), then brine (3×20 mL), dried (MgSO$_4$) to give the titled compound.

MS (DCI/NH$_3$) m/e: 352 (M+H)$^+$; $^1$H NMR (300 MHz, DMSO-d$_6$) δ 3.80 (s, 3H), 6.55 (m, 1H), 7.30 (d, 2H), 7.42 (d, 1H), 7.75 (d, 1H), 7.90 (d, 2H), 8.25 (s, 1H), 8.50 (d, 1H), 9.22 (s, 1H).

EXAMPLE 218B

N-Methyl-4-[4-(1H-pyrazol-1-yl)phenoxy]thieno[2,3-c]pyridine-2-carboxamide

Example 218A was dissolved in 2 M methanolic methylamine and warmed at 50° C. in a round bottom flask for 4 hours. The reaction was then evaporated and crystallized from methanol to give the titled compound.

mp 192–194° C.; MS (DCI/NH$_3$) m/e: 351 (M+H)$^+$; $^1$H NMR (300 MHz, DMSO-d$_6$) δ 2.70 (d, 3H), 6.55 (m, 1H), 7.25 (d, 2H), 7.75 (br s, 1H), 7.90 (d, 2H), 8.12 (s, 1H), 8.20 (s, 1H), 8.50 (d, 1H), 9.00 (m, 1H), 9.18 (s, 1H); Anal. Calcd for C$_{18}$H$_{14}$N$_4$O$_2$S 0.25 H$_2$O: C, 60.15; H, 4.21; N, 15.59. Found: C, 60.30; H, 3.93; N, 15.73.

EXAMPLE 219

N-Methyl-4-[4-(1H-1,2,4-triazol-1-yl)phenoxy] thieno[2,3-c]pyridine-2-carboxamide Example 17A and 4-(1H-1,2,4-triazol-1-yl)phenol were processed as in Example 218 to provide the title compound.

mp 214–215° C.; MS (DCI/NH$_3$) m/e: 352 (M+H)$^+$; $^1$H NMR (300 MHz, DMSO-d$_6$) δ 2.70 (d, 3H), 7.30 (d, 2H), 7.55 (b, 1H), 7.90 (d, 2H), 8.12 (s, 1H), 8.25 (d, 1H), 9.00 (q, 1H), 9.30 (s, 1H).

EXAMPLE 220

N-Methyl-4-{4-[5-(trifluoromethyl)-1,2,4-oxadiazol-3-yl]phenoxy}thieno[2,3-c]pyridine-2-carboxamide

EXAMPLE 220A

N-Methyl-4-[4-(N-hydroxyamindino)phenoxy] thieno[2,3-c]pyridine-2-carboxamide

A solution of Example 186 (500 mg, 1.62 mmol) in a mixture of DMF (10 mL) and EtOH (10 mL) was treated with triethylamine (279 mg, 2.75 mmol) and hydroxylamine hydrochloride (169 mg, 2.43 mmol) at room temperature for 18 hours. The formed white solid was collected by filtration, washed with EtOH, dried to provide the designated compound (376 mg, 68%).

MS (ESI/NH$_3$) m/e: 343 (M+H)$^+$.

EXAMPLE 220B

N-Methyl-4-{4-[5-(trifluoromethyl)-1,2,4-oxadiazol-3-yl]phenoxy}thieno[2,3-c]pyridine-2-carboxamide A suspension of Example 220A (200 mg, 0.58 mmol) in pyridine (8 mL) was treated with trifluoroacetic anhydride (178 mg, 0.85 mmol) at room temperature for 1 hour. The resultant yellow solution was heated at 120° C. for 18 hours, and was then concentrated. The residue was separated by HPLC (C-18, CH$_3$CN/H$_2$O containing 0.1% TFA) to provide the title compound (169 mg, 69%).

mp 174–176° C.; MS (ESI/NH$_3$) m/e: 421 (M+H)$^+$; $^1$H NMR (300 MHz, DMSO-d$_6$) δ 2.78 (d, 3H, J=4.4 Hz), 7.26 (d, 2H, J=8.8 Hz), 8.03 (s, 1H), 8.10 (d, 2H, J=8.8 Hz), 8.38 (s, 2H), 8.96 (q, 1H, J=4.4 Hz), 9.25 (s, 1H); Anal. calcd for C$_{18}$H$_{11}$N$_4$O$_3$SF$_3$: C, 51.43; H, 2.64; N, 13.33. Found: C, 51,56; H, 2.76; N, 13.32.

EXAMPLE 221

4-[4-(4,5-Dihydro-1H-imidazol-2-yl)phenoxy]-N-methylthieno[2,3-c]pyridine-2-carboxamide A solution of Example 186 (800 mg, 2.6 mmol) in a mixture of MeOH (30 mL), Et$_2$O (20 mL), and CH$_2$Cl$_2$ (30 mL) was introduced hydrogen chloride gas at 0° C. for 1.5 hours, stirred at room temperature for 24 hours, and concentrated. The residue was dissolved in MeOH (30 mL) and ethylenediamine (3 mL), and heated at 70° C. for 2 hours. After the reaction was cooled, the resultant white solid was collected by filtration, washed with methanol, and dried to provide the title compound (804 mg, 88%).

mp >280° C.; MS (ESI/NH$_3$) m/e: 353 (M+H)$^+$; $^1$H NMR (300 MHz, DMSO-d$_6$) δ 2.78 (d, 3H, J=4.4 Hz), 3.32 (br s, 4H), 6.88 (br s, 1H), 7.11 (d, 2H, J=8.8 Hz), 7.85 (d, 2H, J=8.8 Hz), 8.04 (s, 1H), 8.22 (s, 2H), 8.93 (q, 1H, J=4.4 Hz), 9.17 (s, 1H); Anal. calcd for C$_{18}$H$_{16}$N$_4$O$_2$S: C, 59.36; H, 4.46; N, 14.57. Found: C, 59.60; H, 4.55; N, 14.40.

EXAMPLE 222

N-Methyl-4-[4-(2-thienyl)phenoxy]thieno[2,3-c] pyridine-2-carboxamide

A flask, purged with nitrogen, was charged with Example 190B (200 mg, 0.48 mmol), Pd(OAc)$_2$ (11 mg, 0.048 mmol), tri-o-tolylphosphine (44 mg, 0.14 mmol), dry degassed DMF (10 mL), 2-tributylstannylthiophene (305 mL, 0.96 mmol), and triethylamine (334 mL, 2.4 mmol). This suspension was stirred at 80° C. for 15 hours. After diluting with ethyl acetate, the reaction mixture was washed with brine, $H_2O$, dried ($MgSO_4$), and concentrated. The residue was separated by HPLC (C-18, $CH_3CN/H_2O$ containing 0.11% TFA) to provide the title compound (212 mg, 90%).

MS (ESI/$NH_3$) m/e: 367 (M+H)$^+$; $^1$H NMR (300 MHz, DMSO-$d_6$) δ 2.80 (d, 3H, J=4.4 Hz), 7.13 (m, 1H), 7.17 (d, 2H, J=8.8 Hz), 7.48 (d, 1H, J=3.7 Hz), 7.54 (d, 1H, J=5.1 Hz), 7.71 (d, 2H, J=8.8 Hz), 8.15 (s, 1H), 8.24 (s, 1H), 9.02 (q, 1H, J=4.4 Hz), 9.22 (s, 1H).

EXAMPLE 223

4-([1,1'-Biphenyl]-4-yloxy)-N-methylthieno[2,3-c]pyridine-2-carboxamide

Example 223 was prepared as in Example 222 but substituting tributylphenyltin for (tributylstannyl)thiophene to provide the title compound.

MS (ESI/$NH_3$) m/e: 361 (M+H)$^+$; $^1$H NMR (300 MHz, DMSO-$d_6$) δ 2.80 (d, 3H, J=4.5 Hz), 7.19 (d, 2H, J=8.8 Hz), 7.36 (t, 1H, J=7.4 Hz), 7.47 (t, 2H, J=7.3 Hz), 7.66 (d, 2H, J=7.3 Hz), 7.72 (d, 2H, J=8.8 Hz), 8.15 (s, 1H), 8.23 (s, 1H), 9.00 (q, 1H, J=4.4 Hz), 9.19 (s, 1H).

EXAMPLE 224

N-Methyl-4-[4-(1-methyl-1H-imidazol-5-yl)phenoxy]thieno[2,3-c]pyridine-2-carboxamide Example 224 was prepared as in Example 222 but substituting 1-methyl-(5-tributylstannyl)imidazole, which was prepared according to a literature method (K. Gaare, et al., Acta Chem. Scand. 1993, 47, 57), for 2-tributylstannylthiophene to provide the title compound.

mp 256–258° C.; MS (ESI/$NH_3$) m/e 365(M+H)$^+$; $^1$H NMR (300 MHz, DMSO-$d_6$) δ 2.80 (d, 3H, J=2.1 Hz), 3.67 (s, 3H), 7.03 (s, 1H), 7.17 (d, 2H, J=8.8 Hz), 7.53 (d, 2H, J=8.8 Hz), 7.69 (s, 1H), 8.12 (s, 1H), 8.22 (s, 1H), 9.00 (q, 1H, J=2.1 Hz), 9.16 (s, 1H); Anal. calcd for $C_{19}H_{16}N_4O_2S$: C, 62.62; H, 4.43; N, 15.37. Found: C, 62.38; H, 4.23; N, 15.13.

EXAMPLE 225

4-{4-[1-(Hydroxymethyl)cyclopropyl]phenoxy}-N-methylthieno[2,3-c]pyridine-2-carboxamide

EXAMPLE 225A 4-(1-Hydroxymethylcyclopropyl)anisole

A solution of 1-(4-methoxyphenyl)-1-cyclopropanecarboxylic acid (5.0 g, 26 mmol) in THF (100 mL) was slowly treated with $LiAlH_4$ (0.95 g, 25 mmol) at –20° C. for 0.5 hour, and was then warmed to room temperature for 2 hours. The excess $LiAlH_4$ was consumed by slowly adding EtOH. After diluting with ether, the reaction mixture was washed with 2% HCl in brine, water, dried ($MgSO_4$) and concentrated to provide the designated compound (5.0 g, 100%).

MS (DCI/$NH_3$) m/e: 196 (M+$NH_4$)$^+$.

EXAMPLE 225B 4-(1-Hydroxymethylcyclopropyl)phenol

To a suspension of NaH (60% in mineral oil, 392 mg, 9.8 mmol) in DMF (10 mL) was slowly added neat ethanethiol (610 mg, 9.8 mmol) at room temperature. The reaction mixture was stirred for 10 minutes to form a clear solution. Example 225A (500 mg, 2.8 mmol) was then added, and the mixture was heated at 145° C. for 4 hours. After diluting with ether, the reaction mixture was washed with 2% HCl in brine, dried ($MgSO_4$) and concentrated. The residue was flash chromatographed on silica gel with 50% EtOAc/hexane to provide the designated compound (373 mg, 81%).

MS (DCI/$NH_3$) m/e: 182 (M+$NH_4$)$^+$.

EXAMPLE 225C 4-(1-Triphenylmethoxymethylcyclopropyl)phenol

A solution of Example 225B (1.0 g, 6 mmol) in pyridine (7 mL) was treated with triphenylmethyl chloride (1.87 g, 6.7 mmol) at room temperature for 18 hours. After diluting with ether, the reaction mixture was washed 1% aqeous HCl, water and dried ($MgSO_4$). The residue was flash chromatographed on silica gel with 12% EtOAc/hexane to provide the designated compound.

MS (DCI/$NH_3$) m/e: 407 (M+H)$^+$.

EXAMPLE 225D

Methyl 4-[4-(1-triphenylmethoxymethyl)cyclopropyl]phenoxy-[2,3-c]pyridine-2-carboxylate Example 225D was prepared as in Example 61A but substituting Example 225C for 4-chlorophenol to provide the designated compound.

MS (DCI/$NH_3$) m/e: 598 (M+H)$^+$.

EXAMPLE 225E

Methyl 4-[4-(1-hydroxymethyl)cyclolprolpyl]phenoxy-[2,3-c]pyridine-2-carboxylate A solution of Example 225D (230 mg, 0.38 mmol) in a mixture of $CH_2Cl_2$ (10 mL) and MeOH (5 mL) was treated with trifluoroacetic acid (1 mL) at 0° C. for 1 hour, allowed to warm to room temperature and stir for for 1 hour, and was poured into aqeous $NaHCO_3$ solution. The mixture was extracted with methylene chloride. The combined organic phases were washed with water, and dried ($MgSO_4$). The residue was flash chromatographed on silica gel with 65% EtOAc/hexane to provide the designated compound (78 mg, 58%).

MS (DCI/$NH_3$) m/e: 356 (M+H)$^+$.

EXAMPLE 225F

4-[4-(1-Hydroxymethyl)cyclopropyl]phenoxy-N-methylthieno[2,3-c]pyridine-2-carboxamide Example 225F was prepared as in Example 103 but substituting Example 225E for Example 61A to provide the designated compound.

MS (ESI/$NH_3$) m/e: 355 (M+H)$^+$; $^1$H NMR (300 MHz, DMSO-$d_6$) δ 0.72 (m, 2H), 0.82 (m, 2H), 2.80 (d, 3H, J=4.7 Hz), 3.51 (d, 2H, J=5.8 Hz), 4.66 (t, 1H, J=5.8 Hz), 7.01 (d, 2H, J=8.8 Hz), 7.34 (d, 2H, J=8.8 Hz), 8.06 (s, 1H), 8.13 (s, 1H), 8.96 (q, 1H, J=4.7 Hz), 9.10 (s, 1H).

EXAMPLE 226

4-[4-(1-{[2-(2-Ethoxyethoxy)ethoxy]methyl}cyclopropyl)phenoxy]-N-methylthieno[2,3-c]pyridine-2-carboxamide

EXAMPLE 226A 4-(2-(2-Ethoxyethoxy)ethoxy)methylcyclopropyl)anisole

A solution of Example 225A (1.0 g, 5.6 mmol) in THF (15 mL) was treated with NaH (60% in mineral oil, 312 mg, 7.8 mmol) and 15-crown-5 (1.33 mL, 6.7 mmol) at room temperature for 15 minutes follwed by addition of 2-(2-ethoxyethoxy)ethyl tosylate (1.93 g, 6.7 mmol) which was prepared according to literature method (C. Almansa, et al., Tetrahedron 1991, 47, 5867). The brown slurry was stiffed at room temperature for 5 hours and was poured into brine. The mixture was extracted with $CH_2Cl_2$, and the combined organic phases were dried ($MgSO_4$) and concentrated. The residue was flash chromatographed on silica gel with 25% EtOAc/hexane to provide the designated compound (1.58 g, 95%).

MS (ESI/$NH_3$) m/e: 312(M+$NH_4$)$^+$.

EXAMPLE 226B 4-(2-(2-Ethoxyethoxy)ethoxcy)methylcyclopropyl) phenol

A solution of Example 226A (1.5 g, 5.1 mmol) in DMF (15 mL) was treated with sodium thiomethoxide (1.25 g, 17.8 mmol) at 145° C. for 5 hours. After cooling to room temperature methylene chloride (100 mL) was added, and the mixture was washed with 2% HCl in brine. The organic layer was dried ($MgSO_4$), concentrated and the residue was flash chromatographed on silica gel with 35% EtOAc/hexane to provide the designated compound (1.33 g, 93%).

MS (ESI/$NH_3$) m/e: 298(M+$NH_4$)$^+$.

EXAMPLE 226C

Methyl 4-[4-(1-{[2-(2-Ethoxyethoxy)ethoxy] methyl}cyclopropyl)phenoxy]-N-metholthieno[2,3-c]pyridine-2-carboxylate Example 226C was prepared as in Example 61A but substituting Example 226B for 4-chlorophenol to provide the designated compound.

MS (ESI/$NH_3$) m/e: 472(M+H)$^+$.

EXAMPLE 226D

4-[4-(1-{[2-(2-Ethoxyethoxy)ethoxy] methyl}cyclopropyl)phenoxy]-N-methylthieno[2,3-c]pyridine-2-carboxamide Example 226D was prepared as in Example 103 but substituting Example 226C for Example 61 A to provide the title compound.

MS (ESI/$NH_3$) m/e: 471(M+H)$^+$. $^1$H NMR (300 MHz, DMSO-$d_6$) δ 0.84 (m, 2H), 0.87 (m, 2H), 1.06 (t, 3H, J=6.7 Hz), 2.82 (d, 3H, J=4.4 Hz), 3.37 (t, 2H, J=6.7 Hz), 3.39–3.55 (m, 10H), 7.07 (d, 2H, J=8.8 Hz), 7.36 (d, 2H, J=8.8 Hz), 8.13 (s, 1H), 8.26 (s, 1H), 9.10 (q, 1H, J=4.4 Hz), 9.28 (s, 1H); Anal. calcd for $C_{25}H_{30}N_4O_5S$: C, 59.22; H, 6.16; N, 5.52. Found: C, 59.50; H, 6.16; N, 5.26.

EXAMPLE 227

N-Methyl-4-[4-(trifluoromethoxy)phenoxy]thieno[2, 3-c]pyridine-2-carboxamide

Example 227 was prepared as in Example 103 but substituting 4-trifluoromethoxyphenol for 4-chlorophenol to provide the title compound.

mp 132–133° C.; MS (ESI/$NH_3$) m/e: 368 (M+H)$^+$; $^1$H NMR (300 MHz, DMSO-$d_6$) δ 2.80 (d, 3H, J=4.4 Hz), 7.20 (d, 2H, J=9.2 Hz), 7.41 (d, 2H, J=9.2 Hz), 8.08 (s, 1H), 8.21 (s, 1H), 8.95 (q, 1H, J=4.4 Hz), 9.18 (s, 1H); Anal. calcd for $C_{16}H_{11}N_2O_3SF_3$: C, 52.17; H, 3.01; N, 7.61. Found: C, 52.21; H, 3.26; N, 7.29.

EXAMPLE 228

5-{4-[4-(1-{[2-(2-(2-Ethoxyethoxy)ethoxy] methyl}cyclopropyl)phenoxy]thieno[2,3-c]pyridin-2-yl-56 -1,3,4-oxadiazol-2-amine Example 228 was prepared as in Example 275 and Example 156 but substituting Example 226C for Example 61A to provide the title compound.

mp 113–114° C.; MS (ESI/$NH_3$) m/e: 497 (M+H)$^+$; $^1$H NMR (300 MHz, DMSO-$d_6$) δ 0.82 (m, 2H), 0.85 (m, 2H), 1.05 (t, 3H, J=7.1 Hz), 3.40 (t, 2H, J=7.1 Hz), 3.42–3.54 (m, 10H), 7.00 (d, 2H, J=8.8 Hz), 7.33 (d, 2H, J=8.8 Hz), 7.55 (s, 1H), 7.58 (s, 2H), 8.18 (br s, 1H), 9.15 (br s, 1H).

EXAMPLE 229

4-[4-(1,1-Difluoro-2-hydroxyethyl)phenoxy]-N-methylthieno[2,3-c]pyridine-2-carboxamide

EXAMPLE 229A

4-[4-(1,1-Ddifluoro-2-ethoxy-2-oxoethyl)phenoxy]-N-methylthieno[2,3-c]pyridine-2-carboxamide A suspension of activated copper (512 mg, 8 mmol) in dry DMSO (5 mL) was treated with ethyl iododifluoroacetate (1.0 g, 4 mmol) at room temperature for 10 minutes. Phenol (188 mg, 2 mmol) and Example 190B were then added. The reaction mixture was stirred at room temperature for 20 hours. After diluted with 1:1 ether/EtOAc, the mixture was washed with 1% HCl in brine, water, dried ($MgSO_4$) and concentrated. The residue was flash chromatographed on silica gel with 65% EtOAc/hexane, and was further purified on HPLC (C-18, $CH_3CN/H_2O$ containing 0.1% TFA) to provide the designated compound (85 mg, 15%).

MS (ESI/$NH_3$) m/e: 407 (M+H)$^+$.

EXAMPLE 229B

4-[4-(1,1-Difluoro-2-hydroxyethyl)phenoxy]-N-methylthieno[2,3-c]pyridine-2-carboxamide A solution of Example 229A (40 mg, 0.1 mmol) in MeOH (5 mL) was treated $NaBH_4$ (50 mg) at room temperature for 2 hours. Brine was added, and the mixture was extracted with EtOAc. The combined organic phases were dried ($Na_2SO_4$) and concentrated. The residue was purified by HPLC (C-18, $CH_3CN/H_2O$ containing 0.1% TFA) to provide the title compound (44.4 mg, 94%).

MS (ESI/$NH_3$) m/e: 365 (M+H)$^+$; $^1$H NMR (300 MHz, $CD_3OD$) δ 2.94 (s, 3H), 3.93 (t, 2H, J=13.5 Hz), 7.27 (d, 2H, J=9.2 Hz), 7.65 (d, 2H, J=9.2 Hz), 8.15 (s, 2H), 9.24 (s, 1H); Anal. calcd for $C_{17}H_{14}N_2O_3SF_2$·TFA: C, 47.70; H, 3.16; N, 5.86. Found: C, 47.67; H, 3.10; N, 5.76.

EXAMPLE 230

4-(4-{2-[2-(2-Ethoxyethoxy)ethoxy]-1,1-difluoroethyl}phenoxy)-N-methylthieno[2,3-c] pyridine-2-carboxamide A solution of Example 229B (40 mg, 0.11 mmol) in THF (3 mL) was treated with NaH (60% in mineral oil, 7 mg, 0.16 mmol) and 15-crown-5 (35 mg, 0.16 mmol) at room temperature for 15 minutes. 2-(2-ethoxyethoxy)ethyl tosylate (46 mg, 0.16 mmol) which was prepared according to literature method (C. Almansa, et al, Tetrahedron 1991, 47, 5867), was then added. The reaction mixture was stirred at room temperature for 15 hours, and was then directly separated on HPLC (C-18, $CH_3CN/H_2O$ containing 0.1% TFA) to provide the title compound (46 mg, 81%).

MS (ESI/$NH_3$) m/e: 481 (M+H)$^+$; $^1$H NMR (300 MHz, $CD_3OD$) δ 1.16 (t, 3H, J=7.1 Hz), 2.97 (s, 3H), 3.49 (q, 2H, J=7.1 Hz), 3.57 (m, 6H), 3.70 (m, 2H), 4.01 (t, 2H, J=12.7 Hz), 7.37 (d, 2H, J=8.8 Hz), 7.72 (d, 2H, J=8.8 Hz), 8.22 (s, 1H), 8.33 (s, 1H), 9.46 (s, 1H).

EXAMPLE 231

4-(4-Chlorophenoxy)-6-{[(2,2-dimethylbropanoyl)oxy]methyl}-2-[(meth lamino)carbonyl]thieno[2,3-c]pyridin-6-ium Trifluoroacetate Example 103 (47.4 mg, 0.149 mmol) was dissolved (under $N_2$ atmosphere) in 1.5 mL dry acetonitrile (with warming), and chloromethyl pivalate (25 mg, 0.167 mmol) was added at room temperature. The reaction was stirred for 16 hours, then tetrabutylammonium iodide (1 mg) was added, and then the solution was warmed to reflux for 48 hours. The reaction mixture was concentrated under reduced pressure, and the residue was purified by preparative HPLC (C-18 column, gradient eluent 20–70% acetonitrile-0.1% aqueous TFA, 60 minutes elution) to provide 24 mg (34%) of the title compound as a foam.

HPLC: Supelco C-18 column, gradient eluent of 0.1% aqueous TFA:acetonitrile 0:90–90:0 over 30 minutes, detection at 254 nm, flow rate of 0.8 mL/min, RT 20.0 minutes. MS (APCI+) m/e: 433 (M)$^+$; $^1$H NMR (300 MHz, DMSO-$d_6$) δ 1.18 (s, 9H), 3.01 (s, 3H), 6.4–6.6 (br s, 2H), 7.1–7.3 (br s, approx. 2H), 7.49 (br s, 2H), 7.74 (br s, 1H), 8.41 (br s, 1H), 8.64 (br s, 1H), 9.3–9.9 (vbr s, 1H); Anal. calcd for $C_{23}H_{22}F_3Cl_2O_6S$: C, 45.43; H, 3.51; N, 4.24. Found: C, 45.93; H, 3,70; N, 4.34.

EXAMPLE 232

4-(4-Bromophenoxy)-6-{[(2,2-dimethylpropanoyl)oxy]methyl}-2-[(methylamino)carbonyl]thieno[2,3-c]pylidin-6-ium Example 171 (69.4 mg, 0.191 mmol) was dissolved in 2 mL acetonitrile, then tetrabutylammonium iodide (1 mg) was added, followed by chloromethyl pivalate (22 mg, 0.146 mmol). The reaction solution was warmed to reflux for 24 hours. An additional portion of chloromethyl pivalate (11 mg, 0.073 mmol) was added, and the reaction was refluxed for an additional 72 hours. The reaction was concentrated under reduced pressure, and the solid was partitioned between 15 mL water and 15 mL EtOAc. The aqueous phase was extracted with 2×15 mL EtOAc, then the aqueous phase was concentrated under reduced pressure to a yellow solid (93.5 mg). HPLC purification (C-18 column, 20–75% acetonitrile-0.1% aqueous TFA) provided pure title compound (55.9 mg, 49%).

HPLC: Supelco C-18 column, gradient eluent of 0.1% aqueous TFA:acetonitrile 0:90–90:0 over 30 minutes, detection at 254 nm, flow rate of 0.8 mL/min, RT 20.3 minutes; MS (APCI−) m/e: 475, 477 (M−H)$^-$; $^1$H NMR (300 MHz, DMSO-$d_6$) δ 1.17 (s, 9H), 3.02 (br m, 3H), 6.0–6.7 (vbr s, 2H), 7.14 (br d, 2H), 7.64 (br d, 2H), 7.78 (s, 1H), 8.07–8.17 (br s, 1H), 8.34 (s, 1H), 9.44–9.65 (vbr s, 1H); Anal. calcd for $C_{23}H_{22}F_3BrN_2O_6S \cdot 1.5\ H_2O$: C, 40.99; H, 3.58; N, 3.82. Found: C, 40.94; H, 3.25; N, 3.76.

EXAMPLE 233

2-(Aminocarbonyl)-4-(4-chlorophenoxy)-6-{[(isoproipoxycarbonyl)oxy]methyl}thieno[2,3-c]pyridin-6-ium To a solution of Example 61 (300 mg, 0.94 mmol) in acetonitrile (15 mL) under a nitrogen atmosphere was added tetraphenylboron sodium (387 mg, 1.13 mmol), sodium iodide (169 mg, 1.13 mmol), and [(isopropyloxycarbonyl)oxy]methyl chloride (172 mg, 1.13 mmol). The reaction mixture was heated at reflux for 4 hours, cooled to room temperature and diluted with acetonitrile (100 mL) before filtering through Celite®. The filtrate was concentrated to a foam that was triturated in methanol to afford the pyridinium tetraphenylborate salt (550 mg) as a yellow solid. The tetraphenylborate salt dissolved in 1:1 $CH_3CN$:i-PrOH and passed over an ion exchange column using Dowex 1×2 chloride, 50–100 mesh. The eluent was concentrated and the resulting residue triturated with $Et_2O$ to afford example 233 as a white solid (210 mg, 49%).

MS (FAB) m/e: 421 (M+H)$^+$; $^1$H NMR (300 MHz, DMSO-$d_6$) δ 1.26 (d, J=7 Hz, 6H), 4.81 (q, J=7 Hz, 1H), 6.44 (s, 2H), 7.41 (m, 2H), 7.62 (m, 2H), 8.31 (br s, 1H), 8.59 (s, 1H), 8.68 (s, 1H), 9.98 (s, 1H); Anal. calcd for $C_{19}H_{18}Cl_2N_2O_5S$: C, 49.90; H, 3.96; N, 6.13. Found: C, 49.74; H, 3.95; N, 6.14.

EXAMPLE 234

4-(Cyclopentyloxy)-N-methylthieno[2,3-c]pyridine-2-carboxamide

EXAMPLE 234A 5-chloro-3-cyclopentyloxypyridine

The title compound (5.91 g, 77%) was prepared as described in Example 236A except substituting cyclopentanol (4.2 mL, 46.31 mmol) for benzyl alcohol.

MS (APCI) m/e: 198 (M+H)$^+$; $^1$H NMR (300 MHz, DMSO-$d_6$) δ 1.53–1.76 (m, 6H), 1.86–2.02 (m, 2H), 4.92–4.99 (m, 1H), 7.55 (t, J=2.25 Hz, 1H), 8.18 (d, J=2.25 Hz, 1H), 8.22 (d, J=3 Hz, 1H).

EXAMPLE 234B

5-Chloro 3-cyclopentylloxy pyridine-4-carboxaldehyde

The title compound (5.22 g, 77%) was prepared as described in Example 236B except substituting Example 234A (5.9 g, 30 mmol) for Example 236A.

MS (APCI) m/e: 226 (M+H)$^+$; $^1$H NMR (300 MHz, DMSO-$d_6$) δ 1.55–1.85 (m, 6H), 1.93–2.04 (m, 2H), 5.14–5.22 (m, 1H), 8.36 (s, 1H), 8.63 (s, 1H), 10.31 (s, 1H).

EXAMPLE 234C

Methyl 4-[cyclopentyloxy]thieno[2,3-c]pyridine-2-carboxylate

The title compound (4.31 g, 67%) was prepared as described in Example 236C except substituting 234B (5.2 g, 23.11 mmol) for Example 236B.

MS (APCI) m/e: 278 (M+H)$^+$; $^1$H NMR (400 MHz, DMSO-$d_6$) δ 1.59–1.69 (m, 2H), 1.74–1.81 (m, 2H), 1.83–1.90 (m, 2H), 1.97–2.07 (m, 2H), 3.93 (s, 3H), 5.12–5.17 (m, 1H), 8.05 (s, 1H), 8.24 (s, 1H), 8.94 (s, 1H); $^{13}$C NMR (100 MHz, DMSO-$d_6$) δ 23.63 ($CH_2$), 32.30 ($CH_2$), 52.98 ($OCH_3$), 80.33 (CH), 125.52 (CH), 127.09 (CH), 134.72 (C), 136.45 (C), 137.44 (CH), 138.05 (C), 149.27 (C), 161.90 (C=O).

EXAMPLE 234D

4-[Cyclopentyloxy]thieno[2,3-c]pyridine-2-N-methylamide

Example 234C (1.6 g, 61%) was prepared as described in Example 171 except substituting Example 234C (2.6 g, 9.4 mmol) for Example 73A.

mp 216–217° C.; MS (APCI) m/e: 277 (M+H)+, 244 (M+Cl)−; $^1$H NMR (400 MHz, DMSO-d$_6$) δ 1.60–1.69 (m, 2H), 1.73–1.90 (m, 4H), 1.97–2.08 (m, 2H), 2.83 (d, J=4 Hz, 3H), 5.10–5.17 (m, 1H), 8.11 (s, 1H), 8.19 (s, 1H), 8.93 (d, J=4 Hz, 1H); $^{13}$C NMR (100 MHz, DMSO-d$_6$) δ 23.60 (CH$_2$), 26.14 (NCH$_3$), 32.34 (CH$_2$), 80.14 (CH), 119.68 (CH), 126.91 (CH), 135.73 (C), 137.17 (CH), 144.2 (C), 149.02 (C), 161.18 (C).

EXAMPLE 235

4-(2-Cyclohexen-1-yloxy)-N-methylthieno[2,3-c]pyridine-2-carboxamide

EXAMPLE 235A

Methyl 4-[2-cyclohexene-3-oxyl]thieno[2,3-c]pyridine-2-carboxylate

The title compound (158 mg, 57%) was prepared as described in Example 99A except substituting 2-cyclohexenol (0.113 mL, 0.115 mmol) for 3-hydroxy tetrahydrofuran. Pure product was obtained by flash chromatography on silica gel eluting with 10% acetone-hexane.

MS (APCI) m/e: 290 (M+H)+, 288 (M−H)−, 324 (M+Cl)−; $^1$H NMR (300 MHz, DMSO-d$_6$) δ 1.95–1.62 (m, 1H), 1.66–2.14 (m, 5H), 3.92 (s, 3H, OCH$_3$), 5.22–5.26 (m, 1H), 5.91–5.99 (m, 2H), 8.03 (s, 1H, CH), 8.36 (s, 1H, CH), 8.95 (s, 1H, CH).

EXAMPLE 235B 4-(2-Cyclohexen-1-yloxy)-N-methylthieno[2,3-c]pyridine-2-carboxamide The title compound Example 235 (59 mg, 40%) was prepared from Example 235A (150 mg, 0.519 mmol) as described in Example 171.

MS (APCI) m/e: 289 (M+H)+, 287 (M−H)−, 323 (M+Cl)−; $^1$H NMR (500 MHz, DMSO-d$_6$) δ 1.62–1.70 (m, 1H), 1.78–1.91 (m, 2H), 1.96–2.17 (m, 3H), 2.82 (d, J=5 Hz, 3H), 5.21 (br s, 1H), 5.93–5.98 (m, 1H), 6.01–6.05 (m, 1H), 8.14 (s, 1H), 8.30 (s, 1H), 8.87 (s, 1H), 8.75 (d, J=5 Hz, 1H); $^{13}$C NMR (75 MHz, DMSO-d$_6$) δ 18.2 (CH$_2$), 24.6 (CH$_2$), 26.2 (CH$_3$), 27.7 (CH$_2$), 71.3 (CH), 119.7 (CH), 125.6 (CH), 127.4 (CH), 132.6 (CH), 136.0 (C), 137.3 (C), 137.4 (CH), 144.1 (C), 149.0 (C), 161.2 (C).

EXAMPLE 236

4-(Benzyloxy)thieno[2,3-c]pyridine-2-carboxamide

EXAMPLE 236A

5-Chloro-3-benzyloxypyridine

To a stirred solution of 5-chloro-3-pyridinol (10 g, 77.19 mmol) in anhydrous tetrahydrofuran (155 mL) at 0° C. and under nitrogen atmosphere was added benzyl alcohol (9.6 mL, 92.63 mmol), triphenylphosphine (26.32 g, 100.35 mmol)) and diethyl azodicarboxylate (15.8 mL, 100.35 mmol). The reaction mixture was stirred at room temperature overnight and the solvent was removed under reduced pressure. The residue (70 g) obtained was treated with diethyl ether (2×300 mL) and the solids were removed by filtration. The filtrate obtained was concentrated under reduced pressure and the residue was purified by silica gel flash chromatography eluting with 5% acetone and hexane to obtain the title compound in 36% (5.8 g) yield.

MS (APCI) m/e: 220 (M+H)+; $^1$H NMR (300 MHz, DMSO-d$_6$) δ 5.22 (s, 2H), 7.33–7.49 (m, 5H), 7.77 (t, J=5 Hz, 1H), 8.23 (d, J=5 Hz, 1H), 8.34 (d, J=5 Hz, 1H).

EXAMPLE 236B

5-Chloro 3-benzyloxy pyridine-4-carboxaldehyde

To a stirred solution of diisopropylamine (4.5 mL, 31.78 mmol) in anhydrous tetrahydrofuran (20 mL) under nitrogen atmosphere at −5° C. was added dropwise n-BuLi in hexanes (2.5 M solution, 12.8 mL, 31.78 mmol) maintaining internal temperature of the reaction mixture below 0° C. The reaction mixture was stirred at −10° C. for 10 minutes, then at 0° C. for 30 minutes. This was cooled to −78° C. and a solution of Example 236A (5.8 g, 26.5 mmol) in anhydrous tetrahydrofuran (30 mL) was added slowly. Stirring at −78° C. was continued for 1 hour. Then the reaction was quenched with dropwise addition of methyl formate (5 mL, 79.5 mmol) in anhydrous THF (15 mL) and stirred at −78° C. for 3.5 hours. Internal temperature of the reaction mixture was maintained at or below −74° C. throughout the reaction. After 3.5 hours, the reaction mixture was poured into an ice cold saturated aqueous solution of NaHCO$_3$ (200 mL) and stirred for 15 minutes. The mixture was partitioned with ethyl acetate (250 mL), organic layer was separated and washed with brine (2×60 mL). The dried (MgSO$_4$) organic layer was concentrated under reduced pressure to obtain the crude product (8.5 g). The title compound was obtained in 75% yield (4.2 g) by flash chromatography on silica gel eluting with 6% acetone-hexane.

MS (APCI) m/e: 248 (M+H)+; $^1$H NMR (300 MHz, DMSO-d$_6$) d: 5.42 (s, 2H), 7.33–7.45 (m, 3H), 7.48–7.52 (m, 2H), 8.41 (s, 1H), 8.72 (s, 1H), 10.39 (s, 1H).

EXAMPLE 236C

Methyl 4-benzyloxythieno[2,3-c]pyridine-2-carboxylate

To an ice cold solution of Example 236B (4.2 g, 17 mmol) in anhydrous tetrahydrofuran (42 mL) under nitrogen atmosphere was added methyl thioglycolate (1.83 mL, 20.4 mmol) followed by powdered cesium carbonate (6.65 g, 20.4 mmol). Then the reaction mixture was allowed to warm to room temperature with stirring under nitrogen. After 30 minutes the reaction was refluxed for 15 minutes and cooled to room temperature. The reaction mixture was quenched with ice (50 mL) and partitioned with ethyl acetate (250 mL). The organic layer separated was washed with an ice cold solution of saturated NaCl (3×60 mL), dried (Na$_2$SO$_4$), and concentrated under reduced pressure to obtain the crude product which was recrystallized from methanol. The mother liquor was purified by flash chromatography on silica gel eluting with 7% acetone-hexane. The combined fractions gave the title compound in 55% yield (3.07 g). MS (APCI) m/e: 300 (M+H)+; $^1$H NMR (300 MHz, DMSO-d$_6$) d: 3.92 (s, 3H), 5.42 (s, 2H), 7.35–7.47 (m, 3H), 7.52–7.57 (m, 2H, Ar—CH), 8.12 (s, 1H,), 8.36 (s, 1H), 8.98 (s, 1H).

EXAMPLE 236D

Methyl 4-hydroxythieno[2,3-c]pyridine-2-carboxylate

To a suspension of 10 wt % Pd on activated carbon (38 mg, 10% w/w) in absolute ethanol (3 mL) was added a cold solution of Example 236C (380 mg, 1.3 mmol) in ethanol (82 mL) under nitrogen atmosphere. Then the reaction mixture was degassed and stirred at room temperature under hydrogen atmosphere. After one over night reaction mixture was treated with additional 10 wt % Pd on activated carbon (190 mg, 50% w/w) and stirred under hydrogen atmosphere. Additional catalyst (100 mg, 26% w/w) was added to the reaction mixture after 48 hours. The reaction mixture was stirred under hydrogen atmosphere for further 24 hours and filtered through Celite®. The filtrate was evaporated to dryness under reduced pressure to obtain the crude product (320 mg). The title compound Example 236E was obtained in 75% yield (200 mg) by flash chromatography on silica gel eluting with 5% acetone-hexane followed by 40% acetone-hexane.

MS (APCI) m/e: 210 (M+H)$^+$, 208 (M−H)$^-$, 244 (M+Cl)$^-$; $^1$H NMR (300 MHz, DMSO-d$_6$) δ 3.93 (s, 3H), 8.08 (s, 1H), 8.21 (s, 1H), 8.81 (s, 1H), 10.66–10.90 (br.s, 1H).

EXAMPLE 236E

4-Benzyloxythieno[2,3-c]pyridine-2-carboxamide

The title compound (50 mg, 67%) was prepared as described in Example 44 using Example 236C (75 mg, 0.25 mmol).

MS (APCI) m/e: 285 (M+H)$^+$, 319 (M+Cl)$^-$; $^1$H NMR (400 MHz, DMSO-d$_6$) δ 5.43 (s, 2H), 7.49–7.50 (m, 3H), 7.58–7.63 (m, 2H), 7.79 (br s, 1H), 8.30 (s, 1H), 8.36 (s, 1H,), 8.48 (br s, 1H), 8.93 (s, 1H); $^{13}$C NMR (100 MHz, DMSO-d$_6$) d: 70.13 (CH$_2$), 120.56 (CH), 126.21 (CH), 127.5 (CH), 128.14 (CH), 128.51 (CH), 135.30 (C), 136.35 (C), 137.48 (C), 137.86 (CH), 144.75 (C), 149.82 (C), 162.61 (C).

EXAMPLE 237

4-(4-Chlorobenzoyl)-N-methylthieno[2,3-c]pyridine-2-carboxamide

EXAMPLE 237A

Methyl 4-chlorothieno[2,3-c]pyridine-2-carboxylate

Example 17A (15.00 g, 85.22 mmol) was dissolved in THF (80 mL) and cesium carbonate (27.77 g, 85.22 mmol) added. Methyl thioglycolate (7.62 mL, 85.22) diluted in THF (20 mL) was added dropwise over a period of 20 minutes. The reaction was stirred for 1.5 hours then heated to 40° C. for 1 hour. The reaction mixture was poured into 850 mL of stirring water. After 10 minutes, the precipitate was collected by filtration and washed twice with water. The product was dried in a desiccator to yield the title compound as a solid (15.2 g, 78%).

MS (DCI/NH$_3$) m/e: 228 (M+H)$^+$; $^1$H NMR (300 MHz, DMSO-d$_6$) δ 3.96 (s, 3H), 8.15 (s, 1H), 8.65 (s, 1H), 9.38 (s, 1H).

EXAMPLE 237B

4-Chlorothieno[2,3-c]pyridine-2-carboxylic acid

Example 237A (15.17 g, 66.63 mmol) was suspended in a solution of 1:4 MeOH/water (500 mL) and LiOH hydrate (4.34 g, 103.50 mmol) was added. The reaction was stirred 1.5 hours then concentrated (100 mL). The aqueous phase was washed with Et$_2$O and then acidified to pH 5 with 1 N HCl (aq). The precipitate was isolated by filtration, washed once with water, then twice with acetonitrile. The product was dried in a desiccator to yield 4-chlorothieno[2,3-c] pyridine-2-carboxylic acid as a solid (12.10 g, 85%).

MS (DCI/NH$_3$) m/e: 214 (M+H)$^+$; $^1$H NMR (300 MHz, DMSO-d$_6$) δ 8.05 (s, 1H), 8.62 (s, 1H), 9.34 (s, 1H).

EXAMPLE 237C

Dimethylethyl 4-chlorothieno[2,3-c]pyridine-2-carboxylate

To a suspension of Example 237B (12.07 g, 56.50 mmol) in THF (200 mL) at 0° C., was added tert-butyl 2,2,2-trichloroacetamidate (25.00 g, 114.41 mmol) followed by dropwise addition of boron trifluoride-diethyl etherate (2.14 mL, 16.95 mmol). The reaction was allowed to warm to room temperature and stirred 18 hours. Additional tert-butyl 2,2,2-trichloroacetamidate (12.50 g, 57.21 mmol) was added and the reaction was stirred 3 hours. The stirred reaction was treated with NaHCO$_3$ (14 g) and then diluted with water (300 mL). The reaction was partitioned between water (300 mL) and 50% EtOAc/Et$_2$O. Organic layer was washed with sat. NaHCO$_3$, washed with brine, partially dried (Na$_2$SO$_4$), filtered, and concentrated. The residue was purified by flash chromatography on silica gel neutralized with Et$_3$N using EtOAc/hexane as eluent. The title compound was isolated as a solid (10.04 g, 66%).

MS (DCI/NH$_3$) m/e: 270 (M+H)$^+$; $^1$H NMR (300 MHz, DMSO-d$_6$) δ 1.59 (s, 9H), 8.04 (s, 1H), 8.64 (s, 1H), 9.35 (s, 1H).

EXAMPLE 237D

Dimethylethyl 4-(ethoxycarbonyl)thieno[2,3-c] pyridine-2-carboxylate

To a solution of Example 237C (1.00 g, 3.71 mmol), 1,3-bis(diphenylphosphino)propane (0.46 g, 1.11 mmol), triethylamine (1.55 mL, 11.13 mmol), in 2:3 EtOH/DMF (25 mL), was added palladium(II) acetate (0.25 g, 1.11 mmol). The reaction was aspirated with a stream of CO(g) for 15 minutes. A balloon of CO(g) was applied and reaction heated to 105° C. for 16 hours then cooled to room temperature. The reaction was poured into water (400 mL). The aqueous was diluted with brine (25 mL) and sat. NaHCO$_3$ (25 mL), then extracted with EtOAc (4×50 mL). The organic extracts were combined, washed with 20% sat.NaHCO$_3$ (2×200 mL), brine (2×100 mL), partially dried (Na$_2$SO$_4$), filtered, and concentrated. The residue was purified by flash chromatography on silica gel using EtOAc/hexane as eluent to provide the title compound as a solid (0.60 g, 53%), MS (APCI) m/e: 308 (M+H)$^+$; $^1$H NMR (300 MHz, CD$_2$Cl$_2$) δ 1.44 (t, J=7.1 Hz, 3H), 1.59 (s, 9H), 4.44 (q, J=7.1 Hz, 2H), 8.65 (s, 1H), 9.12 (s, 1H), 9.25 (s, 1H).

EXAMPLE 237E

Dimethylethyl 4-formylthieno[2,3-c]pyridine-2-carboxylate

To a stirred solution of NaBH$_4$ (0.18 g, 4.89 mmol) in anhydrous 50% MeOH/THF at 0° C. was added powdered CaCl$_2$ (0.54 g, 4.89 mmol). The suspension was stirred 20 minutes and a solution of Example 237D (0.50 g, 1.63 mmol) in anhydrous 50% MeOH/THF was slowly added over a period of 10 minutes. The reaction stirred 1 hour at 0° C. followed by 16 hours at room temperature. Reaction was quenched into a slurry of dilute AcOH (aq)/ice. After all gas evolution ceased with occasional stirring, aqueous was made basic with sat. NaHCO$_3$. Aqueous was extracted with dichloromethane (3×40 mL) and extracts combined. The organic phase was dried (Na$_2$SO$_4$), filtered, and concentrated. The residue was purified by flash chromatography on silica gel using EtOAc/hexane as eluent to provide dimethylethyl 4-(hydroxymethyl)-thieno[2,3-c]pyridine-2-carboxylate compound as a solid (0.14 g, 32%).

MS (APCI) m/e: 266 (M+H)$^+$; $^1$H NMR (300 MHz, CD$_2$Cl$_2$) δ 1.54 (s, 9H), 4.94 (s, 2H), 8.08 (s, 1H), 8.40 (s, 1H), 9.02 (s, 1H).

To a stirred solution of oxalyl chloride (0.10 mL, 1.17 mmol) in anhydrous dichloromethane (10 mL) at −78° C. was added DMSO (0.19 mL, 2.65 mmol). After 20 minutes, a solution of dimethylethyl 4-(hydroxymethyl)thieno[2,3-c]pyridine-2-carboxylate (0.28 g, 1.06 mmol) in anhydrous dichloromethane (4 mL) was added dropwise. The reaction was stirred 1 hours at −78° C. then treated with triethylamine (0.74 mL, 5.30 mmol). After 5 minutes, reaction was allowed to warm to room temperature over 30 minutes. The reaction was quenched with water (5 mL) and partitioned between dichoromethane (50 mL) and 50% sat. aq NaHCO$_3$ (50 mL). The organic phase was washed with 50% sat. aq NaHCO$_3$ (1×50 mL), dried (Na$_2$SO$_4$), filtered, and concentrated and dried in a desiccator to yield the title as a solid (0.25 g, 90%).

MS (APCI) m/e: 264 (M+H)$^+$; $^1$H NMR (300 MHz, CD$_2$Cl$_2$) δ 1.59 (s, 9H), 8.74 (s, 1H), 8.91 (s, 1H), 9.31 (s, 1H), 10.24 s, 1H).

EXAMPLE 237F

Dimethylethyl 4-[(4-chlorophenyl)(hydroxy)methyl]thieno[2,3-c]pyridine-2-carboxylate To a solution of Example 237E (0.25 g, 0.95 mmol) in anhydrous THF (5 mL) at −5° C. was slowly a dded a 1 M solution of p-chlorophenylmagnesium bromide in diethyl ether (2.85 mL, 2.85 mmol). The reaction was quench after 10 minutes with dropwise addition of water (1 mL) and partitioned between dichloromethane (25 mL) and 50% sat. aq NaHCO$_3$ (50 mL). The aqueous phase was extracted with dichloromethane (25 mL) and the organic extracts combined, dried (Na$_2$SO$_4$), filtered, and concentrated. The residue was purified by flash chromatography on silica gel using EtOAc/hexane as eluent to provide the title compound as a foam, which was crushed and dried in a desiccator to yield a powder (0.36 g, 100%).

MS (APCI) m/e: 376 (M+H)$^+$; $^1$H NMR (300 MHz, CD$_2$Cl$_2$) δ 1.52 (s, 9H), 6.18 (d, 1H), 7.25–7.34 (series of m, 4H), 7.96 (s, 1H), 8.47 (s, 1H), 9.03 (s, 1H).

EXAMPLE 237G

Methyl 4-[(4-chlorophenyl)(hydroxy)methyl]thieno[2,3-c]pyridine-2-carboxylate

Example 237F (0.1 2 g, 0.32 mmol) was dissolved in a solution of 10% H$_2$SO$_4$/MeOH (10 mL) and heated to 50° C. for 18 hours. The reaction was quenched into sat. NaHCO$_3$ (100 mL). The aqueous phase was extracted with dichloromethane (2×50 mL) and the organic extracts combined. The organic layer was washed with sat. NaHCO$_3$ (1×100 mL), brine (1×100 mL), partially dried (Na$_2$SO$_4$), filtered, and concentrated. The product was dried in a desiccator to yield the title compound as a solid (0.10 g, 94%).

MS (APCI) m/e: 334 (M+H)$^+$; $^1$H NMR (300 MHz, CD$_2$Cl$_2$) δ 3.85 (s, 3H), 6.17 (d, 1H), 7.23–7.33 (series of m, 4H), 8.05 (s, 1H), 8.48 (s, 1H), 9.05 (s, 1H).

EXAMPLE 237H

Methyl 4-(4-chlorobenzoyl)-N-methylthieno[2,3-c]pyridine-2-carboxylate

To a stirred solution of oxalyl chloride (0.023 mL, 0.26 mmol) in anhydrous dichloromethane (1 mL) at −78° C. was added DMSO (0.045'mL, 0.63 mmol). After 15 minutes, a solution of Example 237G (0.07 g, 0.21 mmol) in anhydrous 1:4 DMSO/dichloromethane (5 mL) was added dropwise. The reaction was stirred 1 hour at 78° C. then treated with triethylamine (0.15 mL, 1.05 mmol). After 5 minutes, reaction was allowed to warm to room temperature over 1 hour. The reaction was quenched with water (2 mL) and partitioned between EtOAc (50 mL) and sat. aq. NaHCO$_3$ (50 mL). The organic layer was washed with 50% sat. aq. NaHCO$_3$ (2×50 mL), brine (1×50 mL), dried (Na$_2$SO$_4$), filtered, and concentrated. The product was dried in a desiccator to yield the title compound as a white solid (0.07 g, 100%).

MS (APCI) m/e: 332 (M+H)$^+$; $^1$H NMR (300 MHz, DMSO-d$_6$) δ 3.95 (s, 3H), 7.68 (m, 2H), 7.87 (m, 2H), 8.31 (s, 1H), 8.74 (s, 1H), 9.66 (s, 1H);)$^+$; IR (KBr) 3208, 2959, 1719, 1657, 1585, 1567, 1434, 1308, 1268 cm$^{-1}$.

EXAMPLE 237I 4-(4-Chlorobenzoyl)-N-methylthieno[2,3-c]pyridine-2-carboxamide Example 237H (70 mg, 0.21 mmol) was suspended in MeOH (5 mL) and chloroform was added until the solid dissolved. A balloon of ammonia was applied andreaction heated to 50° C. for 20 hours. The reaction was concentrated and the residue was purified by flash chromatography on silica gel using EtOAc/hexane as eluent. The obtained title compound was dried in a desiccator to yield a white solid (35 mg, 53%).

mp 216–218° C.; MS (APCI) m/e: 317 (M+H)$^+$; $^1$H NMR (DMSO-d$_6$) δ 7.68 (m, 2H), 7.86 (br s, 1H), 7.88 (m, 2H), 8.38 (s, 1H), 8.53 s, 1H), 8.67 (s, 1H), 9.55 (s, 1H); $^{13}$C NMR (DMSO-d$_6$) δ 123.4, 128.0, 129.3, 132.0, 135.9, 137.9, 138.9, 143.2, 145.1, 148.8, 148.9, 162.7, 193.6; IR (KBr) 3289, 3145, 1681, 1655, 1399, 1270 cm$^{-1}$; Anal calcd for C$_{15}$H$_9$ClN$_2$O$_2$S.0.1 C$_6$H$_{14}$: C, 57.59; H, 3.22; N, 8.61. Found: C, 57.58; H, 3.22; N, 8.41.

EXAMPLE 238

N-4-(4-Chlorophenyl)thieno[2,3-c]pyridine-2,4-dicarboxamide

EXAMPLE 238A 4-(Ethoxycarbonyl)thieno[2,3-c]pyridine-2-carboxamide

Example 94 was treated according to the procedure of Example 237D to provide the title compound.

EXAMPLE 238B 4-(Carboxy)thieno[2,3-c]pyridine-2-carboxamide

Example 238A was treated according to the procedure of Example 159A to provide the title compound.

EXAMPLE 238C

N-4-(4-Chlorophenyl)thieno[2,3-c]pyridine-2,4-dicarboxamide

Example 238B was treated according to the procedure of Example 24 to provide the title compound.

mp>270° C.; MS (ESI) m/e: 332 (M+H)$^+$; $^1$H NMR (300 MHz, DMSO-d$_6$) δ 7.46 (m, 2H), 7.84 (br s, 1H), 7.85 (m,

2H), 8.52 (m, 1H), 8.56 (br s, 1H), 8.90 (m, 1H), 9.47 (m, 1H), 10.79 (br s, 1H).

EXAMPLE 239

[4-(4-Bromophenoxy)thieno[2,3-c]pyridin-2-yl] methanol

Example 239 (900 mg, 97%) was prepared as described in Example 90 except substituting Example 73 (1 g, 2.74 mmol) for Example 61A. MS (APCI) m/e: 336; 338 (M+H)$^+$, 370; 372 (M+Cl)$^-$; $^1$H NMR (300 MHz, DMSO-d$_6$) δ 4.78 (d, J=6 Hz, 2H), 5.88 (t, J=6 Hz, 1H), 6.98 (d, J=9 Hz, 2H), 7.14 (s, 1H), 7.55 (d, J=9 Hz, 2H), 8.19 (s, 1H), 9.06 (s, 1H).

EXAMPLE 240

4-(4-Bromophenoxy)thieno[2,3-c]pyridine-2-carbaldehyde

Example 240 (400 mg, 80%) was prepared as described in Example 91A except substituting Example 239 (500 mg, 1.49 mmol) for Example 90.

MS (APCI) m/e: 334; 336 (M+H)$^+$, 333; 335 (M−H)$^-$; $^1$H NMR (300 MHz, DMSO-d$_6$) δ 7.62 (d, J=9 Hz, 2H), 7.62 (d, J=9 Hz, 2H), 8.26 (s, 1H), 8.40 (s, 1H), 9.27 (s, 1H), 10.21 (s, 1H).

EXAMPLE 241

4-(4-Chlorophenoxy)thieno[2,3-c]pyridine-2-carbaldehyde oxime

The title compound was prepared from Example 91A in a manner similar to Example 30.

HPLC: Supelco C-18 column, water:acetonitrile 0:90–90:0, 30 minute elution, flow rate 0.8 mL/min, rt 19.61 min. and 20.28 min; MS (DCI/NH$_3$) m/e: 305 (M+H)$^+$; $^1$H NMR (300 MHz, DMSO-d$_6$) δ 2.40 (s, 3H, toluene), 7.15 (m, 4H), 7.25 (m, 5H, toluene), 7.48 (m, 4H), 7.58 (s, 1H), 7.75 (s, 1H), 8.16 (m, 3H), 8.51 (s, 1H), 9.05 (s, 1H), 9.14 (s, 1H), 11.91 (s, 1H), 12.66 (s, 1H); $^{13}$C NMR (100 MHz, DMSO-d$_6$) δ 119.28, 119.33, 120.58, 122.21, 125.25, 127.51, 128.13, 128.82, 129.99, 133.03, 133.84, 135.37, 136.10, 136.60, 137.11, 139.40, 139.95, 140.83, 141.28, 143.24, 143.66, 146.31, 146.58, 155.69; Anal. calcd for C$_{14}$H$_9$ClN$_2$O$_2$S.0.4 toluene: C, 59.07; H, 3.60; N, 8.20. Found: C, 59.15; H, 3.65; N, 8.25.

EXAMPLE 242

4-(4-Chlorophenoxy)thieno[2,3-c]pyridine-2-carbaldehyde O-methyloxime

Example 242 was prepared from Example 91A similarly to Example 26. Spectral data for E isomer:

HPLC: Supelco C-18 column, water:acetonitrile 0:90–90:0, 30 minute elution, flow rate 0.8 mL/min, rt 22.72 min. and 23.60 min.; MS (ESI) m/e 319 (M+H)$^+$; $^1$H NMR (300 MHz, DMSO-d$_6$) δ 3.94 (s, 3H), 7.12 (m, 2H), 7.47 (m, 2H), 7.65 (s, 1H), 8.18 (s, 1H), 8.61 (s, 1H), 9.08 (s, 1H); $^{13}$C NMR (100 MHz, DMSO-d$_6$) δ 62.29, 119.35, 122.26, 124.01, 127.60, 130.01, 133.77, 136.85, 140.91, 141.38, 144.34, 146.46, 155.58.

EXAMPLE 243A

Mike Staeger

1-[4-(4-Chlorophenoxy)thieno[2,3-c]pyridin-2-yl]-1-ethanone O-methyloxime

Example 159A was treated similarly to the Example 22 procedure. The derived amide was treated according to Example 33 procedure, to produce the corresponding methyl ketone. This ketone was treated according to the procedure of Example 26 to provide the title compound as a mixture of E- and Z-isomers. The isomers were separated by column chromatography using type H (Sigma) silica gel and eluting with 25% EtOAc:hexanes.

Spectral data for Z-isomer: mp 126–128° C.; MS (APCI) m/e: 333 (M+H)$^+$; $^1$H NMR (300 MHz, DMSO-d$_6$) δ 2.29 (s, 3H), 3.97 (s, 3H), 7.15 (m, 2H), 7.48 (m, 2H), 7.72 (s, 1H), 8.09 (s, 1H), 9.01 (s, 1H); $^{13}$C NMR (100 MHz, DMSO-d$_6$) δ 12.18, 62.32, 118.85, 119.88, 127.77, 130.01, 132.98, 136.94, 136.98, 140.32, 145.60, 146.94, 150.84, 155.40; Anal. calcd for C$_{16}$H$_{13}$ClN$_2$O$_2$S: C, 57.74; H, 3.94; N, 8.42. Found: C, 58.03; H, 3.92; N, 8.14.

EXAMPLE 243B

1-[4-(4-Chlorophenoxy)thieno[2,3-c]pyridin-2-yl]-1-ethanone O-methyloxime

E-isomer isolated from Example 243A preparation: MS (APCI) m/e: 333 (M+H)$^+$; $^1$H NMR (300 MHz, DMSO-d$_6$) δ 2.38 (s, 3H), 4.04 (s, 3H), 7.18 (m, 2H), 7.48 (m, 2H), 7.82 (s, 1H), 8.11 (s, 1H), 9.12 (s, 1H); $^{13}$C NMR (100 MHz, DMSO-d$_6$) δ 19.25, 62.16, 119.88, 120.17, 121.60, 127;95, 130.04, 131.98, 134.49, 136.52, 138.85, 140.68, 146.21, 147.39, 155.22;

EXAMPLE 244A

1-[4-(4-Chlorophenoxy)thieno[2,3-c]pyridin-2-yl]-1-ethanone oxime

Example 244A was prepared similarly to Example 243A, with the substitution of hydroxylamine hydrochloride for methoxylamine hydrochloride.

MS (APCI) m/e: 319 (M+H)$^+$; $^1$H NMR (300 MHz, DMSO-d$_6$) δ 2.23 (s, 3H), 7.15 (m, 2H), 7.48 (m, 2H), 7.62 (s, 1H), 8.10 (s, 1H), 9.02 (s, 1H), 11.89 (s, 1H); $^{13}$C NMR (100 MHz, DMSO-d$_6$) δ 11.41, 117.45, 119.73, 124.45, 127.65, 129.97, 133.14, 136.78, 137.17, 140.28, 146.72, 147.39, 149.85, 155.51; Anal. calcd for C$_{15}$H$_{11}$ClNO$_2$S: C, 54.96; H, 3.69; N, 8.55. Found: C, 55.37; H, 3.47; N, 8.37.

EXAMPLE 244B

1-[4-(4-Chlorophenoxy)thieno[2,3-c]pyridin-2-yl]-1-ethanone oxime

Z-isomer isolated from Example 244A.

MS (APCI) m/e: 319 (M+H)$^+$; $^1$H NMR (300 MHz, DMSO-d$_6$) δ 2.38 (s, 3H), 7.15 (d, J=9 Hz, 2H), 7.48 (d, J=9 Hz, 2H), 7.73 (s, 1H), 8.10 (s, 1H), 9.12 (s, 1H), 12.35 (s, 1H); $^{13}$C NMR (100 MHz, DMSO-d$_6$) δ 19.32, 118.36, 119.96, 120.01, 127.81, 130.02, 132.08, 134.60, 136.99, 138.95, 140.73, 145.08, 147.18, 155.40.

EXAMPLE 245

1-[4-(4-Chlorophenoxy)thieno[2,3-c]pyridin-2-yl]-1-propanone

Title compound was prepared in analogy to Example 33, substituting ethylmagnesium bromide for methylmagnesium bromide.

mp 101–102° C.; MS (APCI) m/e: 318 (M+H)$^+$; $^1$H NMR (300 MHz, DMSO-d$_6$) δ 1.11 (t, J=8 Hz, 3H), 3.18 (d, J=8 Hz, 2H); 7.21 (m, 2H), 7.51 (m, 2H), 8.13 (s, 1H), 8.32 (s, 1H), 9.19 (s, 1H).

EXAMPLE 246

1-[4-(4-Chlorophenoxy)thieno[2,3-c]pyridin-2-yl]-1-propanone oxime

The title compound was prepared from Example 245 in analogy to Example 26, substituting hydroxylamine hydrochloride to provide a mixture of E- and Z-oxime isomers.

mp 195–198° C. (dec); MS (APCI) m/e: 333 (M+H)$^+$; $^1$H NMR (300 MHz, DMSO-d$_6$) δ 1.10 (m, 6H), 2.77 (m, 4H), 7.17 (m, 4H), 7.48 (m, 4H), 7.61 (s, 1H), 7.71 (s, 1H), 8.09 (s, 1H), 8.11 (s, 1H), 9.00 (s, 1H), 9.12 (s, 1H), 11.88 (s, 1H), 12.42 (s, 1H); HPLC Supelco C-18 column, water:acetonitrile 0:90–90:0 in 30 minutes, detection at 254 nm, flow rate of 0.8 mL/min, RT=20.20 min and 21.10 min (E- and Z-isomers); Anal. calcd for C$_{16}$H$_{13}$ClN$_2$O$_2$S: C, 57.74; H, 3.94; N, 8.42. Found: C, 57.51; H, 4.12; N, 8.22.

EXAMPLE 247

2-[4-(4-Chlorophenoxy)thieno[2,3-c]pyridin-2-yl]-N-methoxy-N-methyl-2-oxoacetamide Example 88 (0.38 mmol) was prepared as reported in Example 42 and then combined with THF (1.0 mL) and LDA (0.92 mL of a freshly prepared 0.5 M solution in THF, 0.46 mmol) at −78° C. The clear, pale yellow solution was stirred at −78° C. for 1.25 hours before the solution was transferred by canula to a solution of bis(N,O-dimethylhydroxyl)oxamide (88 mg, 0.50 mmol) in THF (1.0 mL) at −78° C. The solution was slowly warmed to room temperature, diluted with 2N aqueous HCl (20 mL), and extracted with CH$_2$Cl$_2$ (3×20 mL). The organic extracts were combined, washed with brine (1×$_1$0 mL), dried (MgSO$_4$), and concentrated to a yellow solid. Flash silica gel column chromatography (15% acetone in hexane) gave the title compound (25 mg, 17% yield) as a yellow solid.

mp 135.0–137.8° C.; MS (DCI/NH$_3$) m/e: 377 ($^{35}$Cl)/379 ($^{37}$Cl); $^1$H NMR (300 MHz, DMSO-d$_6$) δ 3.31 (s, 3H), 3.64 (s, 3H), 7.27 (d, J=8.8 Hz, 2H), 7.52 (d, J=8.8 Hz, 2H), 8.15 (s, 1H), 8.22 (s, 1H), 9.26 (s, 1H).

EXAMPLE 248

4-(4-Chlorophenoxy)thieno[2,3-c]pyridine-2-carbonitrile

A solution of the resultant compound from Example 61B (500 mg, 1.64 mmol) in pyridine (7 mL) under nitrogen at −78° C. was treated with trifluoroacetic anhydride (1 mL, 6.6 mmol), stirred at −78° C. for 40 minutes, allowed to slowly warm to room temperature, and stirred an additional two hours. This mixture was diluted with ethyl acetate, washed with saturated NaHCO$_3$, brine, dried (MgSO$_4$) and concentrated. The resultant light purple solid was dissolved in a minimal amount of ethyl acetate, filtered through a plug of silica, washed through with 50/50 hexane/ethyl acetate and concentrated to give 395 mg of the title compound as a white solid (84%).

mp 140–142° C.; MS (APCI-NH$_3$) m/e: 287 (M+H)$^+$; $^1$H NMR (300 MHz, CDCl$_3$) δ 7.04 (d, 2H), 7.40 (d, 2H), 8.00 (s, 1H), 8.14 (s, 1H), 8.96 (s, 1H); Anal. calcd for C$_{14}$H$_7$ClN$_2$OS: C, 58.64; H, 2.46; N, 9.77. Found: C, 58.45; H, 2.62; N, 9.52.

EXAMPLE 249

4-(4-Chlorophenoxy)-N'-hydroxythieno[2,3-c]pyridine-2-carboximidamide

A solution of the resultant compound from Example 248 (100 mg, 0.35 mmol) in ethanol (2 mL) under nitrogen at room temperature was treated with triethylamine (90 mL, 0.6 mmol), hydroxylamine hydrochloride (40 mg, 0.53 mmol) and stirred for 18 hours. The resultant white, heterogeneous mixture was diluted with ethyl acetate, washed with saturated NaHCO$_3$, brine, dried (MgSO$_4$), and concentrated to give 120 mg of an off-white foam. This foam was dissolved in ethyl acetate, filtered through a plug of silica and concentrated to give the title compound as a white solid (110 mg, 98%).

mp 194–196° C.; MS (APCI-NH$_3$) m/e: 320 (M+H)$^+$; $^1$H NMR (300 MHz, DMSO-d$_6$) δ 10.23 (s, 1H), 9.02 (s, 1H), 8.13 (s, 1H), 7.87 (s, 1H), 7.46 (d, 2H), 7.11 (d, 2H), 6.26 (br s, 2H); Anal. calcd for C$_{14}$H$_{10}$ClN$_3$O$_2$S: C, 52.59; H, 3.15; N, 13.14. Found: C, 52.72; H, 3.05; N, 12.82.

EXAMPLE 250

4-(4-Chlorophenoxy)-N'-cyanothieno[2,3-c]pyridine-2-carboximidamide

A solution of the resultant compound from Example 248 (100 mg, 0.35 mmol) in THF (2 mL) under nitrogen at ambient temperature was treated with cyanamide (74 mg, 1.75 mmol), 1,8-diazabicylco[5.4.0]undec-7-ene (52 mL, 0.35 mmol) and stirred for 24 hours. The resultant yellow, homogeneous solution was diluted with ethyl acetate, washed with saturated NaHCO$_3$, brine, dried (MgSO$_4$), concentrated to give a light yellow solid, triturated with CH$_2$Cl$_2$ to give 123 mg of a white powder, dissolved in ethyl acetate and THF, washed with distilled water, brine, dried (MgSO$_4$), concentrated to give 99 mg of a white powder (MgSO$_4$) which was triturated with CH$_2$Cl$_2$ and then placed in a vacuum oven overnight at 60° C. to give the title compound as a white powder (78 mg, 69%).

mp 265–268° C.; MS (APCI-NH$_3$) m/e: 329 (M+H)$^+$; $^1$H NMR (300 MHz, DMSO-d$_6$) δ 9.58 (br s, 1H), 9.17 (s, 1H), 9.05 (br s, 1H), 8.41 (s, 1H), 8.19 (s, 1H), 7.48 (d, 2H), 7.15 (d, 2H); Anal. calcd for C$_{15}$H$_9$ClN$_4$OS: C, 54.80; H, 2.76; N, 17.04. Found: C, 54.50; H, 3.01; N, 17.16.

EXAMPLE 251

(2-Aminophenyl)[4-(4-chlorophenoxy)thieno[2,3-c]pyridin-2-yl]methanone

EXAMPLE 251A

[4-(4-Chlorophenoxy)thieno[2,3-c]pyridin-2-yl](2-nitrophenyl)methanol

To a stirred solution of Example 124A (1.00 g, 3.82 mmol) in THF (40 mL) at −78° C., a 1.3 M suspension of sec-butyllithium in cyclohexane (3.52 mL, 4.58 mmol) was added dropwise over a 10-minute period. After 40 minutes, the reaction was transferred via cannula into a stirred solution of 2-nitrobenzaldehyde (1.43 g, 9.55 mmol) in THF (10 mL) at −48° C. After 20 minutes, the reaction was quenched by slow addition of MeOH (6 mL). The reaction was diluted with EtOAc (125 mL) and the organic washed with 1:1 sat. NaHCO$_3$/water (1×75 mL), brine (1×75 mL), partially dried (Na$_2$SO$_4$), and concentrated. The residue was purified by flash chromatography on silica gel using EtOAc/hexane as eluant to yield the title compound as a solid (1.49 g, 95%).

mp 85–90° C.; MS (APCI) m/e: 413 (M+H)$^+$; $^1$H NMR (300 MHz, DMSO-d$_6$) δ 6.54 (s, 1H), 6.95 (s, 1H), 7.03 (m, 1H), 7.06 (m, 2H), 7.42 (m, 2H), 7.60 (m, 1H), 7.78 (m, 1H), 7.85 (m, 1H), 7.98 (m, 1H), 8.12 (s, 1H), 9.02 (s, 1H); Anal. calcd for C$_{20}$H$_{13}$ClN$_2$O$_4$S.0.3 H$_2$O: C, 57.43; H, 3.28; N, 6.70. Found: C, 57.42; H, 3.45; N, 6.42.

EXAMPLE 251B (2-Aminophenyl)[4-(4-chlorophenoxy)thieno[2,3-c]pyridin-2-yl]methanol Example 251A (0.10 g, 0.24 mmol) was dissolved in EtOH (1.7 mL) and a solution of tin(II) chloride dihydrate (0.43 g, 1.92 mmol) in concentrated HCl (0.70 mL) was slowly added. The reaction was stirred 18 hours, then partitioned between CHCl$_3$ (50 mL) and sat. NaHCO$_3$ (75 mL). The aqueous layer was extracted with EtOAc (1×50 mL) and all organic extracts combined, partially dried (Na$_2$SO$_4$), and concentrated. The residue was purified by flash chromatography on silica gel using EtOAc/hexane as eluent to yield the title compound as a lightly colored solid (0.08 g, 87%).

mp 92–96° C.; MS (APCI) m/e: 383 (M+H)$^+$; $^1$H NMR (300 MHz, DMSO-d$_6$) δ 5.08 (br s, 2H), 6.10 (d, J=4.3 Hz, 1H), 6.54 (d, J=4.3 Hz, 1H), 6.55 (m, 1H), 6.61 (m, 1H), 6.98 (m, 1H), 7.05 (m, 2H), 7.13 (m, 1H), 7.19 (m, 1H), 7.42 (m, 2H), 8.09 (s, 1H), 8.98 (s, 1H);

Anal. calcd for C$_{20}$H$_{15}$ClN$_2$O$_2$S: C, 62.74; H, 3.95; N, 7.32. Found: C, 63.09; H, 4.05; N, 7.06.

EXAMPLE 251C (2-Aminophenyl)[4-(4-chlorophenoxy)thieno[2,3-c]pyridin-2-yl]methanone To an anhydrous stirred suspension of silica gel (0.13 g) and celite (0.13 g) in dichloromethane (6 mL) was added pyridinium chlorochromate (0.13 g, 0.59 mmol). A solution of Example 251B (0.15 g, 0.39 mmol) in anhydrous dichloromethane (9 mL) was slowly added dropwise. After 1 hour, sat. NaHCO$_3$ (5 mL) was added, and the reaction stirred for 1 hour. The reaction was filtered and the black solid was crushed and washed with 5% MeOH/dichloromethane (3×20 mL). The organic filtrate and washes were combined and washed with sat. NaHCO$_3$ (2×100 mL), brine (1×75 mL), partially dried (Na$_2$SO$_4$), and concentrated. The residue was purified by flash chromatography on silica gel using EtOAc/hexane as eluent to yield the title compound as a brightly colored solid (45 mg, 39%).

mp 152–154° C.;

MS (APCI) m/e: 381 (M+H)$^+$;

$^1$H NMR (300 MHz, DMSO-d$_6$) δ 6.54 (m, 1H), 6.87 (m, 1H), 7.05 (broad s, 2H), 7.18 (m, 2H), 7.33 (m, 1H), 7.47 (m, 2H), 7.57 (s, 1H), 7.58 (m, 1H), 8.24 (s, 1H), 9.21 (s, 1H); $^{13}$C NMR (300 MHz, DMSO-d$_6$) δ 114.5, 115.9, 117.1, 120.1, 123.8, 128.0, 130.0, 132.5, 133.0, 134.9, 136.0, 138.2, 141.2, 147.8, 148.5, 151.8, 155.3, 188.5; IR (KBr) 3440, 3411, 3293, 3190, 1616, 1587, 1552, 1483, 1409, 1267, 1245, 1219, 1155 cm$^{-1}$; Anal. calcd for C$_{20}$H$_{13}$ClN$_2$O$_2$S: C, 63.08; H, 3.44; N, 7.36. Found: C, 62.94; H, 3.51; N, 7.25.

EXAMPLE 252

(3-Aminophenyl)[4-(4-chlorophenoxy)thieno[2,3-c]pyridin-2-yl]methanone

EXAMPLE 252A

[4-(4-Chlorophenoxy)thieno[2,3-c]pyridin-2-yl](3-nitrophenyl)methanol

The procedure of Example 251A was used, substituting 3-nitrobenzaldehyde for 2-nitrobenzaldehyde.

mp 79–83° C.; MS (APCI) m/e: 413 (M+H)$^+$; $^1$H NMR (300 MHz, DMSO-d$_6$) δ 6.33 (d, J=4.4 Hz, 1H), 6.99 (d, J=4.4 Hz, 1H), 7.07 (m, 2H), 7.27 (m, 1H), 7.43 (m, 2H), 7.66 (m, 1H), 7.92 (m, 1H), 8.13 (s, 1H), 8.15 (m, 1H), 8.34 (m, 1H), 9.01 (s, 1H); Anal. calcd for C$_{20}$H$_{13}$ClN$_2$O$_4$S: C, 58.19; H, 3.17; N, 6.79. Found: C, 57.97; H, 3.23; N, 6.70.

EXAMPLE 252B (3-Aminophenyl)[4-(4-chlorophenoxy)thieno[2,3-c]pyridin-2-yl]methanol Example 252A was treated according to the procedure of Example 251B to provide the title compound.

mp 73–78° C.; MS (APCI) m/e: 383 (M+H)$^+$; $^1$H NMR (300 MHz, DMSO-d$_6$) δ 5.03 (s, 2H), 5.88 (s, 1H), 6.45 (series of m, 2H), 6.57 (m, 1H), 6.64 (m, 1H), 6.96 (m, 1H), 7.06 (m, 2H), 7.11 (m, 1H), 7.42 (m, 2H), 8.08 (s, 1H), 8.97 (s, 1H); Anal. calcd for C$_{20}$H$_{15}$ClN$_2$O$_2$S: C, 62.74; H, 3.95; N, 7.32. Found: C, 63.06; H, 4.22; N, 6.92.

EXAMPLE 252C (3-Aminophenyl)[4-(4-chlorophenoxy)thieno[2,3-c]pyridin-2-yl]methanone Example 252B was treated according to the procedure of Example 251C to provide the title compound.

mp 174–178° C.; MS (APCI) m/e: 481 (M+H)$^+$; $^1$H NMR (300 MHz, DMSO-d$_6$) δ 5.47 (br s, 2H), 6.86–6.96 (series of m, 2H), 7.06 (m, 1H), 7.16–7.23 (series of m, 3H), 7.48 (m, 2H), 7.77 (s, 1H), 8.20 (s, 1H), 9.22 (s, 1H).

EXAMPLE 253

4-(4-Bromophenoxy)-2-vinylthieno[2,3-c]pyridine

To a stirred suspension of methyl triphenylphosphonium bromide (113 mg, 0.314 mmol) in anhydrous tetrahydrofuran (2 mL) at −78° C. was added dropwise a solution of n-BuLi (2.5 M solution in hexanes, 0.125 mL, 0.314 mmol) under nitrogen atmosphere. Then the reaction mixture was stirred at 0° C. for 40 minutes and cooled down to −78° C. To this a solution of Example 240 (100 mg, 0.3 mmol) in anhydrous tetrahydrofuran (2 mL) was added while maintaining the internal temperature below −72° C. Once the addition was completed the reaction mixture was stirred at 0° C. for 15 minutes and at ambient temperature for 1 hour. Then the reaction mixture was partitioned between ethyl acetate (60 mL) and brine (20 mL). The organic layer was washed with brine (2×20 mL), dried (MgSO$_4$) and evaporated to dryness under reduced pressure to obtain the crude product (145 mg). The title compound was obtained in 26% yield (26 mg) by flash chromatography on silica gel eluting with 25% acetone-hexane.

MS (APCI) m/e: 332; 334 (M+H)$^+$; $^1$H NMR (400 MHz, DMSO-d$_6$) δ 5.53 (d, J=10 Hz, 1H), 5.86 (d, J=16 Hz, 1H), 7.02 (d, J=9 Hz, 2H), 7.06–7.14 (m, 1H), 7.37 (s, 1H), 7.57 (d, J=9 Hz, 1H), 8.17 (s, 1H), 9.04 (s, 1H).

EXAMPLE 254

1-[4-(4-Chlorophenoxy)thieno[2,3-c]pyridin-2-yl]-1,2-ethanediol

EXAMPLE 254A 4-(4-Chlorolphenoxy)-2-ethenylthieno[2,3-c]pyridine

Example 254A (70 mg, 10%) was prepared as in Example 253 except substituting Example 91A (700 mg, 2.42 mmol)

for Example 240. $^1$H NMR (300 MHz, DMSO-d$_6$) δ 5.53 (d, J=10.5 Hz, 1H), 5.86 (d, J=18 Hz, 1H), 7.04–7.14 (m, 1H), 7.10 (d, J=9 Hz, 2H), 7.38 (s, 1H), 7.45 (d, J=9 Hz, 2H), 8.16 (s, 1H), 9.04 (s, 1H).

EXAMPLE 254B

1-[4-(4-Chlorolphenoxy)thieno[2,3-c]pyridin-2-yl]-1,2-ethanediol

Example 254A (22 mg, 28%) was prepared as in Example 255 except substituting Example 254A (70 mg, 0.26 mmol) for Example 253.

MS (APCI) m/e: 322 (M+H)$^+$, 356 (M+Cl)$^-$; $^1$H NMR (400 MHz, DMSO-d$_6$) δ 3.50–3.64 (m, 2H), 4.86–4.91 (m, 1H), 5.0 (t, J=6 Hz, 1H), 6.04 (d, J=4 Hz, 1H), 7.07 (d, J=9 Hz, 2H), 7.21 (s, 1H), 7.43 (d, J=9 Hz, 2H), 8.14 (s, 1H), 9.04 (s, 1H); $^{13}$C NMR (100 MHz, DMSO-d$_6$) d: 66.52 (CH$_2$), 70.24 (CH), 114.60 (CH), 119.06 (CH), 127.22 (C), 129.91 (CH), 133.36 (CH), 137.16 (C), 137.42 (C), 140.79 (CH), 145.79 (C), 155.91 (C), 156.59 (C).

EXAMPLE 255

1-[4-(4-Bromophenoxy)thieno[2,3-c]pyridin-2-yl]-1,2-ethanediol

To a solution of Example 253 (90 mg, 0.271 mmol) in tetrahydrofuran (2 mL) was added 4-methylmorpholine N-oxide (63.5 mg, 0.542 mmol) and osmium tetroxide (14 mg, 0.054 mmol) in water (0.5 mL) at room temperature. The reaction mixture was stirred for 48 hours and solvents were removed. The residue obtained was directly purified by flash chromatography on silica gel eluting with 20% acetone-hexane to obtain the title compound (52 mg, 53%).

MS (APCI) rate: 366;368 (M+H)$^+$, 402 (M+Cl)$^-$; $^1$H NMR (400 MHz, DMSO-d$_6$) δ 3.50–3.64 (m, 2H), 4.89 (m, 1H), 5.01 (t, J=6 Hz, 1H), 6.05 (d, J=4 Hz, 1H), 7.01 (d, J=9 Hz, 2H), 7.21 (s, 1H), 7.55 (d, J=9 Hz, 2H), 8.15 (s, 1H), 9.04 (s, 1H); $^{13}$C NMR (100 MHz, DMSO-d$_6$) δ 66.52 (CH$_2$), 70.25 (CH), 114.60 (CH), 115.08 (C), 119.24 (CH), 132.84 (CH), 133.49 (CH), 137.18 (C), 137.48 (C), 140.87 (CH), 145.67 (C), 156.46 (C), 156.65 (C).

EXAMPLE 256

[4-(4-Chlorophenoxy)thieno[2,3-c]pyrdin-2-yl] methanamine

Diethyl azodicarboxylate (180 mL, 1.13 mmol) was added to Example 90 (220 mg, 0.750 mmol), THF (7.5 mL), triphenyl phosphine (297 mg, 1.13 mmol), and phthalimide (1.66 mg, 1.13 mmol). After 16 hours, the orange solution was concentrated under vacuum to an orange solid. Flash silica gel column chromatography (20% acetone in hexane) provided one compound (100% yield) as the major product, which was combined with hydrazine hydrate (230 mL, 7.50 mmol) and ethanol (75 mL) and heated at reflux. After four hours, the solution was cooled to room temperature, concentrated, diluted with 5 N HCl (30 mL), and filtered through a fritted glass funnel. The filtrate was combined with 3 N NaOH until pH>12 and extracted with EtOAc (3×30 mL). The organic extracts were combined, washed once with brine (30 mL), dried (MgSO$_4$), filtered, and concentrated under vacuum to provide the title compound (190 mg, 87% yield) as a white solid.

mp 78.6–79.8° C.; MS (DCI/NH$_3$) m/e: 321 (M+H)$^+$; $^1$H NMR (300 MHz, DMSO-d$_6$) δ 2.24 (br s, 2H), 4.02 (s, 2H), 7.03 (d, J=9.1 Hz, 2H), 7.15 (s, 1H), 7.42 (d, J=9.1 Hz, 2H), 8.14 (s, 1H), 9.01 (s, 1H); Anal. calcd for C$_{14}$H$_{11}$ClN$_2$OS.0.25 H$_2$O: C, 56.95; H, 3.93; N, 9.49. Found: C, 56.86; H, 3.81; N, 9.62.

EXAMPLE 257

[4-(4-Chlorophenoxy)thieno[2,3-c]pyridin-2-yl] methyl carbamate

Example 90 (50 mg, 0.17 mmol) was combined with CH$_2$Cl$_2$ (0.5 mL), sodium cyanate (22 mg, 0.34 mmol), and trifluoroacetic acid (40 mL, 0.34 mmol); gas evolution was observed. After 24 hours, the mixture was partitioned between distilled water (15 mL) and CH$_2$Cl$_2$ (50 mL). The layers were separated, and the organic layer was dried (MgSO$_4$), filtered, and concentrated. Silica gel column chromatography (30% acetone in hexane) provided the title compound (21 mg, 37% yield) as a white solid.

mp 113–115° C.; MS (DCI/NH$_3$) m/e: 335 ($^{35}$Cl)/337 ($^{37}$Cl); $^1$H NMR (300 MHz, DMSO-d$_6$) δ 5.30 (s, 2H), 6.80 (br s, 2H), 7.06 (d, J=9.2 Hz, 2H), 7.37 (s, 1H), 7.45 (d, J=8.8 Hz, 2H), 8.18 (s, 1H), 9.10 (s, 1H).

EXAMPLE 258

N-{[4-(4-Chlorophenoxy)thieno[2,3-c]pyridin-2-yl] methyl}urea

Potassium cyanate (41 mg, 0.50 mmol) was added to a mixture of Example 256 (130 mg, 0.45 mmol), distilled water (2.0 mL), and concentrated HCl (40 mL, 0.45 mmol), and the solution was heated at 50° C. After 3 hours, the solution was slowly cooled to 0° C., and the resulting precipitate was isolated by filtration. Flash silica gel column chromatography (20% acetone in hexane, switching to 10% MeOH in EtOAc) provided the title compound (63 mg, 42% yield) as a white solid.

mp 202–204° C.; MS (DCI/NH$_3$) m/e: 334 (35Cl)$^+$/336 (37Cl)$^+$; $^1$H NMR (300 MHz, DMSO-d$_6$) δ 4.47 (d, J=6.1 Hz, 2H), 5.68 (s, 2H), 6.68 (t, J=6.1 Hz, 1H), 7.05 (d, J=8.8 Hz, 2H), 7.14 (s, 1H), 7.43 (d, J=8.8 Hz, 2H), 8.14 (s, 1H), 9.02 (s, 1H); Anal. calcd for C$_{15}$H$_{12}$ClN$_3$O$_2$S: C, 53.97; H, 3.62; N, 12.59. Found: C, 53.80; H, 3.67; N, 12.37.

EXAMPLE 259

(E)-3-[4-(4-Bromophenoxy)thieno[2,3-c]pyridin-2-yl]propenamide

EXAMPLE 259A

Methyl 3-(4-(4-Bromophenoxy)thieno[2,3-c]pyridine-2-yl)propenoate

Example 259A (590 mg, 57%) was prepared as in Example 91B except substituting Example 240 (890 mg, 2.67 mmol) for Example 91A.

MS (APCI) m/e: 390;392 (M+H)$^+$, 389;391 (M−H)$^-$; $^1$H NMR (300 MHz, DMSO-d$_6$) δ 3.75 (s, 3H), 6.58 (d, J=16 Hz, 1H), 7.07 (d, J=9 Hz, 2H), 7.59 (d, J=9 Hz, 2H), 7.89 (s, 1H), 8.02 (d, J=16 Hz, 1H), 8.17 (s, 1H), 9.12 (s, 1H).

EXAMPLE 259B 3-(4-(4-Bromophenoxy)thieno[2,3-c]pyridine-2-yl) propenoic acid Example 259A and the procedure of Example 88 was used to provide the title compound (270 mg, 93%).

MS (APCI) m/e: 376;378 (M+H)$^+$; $^1$H NMR (300 MHz, DMSO-d$_6$) d: 6.45 (d, J=16 Hz, 1H), 7.07 (d, J=9 Hz, 2H), 7.58 (d, J=9 Hz, 2H), 7.81 (s, 1H), 7.90 (d, J=16 Hz, 1H), 8.16 (s, 1H), 9.10 (s, 1H).

EXAMPLE 259C 3-(4-(4-Bromophenoxy)thieno[2,3-c]pyridine-2-yl) propenamide

Example 259B (222 mg, 81%) and the procedure in Example 92, except substituting Example 259B for Example 91C, was used to provide the title compound.

mp 195–196° C.; MS (APCI) m/e: 375;377 (M+H)$^+$, 409;411 (M+Cl)$^-$; $^1$H NMR (400 MHz, DMSO-d$_6$) δ 6.62 (d, 16 Hz, 1H), 7.04 (d, J=9 Hz, 2H), 7.26 (s, 1H), 7.56 (d, J=9 Hz, 2H), 7.64 (s, 1H), 7.68 (s, 1H), 7.72 (d, J=16 Hz, 1H), 8.13 (s, 1H), 9.05 (s, 1H); $^{13}$C NMR (100 MHz, DMSO-d$_6$) δ 115.55 (C), 119.98 (CH), 122.11 (CH), 126.68 (CH), 131.80 (CH), 132.91 (CH), 133.71 (CH), 136.69 (C), 137.48 (C), 140.84 (CH), 145.79 (C), 146.43 (C), 156.07 (C), 165.37 (C).

EXAMPLE 260

Methyl (E)-3-[4-(4-Bromophenoxy)thieno[2,3-c] pyridin-2-yl]propenamide

Example 260 (25 mg, 50%) was prepared from Example 259A (50 mg, 0.13 mmol) as described in Example 171.

MS (APCI) m/e: 389 (M+H)$^+$; $^1$H NMR (400 MHz, DMSO-d$_6$) δ 2.71 (d, J=4.5 Hz, 3H), 6.62 (d, J=16 Hz, 1H), 7.06 (d, J=9 Hz, 2H), 7.58 (d, J=9 Hz, 2H), 7.69 (s, 1H), 7.74 (d, J=16 Hz, 1H), 8.15 (s, 1H), 8.27 (d, J=4.5 Hz, 1H), 9.08 (s, 1H); $^{13}$C NMR (100 MHz, DMSO-d$_6$) δ 25.7 (CH$_3$), 115.6 (C), 120.0 (CH), 122.1 (CH), 126.4 (CH), 131.1 (CH), 132.9 (CH), 133.7 (CH), 136.7 (C), 137.5 (C), 140.9 (CH), 145.9 (C), 146.4 (C), 156.1 (C), 164.3 (C).

EXAMPLE 261

Methyl 3-[4-(4-Bromophenoxy)thieno[2,3-c] pyridin-2-yl]-2,3-dihydroxypropanamide Example 260 (52 mg, 53%) was prepared as described in Example 255, except substituting Example 260 (90 mg, 0.232 mmol), to provide the title compound.

MS (APCI) m/e: 423;425 (M+H)$^+$, 456 (M+Cl)$^-$; $^1$H NMR (300 MHz, DMSO-d$_6$) δ 2.61 (d, J=4.5 Hz, 3H), 4.09 (br d, J=3 Hz, 1H), 5.27 (br d, J=3 Hz, 1H), 5.68 (d, J=6 Hz, 1H), 6.09 (d, J=6 Hz, 1H), 7.00 (d, J=9 Hz, 2H), 7.23 (s, 1H), 7.56 (d, J=9 Hz, 2H), 7.77 (d, J=4.5 Hz, 1H), 8.14 (s, 1H), 9.04 (s, 1H); $^{13}$C NMR (75 MHz, DMSO-d$_6$) δ 25.5 (CH$_3$), 70.3 (CH), 75.1 (CH), 115.0 (CH), 115.1 (C), 119.5 (CH), 132.9 (CH), 133.5 (CH), 137.5 (C), 137.5 (C), 140.9 (CH), 145.8 (C), 156.3 (C), 156.5 (C), 171.7 (C).

EXAMPLE 262

3-[4-(4-Bromophenoxy)thieno[2,3-c]pyridin-2-yl]-2, 3-dihydroxypropanamide

The procedure of Example 261 and the product from Example 259C may be used to prepare the title compound.

EXAMPLE 263

4-(4-Chlorophenoxy)thieno[2,3-c]pyridin-2-ylamine

A mixture of Example 159A (0.500 g, 1.64 mmol) and 1,8-bis(dimethylamino)naphthalene, N, N, N', N'-tetramethyl-1,8-naphthalenediamnine (0.350 g, 1.64 mmol) in 90 mL of anhydrous THF was warmed until all the solids went into solution. The solution was stirred for 15 m, whereupon diphenylphosphoryl azide (0.450 g, 1.64 mmol) was added. The solution was heated to reflux for 18 hours. The resulting deep red solution was evaporated to dryness under reduced pressure. The product was passed through 5 g of silica gel, eluting with 20% ethyl acetate/hexanes to provide 422 mg of the intermediate isocyanate as a bright orange solid. The resulting product was dissolved in 100 mL of toluene and the solution was heated to reflux for 6 hours. The product was evaporated to dryness. The resulting dark orange solid was dissolved in 20 mL of 2.0 M hydrogen chloride in dioxane. The solution was evaporated, leaving 313 mg (84.9%) of the title compound.

MS (APCI) m/e: 277 (M+H)$^+$; $^1$H NMR (300 MHz, DMSO-d$_6$) δ 6.91 (s, 1H), 7.18 (d, 2H), 7.47 (d, 2H), 8.34 (s, 1H), 9.21 (s, 1H).

EXAMPLE 264

4-(4-Chlorophenoxy)thieno[2,3-c]pyridin-2-ylformamide

A mixture of 5 mL of acetic anhydride and 1.8 mL of 96% formic acid was heated to 70° C. for 3 hours. The solution was allowed to cool whereupon the obtained amine from Example 263 (32 mg, 0.12 mmol) was added. The mixture was stirred for 4 days and then poured into 50 mL of dilute HCl. The mixture was extracted with ethyl acetate, the combined extracts were washed with saturated sodium carbonate and then water, dried (MgSO$_4$), and evaporated. Purification of the resulting product by preparative HPLC using a gradient of 30%–70% acetonitrile/water +0.1% TFA over 40 minutes afforded 18 mg (49%) of the title compound.

MS (APCI) m/e: 305 (M+H)$^+$; $^1$H NMR (300 MHz, CD$_3$OD) δ 7.16 (s, 1H), 7.24 (d, 2H), 7.46 (d, 2H), 8.08 (s, 1H), 8.61 (s, 1H), 9.13 (s, 1H).

EXAMPLE 265

N-[4-(4-Chlorophenoxy)thieno[2,3-c]pyridin-2-yl] urea

A mixture of the obtained isocyanate from Example 263 (110 mg, 0.364 mmol) in 10 mL of ammonium hydroxide was vigorously stirred for 18 hours. The resulting red solid was collected and dried under vacuum, affording 60.7 g (52.2%) of the title compound.

MS (APCI) m/e: 320 (M+H)$^+$; $^1$H NMR (300 MHz, DMSO-d$_6$) δ 7.20 (d, 2H), 7.34 (s, 1H), 7.50 (d, 2H), 7.65–7.79 (m, 4H), 8.06–8.16 (m, 2H), 9.18 (s, 1H).

EXAMPLE 266

N-[4-(4-Chlorophenoxy)thieno[2,3-c]pyridin-2-yl]-N'-methylthiourea

A solution of obtained amine from Example 263 (150 mg, 0.542 mmol) in 5 mL of pyridine was treated with methyl isothiocyanate (198 mg, 2.71 mmol). The solution heated to 100° C. under a nitrogen atmosphere for 5 days. All volatiles were removed under reduced pressure. The resulting product was purified by flash column chromatography on silica gel eluting with chloroform/NH$_4$OH, affording 110 mg (58.1%) of the title compound.

MS (APCI) m/e: 350 (M+H)$^+$; $^1$H NMR (300 MHz, CD$_3$OD) δ 3.31 (s, 3H), 6.61 (bs, 1H), 6.96 (d, 2H), 7.34 (d, 2H), 7.88 (s, 1H), 7.96 (s, 1H), 8.67 (s, 1H).

EXAMPLE 267

Methyl 4-(4-Chlorophenoxy)thieno[2,3-c]pyridine-2-sulfonamide

To a solution of Example 124A (261 mg, 1 mmol) in anhydrous THF (2 mL) at −78° C. was added n-BuLi (2.5 M solution in hexanes, 0.60 mL, 1.5 mmol) under nitrogen atmosphere. This was stirred at −78° C. for 2 hours and a rapid stream of $SO_2$ was introduced on the surface of the reaction mixture. After 15 minutes the reaction mixture was allowed to warm to 0° C. with continuous introduction of $SO_2$. The stream of $SO_2$ gas was discontinued after 10 minutes at 0° C. and the reaction mixture was allowed to warm to 10° C. Then the solvent and excess $SO_2$ gas were removed under reduced pressure to obtain the sulfinic acid lithium salt as a cream colored solid. This material was dissolved in a saturated aqueous solution of $NaHCO_3$ (1 mL) and treated with N-chlorosuccinimide (200 mg, 1.5 mmol) at 0° C. The reaction mixture was stirred at 0° C. for 1 hour and at room temperature for 2 hours. The product formed was extracted into $CH_2Cl_2$ (2×50 mL) and washed with water (2×20 mL). The dried ($Na_2SO_4$) organic layer was evaporated to dryness under reduced pressure to obtain the sulfonyl chloride derivative. A portion of this material (143 mg, 0.398 mmol) was dissolved in $CH_2Cl_2$ (1 mL) at −5° C. and treated with diisopropylethylamine (0.083 mL, 0.478 mmol) and 2 M solution of methylamine in methanol (0.239 mL, 1.2 mmol) under nitrogen atmosphere. The reaction mixture was stirred at room temperature for 1 hour. This was directly purified by silica gel flash chromatography eluting with 10% acetone-hexane followed by 25% acetone-hexane to obtain the title compound (19 mg, 13.5%).

MS (APCI) m/e: 355 (M+H)$^+$, 353 (M−H); $^1$H NMR (300 MHz, DMSO-d$_6$) δ 2.57 (s, 3H), 7.19 (d, J=9 Hz, 2H), 7.49 (d, J=9 Hz, 2H), 7.76 (s, 1H), 8.16 (br d, J=3 Hz, 1H), 8.24 (s, 1H), 9.24 (s, 1H).

EXAMPLE 268

2,3-Dihydroxyipropyl 4-(4-chlorophenoxy)thieno[2,3-c]pyridine-2-sulfonamide

Example 268 (8.6 mg, 7.5%) was prepared as described in Example 267 except substituting 3-amino-1,2-propanediol (0.086 mL, 1.12 mmol) for methylamine.

MS (APCI) m/e: 415 (M+H)$^+$, 413 (M−H)$^-$; $^1$H NMR (300 MHz, DMSO-d$_6$) δ 2.76 (d, J=7.5 Hz, 1H), 2.81 (d, J=7.5 Hz, 1H), 3.02 (d, J=4.5 Hz, 1H), 3.08 (d, J=4.5 Hz, 1H), 3.44–3.55 (m, 1H), 4.47–4.64 (m, 1H), 4.80 (d, J=6 Hz, 1H), 7.17 (d, J=9 Hz, 2H), 7.48 (d, J=9 Hz, 2H), 7.77 (s, 1H), 8.23 (s, 1H), 9.22 (s, 1H).

EXAMPLE 269

2-Hydroxyethyl 4-(4-chlorlphenoxy)thieno[2,3-c]pyridine-2-sulfonamide

Example 269 (25 mg, 16%) was prepared s described in Example 267 except substituting 2-hydroxyethylamine (0.072 mL, 1.2 mmol) for methylamine.

MS (APCI) m/e: 385 (M+H)$^+$, 383 (M−H)$^-$; $^1$H NMR (300 MHz, DMSO-d$_6$) δ 2.97 (t, J=6 Hz, 2H), 3.38–3.45 (m, 2H), 4.69–4.78 (m, 1H), 7.18 (d, J=9 Hz, 2H), 7.48 (d, J=9 Hz, 2H), 7.78 (s, 1H), 8.23 (s, 1H), 9.21 (s, 1H); $^{13}$C NMR (75 MHz, DMSO-d$_6$) δ 45.49(CH$_2$), 59.7 (CH$_2$), 119.9 (CH), 122.2 (CH), 128.0 (C), 130.1 (CH), 133.3 (CH), 135.5 (C), 138.2 (C), 141.4 (CH), 147.5 (C), 148.4 (C), 155.2 (C).

EXAMPLE 270

4-[4-(4-Chlorophenoxy)thieno[2,3-c]pyridin-2-yl] phenol

EXAMPLE 270A

4-[4-(4-Chlorophenoxy)thieno[2,3-c]pyridin-2-boronic acid

A 1.3 M suspension of sec-butyllithium in cyclohexane (3.52 mL, 4.58 mmol) was added to THF (10 mL) at −78° C. A solution of Example 124A (1.00 g, 3.82 mmol) in THF (5 mL) was added dropwise. The reaction was stirred 30 minutes and tributyl borate (1.55 mL, 5.73 mmol) was slowly added. The cold bath was removed and the reaction stirred 45 minutes while warming to room temperature. A solution of 2 N NaOH (15 mL) was added. After 10 minutes, the reaction was diluted with hexane (15 mL) and the aqueous layer collected. The organic layer was extracted with 2 N NaOH (2×5 mL) and all aqueous extracts combined, acidified to pH 2 with 6 N HCl, and extracted with 10% MeOH/CH$_2$Cl$_2$ (4×25 mL). The organic extracts were combined and concentrated. The resulting solid was washed with acetonitrile (1×25 mL) and dried in a desiccator to yield the title compound as a tan solid (0.83 g, 71%).

MS (APCI) m/e: 262 (M+H−B(OH)$_2$)$^+$, m/e: 340 (M+Cl$^-$)$^-$; $^1$H NMR (300 MHz, DMSO-d$_6$) δ 7.15 (m, 2H), 7.48 (m, 2H), 8.03 (s, 1H), 8.24 (s, 1H), 9.29 (s, 1H).

EXAMPLE 270B

4-[4-(4-Chlorophenoxy)thieno[2,3-c]pyridin-2-yl] anisol

A mixture of Example 270A (0.25 g, 0.82 mmol), 4-iodoanisole (0.19 g, 0.82 mmol), [1,1'-bis (diphenylphosphino)ferrocene]dichloropalladium(II) dichloromethane complex (1:1) (0.10 g, 0.12 mmol), cesium fluoride (0.37 g, 2.46 mmol), triethylamine (0.11 mL, 0.82 mmol), in DME (7 mL) was aspirated 10 minutes with anhydrous nitrogen. The reaction was heated to 75° C. for 18 hours and then partitioned between EtOAc (100 mL) and sat. NaHCO$_3$ (100 mL). The organic layer was washed with sat. NaHCO$_3$ (100 mL), brine (75 mL), partially dried (Na$_2$SO$_4$), and concentrated to a colored wet solid. The residue was purified by flash chromatography on silica gel using EtOAc/hexane as eluant to yield a colored solid. The title product was crystallized from hot acetonitrile (0.11 g, 37%).

mp 121–123° C.; MS (APCI) m/e: 368 (M+H)$^+$; $^1$H NMR (300 MHz, DMSO-d$_6$) δ 3.82 (s, 3H), 7.05 (m, 2H), 7.13 (m, 2H), 7.45 (m, 2H), 7.67 (s, 1H), 7.81 (m, 2H), 8.13 (s, 1H), 9.05 (s, 1H); Anal. calcd for C$_{20}$H$_{14}$ClNO$_2$S: C, 65.30; H, 3.84; N, 3.81. Found: C, 65.06; H, 3.69; N, 4.05.

EXAMPLE 270C

4-[4-(4-Chlorophenoxy)thieno[2,3-c]pyridin-2-yl] phenol

To a solution of Example 270B (0.09 g, 0.24 mmmol) in anhydrous CH$_2$Cl$_2$ (4 mL) was added a 1 M solution of boron tribromide in CH$_2$Cl$_2$ (0.96 mL, 0.96 mmol). After 2 hours, the reaction was quenched by slow addition of MeOH (2 mL) and then concentrated. The residue was diluted with CH$_2$Cl$_2$ (50 mL) and organic washed with 1:1 sat. NaHCO$_3$/brine (50 mL), partially dried (Na$_2$SO$_4$), then concentrated. The residue was purified by flash chromatography on silica gel using EtOAc/hexane as eluent to yield the title compound as a solid (0.08, 96%).

mp 213–215° C.; MS (ESI) m/e: 354 (M+H)$^+$; $^1$H NMR (300 MHz, DMSO-d$_6$) δ 6.86 (m, 2H), 7.11 (m, 2H), 7.45 (m, 2H), 7.56 (s, 1H), 7.68 (m, 2H), 8.13 (s, 1H), 9.03 (s, 1H), 9.99 (s, 1H); Anal. calcd for C$_{19}$H$_{12}$ClNO$_2$S. 0.5 H$_2$O: C, 62.90; H, 3.61; N, 3.86. Found: C, 62.96; H, 3.61; N, 3.52.

EXAMPLE 271

3-[4-(4-Chlorophenoxy)thieno[2,3-c]pyridin-2-yl] aniline

EXAMPLE 272

4-[4-(4-Chlorophenoxy)thieno[2,3-c]pyridin-2-yl] aniline

EXAMPLE 272A

4-[4-(4-Chlorophenoxy)thieno[2,3-c]pyridin-2-yl-] nitrobenzene

A mixture of Example 170A (0.25 g, 0.82 mmol), 1-iodo-4-nitrobenzene (0.20 g, 0.82 mmol), [1,1'-bis(diphenylphosphino)ferrocene]dichloropalladium(II) dichloromethane complex (1:1) (0.10 g, 0.12 mmol), cesium fluoride (0.37 g, 2.46 mmol), triethylamine (0.11 mL, 0.82 mmol), in DME (8 mL) was aspirated 10 minutes with anhydrous nitrogen. The reaction was heated to 70° C. for 18 hours and then partitioned between EtOAc (100 mL) and sat. $NaHCO_3$ (100 mL). The organic layer was washed with sat. $NaHCO_3$ (100 mL), brine (75 mL), partially dried ($Na_2SO_4$), and concentrated to a colored oil. The residue was purified by flash chromatography on silica gel using EtOAc/hexane as eluent to yield the title compound as a colored solid (0.15 g, 48%).

mp 193–195° C.; MS (ESI) m/e: 383 (M+H)$^+$; $^1$H NMR (300 MHz, DMSO-$d_6$) δ 7.17 (m, 2H), 7.48 (m, 2H), 8.15 (m, 1H), 8.17 (s, 1H), 8.19 (m, 2H), 8.32 (m, 2H), 9.17 (s, 1H); Anal. calcd for $C_{19}H_{11}ClN_2O_3S$: C, 59.61; H, 2.90; N, 7.32. Found: C, 59.35; H, 2.94; N, 7.22.

EXAMPLE 272B

4-[4-(4-Chlorophenoxy)thieno[2,3-c]pyridin-2-yl] aniline

To a suspension of Example 272A (0.13 g, 0.34 mmol) in EtOH (3.5 mL), a solution of tin(II) chloride dihydrate (0.31 g, 1.36 mmol) in conc. HCl (0.68 mL) was slowly added. The reaction was stirred for 22 hours and partitioned between dichloromethane (75 mL) and 1 N NaOH (75 mL). The organic layer was washed with 1 N NaOH (1×50 mL), brine (1×50 mL), partially dried ($Na_2SO_4$), and concentrated to a colored solid (0.13 g). The desired product was crystallized from acetonitrile to yield colored crystals (0.08 g, 68%).

mp 178–182° C.; MS (APCI) m/e: 353 (M+H)$^+$; $^1$H NMR (300 MHz, DMSO-$d_6$) δ 5.68 (br s, 2H), 6.62 (m, 2H), 7.09 (m, 2H), 7.39 (s, 1H), 7.44 (m, 2H), 7.51 (m, 2H), 8.11 (s, 1H), 8.97 (s, 1H); Anal. calcd for $C_{19}H_{13}ClN_2OS$: C, 64.68; H, 3.71; N, 7.94. Found: C, 64.65; H, 3.73; N, 8.13.

EXAMPLE 273

6-[4-(4-Chlorophenoxy)thieno[2,3-c]pyridin-2-yl]-3-pyridinamine

EXAMPLE 273A

6-[4-(4-Chlorophenoxy)thieno[2,3-c]pyridin-2-yl]-3-nitropyridine

Example 273A (120 mg, 32%) was prepared as in Example 272A substituting 2-bromo-5-nitropyridine for 1-iodo-4-nitrobenzene.

mp 221–223° C.; MS (APCI) m/e: 384 (M+H)$^+$; $^1$H NMR (300 MHz, DMSO-$d_6$) δ 7.20 (m, 2 H), 7.49 (m, 2 H), 8.16 (s, 1 H), 8.50 (s, 1 H), 8.61 (d, J=8.8 Hz, 1 H), 8.70 (dd, J=8.8, 2.4 Hz, 1 H), 9.17 (s, 1 H), 9.44 (d, J=2.4 Hz, 1 H).

EXAMPLE 273B

6-[4-(4-Chlorophenoxy)thieno[2,3-c]pyridin-2-yl]-3-pyridinamine

Example 273B (0.07 g, 59%) was prepared as in Example 272B mp 225–227° C.; MS (APCI) m/e: 354 (M+H)$^+$; $^1$H NMR (300 MHz, DMSO-$d_6$) δ 5.82 (broad s, 2 H), 6.92 (dd, J=8.5, 2.6 Hz, 1 H), 7.05 (m, 2 H), 7.39 (m, 2 H), 7.60 (m, 1 H), 7.79 (d, J=8.5 Hz, 1 H), 7.91 (d, J=2.6 Hz, 1 H), 8.04 (s,1H), 8.93 (s, 1 H); Anal. calcd for $C_{18}H_{12}ClN_3OS$: C, 61.10; H, 3.42; N, 11.88. Found: C, 60.97; H, 3.39; N, 12.08.

EXAMPLE 274

5-[4-(4-Chlorophenoxy)thieno[2,3-c]pyridin-2-yl-]-2-pyridinamine

A mixture of Example 270A (0.20 g, 0.65 mmol), 2-amino-5-bromopyridine (0.11 g, 0.65 mmol), [1,1'-bis(diphenylphosphino)ferrocene]dichloropalladium(II) dichloromethane complex (1:1) (0.11 g, 0.13 mmol), cesium fluoride (0.30 g, 1.95 mmol), triethylamine (0.09 mL, 0.65 mmol), in DME (6 mL) was aspirated 20 minutes with anhydrous nitrogen. The reaction was heated to reflux for 4 hours then concentrated. The residue was dissolved in 10% $^i$PrOH/CHCl$_3$ (100 mL), filtered, and the organic washed with sat. $NaHCO_3$ (2×100 mL), partially dried ($Na_2SO_4$), then concentrated to yield a crude colored solid (0.25 g). The crude material was purified by preparative HPLC using a gradient of 25%–65% acetonitrile/water +0.1% TFA over 40 minutes. The product was neutralized with sat $NaHCO_3$, precipitate collected by filtration, and dried in a desiccator to yield the title compound as a lightly colored solid (54 mg, 23%).

mp 208–210° C.; MS (APCI) m/e: 254 (M+H)$^+$; $^1$H NMR (300 MHz, DMSO-$d_6$) δ 6.50 (br s, 2H), 6.53 (dd, J=8.9, 0.9 Hz, 1H), 7.11 (m, 2H), 7.44 (m, 2H), 7.55 (s, 1H), 7.85 (dd, J=8.9, 2.6 Hz, 1H), 8.11 (s, 1H), 8.41 (dd, J=2.6 Hz, 0.9 Hz, 1H), 9.00 (s, 1H); Anal. calcd for $C_{18}H_{12}ClN_3OS$: C, 61.10; H, 3.42; N, 11.88. Found: C, 60.92; H, 3.45; N, 11.90.

EXAMPLE 275

5-[4-(4-Chlorotphenoxy)thieno[2,3-c]pyridin-2-yl]-1,3,4-oxadiazol-2-amine

Example 156 (0.15 g, 0.47 mmol) was suspended in 1,4-dioxane (3 mL) and a 5 M solution of cyanogen bromide in acetonitrile (0.10mL, 0.50 mmol) was added. The reaction was allowed to stir 10 minutes and a solution of $NaHCO_3$ (0.04 g, 0.50 mmol) in water (1.4 mL) was added dropwise. The colored reaction was stirred 2 hours, then poured into sat. $NaHCO_3$ (75 mL). The aqueous phase was extracted with 10% isopropanol/CHCl$_3$ (4×25 mL). The organic extracts were combined, dried ($Na_2SO_4$), and concentrated to yield a solid (0.13 g). A portion of the crude was purified by HPLC using a gradient of 30%–70% acetonitrile/water +0.1% TFA over 40 minutes to yield the title compound as a tan solid.

mp 262–263° C.; MS (APCI) m/e: 345 (M+H)$^+$; $^1$H NMR (300 MHz, DMSO-$d_6$) δ 7.15 (m, 2H), 7.47 (m, 2H), 7.52 (s, 1H), 7.60 (broad s, 2H), 8.24 (s, 1H), 9.17 (s, 1H); $^{13}$C NMR (DMSO-d$_6$) δ 164.3, 155.6, 153.1, 146.6, 141.2, 137.0, 136.9, 134.0, 131.4, 130.1 (2C), 127.7, 119.5 (2C), 117.5; IR (KBr) 3325, 3234, 3080, 1665, 1578, 1547, 1486, 1411, 1287, 1257, 1229, 1203cm$^{-1}$; Anal calcd for C$_{15}$H$_9$ClN$_4$O$_2$S: C, 52.26; H, 2.63; N, 16.25. Found: C, 52.40; H, 2.68; N, 16.23.

EXAMPLE 276

5-[4-(4-Bromophenoxy)thieno[2,3-c]pyridin-2-yl]-1,3,4-oxadiazol-2-ylamine

Example 157 (0.15 g, 0.41 mimol) was suspended in 1,4-dioxane (4 mL) and a 5 M solution of cyanogen bromide in acetonitrile (0.10 mL, 0.50 nimol) was added. The reaction was allowed to stir 10 minutes and a solution of NaHCO$_3$ (0.04 g, 0.50 mmol) in water (1.4 mL) was added dropwise. The colored reaction was stiffed 3 hours, then poured into sat. NaHCO$_3$ (75 mL). The aqueous was extracted with 10% IPA/CHCl$_3$ (4×25 mL). The organic extracts were combined, partially dried (Na$_2$SO$_4$), and concentrated to yield a solid. A portion of the crude was purified by HPLC using a gradient of 30%–70% acetonitrile/water +0.1% TFA over 40 minutes to yield the title compound as a tan solid.

mp 270–273° C.; MS (APCI) m/e: 389 (M+H)$^+$; $^1$H NMR (300 MHz, DMSO-d$_6$) δ 7.08 (m, 2H), 7.52 (s, 1H), 7.56 (br s, 2H), 7.59 (m, 2H), 8.27 (s, 1H), 9.19 (s, 1H); Anal calcd for C$_{15}$H$_9$BrN$_4$O$_2$S: C, 46.29; H, 2.33; N, 14.39. Found: C, 46.08; H, 2.59; N, 14.12.

EXAMPLE 277

5-[4-(4-Chlorophenoxy)thieno[2,3-c]pyridin-2-yl]-4H-1,2,4-triazol-3-amine

To a dry flask containing 61A (0.33 g, 1.03 mmol) and aminoguanidine hydrochloride (3.45 g, 31.20 mmol) was added slowly a solution of 25% wt NaOMe/MeOH (7.13 mL, 34.32 mmol). The reaction was stirred at ambient temperature for 1 hour then heated to 50° C. for 20 hours, then 70° C. for 24 hours. The reaction was poured into water (200 mL) and aqueous neutralized with 3 N HCl (10 mL). The precipitate was collected by filtration, washed with water (2×20 mL), and dried in a desiccator. The crude material was purified by preparative HPLC using a gradient of 25%–65% acetonitrile/water +0.1% TFA over 40 minutes. The product was neutralized with sat. NaHCO$_3$, and the precipitate was collected by filtration then dried in a desiccator to yield the title compound as a white solid (0.16 g, 45%).

mp>270° C.; MS (APCI) m/e: 344 (M+H)$^+$; $^1$H NMR (300 MHz, DMSO-d$_6$) δ 6.46 (br s, 2H), 7.27 (m, 2H), 7.58 (m, 2H), 7.67 (s, 1H), 8.31 (s, 1H), 9.21 (s, 1H); Anal. calcd for C$_{15}$H$_{10}$ClN$_5$OS: C, 52.41; H, 2.93; N, 20.37. Found: C, 52.21; H, 3.02; N, 20.45.

EXAMPLE 278

5-[4-(4-Chlorophenoxy)thieno[2,3-c]pyridin-2-yl]-1,3,4-thiadiazol-2-amine

Example 88 (0.36 g, 1.18 mmol) was suspended in thionyl chloride (4 mL) and the suspension was heated to 45° C. for 2 hours. The reaction was concentrated and the residue diluted with CH$_2$Cl$_2$ (2×5 mL) and concentrated to yield a colored solid. The crude solid was dissolved in DMF (5 mL) and thiosemicarbazide (2.69 g, 29.50 mmol) was added and the reaction stirred 24 hours. The reaction was poured into water (250 mL) and the aqueous suspension treated with sat. aq. NaHCO$_3$ (10 mL) until pH>7. The precipitate was collected, washed with water (2×20 mL), and dried in a desiccator to yield the corresponding acyl semicarbazate as a solid (0.30 g) [MS (APCI) m/e: 377 (M+H)$^+$]. The crude material (0.20 g) was suspended in toluene (2 mL) and methanesulfonic acid (0.10 mL, 1.60 mmol) added. The reaction was heated to reflux for 4 hours, then allowed to cool to room temperature. The heterogeneous mixture was diluted with hexane (5 mL) and the solvent decanted away from the colored residue. The residue was triturated with hexane (2×10 mL) and dried in-vacuo. The solid was suspended in water (15 mL) and treated with NH$_4$OH until pH 9 was attained. The precipitate was collected and washed with water (2×5 mL). The crude material was partially purified on silica gel by flash chromatography using acetone as eluent. This product was further purified by preparative HPLC using a gradient of 25%–65% acetonitrile/water +0.1% TFA over 40 minutes. The product was neutralized with sat. aq. NaHCO$_3$, and the precipitate collected by filtration, then dried in a desiccator to yield the title compound as a tan solid (0.04 mg, 14% overall). mp>270° C.; MS (APCI) m/e: 361 (M+H)$^+$; $^1$H NMR (300 MHz, DMSO-d$_6$) δ 7.15 (m, 2H), 7.46 (m, 2H), 7.68 (s, 1H), 7.75 (br s, 2H), 8.11 (s, 1H), 9.06 (s, 1H); Anal. calcd for C$_{15}$H$_9$ClN$_4$OS$_2$: C, 49.93; H, 2.51; N, 15.53. Found: C, 49.82; H, 2.64; N, 15.58.

EXAMPLE 279

4-(4-Chlorophenoxy)-2-(5-methyl-1,2,4-oxadiazol-3-yl)thieno[2,3-c]pyridine

A solution of the resultant compound from Example 249 (160 mg, 0.5 mmol) in pyridine (2.0 mL) under nitrogen at ambient temperature was treated with acetyl chloride (50 mL, 0.55 mmol) and heated to reflux for 15 hours. The resultant dark yellow homogeneous solution was diluted with ethyl acetate, washed with saturated NaHCO$_3$, brine, dried (MgSO$_4$), filtered through a plug of silica and concentrated to give 169 mg of an off-white powder. This solid was flash chromatographed on silica gel with 30–50% ethyl acetate/hexane to provide the title compound (150 mg, 87%).

mp 120–121° C.; MS (APCI-NH$_3$) m/e: 344 (M+H)$^+$; $^1$H NMR (300 MHz, DMSO-d$_6$) δ 9.24 (s, 1H), 8.27 (s, 1H), 7.89 (s, 1H), 7.48 (d, 2H), 7.16 (d, 2H), 2.69 (s, 3H); Anal. Calcd for C$_{16}$H$_{10}$ClN$_3$O$_2$S: C, 55.90; H, 2.93; N, 12.22. Found: C, 56.10; H, 3.16; N, 12.01.

EXAMPLE 280

5-{4-[4-(Trifluoromethyl)phenoxy]thieno[2,3-c]pyridin-2-yl}-1,3,4-oxadiazol-2-amine Example 158 was treated according to the procedure of Example 275 to provide the title compound.

MS (APCI) m/e: 358.9 (M+H)$^+$; $^1$H NMR (300 MHz, DMSO-d$_6$) δ 7.22 (d, 2H), 7.51 (s, 1H), 7.60 (s, 2H), 7.79 (d, 2H), 8.40 (s, 1H), 9.25 (s, 1H).

EXAMPLE 281

4-(4-Chlorophenoxy)-2-[5-(methylsulfanyl)-1,3,4-oxadiazol-2-yl]thieno[2,3-c]pyridine

EXAMPLE 281A

5-[4-(4-chlorophenoxy)thieno[2,3-c]pyridin-2-yl]-1,3,4-oxadiazole-2-thiol

The compound from Example 156 (100 mg, 0.31 mmol) was suspended in ethanol (2 ml) and cooled to 0° C. Carbon disulfide (0.04 ml, 0.71 mmol) was added follow by potassium hydroxide (20 mg, 0.31 mmol). The reaction was stirred 1 hr and the cold bath removed. After 1 hr at ambient temperature, the reaction was refluxed for 3 hours then concentrated to a solid. The crude solid was triturated with chloroform (1×5 ml) and concentrated. The residue was dissolved in water (15 ml) and acidified with formic acid. The resulting precipitate was isolated by filtration, washed with water (2×15 ml), and dried in a desiccator to yield the title compound (106 mg, 94%).

mp 236–240° C.; MS (ESI) m/e: 362 (M+H)$^+$; $^1$H NMR (300 MHz, CD$_2$Cl$_2$) δ 7.15 (m, 2H), 7.46 (m, 2H), 7.65 (m, 1H), 8.24 (s, 1H), 9.18 (s,1H); Anal. calcd for C$_{15}$H$_8$ClN$_3$O$_2$S$_2$: C, 47.89; H, 2.57; N, 11.17. Found: C, 47.89; H, 2.49; N, 10.97.

EXAMPLE 281B 4-(4-Chlorophenoxy)-2-[5-(methylsulfanyl)-1,3,4-oxadiazol-2-yl]thieno[2,3-c]pyridine To a stirred suspension of 281A (100 mg, 0.28 mmol) in THF (1 ml) at 0° C. was added an aqueous 1 M sodium hydroxide solution (0.28 ml, 0.28 mmol). After 30 minutes all solid had dissolved and iodomethane (0.02 ml, 0.31 mmol) was slowly added dropwise. The reaction was stirred 30 minutes and water (8 ml) was added. Solid was collected by filtration, washed with water (2×15 ml), and dried in a desiccator to yield 80 mg of a pale yellow solid. The crude product was purified by flash chromatography on silica gel using acetone/hexane as eluent to yield the title compound as a solid (41 mg, 39%).

mp 158–160° C.; MS (ESI) m/e: 376 (M+H)$^+$; $^1$H NMR (300 MHz, CD$_2$Cl$_2$) δ 2.75 (s, 3 H), 7.01 (m, 2 H), 7.33 (m, 2 H), 7.91 (s, 1 H), 8.12 (s, 1 H), 8.93 (s, 1 H); Anal. calcd for C$_{16}$H$_{10}$ClN$_3$O$_2$S$_2$: C, 51.13; H, 2.68; N, 11.18. Found: C, 51.25; H, 3.02; N, 10.89.

EXAMPLE 282

4-(4-Chlorophenoxy)-2-(2-methyl-1,2,3,4-tetrazol-5-yl)thieno[2,3-c]pyridine

EXAMPLE 282A 4-(4-Chlorophenoxy)-2-(1,2,3,4-tetrazol-5-yl)thieno[2,3-c]pyridine A solution of the resultant compound from Example 248 (90 mg, 0.314 mmol) in toluene (1.5 mL) under nitrogen at room temperature was treated with dibutyltin oxide (8 mg, 0.031 mmol), trimethylsilylazide (125 mL, 0.942 mmol) and heated to reflux for 24 hours, then stirred at room temperature an additional 2.5 days. The resultant yellow heterogeneous mixture was concentrated and then flash chromatographed with 20% methanol/dichloromethane to give 105 mg of a light yellow powder. This powder was dissolved in ethyl acetate, extracted with 10% NaHCO$_3$ (2×), the aqueous extracts combined, acidified to pH 2 with 6 N HCl, extracted with ethyl acetate, dried (Na$_2$SO$_4$) and concentrated to give the title compound as a white powder (63 mg, 61%).

mp 250–254° C.; MS (APCI-NH$_3$) m/e: 330 (M+H)$^+$; $^1$H NMR (300 MHz, DMSO-d$_6$) δ 9.26 (s, 1H), 8.27 (s, 1H), 8.01 (s, 1H), 7.48 (d, 2H), 7.19 (d, 2H); Anal. Calcd for C$_{14}$H$_8$ClN$_5$OS 0.25 H$_2$O: C, 50.30; H, 2.56; N, 20.95. Found: C, 50.27; H, 2.69; N, 20.78.

EXAMPLE 282B 4-(4-Chlorophenoxy)-2-(2-methyl-1,2,3,4-tetraazol-5-yl)thieno[2,3-c]pyridine A solution of the resultant compound from Example 282A (100 mg, 0.3 mmol) in methanol (4 mL) under nitrogen at room temperature was treated with diazomethane in diethyl ether (generated from N-methyl-N'-nitro-N-nitrosoguanidine in diethyl ether and 40% KOH) until a yellow color persisted for more than 5 minutes, stirred an additional 15 minutes and then quenched by slow, dropwise addition of glacial acetic acid till yellow color disappeared (vigorous gas evolution) and then concentrated. The resultant light yellow solid was filtered through a plug of silica gel with 5% methanol/dichloromethane and then flash chromatographed on reverse phase silica gel (Dynamax 21.4 mm C-18 column) with 25–65% CH$_3$CN with 0.1% TFA1H$_2$O with 0.1% TFA to provide the title compound as a white powder (40 mg, 39%).

mp 131–133° C.; MS (APCI-NH$_3$) m/e: 344 (M+H)$^+$; $^1$H NMR (300 MHz, DMSO-d$_6$) δ 9.25 (s, 1H), 8.28 (s, 1H), 7.89 (s, 1H), 7.48 (d, 2H), 7.18 (d, 2H), 4.47 (s, 3H); Anal. Calcd for C$_{15}$H$_{10}$ClN$_5$OS 0.25 H$_2$O: C, 51.73; H, 3.04; N, 20.11. Found: C, 51.74; H, 2.93; N, 19.93.

EXAMPLE 283

5-[4-(4-Chlorophenoxy)thieno[2,3-c]pyridin-2-yl]-4-methyl-4H-1,2,4-triazol-3-amine Sodium hydride (60% in oil, 0.02 g, 0.42 mmol) was suspended in DMF (1 mL) at 0° C. A solution of Example 277 (0.11 g, 0.32 mmol) in DMF (1 mL) was added dropwise and the reaction stirred 20 minutes. Iodomethane (0.06 mL, 0.96 mmol) was added and after 30 minutes the reaction was poured into water (75 mL). The resulting precipitate was collected by filtration, washed with water (1×20 mL), and with 50% EtOAc/hexane (2×25 mL). The crude solid was dried to yield a colored solid (0.11 g). The title compound was isolated by preparative HPLC using a gradient of 25%–65% acetonitrile/water +0.1% TFA over 40 minutes. The product was neutralized with sat. aq. NaHCO$_3$, and the precipitates collected by filtration, then dried in a desiccator to provide (31 mg, 27%).

mp 233–235° C.; MS (APCI) m/e: 358 (M+H)$^+$; $^1$H NMR (300 MHz, DMF-d$_7$) δ 3.75 (s, 3H), 6.58 (br s, 2H), 7.23 (m, 2H), 7.54 (m, 2H), 7.61 (s, 1H), 8.27 (s, 1H), 9.18 (s, 1H); Anal. calcd for C$_{16}$H$_{12}$ClN$_5$OS: C, 53.71; H, 3.38; N, 19.57. Found: C, 54.00; H, 3.56; N, 19.68.

EXAMPLE 284

4-(4-Chlorophenoxy)-2-[5-(trifluoromethyl)-1,2,4-oxadiazol-3-yl]thieno[2,3-c]pyridine A solution of the resultant compound from Example 249 (100 mg, 0.31 mmol) in pyridine (1.5 mL) under nitrogen at room temperature was treated with trifluoroacetic anhydride (50 mL, 0.31 mmol), stirred for 20.5 hours, then heated to reflux for three hours. The brown solution was diluted with ethyl acetate, washed with saturated NaHCO$_3$, brine, dried (MgSO$_4$), concentrated, then filtered through a plug of silica gel with 50/50 hexane/ethyl acetate and concentrated to give 120 mg of a yellow residue. This residue was flash chromatographed on silica gel twice using 20–33% ethyl acetate/hexane and then 0–1% methanol/CH$_2$Cl$_2$ to give the title compound as a white solid (67 mg, 54%).

mp 52–54° C.; MS (APCI-NH$_3$) m/e: 398 (M+H)$^+$, 416 (M+NH$_4$)$^+$; $^1$H NMR (300 MHz, DMSO-d$_6$) δ 9.30 (s, 1H), 8.29 (s, 1H), 8.10 (s, 1H), 7.48 (d, 2H), 7.20 (d, 2H); Anal. Calcd for C$_{16}$H$_7$ClF$_3$N$_3$O$_2$S.0.25 H$_2$O: C, 47.77; H, 1.88; N, 10.45. Found: C, 48.15; H, 2.09; N, 10.14.

EXAMPLE 285

5-[4-(4-Chlorophenoxy)thieno[2,3-c]pyridin-2-yl]-1,2,4-oxadiazol-3-amine

A solution of the resultant compound from Example 250 (100 mg, 0.3 mmol) in methanol (1.5 mL) under nitrogen at ambient temperature was treated with hydroxylamine hydrochloride (40 mg, 0.45 mmol), triethylamine (70 mL, 0.5 mmol) and stirred for 18 hours, 4 mL THF was added and stirred for two days, solvent switched to 50/50 dichloromethane/methanol, additional hydroxylamine hydrochloride (100 mg, 1.4 mmol) and triethylamine (200 mL, 2.7 mmol) added, stirred at ambient temperature for 24 hours and then reflux for 8 hours. The reaction mixture was diluted with ethyl acetate, washed with dilute $NaHCO_3$, brine, dried ($MgSO_4$) and concentrated to give 105 mg of an off-white solid. The resultant solid was flash chromatographed twice on reverse phase silica gel (Dynamax 21.4 mm C-18 column) with 25–65% $CH_3CN$ with 0.1% TFA/$H_2O$ with 0.1% TFA, followed by 20–80% $CH_3CN$ with 0.1% TFA/$H_2O$ with 0.1% TFA to provide the title compound as a white powder (26 mg, 25%).

mp 217–219° C.; MS (APCI-$NH_3$) m/e: 345 (M+H)$^+$; $^1$H NMR (300 MHz, DMSO-$d_6$) δ 9.26 (s, 1H), 8.25 (s, 1H), 8.02 (s, 1H), 7.49 (d, 2H), 7.14 (d, 2H), 6.62 (br s, 2H); Anal. Calcd for $C_{15}H_9ClN_4O_2S$: C, 52.25; H, 2.63; N, 16.25. Found: C, 51.94; H, 2.88; N, 15.98.

EXAMPLE 286

5-[4-(4-Chlorophenoxy)thieno[2,3-c]pyridin-2-yl]-N-methyl-1,3,4-thiadiazol-2-amine The title compound (4% overall yield) was prepared as in Example 278, substituting 4-methylthiosemicarbazide for thiosemicarbazide.

mp 226–229° C.; MS (APCI) m/e 375 (M+H)$^+$; $^1$H NMR (300 MHz, DMSO-$d_6$) δ 2.95(d, J=1.7 Hz, 3 H), 7.14 (m, 2 H), 7.45 (m, 2 H), 7.69 (s, 1 H), 8.17 (s, 1 H), 8.19 (br m, 1 H), 9.07 (s, 1 H); Anal. calcd for $C_{16}H_{11}ClN_4OS_2$: C, 51.27; H, 2.96; N, 14.95. Found: C, 51.24; H, 3.03; N, 14.85.

EXAMPLE 287

4-(4-Chlorophenoxy)-2-(1,2,4-oxadiazol-3-yl)thieno[2,3-c]pyridine

EXAMPLE 287A 4-(4-Chlorophenoxy)-N'-(diethoxymethoxy)thieno[2,3,-c]pyridine-2-carboxaimidamide A solution of the resultant compound from Example 249 (100 mg, 0.31 mmol) in triethylorthoformate (1.3 mL) under nitrogen was heated to 140° C. for 5 hours, 160° C. for 2 hours and stirred at room temperature for 14 hours. The resultant light yellow oil (110 mg) was flash chromatographed on silica gel 20–70% ethyl acetate/hexane to provide the title compound as a white solid (50 mg, 38%).

MS (APCI-$NH_3$) m/e: 422 (M+H)$^+$; $^1$H NMR (300 MHz, DMSO-$d_6$) δ 9.05 (s, 1H), 8.15 (s, 1H), 7.97 (s, 1H), 7.46 (d, 2H), 7.10 (d, 2H), 6.65 (br s, 2H), 5.66 (s, 1H), 3.62–3.71 (m, 4H), 1.15 (t, 6H).

EXAMPLE 287B 4-(4-Chlorophenoxy)-2-(1,2,4-oxadiazol-3-yl)thieno[2,3-c]pyridine A solution of the resultant compound from Example 287A (50 mg, 0.119 mmol) in toluene (6 mL) under nitrogen was heated at reflux for 20 hours then allowed to cool and concentrated. The yellow residue (46 mg) was flash chromatographed on silica gel 25–50% ethyl acetate/hexane to provide the title compound as a white solid (39 mg, 100%).

Analytical HPLC: 4.6×250 mm C-18 column, 0.8 mL/min, 254 nm, $CH_3CN$:$H_2O$ with 0.1% TFA, 0:100 (0–3 min), ramp to 90:10 (3–30 min), 90:10 (30–35 min), ra mp to 0:100 (35–40 min), Rt=22.47 min (100% peak area);

mp 151–152° C.; MS (APCI-$NH_3$) m/e: 330 (M+H)$^+$; $^1$H NMR (300 MHz, DMSO-$d_6$) δ 9.86 (s, 1H), 9.26 (s, 1H), 8.27 (s, 1H), 7.98 (s, 1H), 7.48 (d, 2H), 7.19 (d, 2H).

EXAMPLE 288

2-(1,3,4-Oxadiazol-2-yl)-4-[4-(trifluoromethyl)phenoxy]thieno[2,3-c]pyridine

A solution of Example 183 (100 mg, 0.283 mmol) in triethyl orthoformate (15 mL) was heated to reflux under an atmosphere of nitrogen for 28 hours. All volatiles were removed under reduced pressure. The resulting oil was purified by flash column chromatography eluting with hexane/ethyl acetate (2:1), affording 65 mg (63%) of the title compound as a colorless oil that solidified on standing.

MS (ESI) m/e: 364 (M+H)$^+$; $^1$H NMR (300 MHz, $CDCl_3$) δ 7.14 (d, 2H), 7.66 (d, 2H), 8.05 (s, 1H), 8.24 (s, 1H), 8.50 (s, 1H), 9.07 (s, 1H); Anal. calcd for $C_{16}H_8N_3F_3O_2S$: C, 52.89; H, 2.22; N, 11.57. Found: C, 53.03; H, 2.25; N, 11.48.

EXAMPLE 289

3-[4-(4-Chlorophenoxy)thieno[2,3-c]pyridin-2-yl]-1,2,4-oxadiazol-5-amine

EXAMPLE 289A

3-[4-(4-Chlorophenoxy)thieno[2,3-c]pyridin-2-yl]-5-(trichloromethyl-1,2,4-oxadiazole A solution of the resultant compound from Example 249 (50 mg, 0.156 mmol) pyridine (2 mL) under nitrogen at ambient temperature was treated with trichloroacetyl chloride (20 mL, 0.17 mmol) and heated at reflux for 1.5 hours, allowed to cool to room temperature, stirred overnight, treated with additional trichloroacetyl chloride (100 mL, 0.86 mmol) and stirred 4 hours. The reaction mixture was then diluted with ethyl acetate, washed with saturated $NaHCO_3$, brine, dried ($MgSO_4$) and concentrated. The resultant brown residue was flash chromatographed on silica gel with 25–50% ethyl acetate/hexane to give the title compound as a clear residue (37 mg, 53%). MS (APCI-$NH_3$) m/e: 448 (M+H)$^+$; $^1$H NMR (300 MHz, DMSO-$d_6$) δ 9.25 (s, 1H), 8.24 (s, 1H), 8.09 (s, 1H), 7.46 (d, 2H), 7.18 (d, 2H).

EXAMPLE 289B

3-[4-(4-Chlorophenoxy)thieno[2,3-c]pyridin-2-yl]-1,2,4-oxadiazol-5-amine

A solution of the resultant compound from Example 289A (30 mg, 0.067 mmol) in 2.0 M ammonia in methanol (6 mL) in a pressure tube was heated to 60° C. for 15 hours then allowed to cool ambient temperature, rinsed out of the flask with methanol and distilled water. The bulk of the methanol was removed under vacuum and the cloudy white mixture was filtered and washed with distilled water. The resultant yellow-brown solid was flash chromatographed twice on reverse phase silica gel (Dyanamax C-18, 21.4 mm column) with 25–65%, and then 20–80% $CH_3CN$ with 0.1% TFA/$H_2O$ with 0.1% TFA to give the title compound as a white solid (4 mg, 17%). Analytical HPLC: 4.6×250 mm C-18 column, 0.8 mL/min, 254 nm, $CH_3CN$:$H_2O$ with 0.1% TFA, 0:100 (0–3 min), ramp to 90:10 (3–30 min), 90:10 (30–35 min), ramp to 0:100 (35–40 min), Rt=19.44 min (100% peak area);

mp 268–270° C.; MS (APCI-NH$_3$) m/e: 345 (M+H)$^+$; $^1$H NMR (300 MHz, DMSO-d$_6$) δ 9.21 (s, 1H), 8.27 (s, 1H), 8.22 (br s, 2H), 7.67 (s, 1H), 7.47 (d, 2H), 7.15 (d, 2H).

EXAMPLE 290

2-(5-Methyl-1,3,4-oxadiazol-2-yl)-4-[4-(trifluoromethyl)phenoxy]thieno[2,3-c]pyridine The title compound was prepared as described for Example 288 using triethyl orthoacetate as the solvent. Reflux was maintained for 5 days with the yield being 29%.

MS (APCI) m/e: 377 (M+H)$^+$; $^1$H NMR (300 MHz, CDCl$_3$) δ 2.65 (s, 3H), 7.13 (d, 2H), 7.65 (d, 2H), 7.94 (s, 1H), 8.27 (s, 1H), 9.06 (s, 1H).

EXAMPLE 291

4-(4-Chlorophenoxy)-2-(2-furyl)thieno[2,3-c]pyridine

A mixture of Example 270A (0.30 g, 0.98 mmol), 2,5-dibromofuran (0.66 g, 2.94 mmol), cesium fluoride (0.45 g, 2.94 mmol), triethylamine (0.14 mL, 0.98 mmol), in DME (9 mL) was aspirated 25 minutes with anhydrous nitrogen and [1,1'-bis(diphenylphosphino)ferrocene] dichloropalladium(II) dichloromethane complex (1:1) (0.16 g, 0.20 mmol) was added. The reaction was heated to reflux for 4 hr and then stirred at ambient temperature overnight. The reaction was diluted with EtOAc (100 mL) and filtered. The organic layer was washed with sat. NaHCO$_3$ (3×50 mL), brine (75 mL), partially dried (Na$_2$SO$_4$), and concentrated to a colored oil. The residue was purified by flash chromatography on silica gel using EtOAc/hexane as eluent to yield a colored oil (0.12 g, 0.30 mmol) [MS (APCI) m/e 406 (M+H)$^+$]. This material was dissolved in EtOH (10 mL) and 5% Pd/C (3 mg, 0.02 mmol) was added. A balloon of hydrogen gas was applied and reaction stirred 3 days at ambient temperature. Reaction was filtered through celite and celite wash with MeOH (10 mL) and dichloromethane (10 mL). The filtrate and washes were combined and concentrated to a colored wet foam. The crude material was purified by preparative HPLC using a gradient of 30%–70% acetonitrile/water +0.1% TFA over 40 minutes. The product was neutralized with sat NaHCO$_3$, precipitate collected by filtration, and dried in a desiccator to yield the title compound as a lightly colored solid (15 mg, 5% overall yield).

mp 75–77° C.; MS (APCI) m/e: 328 (M+H)$^+$; $^1$H NMR (300 MHz, DMSO-d$_6$) δ 6.70 (dd, J=3.4, 1.7 Hz, 1 H), 7.12 (m, 2 H), 7.24 (d, J=3.4 Hz, 1 H), 7.46 (m, 2 H), 7.59 (s, 1 H), 7.88 (d, J=1.7 Hz, 1 H), 8.16 (s, 1 H), 9.08 (s, 1H).

EXAMPLE 292

4-(4-Chlorophenoxy)-2-(2-thienyl)thieno[2,3-c]pyridine

Example 292 (50 mg, 22%) was prepared as in Example 272A, substituting 2-iodothiophene for 1-iodo-4-nitrobenzene.

mp 101–103° C.; MS (APCI) m/e: 344 (M+H)$^+$; $^1$H NMR (300 MHz, DMSO-d$_6$) δ 7.14 (m, 2 H), 7.19 (dd, J=5.0, 3.4 Hz, 1 H), 7.46 (m, 2 H), 7.54 (d, J=0.9 Hz, 1 H), 7.67 (dd, J=3.4, 1.3 Hz, 1 H), 7.73 (dd, J=5.0, 1.3 Hz, 1 H), 8.14 (s, 1 H), 9.05 (s, 1 H); Anal. calcd for C$_{17}$H$_{10}$ClNOS$_2$.0.2H$_2$O: C, 58.77; H, 3.02; N, 4.03. Found: C, 58.74; H, 2.84; N, 3.72.

EXAMPLE 293

2-[4-(4-Chlorophenoxy)thieno[2,3-c]pyridin-2-yl]-1,3-thiazole-4-carboxamide

EXAMPLE 293A

Ethyl 2-[4-(4-Chlorophenoxy)thieno[2,3-c]pyridin-2-yl]-1,3-thiazole-4-carboxylate Ethyl bromopyruvate (390 mL, 2,30 mmol) was combined with Example 146 (672 mg, 2.09 mmol) and absolute ethanol (100 mL), and the orange, homogenous solution was heated at 60° C. After 48 hours, the mixture was cooled to ambient temperature and concentrated under vacuum. Purification was achieved by means of flash silica gel chromatography (15% acetone in hexane), and the title compound (297 mg, 34% yield) was obtained as a white solid.

MS (DCI/NH$_3$) m/e: 417 ($^{35}$Cl)/419 ($^{37}$Cl); $^1$H NMR (300 MHz, CDCl$_3$) δ 8.94 (s, 1H), 8.24 (s, 1H), 8.12 (s, 1H), 7.88 (s, 1H), 7.36 (d, J=8.8 Hz, 2H), 7.04 (d, J=8.8 Hz, 2H), 4.45 (q, J=7.0 Hz, 2H), 1.45 (t, J=7 Hz, 3H).

EXAMPLE 293B

2-[4-(4-Chlorophenoxy)thieno[2,3-c]pyridin-2-yl]-1,3-thiazole-4-carboxamide

Example 293A (32 mg, 77 mmol) was combined with ammonia in methanol (4 mL of a 2.0 M solution), and the solution was heated in a sealed tube at 40° C. After 16 hours, the homogeneous solution was cooled to room temperature and concentrated to a brown solid that was dry-loaded on flash silica gel and eluted with 20% acetone in hexane, followed by 40% acetone in hexane to recover the title compound (8 mg, 27% yield).

mp 215–218° C.; MS (DCI/NH$_3$) m/e: 388 (M+H)/405 (M+NH$_3$), 407 ($^{37}$Cl+NH$_3$); $^1$H NMR (300 MHz, CDCl$_3$) δ 5.67 (br s, 2H), 7.06 (d, J=8.5 Hz, 2H), 7.38 (d, J=8.8 Hz, 2H), 8.09 (s, 1H), 8.25 (s, 1H), 8.94 (s, 1H).

EXAMPLE 294 tert-Butyl 2-[4-(4-Chlorophenoxy)thieno[2,3-c]pyridin-2-yl]-1,3-thiazol-4-ylcarbamate Example 293 was converted to the corresponding carboxylic acid in a similar manner as described in Example 18. Diphenyl phosphorylazide (25 μL, 0.10 mmol) was added to a mixture of the carboxylic acid (40 mg, 0.10 mmol), tert-butanol (10 mL), and triethyl amine (20 μL, 0.10 mmol), and the solution was heated at 80° C. After 18 hours, the solution was cooled and concentrated. The yellow residue was dissolved in CH$_2$Cl$_2$ (30 mL), washed sequentially with 0.5 N aqueous HCl (40 mL) and saturated aqueous NaHCO$_3$ (25 mL), and brine (25 mL). The combined aqueous washes were back-extracted with CH$_2$Cl$_2$ (2×25 mL). The organic layers were combined, dried (MgSO$_4$), filtered, and concentrated to a yellow residue. Flash silica gel flash column chromatography (15% acetone in hexane) provided the title compound (13 mg, 28% yield) as a bright yellow solid.

MS (APCI) m/e: 460 ($^{35}$Cl)/462 ($^{37}$C); $^1$H NMR (300 MHz, CDCl$_3$) δ 8.91 (s, 1H), 8.11 (s, 1H), 7.71 (s, 1H), 7.35 (d, J=8.9 Hz, 2H), 7.03 (d, J=8.9 Hz, 2H), 3.97 (d, J=11.4 Hz, 2H), 1.54 (s, 9H).

EXAMPLE 295

2-[4-(4-Chlorophenoxy)thieno[2,3-c]pyridin-2-yl]-1,3-thiazol-4-amine

Trifluoroacetic acid (0.5 mL) was added to Example 294 (9.0 mg, 20 μmol) in CH$_2$Cl$_2$ (1.5 mL) at 0° C. After 1 h, the volatiles were removed, and the orange residue was dissolved in 0.5 N aqueous HCl (35 mL). The aqueous phase was washed once with Et$_2$O (10 mL); the ether wash was extracted with 1 N HCl (2×20 mL). The acidic layers were combined, and saturated aqueous potassium carbonate was added until the solution was basic (pH>12). The alkaline phase was extracted with EtOAc (3×40 mL); the organic extracts were combined, dried (MgSO$_4$), filtered, and concentrated to a dark brown solid (9 mg). Purification by flash silica gel column chromatography (20% acetone in hexane) provided the title compound as a bright yellow solid (6.8 mg, 97% yield).

mp 168–170° C. (decomposes); MS (APCI) m/e: 360 ($^{35}$Cl)/362 ($^{37}$Cl); $^1$H NMR (300 MHz, CDCl$_3$) δ 8.90 (s, 1H), 8.11 (s, 1H), 7.68 (s, 1H), 7.35 (d, J=9.2 Hz, 2H), 7.02 (d, J=8.9 Hz, 2H), 6.07 (s, 1H), 3.89 (br s, 2H).

EXAMPLE 296

4-(4-Chlorophenoxy)-2-(4,5-dihydro-1,3-oxazol-2-yl)thieno[2,3-c]pyridine

To a solution of Example 150 (0.14 g, 0.38 mmol) in anhydrous dichloromethane (4 mL) was added 1,8-diazabicyclo[5.4.0]undec-7-ene (DBU) (0.09 mL, 0.57 mmol). The reaction was stirred 24 hours and an excess of morpholine (0.2 mL) was added to react with any remaining starting material. The reaction was stirred 4 hours then partitioned between EtOAc (100 mL) and H$_2$O (100 mL). The organic layer was washed with dilute NaH$_2$PO$_4$ (100 mL), sat. NaHCO$_3$ (100 mL), brine (100 mL), partially dried (Na$_2$SO$_4$), and concentrated to a solid. The crude product was purified by flash chromatography on silica gel using EtOAc/hexane as eluant to yield the title compound as a solid (0.07 g, 55%).

mp 158–160° C. (dec); MS (APCI) m/e: 331 (M+H)$^+$; $^1$H NMR (300 MHz, DMSO-d$_6$) δ 4.01 (t, J=9.6 Hz, 2 H), 4.48 (t, J=9.6 Hz, 2 H), 7.14 (m, 2 H), 7.47 (m, 2 H), 7.62 (s, 1 H), 8.24 (s, 1 H), 9.19 (s, 1 H); Anal. calcd for C$_{16}$H$_{11}$ClN$_2$O$_2$S: C, 58.09; H, 3.35; N, 8.47. Found: C, 58.16; H, 3.31; N, 8.27.

EXAMPLE 297

4-(4-Chlorophenoxy)-2-(1,3-oxazol-2-yl)thieno[2,3-c]pyridine

The title compound may be produced from Example 296 according to the procedure of Ishibashi, Y., et al. (Tetrahedron Lett. 1996, 37(17), 2997–3000).

EXAMPLE 298

4-(4-Chlorophenoxy)-2-(4,5-dihydro-1H-imidazol-2-yl)thieno[2,3-c]pyridine

A suspension of Example 154 (0.15 g, 0.43 mmol) and calcium oxide (0.12 g, 2.15 mmol) in phenyl ether (10 mL) was heated to 220–250° C. The reaction was stirred 45 minutes over which reaction volume decreased due to evaporation of solvent. The reaction was cooled to room temperature and diluted with 10% MeOH/dichloromethane (25 mnL) then filtered. The filtrate was concentrated and residue was purified by preparative HPLC using a gradient of 30%–90% acetonitrile/water +0.1% TFA over 40 minutes. The product containing fractions were combined and neutralized with sat NaHCO$_3$. The product crystalized upon standing for 3 days and was collected by filtration, and dried in a desiccator to yield the title compound as a tan needles (23 mg, 16%).

mp 154–155° C.; MS (APCI) m/e: 330 (M+H)$^+$; $^1$H NMR (300 MHz, DMSO-d$_6$) δ 3.46 (td, J=9.9, 1.7 Hz, 2H), 3.83 (t, J=9.9 Hz, H), 7.12 (m, 2H), 7.34 (br s, 1H), 7.46 (m, 2H), 7.81 (s, 1H), 8.17 (s, 1H), 9.11 (s, 1H); Anal. calcd for C$_{16}$H$_{12}$ClN$_3$OS: C, 58.27; H, 3.67; N, 12.74. Found: C, 58.15; H, 3.50; N, 12.73.

EXAMPLE 299

4-(4-chlorophenoxy)-2-(1H-imidazol-2-yl)thieno[2,3-c]pyridine

The title compound may be produced from Example 298 according to the procedure of Zimmerman, S. C., et al. (J. Org. Chem. 1989, 54(6), 1256–1264).

EXAMPLE 300

4-Chloro-3-methylthieno[2,3-c]pyridine-2-carboxamide

Example 300 was prepared as in Example 125 from the corresponding 4-chloro methyl ester which was isolated as a by-product from example 125A.

MS (DCI/NH$_3$) m/e: 227 (M+H)$^+$; $^1$H NMR (300 MHz, DMSO-d$_6$) δ 2.55 (s, 3H), 6.95 (d, 2H), 7.57 (d, 2H), 7.90 (b, 1H), 8.00 (b, 1H), 8.27 (s, 1H), 9.15 (s, 1H).

EXAMPLE 301

3-Amino-4-chlorothieno[2,3-c]pyridine-2-carboxamide

Methyl 3-amino-4-chlorothieno[2,3-c]pyridine-2-carboxylate was isolated from the crude product mixture of Example 131B. The mixture was hydrolyzed as described in Example 18, and the resultant acid was coupled with ammonium chloride using the procedure for Example 92. The product was isolated by filtration and washed with water after precipitating the reaction mixture by pouring it into 5% sodium bicarbonate solution.

MS (DCI/NH3) m/e: 228 (M+H)$^+$; $^1$H NMR (300 MHz, DMSO-d$_6$) δ 7.01 (br s, 2H), 7.49 (br s, 2H), 8.42 (s, 1H), 9.11 (s, 1H).

EXAMPLE 302

9-(4-Chlorophenoxy)pyrido[4',3':4,5]thieno[3,2-d]pyrimidine-2,4(1H,3H)-dione

To a suspension of Example 131D (70 mg, 0.22 mmol) in anhydrous tetrahydrofuran (5 mL) under nitrogen atmosphere was added 1,1-carbonyldiimidazole (71 mg, 0.44 mmol) and triethylamine (60 µL, 0.44 mmol). The reaction mixture was stirred at reflux for 48 hours and then ambient temperature for an additional 24 hours. The reaction mixture was poured into a 1:1 solution of water: saturated NH$_4$Cl and the resulting solid collected by filtration. This material was purified by flash chromatography on silica gel eluting with 20% acetone-hexane. The desired fractions were combined, evaporated and slurried in hot EtOAC to obtain title compound (39 mg) in 51% yield.

MS (APCI) m/e: (M–H)$^-$344; $^1$H NMR (300 MHz, DMSO-d$_6$) δ 7.32 (m, 2H), 7.55 (m, 2H), 7.92 (s, 1H), 9.09 (s,1H), 11.22 (br s, 1H), 11.72 (br s, 1H); HPLC: Supelco C-18 column, water:acetonitrile 0:90–90:0, 30 minute elution, flow rate 0.8 mL/min, rt 20.33 min.

EXAMPLE 303

4-(4-Chlorophenoxy)-N,3-dimethylthieno[2,3-c]pyridine-2-carboxamide

Example 125A was prepared as in Example 218 to provide the title compound.

MS (DCI/NH$_3$) m/e: 333 (M+H)$^+$; $^1$H NMR (300 MHz, DMSO-d$_6$) δ 2.55 (s, 3H), 2.80 (d, 3H), 7.05 (d, 2H), 7.45 (d, 2H), 8.20 (s, 1H), 8.55 (b, 1H), 9.18 (s, 1H);

EXAMPLE 304

4-(4-Bromophenoxy)-3-methylthieno[2,3-c] pyridine-2-carboxamide

Example 17A and 4-bromophenol were processed as in Example 125 to provide the title compound.

mp 177–178° C.; MS (DCI/NH$_3$) m/e: 364 (M+H)$^+$; $^1$H NMR (300 MHz, DMSO-d$_6$) δ 2.55 (s, 3H), 6.95 (d, 2H), 7.57 (d, 2H), 7.90 (m, 1H), 8.00 (m, 1H), 8.27 (s, 1H), 9.15 (s, 1H); Anal. Calcd for C$_{15}$H$_{11}$BrN$_2$O$_2$S: C, 49.60; H, 3.05; N, 7.71. Found: C, 49.36; H, 3.24; N, 7.61.

EXAMPLE 305

7-Chloro-4-(4-chlorophenoxy)-3-methylthieno[2,3-c]pyridine-2-carboxamide

EXAMPLE 305A

Methyl 4-(4-Chlorophenoxy)-3-methylthieno[2,3-c] pyridine-2-carboxylate, N-oxide Example 125A was prepared according to the procedure of Example 123A to provide the title compound.

MS (DCI/NH$_3$) m/e: 350 (M+H)$^+$; $^1$H NMR (300 MHz, DMSO-d$_6$) δ 2.78 (s, 3H), 3.88 (s, 3H), 7.28 (m, 2H), 7.51 (m, 2H), 7.68 (br s, 1H), 8.92 (br s, 1H).

EXAMPLE 305B

Methyl 7-Chloro-4-(4-chlorophenoxy)-3-methylthieno[2,3-c]pyridine-2-carboxamide

Example 305A was prepared according to the procedure of Example 1C to provide the title compound.

HPLC: Supelco C-18 column, gradient elution 0.1% aqueous TFA:acetonitrile 0:90–90:0 over 30 minutes, detection at 254 nm, flow rate of 0.8 mL/min, RT 31.64 minutes; MS (DCI/NH$_3$) m/e: 368 (M+H)$^+$; $^1$H NMR (300 MHz, DMSO-d$_6$) δ 2.78 (s, 3H), 3.92 (s, 3H), 7.18 (m, 2H), 7.48 (m, 2H), 8.01 (s, 1H).

EXAMPLE 305C

7-Chloro-4-(4-chlorophenoxy)-3-methylthieno[2,3-c]pyridine-2-carboxylic acid

Example 305B was prepared according to the procedure of Example 18 substituting tetrahydrofuran for isopropanol to provide the title compound.

HPLC: Supelco C-18 column, gradient elution 0.1% aqueous TFA:acetonitrile 0:90–90:0 over 30 minutes, detection at 254 nm, flow rate of 0.8 mL/min, RT 27.25 minutes; MS (APCI) m/e: 354 (M+H)$^+$; $^1$H NMR (300 MHz, DMSO-d$_6$) δ 2.72 (s, 3H), 7.16 (m, 2H), 7.49 (m, 2H), 8.01 (s, 1H).

EXAMPLE 305D

7-Chloro-4-(4-chlorophenoxy)-3-methylthieno[2,3-clipyridine-2-carboxamide

Example 305C was prepared according to Example 92 to provide the title compound.

HPLC: Supelco C-18 column, gradient elution 0.1% aqueous TFA:acetonitrile 0:90–90:0 over 30 minutes, detection at 254 nm, flow rate of 0.8 mL/min, RT 24.75 minutes; MS (DCI/NH$_3$) m/e: 353 (M+H)$^+$; $^1$H NMR (300 MHz, DMSO-d$_6$) δ 2.58 (s, 3H), 7.10 (m, 2H), 7.47 (m, 2H), 8.0 (br s, 1H), 8.02 (s, 1H), 8.03 (br s, 1H).

EXAMPLE 306 tert-Butyl 2-(aminocarbonyl)-4-(4-chlorophenoxy) thieno[2,3-c]pyridine-3-carboxylate

EXAMPLE 306A tert-Butyl 3,5-Dichloropyridine-4-oxalate

Example 17A was followed except for replacing the methyl formate with t-Butyl chlorooxalate to provide the titled compound.

MS (DCI/NH$_3$) m/e: 241 (M+H)$^+$; $^1$H NMR (300 MHz, DMSO-d$_6$) δ 1.5 (s, 9H), 8.85 (s, 2H).

EXAMPLE 306B tert-Butyl 2-(Methoxycarbonyl)-4-(4-chlorophenoxy)thieno[2,3-clipyidine-3-carboxylate Example 306A and 4-chlorophenol were processed as in Example 61 to provide the title compound.

MS (DCI/NH$_3$) m/e: 420 (M+H)$^+$; $^1$H NMR (300 MHz, DMSO-d$_6$) δ 1.42 (s, 9H), 3.95 (s, 3H), 7.18 (d, 2H), 7.50 (d, 2H), 8.05 (s, 1H), 9.20 (s, 1H).

EXAMPLE 306C tert-Butyl 2-(Aminocarbonyl)-4-(4-chlorophenoxy) thieno[2,3-c]pyridine-3-carboxylate Example 306B was prepared as in Example 217 to provide the title compound.

MS (DCI/NH$_3$) m/e: 405 (M+H)$^+$; $^1$H NMR (300 MHz, DMSO-d$_6$) δ 1.35 (s, 9H), 7.10 (d, 2H), 7.45 (d, 2H), 7.95 (m, 1H), 8.08 (s, 1H), 8.14 (m, 1H), 9.18 (s, 1H).

EXAMPLE 306D 2-(Aminocarbonyl)-4-(4-chlorophenoxy)thieno[2,3-c]pyridine-3-carboxylic acid Example 306C (0.08 g, 0.2 mmol) was placed in a cold solution of trifluoroacetic acid (0.5 mL) and methylene chloride (0.5 mL) and stirred for 1 hour. The solution was evaporated and treated slowly with a cold solution of sodium bicarbonate (20 mL), and then the mixture was extracted with ethyl acetate (3×20 mL). The ethyl acetate extract was dried and evaporated to provide the title compound.

MS (DCI/NH$_3$) m/e: 349 (M+H)$^+$; $^1$H NMR (300 MHz, DMSO-d$_6$) δ 7.05 (d, 2H), 7.45 (d, 2H), 7.95 (b, 1H), 8.05 (m, 1H), 8.15 (s, 1H), 9.20 (s, 1H).

EXAMPLE 307

Methyl 4-(4-toluidino)thieno[2,3-c]pyridine-2-carboxamide

A mixture of Example 93C (271 mg, 1 mmol), 4-methyl aniline (150 mg, 1.4 mmol), sodium t-butoxide (134.5 mg, 1.4 mmol), 18-crown-6 (370 mg, 1.4 mmol), Pd$_2$(dba)$_3$ (46 mg, 5 mol %) and BINAP (31 mg, 5 mol %) were combined in a three necked round bottom flask equipped with a condenser, internal temperature probe and a N$_2$ inlet. This was evacuated under nitrogen and anhydrous tetrahydrofuran (5 mL) was added. The reaction mixture was warmed at 45° C. for three days, solid materials were filtered through celite and washed with a mixture of ethyl acetate and acetone. The filtrate was diluted with ethyl acetate (100 mL), washed with brine (2×50 mL), dried (MgSO$_4$) and evaporated to dryness under reduced pressure. The title compound was obtained in 29% yield (86 mg), by flash chromatography on silica gel eluting with 30% acetone-hexane.

MS (DCI/NH$_3$) m/e: 298 (M+H)$^+$; $^1$H NMR (300 MHz, DMSO-d$_6$) δ 2.25 (s, 3H), 2.80 (d, J=6 Hz, 3H), 7.02 (d, J=9 Hz, 2H), 7.10 (d, J=9 Hz, 2H), 8.13 (s, 1H), 8.26 (s, 1H), 8.36 (m, 1H), 8.76 (br s, 1H); $^{13}$C NMR (75 MHz, DMSO-d$_6$) δ 20.4 (CH$_3$), 26.4 (CH$_2$), 118.2 (CH), 118.2 (CH), 122.1 (CH), 129.8 (CH), 130.0 (C), 130.6 (CH), 130.7 (C), 135.9 (C), 136.5 (CH), 137.1 (C), 140.3 (C), 142,3 (C), 161.6 (CO).

EXAMPLE 308

4-(4-Chloroanilino)-N-methylthieno[2,3-c]pyridine-2-carboxamide

The title compound (500 mg, 84%) was prepared as in Example 307 except substituting 4-chloroaniline (510 mg, 4 mmol) for 4-methylaniline and reaction was warmed at 60° C. for 20 hours.

MS (APCI) m/e: 318 (M+H)$^+$, 352 (M+Cl)$^-$; $^1$H NMR (400 MHz, DMSO-d$_6$) d: 2.83 (d, J=4 Hz, 3H), 7.07 (d, J=9 Hz, 2H), 7.32 (d, J=9 Hz, 2H), 8.11 (s, 1H), 8.38 (s, 1H), 8.67 (s, 1H), 8.85 (d, J=4 Hz, 1H), 8.91 (s,1H); $^{13}$C NMR (100 MHz, DMSO-d$_6$) δ 26.3 (CH$_3$), 118.1 (2×CH), 121.7 (CH), 123.6 (C), 129.1 (2×CH), 133.0 (CH), 134.4 (C), 137.1 (C), 137.2 (C), 138.2 (CH), 142.6 (C), 143.2 (C), 161.4 (C).

EXAMPLE 309

Methyl 4-(4-morpholinyl)thieno[2,3-c]pyridine-2-carboxamide

The title compound (105 mg, 38%) was prepared as in Example 308 except substituting morpholine (0.175 mL, 2 mmol) for 4-chloroaniline.

MS (APCI) m/e: 278 (M+H)$^+$, 312 (M+Cl)$^-$; $^1$H NMR (400 MHz, DMSO-d$_6$) δ 2.91 (d, J=4 Hz, 3H), 3.23 (m, 4H), 3.91 (m, 4H), 8.14 (s, 1H), 8.18 (s, 1H), 8.96 (s, 1H), 8.99 (d, J=4 Hz, 1H); $^{13}$C NMR (100 MHz, DMSO-d$_6$) δ 26.1 (CH$_3$), 51.6 (2×CH$_2$), 66.3 (CH$_2$), 121.2 (CH), 131.6 (CH), 137.1 (C), 137.9 (C), 139.0 (C), 143.3 (C), 143.9 (C), 161.3 (CO).

EXAMPLE 311

7-Chloro-4-(4-chlorophenoxy)thieno[2,3-c]pyridine-2-carboxamide

EXAMPLE 311A

Methyl 7-chloro-4-(4-chlorophenoxy)thieno[2,3-c]pyridine-2-carboxylate

Example 61A was prepared as in Example 1C to provide the title compound.

HPLC: Supelco C-18 column, gradient elution of 0.1% aqueous TFA:acetonitrile 0:90–90:0 over 30 minutes, detection at 254 nm, flow rate of 0.8 ml/minutes RT 30.35 minutes; MS (DCI/NH$_3$) m/e: 354 (M+H)$^+$; $^1$H NMR (300 MHz, DMSO-d$_6$) δ 3.91 (s, 3H), 7.14 (m, 2H), 7.45 (m, 2H), 7.91 (s, 1H); 8.24 (s, 1H); 9.21 (s, 1H).

EXAMPLE 311B

7-Chloro-4-(4-chlorophenoxy)thieno[2 3-c]pyridine-2-carboxamide

Example 311A was prepared according to the procedure of Example 44 to provide the title compound.

MS (DCI/NH$_3$) m/e: 339 (M+H)$^+$; $^1$H NMR (300 MHz, DMSO-d$_6$) δ 7.20 (m, 2H), 748 (m, 2H), 7.94 (br s, 1H), 8.04 (s, 1H) 8.22 (s, 1H), 8.49 (br s, 1H); Anal. calcd for C$_{14}$H$_8$Cl$_2$N$_2$O$_2$S: C, 56.42; H, 3.28; N, 10.12. Found: C, 56.31; H, 3.22; N, 10.01;

EXAMPLE 312

7-Chloro-4-(4-chlorophenoxy)-N-methylthieno[2,3-c]pyridine-2-carboxamide

Example 311A was prepared as described in Example 171 to provide the title compound.

MS (DCI/NH$_3$) m/e: 353 (M+H)$^+$; $^1$H NMR (300 MHz, DMSO-d$_6$) δ 2.80 (d, 3H); 7.16 (m, 2H), 7.49 (m, 2H), 8.05 (s, 1H), 8.17 (s, 1H), 9.04 (br s, 2H).

EXAMPLE 313

7-Chloro-4-(4-chlorophenoxy)-N-(2-hydroxyethyl)thieno[2,3-c]pyridine-2-carboxamide Example 311A was prepared according to the procedure of Example 114 to provide the title compound.

HPLC: Supelco C-18 column, gradient elution of 0.1% aqueous TFA:acetonitrile 0:90–90:0 over 30 minutes, detection at 254 nm, flow rate of 0.8 mL/minutes RT 23.49 minutes; mp 129–132° C.; MS (DCI/NH$_3$) m/e: 382 (M+H)$^+$; $^1$H NMR (300 MHz, DMSO-d$_6$) δ 3.33 (m, 2H), 3.51 (m, 2H), 4.82 (t, 1H), 7.19 (m, 2H), 7.48 (m, 2H), 8.08 (s, 1H), 8.27 (s, 1H), 9.12 (br t, 1H), 9.18 (s, 1H), 12.81 (br s, 1H).

EXAMPLE 314

7-Bromo-4-(4-chlorophenoxy)thieno[2,3-c]pyridine-2-carboxamide

EXAMPLE 314A

Methyl 7-Bromo-4-(4-chlorophenoxy)thieno[2,3-c]pyridine-2-carboxylate

Example 123A was prepared as in Example 1C substituting phosphorous oxybromide for phosphorous oxychloride to provide the title compound.

MS (ESI) m/e: 400 (M+H)$^+$; $^1$H NMR (300 MHz, DMSO-d$_6$) δ 3.91 (s, 3H), 7.22 (m, 2H), 7.48 (m, 2H), 8.19 (s, 1H), 8.20 (s, 1H).

EXAMPLE 314B

7-Bromo-4-(4-chlorophenoxy)thieno[2,3-c]pyridine-2-carboxamide

Example 314A was prepared according to Example 44 to provide the title compound.

HPLC: Supelco C-18 column, gradient elution of 0.1% aqueous TFA:acetonitrile 0:90–90:0 over 30 minutes, detection at 254 nm, flow rate of 0.8 mL/min, RT 24.95 minutes; MS (DCI/NH$_3$) m/e: 385 (M+H)$^+$; $^1$H NMR (300 MHz, DMSO-d$_6$) δ 7.22 (m, 2H), 7.44 (m, 2H), 7.95 (s, 1H), 8.02 (s, 1H), 8.29 (s, 1H); 8.51 (br s, 1H).

EXAMPLE 315

7-Bromo-4-(4-chlorophenoxy)-N-methylthieno[2,3-c]pyridine-2-carboxamide

Example 314A was prepared according to the procedure of Example 171 to provide the title compound.

HPLC: Supelco C-18 column, gradient elution of 0.1% aqueous TFA:acetonitrile 0:90–90:0 over 30 minutes, detection at 254 nm, flow rate of 0.8 mL/min, RT 25.40 minutes; MS (DCI/NH$_3$) m/e: 397 (M+H)$^+$; $^1$H NMR (300 MHz, DMSO-d$_6$) δ 2.81 (d, 3H), 3.97 (s, 3H), 7.19 (m, 2H), 7.48 (m, 2H), 8.04 (s, 1H), 8.21 (s, 1H), 9.05 (br s, 1H).

EXAMPLE 316

4-(4-Bromophenoxy)-7-chlorothieno[2,3-c]pyridine-2-carboxamide

Example 316 was prepared as in Example 311 but substituting 4-bromophenol for 4-chlorophenol to provide the title compound.

MS (DCI/NH$_3$) m/e: 383, 385 (M+H)$^+$; $^1$H NMR (300 MHz, DMSO-d$_6$) δ 7.14 (d, 2H, J=8.9 Hz), 7.61 (d, 2H, J=8.8 Hz), 7.98 (br s, 1H), 8.05 (s, 1H), 8.22 (s, 1H), 8.52 (br s, 1H); Anal. calcd for C$_{14}$H$_8$N$_2$O$_2$SBrCl.0.5 H$_2$O: C, 42.82; H, 2,31; N, 7.10. Found: C, 42.62; H, 2.26; N, 6.82.

EXAMPLE 317

4-(4-Bromophenoxy)-7-chloro-N-methylthieno[2,3-c]pyridine-2-carboxamide

Example 317 was prepared as in Example 312 but substituting 4-bromophenol for 4-chlorophenol to provide the title compound.

MS (DCI/NH$_3$) m/e: 397, 399 (M+H)$^+$; $^1$H NMR (300 MHz, DMSO-d$_6$) δ 2.80 (d, 3H, J=4.7 Hz), 7.13 (d, 2H, J=9.2 Hz), 7.60 (d, 2H, J=9.2 Hz), 8.07 (s, 1H), 8.13 (s, 1H), 9.03 (q, 1H, J=4.7 Hz); Anal. calcd for C$_{15}$H$_{10}$N$_2$O$_2$SBrCl: C, 45.30; H, 2.53; N, 7.04. Found: C, 45.25; H, 2,31; N, 6.86.

EXAMPLE 318

7-Chloro-4-[4-(trifluoromethyl)phenoxy]thieno[2,3-c]pyridine-2-carboxamide

Example 17A and 4-trifluoromethylphenol were processed as in Example 311 to provide the title compound.

mp 175–176° C.; MS (DCI/NH$_3$) m/e: 373 (M+H)$^+$; $^1$H NMR (300 MHz, DMSO-d$_6$) δ 7.30 (d, 2H), 7.80 (d, 2H), 8.00 (s, 1H), 8.20 (s, 1H), 8.25 (s, 1H), 8.55 (s, 1H); Anal. Calcd for C$_{16}$H$_{10}$ClF$_3$N$_2$O$_2$S: C, 48.33; H, 2.16; N, 7.52. Found: C, 48.26; H, 2.25; N, 7.40.

EXAMPLE 319

7-Chloro-N-methyl-4-[4-(trifluoromethyl)phenoxy]thieno[2,3-c]pyridine-2-carboxamide Example 17A and 4-trifluoromethylphenol were processed as in Example 312 to provide the title compound.

mp 178–179° C.; MS (DCI/NH$_3$) m/e: 387 (M+H)$^+$; $^1$H NMR (300 MHz, DMSO-d$_6$) δ 2.80 (s, 3H), 7.30 (d, 2H), 7.80 (d, 2H), 8.00 (s, 1H), 8.25 (s, 1H), 8.55 (m, 1H); Anal. Calcd for C$_{16}$H$_{10}$ClF$_3$N$_2$O$_2$S: C, 49.68; H, 2.61; N, 7.24. Found: C, 49.58; H, 2.54; N, 6.94.

EXAMPLE 320

7-Chloro-N-(2-hydroxyethyl)-4-[4-(trifluoromethyl)phenoxy]thieno[2,3-c]pyridine-2-carboxamide Example 320 was prepared according to the procedure of Example 319, with the substitution of aminoethanol for methylamine.

mp 96–97° C.; MS (ESI/NH$_3$) m/e: 415 (M+H)$^+$; $^1$H NMR (300 MHz, CDCl$_3$) δ 3.66 (t, 2H, J=4.8 Hz), 3.87 (t, 2H, J=4.8 Hz), 6.63 (m, 1H), 7.11 (d, 2H, J=8.5 Hz), 7.64 (d, 2H, J=8.5 Hz), 7.72 (s, 1H), 8.02 (s, 1H).

EXAMPLE 321

4-(4-Chlorophenoxy)-N,7-dimethylthieno[2,3-c]pyridine-2-carboxamide

EXAMPLE 321A

Methyl 4-(4-Chlorophenoxy)-N,7-dimethylthieno[2,3-c]pyridine-2-carboxylate

Example 311A was prepared as Example 95A but substituting methyl boronic acid for 4-(triflouoromethyl)phenyl boronic acd and substituting dichlorobis(tricyclohexylphosphine)palladium for tetrakis(triphenylphosphine)palladium and substituting NMP for DME to provide the title compound.

MS (DCI/NH$_3$) m/e: 334 (M+H)$^+$; $^1$H NMR (300 MHz, DMSO-d$_6$) δ 2.74 (d, 3H), 3.91 (s, 3H), 7.14, (m, 2H), 7.44 (m, 2H), 7.91 (s, 1H), 8.22 (s, 1H).

EXAMPLE 321B 4-(4-Chlorophenoxy)-N,7-dimethylthieno[2,3-c]pyridine-2-carboxamide Example 321A was prepared according to the procedure of Example 171 to provide the title compound.

HPLC Supelco C-18 column, gradient elution of 0.1% aqueous TFA:acetonitrile 0:90–90:0 over 30 minutes, detection at 254 nm, flow rate of 0.8 mL/minutes RT 20.70 minutes; MS (DCI/NH$_3$) m/e: 334 (M+H)$^+$; $^1$H NMR (300 MHz, DMSO-d$_6$) δ 2.82 (d, 3H), 7.04 (m, 2H), 7.41 (m, 2H), 8.04, (s, 1H), 8.11 (s, 1H), 8.92 (br s, 1H).

EXAMPLE 322

4-(4-Chlorophenoxy)-7-methoxythieno[2,3-c]pyridine-2-carboxamide

EXAMPLE 322A 4-(4-Chlorophenoxy)-7-methoxythieno[2,3-c]pyridine-2-carboxylic acid Example 311A (100 mg, 0.28 mmol) was dissolved in 25% sodium methoxide in methanol (10 mL) and was warmed to 60° C. in a pressure tube for 3 days. The solvent was removed under reduced pressure and the residue was redissolved in methylene chloride and acidified with formic acid. The organic layer was washed with H$_2$O and brine, dried (Na$_2$SO$_4$) and the solvent removed under reduced pressure to afford the title compound (50 mg, 54%) as an off-white solid.

MS (DCI) m/e 336 (M+H)$^+$; $^1$H NMR (300 MHz, DMSO-d$_6$) δ 4.18 (s, 3H), 6.92 (m, 2H), 7.31 (m, 2H), 7.54 (s, 1H), 7.69 (s, 11H).

EXAMPLE 322B 4-(4-Chloroiphenoxy)-7-methoxythieno[2,3-c]pyridine-2-carboxarmide Example 322A (40 mg, 0.12 mmol) was treated according to the procedure of Example 92 to provide the title compound (23 mg, 0.58 mmol) as a white solid.

mp >250° C.; MS (DCI/NH$_3$) m/e: 335 (M+H)$^+$; $^1$H NMR (300 MHz, DMSO-d$_6$) δ 4.08 (s, 3H), 7.01 (m, 2H), 7.38 (m, 2H), 7.82 (br s, 1H), 7.90 (s, 1H), 8.04 (s, 1H), 8.43 (s, 1H).

EXAMPLE 323

4-(4-ChlorophenoxU)-7-oxo-6,7-dihydrothieno[2,3-c]pyridine-2-carboxamide

EXAMPLE 323A

Methyl 4-(4-Chlorophenoxy)-7-oxo-6,7-dihydrothieno[2,3-c]pyridine-2-carboxylate

A solution of Example 311A (200 mg, 0.597 mmol) in acetic anhydride (20 mL) was heated at reflux for 18 hours. The reaction was cooled and poured over ice. The mixture was allowed to stir 1 hour before CH$_2$Cl$_2$ (100 mL) was added. The organic extracts were washed with 1 N NaOH (100 mL), H$_2$O (50 mL) brine (50 mL), dried (Na$_2$SO$_4$), filtered and rotoevaporated to afford a crude brown residue. This residue was directly dissolved in DMF (20 mL) and H$_2$O (3 mL), treated with K$_2$CO$_3$ and warmed to 60° C. for 2 hours. The reaction was allowed to cool to room temperature and then was rotoevaporated. The crude residue was purified by column chromatography on silica gel eluting with 10% ethyl acetate/hexane with a gradient to 50% ethyl acetate/hexane to provide the title compound.

MS (DCI/NH$_3$) m/e: 336 (M+H)$^+$; $^1$H NMR (300 MHz, DMSO-d$_6$) δ 3.82 (s, 3H), 7.09 (m, 2H), 7.38 (m, 2H), 7.42 (s, 1H), 7.52 (s, 1H), 11.84 (br s, 1H).

EXAMPLE 323B 4-(4-Chlorophenoxy)-7-oxo-6,7-dihydrothieno[2,3-c]pyridine-2-carboxamide Example 323A was prepared according to Example 44 to provide the title compound.

HPLC: Supelco C-18 column, eluent gradient of water-:acetonitrile 0:90–90:0 over 30 minutes, detection at 254 nm, flow rate of 0.8 mL/min, RT 18.61 minutes; mp >250° C.; MS (APCI) m/e: 321 (M+H)$^+$; $^1$H NMR (300 MHz, DMSO-d$_6$) δ 7.04 (m, 2H), 7.38 (m, 2H), 7.40 (s, 1H), 7.75 (s, 1H), 8.32 (br s, 1H).

EXAMPLE 324

4-(4-Chlorophenoxy)-N-methyl-7-(methylamino)thieno[2,3-c]pyridine-2-carboxamide

Example 311A (27 mg, 76 mmol) was treated according to the procedure of Barraclough, et. al (J. Med. Chem. 1990, 33, 2231) to afford the title compound (12 mg, 45% yield).

MS (DCI/NH$_3$) m/e: 348 ($^{35}$Cl)/350 ($^{37}$Cl); $^1$H NMR (CDCl$_3$, 300 MHz) δ 2.98 (d, 3H), 3.16 (d, 3H), 4.65 (d,1H), 6.56 (d, 1H), 6.83 (d, 2H), 7.27 (d, 2H), 7.47 (s, 1H), 7.86 (s, 1H).

EXAMPLE 325

N-Methyl-7-(4-methylphenoxy)[1,3]thiazolo[5,4-c]pyridine-2-carboxamide

Example 142D (10 mg, 33 mmol) was treated according to the procedure of Example 96 to give the title compound (1.5 mg, 75%) as a white solid.

MS (DCI/NH$_3$) m/e: 300 (M+H)$^+$, 317 (M+NH$_3$)$^+$; $^1$H NMR (CDCl$_3$, 300 MHz) δ 2.39 (s, 3H), 3.07 (d, J=5.1 Hz, 3H), 7.06 (d, J=8.8 Hz, 2H), 7.23 (d, J=8.5 Hz, 2H), 7.52 (d, J=5.5 Hz, 1H), 8.18 (s, 1H), 9.02 (s, 1H).

EXAMPLE 327

4-(4-Chlorophenoxy)furo[2,3-c]pyridine-2-carboxamide

EXAMPLE 327A

Ethyl 4-(4-Chlorolphenoxy)furo[2,3-c]pyridine-2-carboxylate

To a solution of 4-chlorophenol (1.08 g, 8.7 mmol) in anhydrous tetrahydrofuran (25 mL) under nitrogen atmosphere at 0° C. was added dropwise a solution of potassium tert-butoxide (1.0 M solution in THF, 8.7 mL, 8.7 mmol). The reaction mixture was then stirred and heated at 65° C. for 2 hours, cooled to 0° C., then treated with Example 17A (1.0 g, 5.7 mmol) in anhydrous tetrahydrofuran (10 mL) and warmed at 65° C. for 2 hours. The reaction was cooled to 0° C., ethyl glycolate (1.07 mL, 11.4 mmol) and cesium carbonate (3.0 g, 9.2 mmol) were added, and the mixture was heated at 65° C. for 3 hours. The reaction was cooled and concentrated, and the residue was then diluted with ethyl acetate (50 mL) and washed with brine (3×50 mL), then dried (MgSO$_4$). The ethyl acetate was then evaporated to give an oil. Purification by flash chromatography on silica gel eluting with 10% ethyl acetate-hexane yielded 0.110 g (6.1%) of the title compound as a glassy residue.

MS (DCI/NH$_3$) m/e: 318 (M+H)$^+$; $^1$H NMR (300 MHz, DMSO-d$_6$) δ 1.35 (t, 2H, CH$_2$), 4.4 (q, 3H, CH$_3$), 7.2 (d, J=9 Hz, 2H), 7.5 (d, J=9 Hz, 2H), 8.09 (s, 1H), 8.23 (s, 1H), 9.25 (s, 1H).

EXAMPLE 327B 4-(4-Chlorophenoxy)furo[2,3-c]pyridine-2-carboxylic acid

To a solution of lithium hydroxide monohydrate (0.0113 g, 0.5 mmol), in tetrahydrofuran (5 mL) and water (1 mL) was added Example 327A (0.1 g, 0.3 mmol), and the mixture was heated at 50° C. for 2 hours. The mixture was cooled, and then fonnic acid was added until it was acidic (pH?). The mixture was then extracted with ethyl acetate (50 mL), and the extract was washed with brine (2×20 mL), dried (MgSO$_4$), and evaporated. Purification by flask chromatography on silica gel eluting with 20% acetone-hexane yielded 0.710 g (81.6%) of the title compound as a glassy residue.

MS (DCI/NH$_3$) m/e: 290 (M+H)$^+$; $^1$H NMR (300 MHz, DMSO-d$_6$) δ 3.4 (br s, 1H), 7.2 (d, J=9 Hz, 2H), 7.5 (d, J=9 Hz, 2H), 8.09 (s, 1H), 8.23 (s, 1H), 9.25 (s, 1H).

EXAMPLE 327C 4-(4-Chlorophenoxy)furo[2,3-c]pyridine-2-carboxamide

A solution of Example 327B (0.15 g, 0.5 mmol) in DMF (10 mL) was treated with 1-hydroxybenzotriazole hydrate (0.104 g, 0.66 mmol), NH$_4$Cl (0.0948 g, 0.017 mmol), and 4-methylmorpholine (0.141 g, 0.14 mmol). The solution was cooled to 0° C. and treated with 1-[3-(dimethylamino)propyl]-3-ethylcarbodiimide hydrochloride (0.115 g, 0.6 mmol), warmed to room temperature, stirred overnight, poured into saturated NaHCO$_3$, filtered, washed with brine (3×20 mL), dried (MgSO$_4$), and evaporated. Purification by flask chromatography on silica gel eluting with 20% acetone-hexane yielded 0.030 g (21%) of the title compound as a glassy residue.

MS (DCI/NH$_3$) m/e: 289 (M+H)$^+$; $^1$H NMR (300 MHz, DMSO-d$_6$) δ 7.18 (d, 2H), 7.29 (s, 1H), 7.5 (d, 2H), 7.82 (br s, 1H), 8.25 (s, 1H), 8.35 (br s, 1H), 8.95 (s, 1H);

EXAMPLE 328

4-(4-Chlorophenoxy)furo[2,3-c]pyridine-2-carbothioamide

To a solution of Example 327 (0.06 g, 0.2 mmol) in toluene (5 mL) was added Lawesson's reagent (0.1 g, 0.2 mmol). The reaction was then refluxed for 1 hour, then cooled, evaporated and dissolved in ethyl acetate. The ethyl acetate solution was washed with brine (3×15 mL), dried (MgSO$_4$), and evaporated. Purification by flask chromatography on silica gel eluting with 20% acetone-hexane yielded 0.022 g (37%) of the title compound as a light yellow solid.

MS (DCI/NH$_3$) m/e: 305 (M+H)$^+$; $^1$H NMR (300 MHz, DMSO-d$_6$) δ 7.20 (d, 2H), 7.29 (s, 1H), 7.5 (d, 2H), 8.25 (s, 1H), 8.82 (s, 1H), 9.95 (b, 2H).

EXAMPLE 329

4-(2-Phenylethenyl)thieno[2,3-c]pyridine-2-carboxamide

EXAMPLE 329A tert-Butyl E- and Z-4-(2-phenylethenyl)thieno[2,3-c]pyridine-2-carboxylate

To a stirred solution of diethyl benzylphosphonate (0.08 mL, 0.38 mmol) in dichloromethane (2 mL) at −78° C., a 0.5 M solution of potassium bis(trimethylsilyl)amide in toluene (0.84 mL, 0.42 mmol) was added dropwise. After 45 min, a solution of Example 237E (0.10 g, 0.38 mmol) in dichloromethane (3 mL) was slowly added and reaction stirred 1 hour. Bath was removed and reaction stirred 20 minutes. Reaction was quenched into a dilute aqueous solution of NaHCO$_3$. Aqueous was extracted with dichloromethane (2×25 mL), ethyl acetate (2×25 mL). All organic phases were combined, dried (Na$_2$SO$_4$), and concentrated to yield a colored oil. The residue was purified by flash chromatography on silica gel using EtOAc/hexane as eluent. The mixture of stereoisomers was dried in a desiccator to yield a solid (0.07 g, 55%): MS (APCI) m/e: 338 (M+H)$^+$.

EXAMPLE 329B

E-4-(2-Phenylethenyl)thieno[2,3-c]pyridine-2-carboxamide

Example 329A (0.07 g, 0.21 mmol) was dissolved in a solution of 10% H$_2$SO$_4$/MeOH (10 mL). Solution was heated to reflux for 6 hours then stirred at room temperature for 16 hours. The reaction was concentrated under reduced pressure, then basified with sat. NaHCO$_3$ (50 mL). The aqueous phase was extracted with dichloromethane (2×50 mL) and the organic extracts were combined. The organic layer was washed with a dilute brine solution (100 mL), dried (Na$_2$SO$_4$), filtered, and concentrated under reduced pressure to a colored residue. The residue was dissolved in methanol (8 mL) and chloroform (1 mL). A balloon of ammonia gas was applied and reaction heated to 35° C. for 24 hours. The reaction was concentrated and the residue was purified by HPLC using a gradient of 25%–65% acetonitrile/water +0.1% TFA over 40 minutes. Products were neutralized with Sat. NaHCO$_3$ to yield the title compound (27 mg, 46%), and additionally the corresponding Z-isomer (14 mg, 24%).

mp 257–258° C.; MS (DCI/NH$_3$) m/e: 281 (M+H)$^+$; $^1$H NMR (300 MHz, DMSO-d$_6$) δ 7.34 (dd, J=7.6, 7.2 Hz, 1H), 7.46 (dd, J=7.6, 7.2 Hz, 2H), 7.55 (d, J=16.5 Hz, 1H), 7.64 (d, J=16.5 Hz, 1H), 7.73 (d, J=7.2 Hz, 2H), 7.78 (br s, 1H), 8.37 (br s, 1H), 8.62 (s, 1H), 8.85 (br s, 1H), 9.18 (s, 1H); Anal calcd for (C$_{16}$H$_{12}$N$_2$OS 0.2 H$_2$O): C, 67.68; H, 4.40; N, 9.87. Found: C, 67.47; H, 4.18; N, 9.84.

EXAMPLE 330

4-(4-Chlorophenyl)thieno[2,3-c]pyridine-2-carboxamide

EXAMPLE 330A

4-(4-Chlorophenyl)thieno[2,3-c]pyridine-2-carboxalate

The title compound (160 mg, 53%) was prepared as in Example 95A but substituting 4-cholorophenyl boronic acid for 4-(trifluoromethyl)phenyl boronic acid.

MS (APCI) m/e: 304 (M+H)$^+$; $^1$H NMR (300 MHz, DMSO-d$_6$) δ 3.92 (s, 3H), 7.69 (m, 4H), 8.30 (s, 1H), 8.60 (s, 1H), 9.42 (s, 1H).

EXAMPLE 330B

4-(4-Chlorophenyl)thieno[2,3-c]pyridine-2-carboxamide

Example 330A was prepared as in Example 44 to provide the title compound (60 mg, 60%).

MS (APCI) m/e: 289 (M+H)$^+$; $^1$H NMR (400 MHz, DMSO-d$_6$) δ 7.63 (d, J=8 Hz, 2H), 7.69 (d, J=8 Hz, 2H), 7.77 (s, 1H), 8.19 (s, 1H), 8.41 (s, 1H), 8.51 (s, 1H), 9.30 (s, 1H).

EXAMPLE 331

4-[3-(Trifluoromethyl)phenyl]thieno[2,3-c]pyridine-2-carboxalamide

EXAMPLE 331A

4-[3-(trifluoromethyl)phenyl]thieno[2,3-c]pyridine-2-carboxalate

The title compound (100 mg, 30%) was prepared as in Example 95A but substituting 4-(trifluoromethy)lphenyl boronic acid for 4-(trifluoromethyl)phenyl boronic acid.

MS (APCI) m/e: 338 (M+H)$^+$; $^1$H NMR (300 MHz, DMSO-d$_6$) δ 3.92 (s, 3H), 7.81–7.93 (m, 4H), 8.01 (s, 1H), 8.67 (s, 1H), 9.46 (s, 1H).

EXAMPLE 331B

4-[3-(trifluoromethyl)phenyl]thieno[2,3-c]pyridine-2-carboxalamide

Example 331A was prepared as in Example 44 to provide the title compound (90 mg, 94%).

MS (APCI) m/e: 323(M+H)$^+$; $^1$H NMR (400 MHz, DMSO-d$_6$) δ 7.85 (s, 1H), 7.90–7.97 (m, 4H), 8.25 (s, 1H), 8.46 (s, 1H), 8.69 (s, 1H), 9.38 (s, 1H).

EXAMPLE 332

4-(3-Chlorophenyl)thieno[2,3-c]pyridine-2-carboxamide

EXAMPLE 332A

4-(3-Chlorophenyl)thieno[2,3-c]pyridine-2-carboxalate

The title compound (130 mg, 43%) was prepared as in Example 95A but substituting 3-chlorophenyl boronic acid for 4-chlorophenyl boronic acid.

MS (APCI) m/e: 304 (M+H)+; 1H NMR (300 MHz, DMSO-d6) δ 3.92 (s, 3H), 7.59–7.68 (m, 3H), 7.75 (s, 1H), 8.02 (s, 1H), 8.62 (s, 1H), 9.43 (s, 1H).

EXAMPLE 332B 4-(3-Chlorophenyl)thieno[2,3-c]pyridine-2-carboxamide

Example 332A was prepared as in Example 44 to provide the title compound (82 mg, 86%).

MS (APCI) m/e: 288 (M+H)+; 1H NMR (400 MHz, DMSO-d6) δ 7.58–7.62 (m, 3H), 7.62 (s, 1H), 7.69 (s, 1H), 8.19 (s, 1H), 8.49 (s, 1H), 8.51 (s, 1H), 9.31 (s, 1H).

EXAMPLE 333

4-(4-Bromophenyl)thieno[2,3-c]pyridine-2-carboxamide

EXAMPLE 333A 4-(4-Bromophenyl)thieno[2,3-c]pyridine-2-carboxalate

The title compound (148 mg, 42%) was prepared as in Example 95A but substituting 4-bromophenyl boronic acid for 4-(trifluoromethyl)phenyl boronic acid.

MS (APCI) m/e 305 (M+H)+; 1H NMR (300 MHz, DMSO-d6) δ 3.91 (s, 3H), 7.61 (d, J=7.5 Hz, 2H), 7.77 (d, J=7.5 Hz, 2H), 8.02 (s, 1H), 8.57 (s, 1H), 9.40 (s, 1H).

EXAMPLE 333B 4-(4-bromophenyl)thieno[2,3-c]pyridine-2-carboxamide

Example 333A was prepared as in Example 44 to provide the title compound (118 mg, 88%).

MS (APCI) m/e: 333, 335 (1:1) (M+H)+; 1H NMR (300 MHz, DMSO-d6) δ 7.63 (d, J=7.5 Hz, 2H), 7.79 (d, J=7.5 Hz, 2H), 7.84 (s, 1H), 8.22 (s, 1H), 8.46 (s, 1H), 9.33 (s, 1H).

EXAMPLE 334

4-(3-Aminophenyl)thieno[2,3-c]pyridine-2-carboxamide

EXAMPLE 334A 4-(3-Aminoophenyl)thieno[2,3-c]pyridine-2-carboxalate

The title compound (90 mg, 32%) was prepared as in Example 95A but substituting 3-aminophenyl boronic acid for 4-(trifluoromethyl)phenyl boronic acid.

MS (APCI) m/e: 285 (M+H)+; 1H NMR (300 MHz, DMSO-d6) δ 3.92 (s, 3H), 5.34 (s, 2H), 6.67–6.76 (m, 2H), 6.81 (m, 1H), 7.22 (t, J=7.5 Hz, 1H), 8.07 (s, 1H), 8.53 (s, 1H), 9.36 (s, 1H).

EXAMPLE 334B 4-(3-Aminophenyl)thieno[2,3-c]pyridine-2-carboxamide

Example 334A was prepared as in Example 44 to provide the title compound (83 mg, 98%).

MS (APCI) m/e 270 (M+H)+; 1H NMR (300 MHz, DMSO-d6) δ 5.30 (s, 2H), 6.67–6.82 (m, 3H), 7.22 (t, J=7.5 Hz, 1H), 7.79 (s, 1H), 8.23 (s, 1H), 8.43 (s, 1H), 8.51 (s, 1H), 9.25 (s, 1H).

EXAMPLE 335

4-(3,5-Dichlorohenyl)thieno[2,3-c]pyridine-2-carboxamide

EXAMPLE 335A 4-(3,5-Dichlorophenyl)thieno[2,3-c]pyridine-2-carboxalate

The title compound (90 mg, 27%) was prepared as in Example 95A but substituting 3,5-dichlorophenyl boronic acid for 4-(trifluoromethyl)phenyl boronic acid.

MS (APCI) m/e: 338 (M+H)+.

EXAMPLE 335B 4-(3,5-Dichlorohenyl)thieno[2,3-c]pyridine-2-carboxamide

Example 335A was prepared as in Example 44 to provide the title compound (21 mg, 24%).

MS (APCI) m/e: 323 (M+H)+; 1H NMR (300 MHz, DMSO-d6) δ 7.73 (d, J=2.25 Hz, 2H), 7.80 (m, 1H), 7.88 (s, 1H), 8.20 (s, 1H), 8.53 (s, 1H), 8.56 (s, 1H), 9.36 (s, 1H).

EXAMPLE 336

4-(2,4-Dichlorohenyl)thieno[2,3-c]pnridine-2-carboxamide

EXAMPLE 336A 4-(2,4-Dichlorophenyl)thieno[2,3-c]pyridine-2-carboxalate

The title compound (100 mg, 30%) was prepared as in Example 95A but substituting 2,4-dichlorophenyl boronic acid for 4-(trifluoromethyl)phenyl boronic acid.

MS (APCI) m/e: 338 (M+H)+; 1H NMR (300 MHz, DMSO-d6) δ 3.38 (s, 3H), 7.59 (s, 1H), 7.61 (d, J=2.25 Hz, 1H), 7.70 (s, 1H), 7.86 (d, J=2.25 Hz, 1H), 8.49 (s, 1H), 9.45 (s, 1H).

EXAMPLE 336B 4-(2,4-Dichlorohenyl)thieno[2,3-c]pyridine-2-carboxamide

Example 336A was prepared as in Example 44 to provide the title compound.

1H NMR (300 MHz, DMSO-d6) δ 7.60 (s, 1H), 7.64 (m, 1H), 7.81 (br.s, 1H), 7.87 (s, 1H), 7.91 (m, 1H), 8.37 (br.s, 1H), 8.45 (s, 1H), 9.37(s, 1H).

EXAMPLE 337

4-(3,4-Dichlorohenyl)thieno[2,3-c]pyridine-2-carboxamnide

EXAMPLE 337A 4-(3,4-Dichluorophenyl)thieno[2,3-c]pyridine-2-carboxalate

The title compound (130 mg, 39%) was prepared as in Example 95A but substituting 3,4-dichlorophenyl boronic acid for 4-(trifluoromethyl)phenyl boronic acid.

MS (APCI) m/e: 338 (M+H)+; 1H NMR (300 MHz, DMSO-d6) δ 3.94 (s, 3H), 7.67–7.76 (m, 1H), 7.85 (m, 1H), 7.79 (d, J=2.25 Hz, 1H), 8.06 (s, 1H), 8.63 (s, 1H), 9.44 (s, 1H).

EXAMPLE 337B 4-(3,4-Dichlorohenyl)thieno[2,3-c]pyridine-2-carboxamide

Example 337A was prepared as in Example 44 to provide the title compound (44 mg, 46%).

MS (APCI) m/e: 323(M+H)+; 1H NMR (300 MHz, DMSO-d6) δ 7.65–7.68 (m, 1H), 7.84–7.87 (m, 2H), 8.96 (d, J=2.25 Hz, 1H), 8.21 (s,1H), 8.47 (s, 1H), 8.56 (s, 1H), 9.35 (s, 1H).

EXAMPLE 338

4-[2,4-Difluorophenyl]thieno[2,3-c]pyridine-2-carboxamide

EXAMPLE 338A

4-[2,4-Difluorophenyl]thieno[2,3-c]pyridine-2-carboxalate

The title compound (130 mg, 42%) was prepared as in Example 95A but substituting 2,4-difluorophenyl boronic acid for 4-(trifluoromethyl)phenyl boronic acid.

MS (APCI) m/e: 306 (M+H)+; 1H NMR (300 MHz, DMSO-d6) δ 3.90 (s, 3H), 7.26 (m, 1H), 7.45 (m, 1H), 7.63 (m, 1H), 7.81 (d, J=3 Hz, 1H), 8.55 (s, 1H), 9.44(s, 1H).

EXAMPLE 338B

4-[2,4-Difluorophenyl]thieno[2,3-c]pyridine-2-carboxamide

Example 338A was processed as in Example 44 to provide the title compound.

MS (APCI) m/e: 291 (M+H)+; 1H NMR (300 MHz, DMSO-d6) δ 7.30 (m, 1H), 7.49 (m,1H), 7.66 (m, 1H), 7.77 (s, 1H), 7.99 (s, 1H), 8.39 (s, 1H), 8.47 (s, 1H), 9.34 (s, 1H).

EXAMPLE 339

4-[4-Fluorphenyl]thieno[2,3-c]pyridine-2-carboxamide

EXAMPLE 339A 4-(4-Fluorolphenyl)thieno[2,3-c]pyridine-2-carboxalate

The title compound (100 mg, 35%) was prepared as in Example 95A but substituting 4-fluorophenyl boronic acid for 4-(trifluoromethyl)phenyl boronic acid.

MS (APCI) m/e: 288 (M+H)+; 1H NMR (300 MHz, DMSO-d6) δ 3.89 (s, 3H), 7.38–7.48 (m, 2H), 7.55–7.64 (m, 1H), 7.78 (d, J=3 Hz, 1H), 8.57 (s, 1H), 9.44 (s, 1H).

EXAMPLE 339B

4-[4-Fluorphenyl]thieno[2,3-c]pyridine-2-carboxamide

Example 339A was processed as in Example 44 to provide the title compound.

MS (APCI) m/e: 273 (M+H)+; 1H NMR (300 MHz, DMSO-d6) δ 7.40–7.50 (m, 2H), 7.57–7.65 (m, 2H), 7.81 (s, 1H), 8.01 (s, 1H), 8.47 (s, 1H), 8.51 (s, 1H), 9.36 (s, 1H).

EXAMPLE 340

5-Chloro-4-(4-chlorophenoxy)thieno[2,3-c]pyridine-2-carboxamide

EXAMPLE 340A 2,3,5-Trichloro-4-formylpyridine

A solution of lithium diisopropylamide (7.3 mL, 1.5 M in cyclohexane, 11 mmol) in 10 mL of dry THF under nitrogen at −78° C. was treated with 2,3,5-trichloropyridine (2 g, 11 mmol) in 20 mL THF over a 30 minute period, stirred an additional 30 minutes, then methyl formate (1.4 mL, 1.3 g, 22 mmol) in 14 mL THF was added slowly to the brown solution over 15 minutes, allowed to slowly warm to room temperature and stirred overnight. The resultant dark brown solution was poured onto ice and saturated NaHCO3, extracted with ethyl acetate, washed with brine, dried (Na2SO4) and concentrated. The brown oil was flash chromatographed on silica gel with 20–33% ethyl acetate/hexane to provide the title compound (1.7 g, 74%).

MS (APCI-NH3) m/e: 211 (M+H)+, 229 (M+NH4)+; 1H NMR (300 MHz, DMSO-d6) δ 10.26 (s, 1H), 8.70 (s, 1H).

EXAMPLE 340B

2-Chloro-3,5-bis(4-bromophenoxy)-4-pyridinecarboxaldehyde

A solution of 4-bromophenol (1.04 g, 6 mmol) in 4 mL THF at 0° C. was treated with potassium t-butoxide (4 mL, 1 M in THF, 4 mmol) via syringe, allowed to warm to room temperature and stirred one hour, cooled to 0° C., Example 340A (390 mg, 2 mmol) in 2 mL THF was added, the reaction heated to 60° C. for two hours, and then allowed to cool to room temperature. The reaction mixture was diluted with ethyl acetate, washed with 1 N NaOH, brine, dried (Na2SO4) and concentrated. The brown residue was flash chromatographed on silica gel twice with 1–2% methanol/dichloromethane and then 5–20% ethyl acetate/hexane to provide the title compound (235 mg, 24%).

MS (APCI-NH3) m/e: 483 (M–H)−, 517 (M+Cl)−; 1H NMR (300 MHz, DMSO-d6) δ 10.20 (s, 1H), 8.24 (s, 1H), 7.63 (m, 2H), 7.53 (m, 2H), 7.24 (m, 2H), 6.99 (m, 2H).

EXAMPLE 340C

Methyl 5-Chloro-4-(4-chlorophenoxy)thieno[2,3-c]yridine-2-carboxyylate

A solution of 340B (227 mg, 0.47 mmol) in 2 mL THF was treated with methyl thioglycolate (50 µL, 0.52 mmol) followed by powdered CS2CO3 (179 mg, 0.55 mmol), stirred at room temperature for 21 hours, heated to 60° C. for 15 minutes, then allowed to cool to room temperature. The reaction was diluted with ethyl acetate and distilled water, washed with 1 M K2CN3, brine, dried (MgSO4) and concentrated. The residue was flash chromatographed on silica gel with 5–20% ethyl acetate/hexane followed by HPLC purification (C-18), gradient eluent of 30–90% CH3CN/H2O with 0.1% TFA to provide the title compound (6 mg, 3%).

MS (APCI-NH3) m/e: 400 (M+H)+; 1H NMR (300 MHz, DMSO-d6) δ 9.20 (s, 1H), 7.78 (s, 1H), 7.51 (d, 2H), 6.93 (d, 2H), 3.90 (s, 3H).

EXAMPLE 340D

5-Chloro-4-(4-chlorophenoxy)thieno[2,3-c]pyridine-2-carboxamide

A solution of 340C (5 mg, 0.013 mmol) in 1 mL methanol and 1 mL dichloromethane was treated with 2M ammonia in methanol (3 mL, 6 mmol) in a pressure tube and heated to 60° C. for 4 hours, allowed to cool to room temperature, and concentrated. The residue was filtered through a plug of silica with 95/5 dichloromethane/methanol, concentrated, then purified by reverse phase HPLC (C-8) 20–75% CH3CN/H2O with 0.1% TFA to provide the title compound (4.2 mg, 84%).

HPLC (C-18, 4.6×250 mm), 0.8 mL/min, λ=254 nm, CH$_3$CN:H$_2$O with) 0.1% TFA 0–90%, RT 23.3 min (98.52% area); MS (APCI-NH$_3$) m/e: 385 (M+H)$^+$; $^1$H NMR (300 MHz, MeOH-d$_4$) δ 8.98 (s, 1H), 7.9 (s, 1H), 7.49 (d, 2H), 6.83 (d, 2H).

The foregoing is merely illustrative and is not intended to limit the invention to the disclosed compounds. Variations and changes which are obvious to one skilled in the art are to be within the scope and nature of the invention which are defined in the appended claims.

What is claimed is:

1. A compound having Formula I

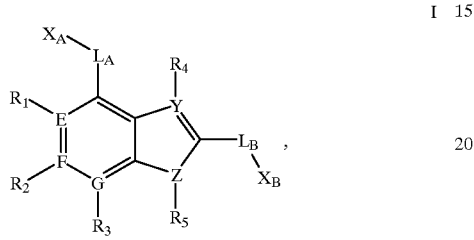

I or a pharmaceutically acceptable salt or prodrug thereof, where

F is selected from nitrogen and N$^+$–O$^-$;

E and G are
  carbon;

Y is carbon; Z is
  S(O)$_t$ where t is 0–2;

L$_A$ is selected from
  (a) —O— and
  (b) —S(O)$_t$—;

X$_A$ is
  aryl,
    where the aryl can be optionally substituted with 1, 2, 3, 4, or 5 substituents independently selected from
    (a) alkyl of one to twenty carbons,
    (b) alkyl of one to ten carbons substituted with 1, 2, or 3 substituents independently selected from
      (i) —OR$_{11}$ where R$_{11}$ is selected from
        hydrogen,
        —C(W)R$_{12}$ where R$_{12}$ is selected from
          alkyl of one to ten carbons,
          cycloalkyl of three to ten carbons, and
          aryl,
      (ii) alkoxy of one to ten carbons optionally substituted with 1 or 2 substituents independently selected from
        alkoxy and
        alkoxyalkoxy,
      (iii) spiroalkyl of three to ten carbons, and
      (iv) halo,
    (c) alkoxy of one to ten carbons optionally substituted with 1 or 2 substituents independently selected from
      (i) alkoxy and
      (ii) alkoxyalkoxy,
    (d) thioalkoxy of one to ten carbons,
    (e) halo,
    (f) perfluoroalkyl of one to three carbons,
    (g) alkenyl of two to ten carbons optionally substituted with 1 or 2 substituents independently selected from
      (i) —C(W)R$_{10}$ where R$_{10}$ is selected from
        hydrogen,
        alkyl of one to ten carbons optionally substituted with 1 or 2 substituents independently selected from
          aryl and
          cycloalkyl of three to ten carbons and
      (ii) —C(W)R$_{12}$,
    (h) —CO$_2$R$_7$ where R$_7$ is selected from
      (i) hydrogen and
      (ii) alkyl of one to ten carbons optionally substituted with 1 or 2 substituents independently selected from
        ary and
        cycloalkyl of three to ten carbons,
    (i) —NR$_8$R$_9$ where R$_8$ and R$_9$ are independently selected from
      (i) hydrogen,
      (ii) alkyl of one to six carbons optionally substituted with 1 or 2 substituents independently selected from
        —OH,
        aryl,
        cycloalkyl of three to ten carbons, and
        —NR$_A$R$_B$ where R$_A$ and R$_B$ are independently selected from
          hydrogen and
          alkyl of one to six carbons optionally substituted with 1 or 2 —OH substituents
      (iii) alkanoyl where the alkyl part is of one to ten carbons,
      (iv) cycloalkyl of three to ten carbons,
      (v) alkoxy, and
      (vi) aryl, where the aryl is substituted with 1 or 2 substituents independently selected from
        alkyl of one to six carbons and
        halo,
    (j) aryl,
    (k) —C(W)R$_{12}$,
    (l) —CHO,
    (m) —C(O)NR$_8$R$_9$,
    (n) —CN,
    (o) —C(W)R$_{10}$,
    (p) ethylenedioxy, and
    (q) —OCF$_3$;

L$_B$ is
  —C(W)— where W is selected from O and S;

X$_B$ is —NR$_{17}$R$_{18}$ where R$_{17}$ and R$_{18}$ are independently selected from
  (a) hydrogen,
  (b) alkyl of one to ten carbons optionally substituted with 1, 2, or 3 substituents independently selected from
    (i) —OH,
    (ii) —C(W)R$_{10}$,
    (iii) —NR$_A$C(=NR$_{13}$)NR$_B$R$_{19}$
    where R$_{13}$ is selected from
      hydrogen,
      —NO$_2$,
      —CN, and
      —OR$_{14}$ where R$_{14}$ is selected from
        hydrogen,
        aryl, and
        alkyl of one to ten carbons optionally substituted with 1 or 2 substituents independently selected from
          aryl and —C(O)R$_{15}$ where R$_{15}$ is selected from
  hydrogen,
  —OH,
  alkoxy, and
  NR$_A$R$_B$ and
R$_{19}$ is selected from
  hydrogen,
  alkyl of one to ten carbons, and
  —NO$_2$,
  (iv) heterocycle,
  (v) aryl,
  (vi) halo, and
  (vii) —NR$_A$R$_B$,
(c) alkoxy of one to ten carbons,
(d) aryl optionally substituted with 1, 2, or 3 substituents independently selected from
  (i) halo,
  (ii) alkyl of one to ten carbons,
  (iii) alkoxy of one to ten carbons, and
  (iv) perfluoroalkyl of one to three carbons,
(e) heterocycle,
(f) —NR$_A$R$_B$,
(g) —C(O)R$_{20}$ where R$_{20}$ is selected from
  (i) hydrogen,
  (ii) alkyl of one to ten carbons,
  (iii) —OR$_{12}$, and
  (iv) —NR$_A$R$_B$,
(h) cycloalkyl of three to ten carbons, and
(i) —OH;
R$_1$, R$_3$, and R$_4$ are independently selected from
(a) hydrogen,
(b) alkyl of one to six carbons optionally substituted with 1 or 2 substituents independently selected from
  (i) —OC(O)R$_{22}$, where R$_{22}$ is selected from
    alkyl,
    alkoxy, and
    —NR$_A$R$_B$,
  (ii) alkoxy,
  (iii) —OH,
  (iv) —NR$_A$R$_B$,
  (v) heterocycle, and
  (vi) aryl,
(c) —CO$_2$R$_7$,
(d) —C(O)NR$_A$R$_B$,
(e) —SR$_{23}$ where R$_{23}$ is selected from
  (i) hydrogen,
  (ii) alkyl of one to six carbons,
  (iii) aryl optionally substituted with 1 or 2 substituents selected from
    alkyl of one to six carbons and
    halo,
(f) —NR$_A$R$_B$,
(g) halo,
(h) alkoxy of one to six carbons,
(i) perfluoroalkyl of one to three carbons,
(j) —OH, and
(k) heterocycle; and
R$_2$ and R$_5$ are absent.
2. A compound selected from the group consisting of
4-[(4-methylphenyl)thio]thieno[2,3-c]pyridine-2-carboxamide,
4-[(4-chlorophenyl)thio]thieno[2,3-c]pyridine-2-carboxamide,
N-methoxy-N-methyl-4-[(4-methylphenyl)thio]thieno[2,3-c]pyridine-2-carboxamide,
N-methoxy-4-[(4-methylphenyl)thio]thieno[2,3-c]pyridine-2-carboxamide,
N-(4-chlorophenyl)-4-[(4-methylphenyl)thio]thieno[2,3-c]pyridine-2-carboxamide,
N-(2,3-dihydroxypropyl)-4-[(4-methylphenyl)thio]thieno[2,3-c]pyridine-2-carboxamide,
4-[(4-methylphenyl)thio]thieno[2,3-c]pyridine-2-carboxylic acid, hydrazide,
N$^2$-4-[(4-methylphenyl)thio]thieno[2,3-c]pyridin-2-yl]carbonyl]-N$^6$-[(nitroamino)iminomethyl]-L-lysine, methyl ester,
4-[(4-methylphenyl)thio]thieno[2,3-c]pyridine-2-carbothioamide,
4-[(4-bromophenyl)thio]thieno[2,3-c]pyridine-2-carboxamide,
4-(phenylthio)thieno[2,3-c]pyridine-2-carboxamide,
4-[[4-(trifluoromethyl)phenyl]thio]thieno[2,3-c]pyridine-2-carboxamide,
4-[(2-methylphenyl)thio]thieno[2,3-c]pyridine-2-carboxamide,
4-[(3-methylphenyl)thio]thieno[2,3-c]pyridine-2-carboxamide,
4-[(3,4-dimethylphenyl)thio]thieno[2,3-c]pyridine-2-carboxamide,
4-[(3,5-dimethylphenyl)thio]thieno[2,3-c]pyridine-2-carboxamide,
4-[(2,4-dimethylphenyl)thio]thieno[2,3-c]pyridine-2-carboxamide,
4-[(3,4-dichlorophenyl)thio]thieno[2,3-c]pyridine-2-carboxamide,
4-[(4-methoxyphenyl)thio]thieno[2,3-c]pyridine-2-carboxamide,
4-[(4-methylphenyl)thio]-N-[3-(4-morpholinyl)propyl]thieno[2,3-c]pyridine-2-carboxamide,
4-[(4-methylphenyl)sulfinyl]thieno[2,3-c]pyridine-2-carboxamide,
4-(4-methylphenoxy)thieno[2,3-c]pyridine-2-carboxamide,
4-(4-chlorophenoxy)thieno[2,3-c]pyridine-2-carboxamide,
4-[4-(trifluoromethyl)phenoxy]thieno[2,3-c]pyridine-2-carboxamide,
4-(4-octylphenoxy)thieno[2,3-c]pyridine-2-carboxamide,
4-[4-(1-methylethyl)phenoxy]thieno[2,3-c]pyridine-2-carboxamide,
4-(2-bromo-4-chlorophenoxy)thieno[2,3-c]pyridine-2-carboxamide,
4-(4-ethylphenoxy)thieno[2,3-c]pyridine-2-carboxamide,
4-(4-ethenylphenoxy)thieno[2,3-c]pyridine-2-carboxamide,
4-[4-(1,2-dihydroxyethyl)phenoxy]thieno[2,3-c]pyridine-2-carboxamide,
4-[2-(2-propenyl)phenoxy]thieno[2,3-c]pyridine-2-carboxamide,
4-[2-(2,3-dihydroxypropyl)phenoxy]thieno[2,3-c]pyridine-2-carboxamide,
4-[4-(trifluoromethyl)phenoxy]thieno[2,3-c]pyridine-2-carboxamide, 1-oxide,
4-[3-(pentadecyl)phenoxy]thieno[2,3-c]pyridine-2-carboxamide,
4-(4-bromophenoxy)thieno[2,3-c]pyridine-2-carboxamide,
4-(3-chlorophenoxy)thieno[2,3-c]pyridine-2-carboxamide, 4-(4-t-butylphenoxy)thieno[2,3-c]pyridine-2-carboxamide,
4-(4-chloro-3-methylphenoxy)thieno[2,3-c]pyridine-2-carboxamide,
4-(4-chloro-2-methylphenoxy)thieno[2,3-c]pyridine-2-carboxamide,
4-(4-methoxyphenoxy)thieno[2,3-c]pyridine-2-carboxamide, ethyl 3-[[2-(aminocarbonyl)thieno[2,3-c]pyridin-4-yl]oxy]benzoate,
4-phenoxythieno[2,3-c]pyridine-2-carboxamide,
4-(3-bromophenoxy)thieno[2,3-c]pyridine-2-carboxamide,
4-(4-fluorophenoxy)thieno[2,3-c]pyridine-2-carboxamide,
4-(3,5-dimethylphenoxy)thieno[2,3-c]pyridine-2-carboxamide,
4-(3-chloro-4-methylphenoxy)thieno[2,3-c]pyridine-2-carboxamide,
4-(4-iodophenoxy)thieno[2,3-c]pyridine-2-carboxamide,
4-(4-(methoxymethyl)phenoxy)thieno[2,3-c]pyridine-2-carboxamide,
4-([1,1'-biphenyl]-4-ylthio)thieno[2,3-c]pyridine-2-carboxamide, ethyl 4-[[2-(aminocarbonyl)thieno[2,3-c]pyridin-4-yl]oxy]benzoate,
4-[[2-(aminocarbonyl)thieno[2,3-c]pyridin-4-yl]oxy]benzoic acid,
4-(4-Chlorophenoxy)-N-methylthieno[2,3-c]pyridine-2-carboxamide,
4-(4-chlorophenoxy)-N,N-dimethylthieno[2,3-c]pyridine-2-carboxamide,
4-(4-chlorophenoxy)-N,N-diethylthieno[2,3-c]pyridine-2-carboxamide,
4-(4-chlorophenoxy)-N-cyclopropylthieno[2,3-c]pyridine-2-carboxamide,
4-(4-chlorophenoxy)-N-(2-hydroxyethyl)lthieno[2,3-c]pyridine-2-carboxamide,
4-(4-chlorophenoxy)-N-[1-(hydroxymethyl)ethyl]thieno[2,3-c]pyridine-2-carboxamide,
4-(4-chlorophenoxy)-N-[1,1-bis(hydroxymethyl)ethyl]thieno[2,3-c]pyridine-2-carboxamide,
(D,L)-4-(4-chlorophenoxy)-N-(2-hydroxypropyl)thieno[2,3-c]pyridine-2-carboxamide,
4-(4-chlorophenoxy)-N-[2-(4-morpholinyl)ethyl]thieno[2,3-c]pyridine-2-carboxamide,
4-(4-chlorophenoxy)thieno[2,3-c]pyridine-2-carboxamide, N-oxide,
4-(4-chlorophenoxy)-3-methylthieno[2,3-c]pyridine-2-carboxamide,
3-amino-4-(4-chlorophenoxy)thieno[2,3-c]pyridine-2-carboxamide,
4-(4-chlorophenoxy)thieno[2,3-c]pyridine-2-carbothioamide,
4-(4-chlorophenoxy)-N-ethylthieno[2,3-c]pyridine-2-carboxamide,
4-(4-chlorophenoxy)-N-(2,3-dihydroxypropyl)thieno[2,3-c]pyridine-2-carboxamide,
4-(4-bromophenoxy)-N-(2,3-dihydroxypropyl)thieno[2,3-c]pyridine-2-carboxamide,
N-(2-chloroethyl)-4-(4-chlorophenoxy)thieno[2,3-c]pyridine-2-carboxamide,
4-(4-bromophenoxy)-N-(2-hydroxyethyl)thieno[2,3-c]pyridine-2-carboxamide,
4-(2-bromo-4-chlorophenoxy)-N-(2-hydroxyethyl)thieno[2,3-c]pyridine-2-carboxamide,
N-(2-hydroxyethyl)-4-[4-(trifluoromethyl)phenoxy]thieno[2,3-c]pyridine-2-carboxamide,
N-(2-aminoethyl)-4-(4-chlorophenoxy)thieno[2,3-c]pyridine-2-carboxanide,
4-(4-chlorophenoxy)-N-hydroxythieno[2,3-c]pyridine-2-carboxamide,
4-(4-chlorophenoxy)thieno[2,3-c]pyridine-2-carbohydrazide,
4-(4-bromophenoxy)thieno[2,3-c]pyridine-2-carbohydrazide,
4-[4-(trifluoromethyl)phenoxy]thieno[2,3-c]pyridine-2-carbohydrazide,
4-(4-bromophenoxy)-N-methylthieno[2,3-c]pyridine-2-carboxamide,
4-(4-bromophenoxy)-N,N-dimethylthieno[2,3-c]pyridine-2-carboxamide,
N,N-dimethyl-4-[4-(trifluoromethyl)phenoxy]thieno[2,3-c]pyridine-2-carboxamide,
4-(4-chloro-3-fluorophenoxy)-N-methylthieno[2,3-c]pyridine-2-carboxamide,
4-(4-chloro-3-fluorophenoxy)thieno[2,3-c]pyridine-2-carboxamide,
4-(4-chloro-3-ethylphenoxy)thieno[2,3-c]pyridine-2-carboxamide,
4-(3-fluorophenoxy)thieno[2,3-c]pyridine-2-carboxamide,
4-(2,3-difluorophenoxy)thieno[2,3-c]pyridine-2-carboxamide,
4-(2,3-difluorophenoxy)-N-methylthieno[2,3-c]pyridine-2-carboxamide,
4-(3-fluorophenoxy)-N-methylthieno[2,3-c]pyridine-2-carboxamide,
N-methyl-4-(2,3,4-trifluorophenoxy)thieno[2,3-c]pyridine-2-carboxamide,
4-(2,3,4-trifluorophenoxy)thieno[2,3-c]pyridine-2-carboxamide,
N-methyl-4-[4-(trifluoromethyl)phenoxy]thieno[2,3-c]pyridine-2-carboxamide,
4-[3-(trifluoromethyl)phenoxy]thieno[2,3-c]pyridine-2-carboxamide,
N,N-dimethyl-4-(4-vinylphenoxy)thieno[2,3-c]pyridine-2-carboxamide,
4-(4-cyanophenoxy)-N-methylthieno[2,3-c]pyridine-2-carboxamide,
4-(4-cyanophenoxy)thieno[2,3-c]pyridine-2-carboxamide,
4-(4-aminophenoxy)thieno[2,3-c]pyridine-2-carboxamide,
4-[4-(acetylamino)phenoxy]thieno[2,3-c]pyridine-2-carboxamide,
N-methyl-4-[4-(4-iodophenoxy)]thieno[2,3-c]pyridine-2-carboxamide,
4-[4-(hydroxymethyl)phenoxy]thieno[2,3-c]pyridine-2-carboxamide,
4-[4-(hydroxymethyl)phenoxy]-N-methylthieno[2,3-c]pyridine-2-carboxamide,
4-[4-(methoxymethyl)phenoxy]-N-methylthieno[2,3-c]pyridine-2-carboxamide,
4-{4-[(2-methoxyethoxy)methyl]phenoxy}thieno[2,3-c]pyridine-2-carboxamide, 4-{4-[(2-methoxyethoxy)methyl]phenoxy}-N-methylthieno[2,3-c]pyridine-2-carboxamide, 4-(4-{[2-(2-methoxyethoxy)ethoxy]methyl}phenoxy)thieno[2,3-c]pyridine-2-carboxamide, 4-(4-{[2-(2-methoxyethoxy)ethoxy]methyl}phenoxy)-N-methylthieno[2,3-c]pyridine-2-carboxaamide, 4-(4-acetylphenoxy)-N-methylthieno[2,3-c]pyridine-2-carboxamide, 4-(4-{(E)-3-[(2,3-dihydroxypropyl)amino]-3-oxo-1-propenyl}phenoxy)thieno[2,3-c]pyridine-2-carboxamide, 4-(4-{(E)-3-[(2,3-dihydroxypropyl)amino]-3-oxo-1-propenyl}phenoxy)-N-methylthieno[2,3-c]pyridine-2-carboxamide, 4-{4-[(E)-3-({2-[bis(2-hydroxyethyl)amino]ethyl}amino)-3-oxo-1-propenyl]phenoxy}-N-methylthieno[2,3-c]pyridine-2-carboxamide, 4-{4-[(E)-3-({2-[bis(2-hydroxyethyl)amino]ethyl}amino)-3-oxo-1-propenyl]phenoxy}thieno[2,3-c]pyridine-2-carboxamide, 4-([1,1'-biphenyl]-4-yloxy)-N-methylthieno[2,3-c]pyridine-2-carboxamide, 4-{4-[1-(hydroxymethyl)cyclopropyl]phenoxy}-N-methylthieno[2,3-c]pyridine-2-carboxamide, 4-[4-(1-{[2-(2-ethoxyethoxy)ethoxy]methyl}cyclopropyl)phenoxy]-N-methylthieno[2,3-c]pyridine-2-carboxamide, N-methyl-4-[4-(trifluoromethoxy)phenoxy]thieno[2,3-c]pyridine-2-carboxamide, 4-[4-(1,1-difluoro-2-hydroxyethyl)phenoxy]-N-methylthieno[2,3-c]pyridine-2-carboxamide, 4-(4-{2-[2-(2-ethoxyethoxy)ethoxy]-1,1-difluoroethyl}phenoxy)-N-methylthieno[2,3-c]pyridine-2-carboxamide, 4-(4-chlorophenoxy)-N,3-dimethylthieno[2,3-c]pyridine-2-carboxamide, 4-(4-bromophenoxy)-3-methylthieno[2,3-c]pyridine-2-carboxamide, 7-chloro-4-(4-chlorophenoxy)-3-methylthieno[2,3-c]pyridine-2-carboxamide, tert-butyl 2-(aminocarbonyl)-4-(4-chlorophenoxy)thieno[2,3-c]pyridine-3-carboxylate, 7-chloro-4-(4-chlorophenoxy)thieno[2,3-c]pyridine-2-carboxamide, 7-chloro-4-(4-chlorophenoxy)-N-methylthieno[2,3-c]pyridine-2-carboxamide, 7-chloro-4-(4-chlorophenoxy)-N-(2-hydroxyethyl)thieno[2,3-c]pyridine-2-carboxamide, 7-bromo-4-(4-chlorophenoxy)thieno[2,3-c]pyridine-2-carboxamide, 7-bromo-4-(4-chlorophenoxy)-N-methylthieno[2,3-c]pyridine-2-carboxamide, 4-(4-bromophenoxy)-7-chlorothieno[2,3-c]pyridine-2-carboxamide, 4-(4-bromophenoxy)-7-chloro-N-methylthieno[2,3-c]pyridine-2-carboxamide, 7-chloro-4-[4-(trifluoromethyl)phenoxy]thieno[2,3-c]pyridine-2-carboxamide, 7-chloro-N-methyl-4-[4-(trifluoromethyl)phenoxy]thieno[2,3-c]pyridine-2-carboxamide, 7-chloro-N-(2-hydroxyethyl)-4-[4-(trifluoromethyl)phenoxy]thieno[2,3-c]pyridine-2-carboxamide, 4-(4-chlorophenoxy)-N,7-dimethylthieno[2,3-c]pyridine-2-carboxamide, 4-(4-chlorophenoxy)-7-methoxythieno[2,3-c]pyridine-2-carboxamide, 4-(4-chlorophenoxy)-N-methyl-7-(methylamino)thieno[2,3-c]pyridine-2-carboxamide, 4-(4-bromophenoxy)-5-chlorothieno[2,3-c]pyridine-2-carboxamide.

3. A method for treating reperfusion injuries and inflammatory diseases in a mammal comprising administering to the mammal a therapeutically effective amount of a compound of claim 1.

4. A compound according to claim 1 where $L_A$ is —O—.

5. A compound according to claim 1 where $L_A$ is —S(O)$_t$—.

6. A compound according to claim 1 where $X_A$ is unsubstituted aryl.

7. A compound according to claim 1 where $X_A$ is phenyl.

8. A compound according to claim 1 where $X_A$ is aryl, where the aryl is substituted with one substituent selected from (a) alkyl of one to twenty carbons, (b) alkyl of one to ten carbons substituted with 1 or 2 substituents independently selected from
  (i) —OR$_{11}$ where R$_{11}$ is hydrogen,
  (ii) alkoxy of one to ten carbons optionally substituted with an alkoxy or alkoxyalkoxy substituent,
  (iii) spiroalkyl of three to ten carbons, and
  (iv) halo, (c) alkoxy of one to ten carbons (d) halo, (e) perfluoroalkyl of one to three carbons, (f) alkenyl of two to ten carbons (g) —CO$_2$R$_7$ where R$_7$ is selected from hydrogen and alkyl of one to ten carbons (h) —NR$_8$R$_9$ where R$_8$ and R$_9$ are hydrogen, (i) aryl, (j) —CN, (k) —C(W)R$_{10}$ where R$_{10}$ is alkyl of one to ten carbons, and (l) —OCF$_3$.

9. A compound according to claim 1 where $X_A$ is 2-methylphenyl, 2-(2-propenylphenyl), 3-chlorophenyl, 3-ethoxycarbonylphenyl, 4-methylphenyl, 4-fluorophenyl, 4-chlorophenyl, 4-bromophenyl, 4-iodophenyl, 4-(trifluoromethyl)phenyl, 4-methoxyphenyl, 4-octylphenyl, 4-(1-methylethyl)phenyl, 4-ethylphenyl, 4-ethenylphenyl, 4-(1,2-dihydroxyethyl)phenyl, 4-(2,3-dihydroxypropyl)phenyl, 4-pentadecylphenyl, 4-(1,1-dimethylethyl)phenyl, 4-(methoxymethyl)phenyl, 4-phenylphenyl, 4-carboxyphenyl, 4-cyanophenyl, 4-aminophenyl, 4-(N-acetylamino)phenyl, 4-(hydroxymethyl)phenyl, 4-((2-methoxyethoxy)methyl)phenyl, 4-acetylphenyl, 4-(1-(hydroxymethyl)cycloprop-1-yl)phenyl, 4-(1-((ethoxyethoxy)ethoxy)cycloprop-1-yl)phenyl, 4-(1,1-difluoro-2-hydroxyethyl)phenyl, and 4-((2-ethoxyethoxy)ethoxy)phenyl.

10. A compound according to claim 1 where $X_A$ is aryl, where the aryl is substituted with two substituents independently selected from halo and alkyl of one to twenty carbons.

11. A compound according to claim 1 where $X_A$ is selected from 3,4-dimethylphenyl, 3,5-dimethylphenyl, 2,4-dimethylphenyl, 2,3-difluorophenyl, 3,4-dichlorophenyl, 2-bromo-4-chlorophenyl, 4-chloro-3-methylphenyl, 4-chloro-3-ethylphenyl, 4-chloro-2-methylphenyl, 3-chloro-4-methylphenyl, and 4-chloro-3-fluorophenyl.

12. A compound according to claim 1 where $X_A$ is aryl, where the aryl is substituted with three halo substituents.

13. A compound according to claim 1 where $X_A$ is 2,3,4-trifluorophenyl.

14. A compound according to claim 1 where W is O.

15. A compound according to claim 1 where W is S.

16. A compound according to claim 1 where $R_1$ is selected from hydrogen and halo.

17. A compound according to claim 1 where $R_1$ is selected from hydrogen and chloro.

18. A compound according to claim 1 where $R_3$ is selected from hydrogen, alkoxy of one to six carbons, halo, alkyl of one to six carbons, and —$NR_AR_B$ where $R_A$ is hydrogen and $R_B$ is alkyl of one to six carbons.

19. A compound according to claim 1 where $R_3$ is selected from hydrogen, methoxy, chloro, bromo, methyl, and N-methylamino.

20. A compound according to claim 1 where $R_4$ is selected from hydrogen, alkyl of one to six carbons, —$NR_AR_B$ where $R_A$ and $R_B$ are hydrogen, and —$OC(O)R_{22}$ where $R_{22}$ is alkyl.

21. A compound according to claim 1 where $R_4$ is selected from hydrogen, methyl, —OH, 1-methylethoxy, —$NH_2$, and 1,1-dimethylethoxycarbonyl.

22. A compound according to claim 1 where Z is —$S(O)_t$—, $L_A$ is —O—, $X_A$ is 4-bromophenyl, $R_1$ is hydrogen; $R_3$ is hydrogen, $R_4$ is hydrogen, $R_{17}$ is alkyl of one to ten carbons, and $R_{18}$ is hydrogen.

23. A compound according to claim 22 which is methyl 4-(4-bromophenoxy)thieno[2,3-c]pyridine-2-carboxamide.

24. A compound according to claim 1 where Z is —$S(O)_t$—, $L_A$ is —O—, $X_A$ is 4-(trifluoromethyl)phenyl, $R_1$ is hydrogen, $R_3$ is hydrogen, $R_4$ is hydrogen, $R_{17}$ is alkyl of one to ten carbons, and $R_{18}$ is hydrogen.

25. A compound according to claim 24 which is 4-[3-(trifluoromethyl)phenoxy]thieno[2,3-c]pyridine-2-carboxamide.

* * * * *

UNITED STATES PATENT AND TRADEMARK OFFICE
CERTIFICATE OF CORRECTION

PATENT NO.      : 6,232,320 B1
DATED           : May 15, 2001
INVENTOR(S)     : Andrew O. Stewart et al.

It is certified that error appears in the above-identified patent and that said Letters Patent is hereby corrected as shown below:

<u>Column 224,</u>
Line 14, replace "ary and" with -- aryl and --.

Signed and Sealed this

Tenth Day of June, 2003

JAMES E. ROGAN
*Director of the United States Patent and Trademark Office*